(12) United States Patent
Okazaki et al.

(10) Patent No.: US 6,797,805 B2
(45) Date of Patent: Sep. 28, 2004

(54) ORGANIC POLYMERS AND NOVEL POLYMERIZABLE COMPOUNDS

(75) Inventors: Koju Okazaki, Chiba (JP); Ryouichi Seki, Chiba (JP); Shiro Nakatsuka, Chiba (JP)

(73) Assignee: Mitsui Chemicals, Inc., Tokyo (JP)

( * ) Notice: Subject to any disclaimer, the term of this patent is extended or adjusted under 35 U.S.C. 154(b) by 42 days.

(21) Appl. No.: 10/169,190

(22) PCT Filed: Oct. 30, 2001

(86) PCT No.: PCT/JP01/09503

§ 371 (c)(1),
(2), (4) Date: Jun. 28, 2002

(87) PCT Pub. No.: WO02/36662

PCT Pub. Date: May 10, 2002

(65) Prior Publication Data

US 2003/0166808 A1 Sep. 4, 2003

(30) Foreign Application Priority Data

| Oct. 30, 2000 | (JP) | 2000-331228 |
| Oct. 30, 2000 | (JP) | 2000-331394 |
| Oct. 31, 2000 | (JP) | 2000-331573 |
| Oct. 31, 2000 | (JP) | 2000-331574 |
| Oct. 31, 2000 | (JP) | 2000-331575 |

(51) Int. Cl.$^7$ .................. C08G 73/56; C08G 75/00
(52) U.S. Cl. ............... 528/423; 528/422; 528/425; 528/373; 526/217; 526/273; 546/351
(58) Field of Search ................. 528/423, 422, 528/425, 373; 526/217, 273; 546/351

(56) References Cited

FOREIGN PATENT DOCUMENTS

| EP | 0405308 A2 | 1/1991 |
| GB | 2325467 A | 11/1998 |
| JP | 9-241331 A | 9/1997 |
| JP | 10-139836 A | 5/1998 |
| JP | 10-168125 A | 6/1998 |
| JP | 10-316769 A | 12/1998 |
| JP | 11-5967 A | 1/1999 |
| JP | 11-302421 A | 11/1999 |
| JP | 2000-319406 A | 11/2000 |
| JP | 2001-329018 A | 11/2001 |
| JP | 2001-337298 A | 12/2001 |

OTHER PUBLICATIONS

Reichard et al; Preparation of substituted oximes and hydrazones as neurokinin antagonists; Jul. 2000; Chem Abstract 133: 74037.*

* cited by examiner

*Primary Examiner*—Duc Truong
(74) *Attorney, Agent, or Firm*—Burns, Doane, Swecker & Mathis, L.L.P.

(57) ABSTRACT

Organic polymers having water contact angles of 20° or smaller, preferably 7° or smaller and equipped with both high wettability and high transparency. The organic polymers may contain as partial structures polar structures of about 3 debyes or higher in dipole moment and are available especially from polymerization of polymerizable compounds having alkylene(thio)urea structures.

24 Claims, 68 Drawing Sheets

ORGANIC POLYMERS AND NOVEL POLYMERIZABLE COMPOUNDS

TECHNICAL FIELD

This invention relates to organic polymers having high water wettability, molded or otherwise formed products comprising the organic polymers, novel polymerizable compounds and compositions capable of affording organic polymers having high water wettability, and antifouling materials, anti-mist materials, dew preventing materials, water (liquid) absorbent materials and optical materials, all of which make use of organic polymers and molded or otherwise formed products having high water wettability.

BACKGROUND ART

As a representative physical value expressing water wettability, water contact angle is known. In general, those having water contact angles of less than 90° are classified as hydrophilic materials, and those having water contact angles of greater than 90° are classified as water repellant materials. As the water contact angle approaches from 90° toward 0°, the material can be considered to be higher in water wettability.

High water wettability is extremely effective for water retaining materials or the like, which are useful, for example, for the inhibition of dew-induced misting of windowpanes, mirrors, agricultural vinyl sheets, eyeglass lenses, camera lenses and the like, for the suppression of a reduction in the efficiency of heat exchange due to formation of water droplets and deposition of fouling substances on cooling fins, for the protection of building exterior walls and the like from fouling by improving their property to eliminate (self-clean), with rain or water, fouling (airborne hydrophobic substances) deposited on the building exterior walls, for the improvement of dew preventing property of building interior finish paints and materials and the like, for the improvement of contact lens wear comfort and anti-fouling property, and for water-retention materials used for the greening of deserts or the growth promotion of general plants.

In these applications, the products are large in size or complex in structure, accuracy is required, productivity, controllability and product flexibility and safety are needed, water absorbency is needed, and coloration or dyeing is preferred. Accordingly, difficulties are encountered with inorganic materials in any instances, resulting in an increasingly high demand for organic materials.

Known as organic materials capable of showing high water wettability include polymers such as polyvinyl alcohol [water contact angle: 36°, "Cho-shinsui Cho-hassuika Gijutsu (Superhydrophilicity, Super Water-repellancy Imparting Technology)", Published by Gijutsu Joho Kyokai Co., Ltd., 2001], polyisopropylacrylamide (water contact angle: about 44° Langmuir, 11, 2301, 1995), and polyacrylonitrile (water contact angle: about 53°, Desalination, 72, 263, 1989).

These polymers show the effect by hydroxyl groups, nitrile groups or amide groups which they themselves have. These functional groups are, however, known to be high in reactivity, and in some instances, may tend to cause a quality deterioration or change in final products due to induction of undesired unnecessary reactions such as acetylation with aldehydes, esterification with acids or acid anhydrides, changes into amides or carboxylic acids through hydrolysis and esterification by alcoholysis or the like, and induction of Diels-Alder reaction or Michael addition ["Plastic Jiten (Plastic Dictionary)", Published by Asakura-Shoten Pub., Co., Ltd., 1992]. Such polymers are accompanied by further problems such that they themselves may be dissolved or eluted into water and may be low in mechanical strength or the like.

With a view to solving, for example, problems of dissolution or elution, mechanical strength and the like, it has been proposed to add copolymerizable compounds to form them into network polymers. This modification, however, has a tendency of deteriorating the wettability, and is not considered to be a proposal that assures sufficient strength while retaining high wettability.

As an unconventional material, an agar gel (water contact angle: about 20°, Langmuir, 10, 2435, 1994) is known. It is, however, not considered to be sufficient in physical and chemical properties for its insufficient mechanical strength, insufficient heat resistance and insufficient water resistance and chemical resistance. Practically, it is extremely difficult to use it for such purposes as described above.

As other methods for exhibiting high water wettability, methods which primarily involve surface modifications are known, including a method that provides a photocatalytic reaction layer of titanium oxide (JP 11-58629 A, JP 11-1659 A), a method that coats a coating formulation making use of silanol groups (JP 9-40907 A, JP 9-40908 A, JP 11-21826 A), a method that subsequent to corona discharge treatment, provides a layer containing silyl groups and ionic hydrophilic groups (carboxyl groups) and polyvinyl alcohol (JP 9-76428 A), a method that provides a layer making use of a quaternary ammonium base (JP 10-296895 A), a method that forms a number of micropits on a surface by etching treatment (JP 7-198290 A), a method that introduces active hydrogen groups such as an amido group, carboxyl group and hydroxyl group, or ionic functional groups such as sodium sulfonate, into a surface by graft copolymerization (J. Poly. Sci., Part A: Polym. Chem., 32, 1569, 1994; Macromolecules, 25, 6842, 1992), and a method that treats a surface with a chloric acid-potassium chlorate mixed solution [Polymer (Korea), 24, 877, 2000].

According to these methods, high water wettability can be certainly realized in some instances. However, they tend to cause various problems such as decomposition at the interface with a coated material through a photocatalytic reaction, ineffectiveness in a dark ambient, delamination due to differences in a physical property such as coefficient of linear expansion, flexibility or refractive index, crazing in a coating layer or a coated material, development of interference bands, insufficient strength and weather resistance of a coating layer and a treated surface, and a reduction in performance due to an undesired reaction with active hydrogen groups or ionic groups. On top of these problems, these methods generally require high ingenuity and special apparatus in many instances, and also require a procedure of forming molded or otherwise formed products beforehand and then treating or coating the products further. These surface-modifying methods, therefore, are proposals that lead to cumbersome production and are not considered to be effective, tend to result in high cost, and in some instances, also have some doubts in safety.

In the field of resins, polymers and the like, on the other hand, the possession of excellent transparency is significantly effective. They can be used in the field of optical materials led by spectacle lenses, contact lenses, camera lenses, pickup lenses and organic glasses and the field of transparent materials such as transparent films, and moreover, are expected to develop new markets and high functionality, such as improvements in color vividness and luster, in the field of paints, coating formulations and the like.

Nonetheless, it has been unknown whether or not high-wettability organic polymers with which the present invention are concerned have high transparency.

DISCLOSURE OF THE INVENTION

Namely, it has been extremely difficult to solve the above-mentioned numerous problems and to propose organic polymers, resins and the like having high wettability and high transparency.

With such circumstances in view, the present inventors have proceeded with an extensive investigation. As a result, it has been found that use of a polymerizable compound having a polar structure, the dipolar moment of which is high (about 3 debyes or higher), as a partial structure is effective for solving the problems and also that among such polar structures, an alkylene(thio)urea structure analogous to the structure of polyurea considered to be poor in practical utility for its high cost and low thermal stability ["Plastic Daijiten (Encyclopedia of Plastics)", Published by Kogyo Chosakai Publishing Co., Ltd.] is more effective. The present inventors have also found polymerizable compounds having a novel alkylene(thio)urea structure which can bring about more preferred results.

The present inventors have also found that the wettability of a polymer is drastically improved by copolymerizing a polymerizable compound having the above-described polar structure.

According to the above method, organic polymers which are physically and chemically stable despite their high water wettability and are excellent in transparency can be efficiently obtained without needing special ingenuity and apparatus and a cumbersome procedure such as conversion. organic polymers according to the present invention can be suitably used for applications in antifouling materials (self-cleaning materials), anti-mist materials, dew preventing materials, water (liquid) absorbent materials, optical materials and the like. Described specifically, the present invention relates to:

[3] An organic polymer as defined in [1] or [2], which has a polar structure of 3 debyes or higher in dipole moment.

[4] A molded or otherwise formed product comprising an organic polymer as defined in [1], [2] or [3].

[5] A polymerizable compound comprising, in a molecule thereof, one or more of the following partial structural formula (A):

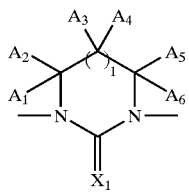

(A)

wherein $A_1$ to $A_6$ each independently represent a hydrogen atom or an alkyl group having 1 to 6 carbon atoms, $X_1$ represents O or S, and l stands for an integer of 0 to 2, and one or more thioepoxy groups, allylthio-carbonyl groups or allyloxycarbonyl groups.

[6] A polymerizable compound comprising, in a molecule thereof, one or more of the following partial structural formula (A):

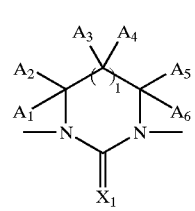

(A)

wherein $A_1$ to $A_6$ each independently represent a hydrogen atom or an alkyl group having 1 to 6 carbon atoms, $X_1$ represents O or S, and l stands for an integer of 0 to 2, and two or more mercapto groups, glycidylthio groups or (meth) acryloylthio groups.

[7] A polymerizable compound represented by the following formula (B):

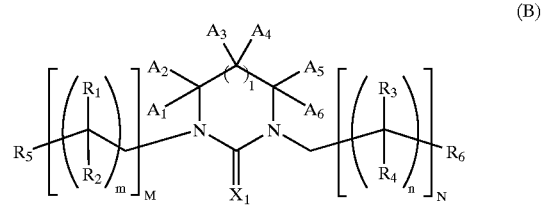

(B)

wherein $A_1$ to $A_6$ each independently represent a hydrogen atom or an alkyl group having 1 to 6 carbon atoms, $X_1$ represents O or S, l stands for an integer of 0 to 2, $R_1$ to $R_4$ each independently represent a hydrogen atom, a hydroxy group, a mercapto group, an alkyl group having 1 to 6 carbon atoms, an alkoxy group having 1 to 6 carbon atoms, an alkylthio group having 1 to 6 carbon atoms, or the below-described formulas (C) to (F), m and n each independently stand for an integer of from 0 to 10, M and N each independently stand for an integer of from 1 to 10, $R_5$ and $R_6$ each independently represent an alkoxy group having 1 to 6 carbon atoms, an alkylthio group having 1 to 6 carbon atoms, or the below-described formulas (C) to (F), with a proviso that any one or more of $R_1$ to $R_4$ are any of the below-described formulas (C) to (E):

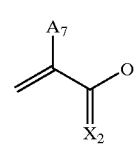

(C)

wherein $A_7$ represents a hydrogen atom or a methyl group, and $X_2$ represents O or S;

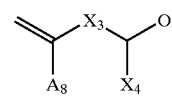

(D)

wherein $A_8$ represents a hydrogen atom or a methyl group, and $X_3$ and $X_4$ each independently represent O or S; and (E)

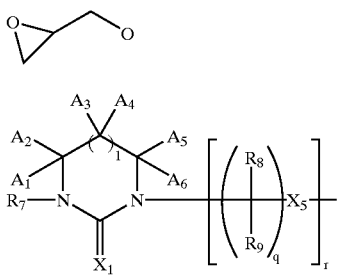

(F)

wherein $A_1$ to $A_6$ each independently represent a hydrogen atom or an alkyl group having 1 to 6 carbon atoms, $X_1$ or $X_5$ represents O or S, l stands for an integer of 0 to 2, $R_7$ each independently represents a hydrogen atom, an alkyl group having 1 to 6 carbon atoms, an alkoxyalkyl group having 2 to 12 carbon atoms or an alkylthioalkyl group having 2 to 12 carbon atoms, $R_8$ and $R_9$ each independently represent a hydrogen atom, a hydroxy group, a mercapto group, an alkyl group having 1 to 6 carbon atoms, an alkoxy group having 1 to 6 carbon atoms or an alkylthio group having 1 to 6 carbon atoms, q stands for an integer of from 1 to 6, and r stands for an integer of an integer of from 0 to 3.

[8] A polymerizable composition comprising a polymerizable compound as defined in [5], [6] or [7].

[9] An organic polymer available from polymerization of a polymerizable compound as defined in [5], [6] or [7] or a polymerizable composition as defined [8] and having a water contact angle of 20° or smaller.

[10] An organic polymer available from polymerization of a polymerizable compound as defined in [5], [6] or [7] or a polymerizable composition as defined in [8] and having a water contact angle of 7° or smaller.

[11] A molded or otherwise formed product comprising an organic polymer as defined in [8] or [9].

[12] Use, as an antifouling material, of an organic polymer as defined in [1], [2], [3], [9] or [10] or a molded or otherwise formed product as defined in [4] or [11].

[13] Use, as an anti-mist material, of an organic polymer as defined in [1], [2], [3], [9]or [10] or a molded or otherwise formed product as defined in [4] or [11].

[14] Use, as a dew preventing material, of an organic polymer as defined in [1], [2], [3], [9] or [10] or a molded or otherwise formed product as defined in [4] or [11].

[15] Use, as a water(liquid) absorbent material, of an organic polymer as defined in [1], [2], [3], [9] or [10] or a molded or otherwise formed product as defined in [4] or [11].

[16] Use, as an optical material, of an organic polymer as defined in [1], [2], [3], [9] or [10] or a molded or otherwise formed product as defined in [4] or [11].

BEST MODES FOR CARRYING OUT THE INVENTION

Figure 1:
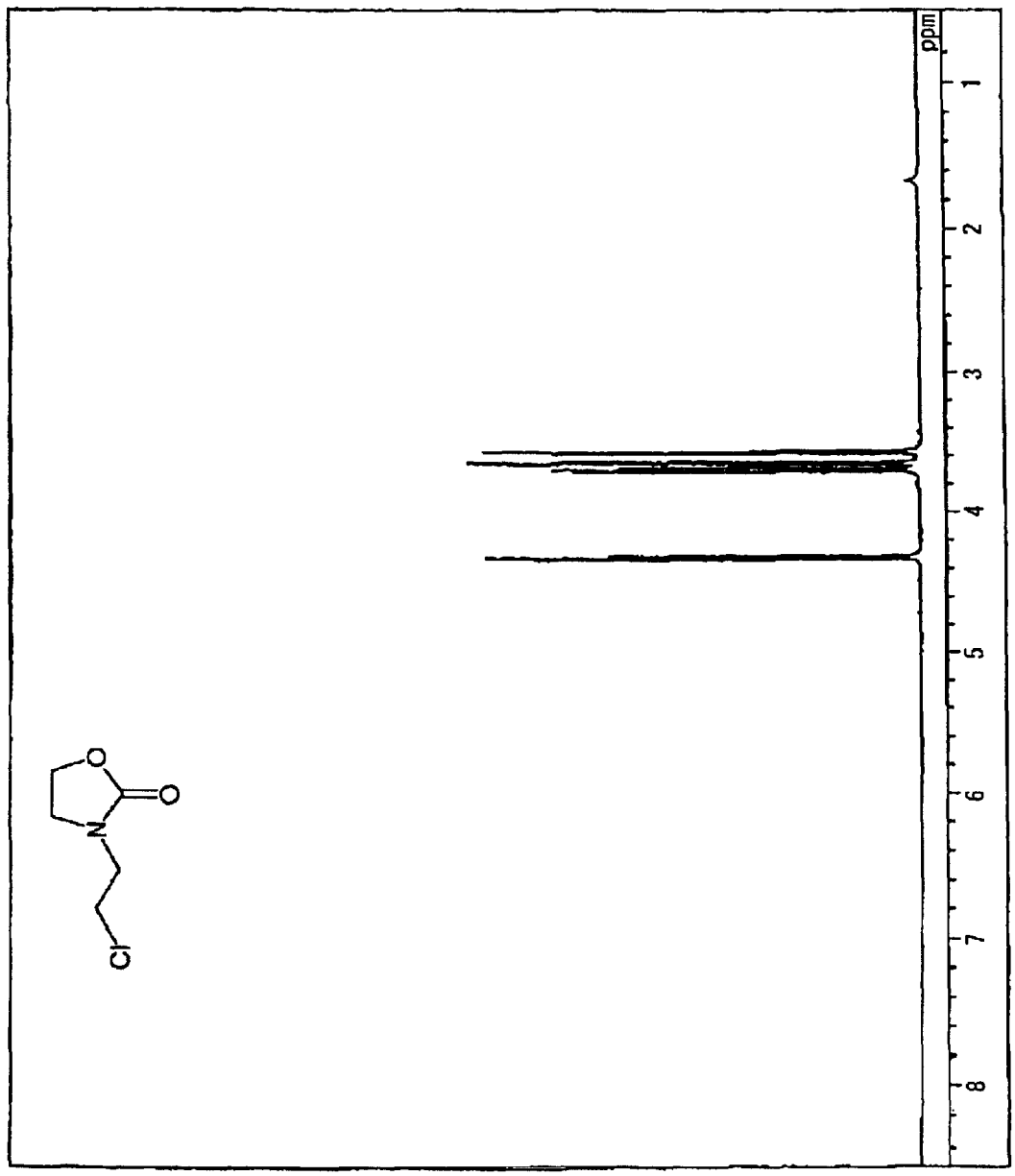
FIG. 1 is a $^1$H-NMR chart of chloroethyloxazolidone obtained in Example 1.

The present invention will hereinafter be described in detail.

The organic polymer having high water wettability, to which the present invention relates, has a water contact angle in a range of from 0 to 20°, preferably in a range of from 0 to 7°. As the water contact angle becomes smaller, antifouling property is improved further. Antifouling property is substantially satisfactory when the water contact angle is about 20° or smaller, and is fully satisfactory when the water contact angle is 10° or smaller. When the water contact angle is 7° or smaller, prevention of misting by steam or the like is also become feasible so that the organic polymer is in a most preferred mode.

The molded or otherwise formed product according to the present invention is a molded or otherwise formed product which comprises an organic polymer having a water contact angle of from 0 to 20° or an organic polymer having a water contact angle of from 0 to 7°. Specifically, it can be, for example, a molded or otherwise formed product comprising only one organic polymer according to the present invention, or a conventional, molded or otherwise formed organic or inorganic product with a coating formulation, paint, laminating material, film or the like, which contains the organic polymer according to the present invention, cured, coated or adhered thereon.

These molded or otherwise molded products may optionally contain, in addition to the organic polymer according to the present invention, other components, for example, stabilizers, colorants, fragrances, bactericides, binders, fillers, organic polymers other than those of the present invention, fillers, glass, metals, metal oxides, organometals, surfactants and the like, as needed depending on desired physical properties, characteristic properties, purposes, applications and the like to extents not causing a problem.

The organic polymers according to the present invention are characterized in that they contain in their molecular structures polar structures the dipolar moments of which are large. Among these, organic polymers having polar structures of 3 debyes or greater are preferred, organic polymers having aprotic polar structures of 3 debyes or greater are more preferred. Particularly effective are structures each of which contains one or more heteroatoms such as oxygen atom(s), nitrogen atom(s), phosphorus atom(s), sulfur atom (s) and/or the like. Illustrative are alkylene(thio)urea structures, oxazolidone structure, pyrrolidone structure, lactone structures, sulfone structures, sulfolane structure, amide structures, alkyl(thio)urea structures, sulfone structures, sulfoxide structures, piperazin-2,3-dione structure, acetyle-neurea structure, caprolactam structures, alkylenecarbonate structures, and phosphate ester structures. For example, a N,N'-dimethyl-ethyleneurea structure which is a sort of alkylene(thio)urea structure is a structure that has high dipolar moment (4.1 debyes), is low in crystallinity and permits relatively easy polyfunctioning (bi- or higher functioning) effective for the retention of mechanical strength and heat resistance.

It is also possible to significantly modify the properties of each organic polymer according to the present invention or to impart one or more new functions to it by adding one or more other components.

One or more new functions can be easily imparted. For example, a high refractive index can be imparted while retaining wettability, hydrophilicity, transparency and the like by newly adding a polymerizable compound, which contains one or more sulfur atoms, as a copolymerizable component. High adhesion property or the like can be imparted while retaining wettability, hydrophilicity, transparency and the like by adding a polymerizable, active-hydrogen-containing component such as (meth)acrylic acid. Further, by adding a metal such as silver or lithium, an organometal salt such as an alkaline metal (meth)acrylate, iodine, an iodonium salt, or the like, antimicrobial property can be imparted while retaining wettability and hydrophilicity although transparency may be impaired in some instances.

A description will next be made about novel polymerizable compounds having alkylene(thio)urea structures of specific structures, which can readily bring about preferred results in the organic polymers according to the present invention.

Described specifically, the novel polymerizable compounds according to the present invention are the compounds described in [5], [6] and [7].

$A_1$ to $A_6$ in the partial structures of the formulas (A), (B) and (F) described in [5], [6] and [7] each independently represents a hydrogen or a linear (or branched) alkyl group having 1 to 6 carbon atoms. From the standpoint of the viscosities and the like of the polymerizable compounds and polymerizable compositions, hydrogen and linear (or branched) alkyl groups having 1 to 3 carbon atoms are preferred, and in some instances, hydrogen and methyl group may be more preferred. $A_1$ to $A_6$ do no contain any cyclic structure such as an aromatic ring, and further, any two or more of them do not fuse together to form a ring structure. In a form having a ring structure, the polymerizable compound may develop inconvenience in that it tends to crystallize by itself, leads to a higher viscosity, or has lower solubility. The alkyl group having 1 to 6 carbon atoms may contain one or more heteroatoms such as oxygen atom(s), sulfur atom(s) and/or nitrogen atom(s) as needed to an extent not causing a problem, and its hydrogen atoms may be substituted partially or wholly by a like number of halogen atoms such as fluorine atoms. Non-inclusion of any heteroatom is, however, desired for hemiacetal forms each of which is susceptible to hydrolysis when one or more heteroatoms are contained.

$X_1$ to $X_5$ in the partial structural formulas (A) to (D) and (F) each independently represents O or S, and selection of one of these heteroatoms can be made appropriately depending on the purpose. From the standpoint of ease in synthesis and cost, O tends to be relatively preferred.

l in the partial structural formulas (A), (B) and (F) stands for an integer of from 0 to 2. Basically, no problem or inconvenience arises with any of 0 (5-membered ring), 1 (6-membered ring) and 2 (7-membered ring). From the standpoint of solubility, crystallinity, cost, ease in synthesis and the like, however, 0 or 1 is relatively preferred, and 0 may be more preferred in some instances.

The partial structural formulas (A) and (B) may each independently be bonded with one or more of polymerizable functional groups {thioepoxy groups, allylthiocarbonyl groups, allyloxycarbonyl groups, mercapto groups, glycidylthio groups, (meth)acryloylthio groups, and the partial structures (C) to (E)}. From the standpoint of cost, ease in synthesis and the like, it is preferred to contain 1 to 6 of these polymerizable functional groups bonded in a molecule, and in some instances, bonding of 1 to 4 of them may be more preferred.

Among these polymerizable functional groups, (meth)acryloylthio group, allylthiocarbonyl group, allyloxycarbonyl group, the partial structural formula (C) and the partial structural formula (D) are relatively preferred from the standpoint of photopolymerization reactivity level, and (meth)acryloylthio group and partial structural formula (C) tend to be more preferred.

From the standpoint of thermopolymerization reactivity level, on the other hand, mercapto group, thioepoxy group, (meth)acryloylthio group, allylthio-carbonyl group, allyloxycarbonyl group, the partial structural formula (C) and the partial structural formula (D) are relatively preferred.

The polymerizable functional group of the partial structural formula (E) in the present invention tends to be relatively low in polymerization reactivity.

When the novel polymerizable compounds according to the present invention contain a bond chain or the like in addition to polymerizable functional group(s) bonded to the partial structural formula (A) or the partial structural formula (B), preferred examples of the partial structural formula can be covalently bonding organic chains such as alkylene, alkylenoxy, poly(alkylenoxy), alkylenethio, poly(alkylenethio), fluoroalkylene, cycloalkylene, arylene and arylalkylene. From the standpoint of solubility, transparency, weather resistance, easy in synthesis, and the like, alkylene, alkylenoxy, poly(alkylenoxy), alkylenethio, poly(alkylenethio) and the like are relatively preferred.

They can be contained either singly or in combination, and can be either linear or branched. It is, however, to be borne in mind that the present invention is not limited only to these bonding organic chains.

In the case of a polymerizable compound containing the partial structural formula (B) and the partial structural formula (F), these formulas are independent from each other. When the partial structural formula (B) is a 5-membered ring, for example, the partial structural formula (F) is not required to be a 5-membered ring but can also be either a 6-membered ring, 7-membered ring or the like without developing any problem or inconvenience.

$R_1$ to $R_4$ in the partial structural formula (B) each independently represents a hydrogen atom, a hydroxyl group, a mercapto group, an alkyl group having 1 to 6 carbon atoms, an alkoxy group having 1 to 6 carbon atoms, an alkylthio group having 1 to 6 carbon atoms, or any one of the partial structural formulas (C) to (F).

The alkyl, alkoxy and alkylthio groups, each of which has 1 to 6 carbon atoms, can independently be either linear or branched. From the standpoint of the viscosities or the like of the polymerizable compound and polymerizable composition, a carbon number in a range of from 1 to 3 is preferred.

Further, the alkyl, alkoxy and alkylthio groups, each of which has 1 to 6 carbon atoms, may each contain one or more heteroatoms such as oxygen atoms, sulfur atoms and nitrogen atoms. Their hydrogen atoms may be substituted partially or wholly by a like number of halogen atoms such as fluorine atoms. Non-inclusion of any heteroatom is, however, desired for hemiacetal forms each of which is susceptible to hydrolysis when one or more heteroatoms are contained.

In the partial structural formula (B), m and n each independently stand for an integer of form 0 to 10, with 1 to 6 being relatively preferred and 1 to 3 being more preferred.

Similarly, M and N each independently stand for an integer of from 1 to 10, with 1 to 3 being relatively preferred and 1 to 2 being more preferred.

$A_7$ and $A_8$ in the partial structural formulas (C) to (E) represent hydrogen or a methyl group, and the hydrogen atoms may be substituted partially or wholly by a like number of halogen atoms such as fluorine atoms as needed to an extent not causing a problem.

In the formula (F), $R_7$ each independently represents a hydrogen atom, an alkyl group having 1 to 6 carbon atoms, an alkoxyalkyl group having 2 to 12 carbon atoms, or an alkylthioalkyl group having 2 to 12 carbon atoms, and $R_8$ and $R_9$ each independently represent a hydrogen atom, a hydroxy group, a mercapto group, an alkyl group having 1 to 6 carbon atoms, an alkoxy group having 1 to 6 carbon atoms, or an alkylthio group.

When $R_7$ in the formula (F) is an alkyl group having 1 to 6 carbon atom or an alkoxyalkyl or alkylthioalkyl group having 2 to 12 carbon atoms, these groups may independently be linear or branched. From the standpoint of the viscosities or the like of the polymerizable compound and polymerizable composition, a carbon number in a range of from 1 to 3 may be preferred in some instances.

When one or each of $R_8$ and $R_9$ in the formula (F) is an alkyl, alkoxy or aralkylthio group having 1–6 carbon atoms, the group can be either linear or branched. Its carbon number may preferably be in a range of from 1 to 3 in some instances.

$R_7$ to $R_9$ in the formula (F) may contain one or more heteroatoms such as oxygen atoms, sulfur atoms or nitrogen atoms as needed to an extent not causing a problem. The hydrogen atoms may be substituted partially or wholly with a like number of halogen atoms such as fluorine atoms. Non-inclusion of any heteroatom is, however, desired for hemiacetal forms each of which is susceptible to hydrolysis when one or more heteroatoms are contained.

In the formula (F), q stands for an integer of from 1 to 6 and r stands for an integer of an integer of from 0 to 3. From ease in synthesis, a combination of 2 to 3 as q and 1 as r is relatively preferred.

In each of the novel polymerizable compounds according to the present invention, the hydrogen atoms which make up the compound may be substituted partially or wholly with halogen atoms such as fluorine atoms as needed to an extent not causing a problem as appreciated from the foregoing.

As described above, the novel polymerizable compounds according to the present invention have been described in detail. To facilitate the understanding further, certain representative polymerizable compounds will be exemplified below. It should, however, be borne in mind that the present invention shall not be limited only to the compounds to be exemplified. For example, the compounds shown in the below-described table can be mentioned. In the table, each compound corresponds to both of the structural formula described before the table.

| m,n/r,r' (not in order) | R7, R7' (not in order) | | | | | | | |
|---|---|---|---|---|---|---|---|---|
| | Methyl, methyl | Methyl, methyl | Methyl, methyl | Methyl, methyl | Methoxyethyl, methyl | Methoxyethyl, methoxyethyl | Methoxyethyl, methoxyethyl | Methylthioethyl, methylthioethyl |
| 2,2,/2,2 | G3 Hydroxy | Mercapto | Hydroxymethyl | Mercaptomethyl | Mercaptomethyl | Mercaptomethyl | Hydroxy | Mercapto |
| | G4 Acryloyloxy | Acryloylthio | Acryloyloxymethyl | Acryloylthiomethyl | Allyloxycarbonylthiomethyl | Allylthiocarbonylthiomethyl | Glycidyloxy | Glycidylthio |
| 2,2,/2,2 | G3 Hydroxy | Mercapto | Hydroxymethyl | Mercaptomethyl | Mercaptomethyl | Mercapto | Mercapto | Hydroxy |
| | G4 Methacryloyloxy | Methacryloylthio | Methacryloyloxymethyl | Methacryloylthiomethyl | Methacryloylthiomethyl | Allyloxycarbonylthio | Allylthiocarbonylthio | Allylthiocarbonyloxy |
| 2,2,/2,2 | G3 Hydroxy | Hydroxymethyl | Mercapto | Mercaptomethyl | Mercaptomethyl | Hydroxymethyl | Hydroxymethyl | Hydroxymethyl |
| | G4 Allyloxycarbonyloxy | Allyloxycarbonyloxymethyl | Allyloxycarbonylthio | Allyloxycarbonylthiomethyl | Acryloylthiomethyl | Methacryloyloxymethyl | Allyloxycarbonyloxymethyl | Allylthiocarbonyloxymethyl |
| 2,2,/2,2 | G3 Hydroxy | Hydroxymethyl | Mercapto | Mercaptomethyl | Hydroxymethyl | Hydroxymethyl | Mercapto | Hydroxy |
| | G4 Allylthio- | Allylthio- | Allylthio- | Allylthio- | Thioglycidyl | Acryloyl | Methacryloyl | Allyloxy |

-continued

| | | | | R7, R7' (not in order) | | | | |
|---|---|---|---|---|---|---|---|---|
| m,n/r,r' (not in order) | | Methyl, methyl | Methyl, methyl | Methyl, methyl | Methyl, methyl | Methoxyethyl, methyl | Methoxyethyl, methoxyethyl | Methoxyethyl, methoxyethyl | Methylthio-ethyl, methylthio-ethyl |
| | | carbonyl oxy | carbonyl oxymethyl | carbonyl thio | carbonyl thiomethyl | thiomethyl | oxymethyl | thio | carbonyl oxy |
| 2,2,/2,2 | G3 | Hydroxy | Mercapto | Hydroxymethyl | Mercaptomethyl | Hydroxymethyl | Mercaptomethyl | Mercapto | Hydroxy |
| | G4 | Glycidyl oxy | Glycidyl thio | Glycidyl oxymethyl | Glycidyl thiomethyl | Thioglycidyl oxymethyl | Glycidyl thiomethyl | Acryloyl thio | Methacryloyl oxy |
| 2,2,/2,2 | G3 | Hydroxy | Hydroxy | Hydroxymethyl | Hydroxymethyl | Hydroxymethyl | Hydroxy | Hydroxy | Hydroxy |
| | G4 | Thioglycidyl oxy | Thioglycidyl thio | Thioglycidyl oxymethyl | Thioglycidyl thiomethyl | Glycidyl oxymethyl | Thioglycidyl thio | Thioglycidyl oxy | Acryloyl oxy |
| 2,2,/2,2 | G3 | Acryloyl oxy | Acryloyl thio | Acryloyl oxymethyl | Acryloyl thiomethyl | Allyloxy carbonyl oxymethyl | Methacryloyl thiomethyl | Methacryloyl oxy | Acryloyl oxy |
| | G4 | Acryloyl oxy | Acryloyl thio | Acryloyl oxymethyl | Acryloyl thiomethyl | Allyloxy carbonyl oxymethyl | Methacryloyl thiomethyl | Methacryloyl oxy | Acryloyl oxy |
| 2,2,/1,1 | G3 | Methacryloyl oxy | Methacryloyl thio | Methacryloyl oxymethyl | Methacryloyl thiomethyl | Allyloxy carbonyl oxy | Methacryloyl thio | Acryloyl thio | Allyloxy carbonyl thio |
| | G4 | Methacryloyl oxy | Methacryloyl thio | Methacryloyl oxy methyl | Methacryloyl thiomethyl | Allyloxy carbonyl oxy | Methacryloyl thio | Acryloyl thio | Allyloxy carbonyl thio |
| 2,2,/1,1 | G3 | Allyloxy carbonyl oxy | Allyloxy carbonyl oxymethyl | Allyloxy carbonyl thio | Allyloxy carbonyl thiomethyl | Methacryloyl oxymethyl | Acryloyl oxymethyl | Allyloxy carbonyl thiomethyl | Glycidyl oxymethyl |
| | G4 | Allyloxy carbonyl oxy | Allyloxy carbonyl oxymethyl | Allyloxy carbonyl thio | Allyloxy carbonyl thiomethyl | Methacryloyl oxymethyl | Acryloyl oxymethyl | Allyloxy carbonyl thiomethyl | Glycidyl oxymethyl |
| 2,2,/1,1 | G3 | Allylthio-carbonyl oxy | Allylthio-carbonyl oxymethyl | Allylthio-carbonyl thio | Allylthio-carbonyl thiomethyl | Acryloyl thiomethyl | Glycidyl oxy | Glycidyl thiomethyl | Thioglycidyl thio |
| | G4 | Allylthio-carbonyl oxy | Allylthio-carbonyl oxymethyl | Allylthio-carbonyl thio | Allylthio-carbonyl thiomethyl | Acryloyl thiomethyl | Glycidyl oxy | Glycidyl thiomethyl | Thioglycidyl thio |
| 2,2,/1,1 | G3 | Glycidyl oxy | Glycidyl thio | Glycidyl oxymethyl | Glycidyl thiomethyl | Allylthio-carbonyl thiomethyl | Allylthio-carbonyl oxy | Allylthio-carbonyl thio | Allylthio-carbonyl oxymethyl |
| | G4 | Glycidyl oxy | Glycidyl thio | Glycidyl oxymethyl | Glycidyl thiomethyl | Allylthio-carbonyl thiomethyl | Allylthio-carbonyl oxy | Allylthio-carbonyl thio | Allylthio-carbonyl oxymethyl |
| 2,2,/1,1 | G3 | Thioglycidyl oxy | Thioglycidyl thio | Thioglycidyl oxymethyl | Thioglycidyl thiomethyl | Glycidyl thio | Thioglycidyl oxy | Thioglycidyl thiomethyl | Thioglycidyl oxymethyl |
| | G4 | Thioglycidyl oxy | Thioglycidyl thio | Thioglycidyl oxymethyl | Thioglycidyl thiomethyl | Glycidyl thio | Thioglycidyl oxy | Thioglycidyl thiomethyl | Thioglycidyl oxymethyl |

| 2,2,/2,2 | G3 | Hydroxy | Mercapto | Hydroxymethyl | Mercaptomethyl | Mercaptomethyl | Mercaptomethyl | Hydroxy | Mercapto |
| | G4 | Acryloyl oxy | Acryloyl thio | Acryloyl oxymethyl | Acryloyl thiomethyl | Allyloxy carbonyl thiomethyl | Allylthio-carbonyl thiomethyl | Glycidyl oxy | Glycidyl thio |
| 2,2,/2,2 | G3 | Hydroxy | Mercapto | Hydroxymethyl | Mercaptomethyl | Mercaptomethyl | Mercapto | Mercapto | Hydroxy |
| | G4 | Methacryloyl oxy | Methacryloyl thio | Methacryloyl oxymethyl | Methacryloyl thiomethyl | Methacryloyl thiomethyl | Allyloxy carbonyl thio | Allylthio-carbonyl thio | Allylthio-carbonyl oxy |
| 2,2,/2,2 | G3 | Hydroxy | Hydroxymethyl | Mercapto | Mercaptomethyl | Mercaptomethyl | Hydroxymethyl | Hydroxymethyl | Hydroxy-methyl |
| | G4 | Allyloxy carbonyl oxy | Allyloxy carbonyl oxymethyl | Allyloxy carbonyl thio | Allyloxy carbonyl thiomethyl | Acryloyl thiomethyl | Methacryloyl oxymethyl | Allyloxy carbonyl oxymethyl | Allylthio-carbonyl oxymethyl |

-continued

| | | | R7, R7' (not in order) | | | | | |
|---|---|---|---|---|---|---|---|---|
| m,n,/r,r' (not in order) | | Methyl, methyl | Methyl, methyl | Methyl, methyl | Methyl, methyl | Methoxyethyl, methyl | Methoxyethyl, methoxyethyl | Methoxyethyl, methoxyethyl | Methylthioethyl, methylthioethyl |
| 2,2,/2,2 | G3 | Hydroxy | Hydroxymethyl | Mercapto | Mercaptomethyl | Hydroxymethyl | Hydroxymethyl | Mercapto | Hydroxy |
| | G4 | Allylthiocarbonyloxy | Allylthiocarbonyloxymethyl | Allylthiocarbonylthio | Allylthiocarbonylthiomethyl | Thioglycidyl thiomethyl | Acryloyl oxymethyl | Methacryloyl thio | Allyloxy carbonyl oxy |
| 2,2,/2,2 | G3 | Hydroxy | Mercapto | Hydroxymethyl | Mercaptomethyl | Hydroxymethyl | Mercaptomethyl | Mercapto | Hydroxy |
| | G4 | Glycidyl oxy | Glycidyl thio | Glycidyl oxymethyl | Glycidyl thiomethyl | Thioglycidyl oxymethyl | Glycidyl thiomethyl | Acryloyl thio | Methacryloyl oxy |
| 2,2,/2,2 | G3 | Hydroxy | Hydroxy | Hydroxymethyl | Hydroxymethyl | Hydroxymethyl | Hydroxy | Hydroxy | Hydroxy |
| | G4 | Thioglycidyl oxy | Thioglycidyl thio | Thioglycidyl oxymethyl | Thioglycidyl thiomethyl | Glycidyl oxymethyl | Thioglycidyl thio | Thioglycidyl oxy | Acryloyl oxy |
| 2,2,/2,2 | G3 | Acryloyl oxy | Acryloyl thio | Acryloyl oxymethyl | Acryloyl thiomethyl | Allyloxy carbonyl oxymethyl | Methacryloyl thiomethyl | Methacryloyl oxy | Acryloyl oxy |
| | G4 | Acryloyl oxy | Acryloyl thio | Acryloyl oxymethyl | Acryloyl thiomethyl | Allyloxy carbonyl oxymethyl | Methacryloyl thiomethyl | Methacryloyl oxy | Acryloyl oxy |
| 2,2,/2,2 | G3 | Methacryloyl oxy | Methacryloyl thio | Methacryloyl oxymethyl | Methacryloyl thiomethyl | Allyloxy carbonyl oxy | Methacryloyl thio | Acryloyl thio | Allyloxy carbonyl thio |
| | G4 | Methacryloyl oxy | Methacryloyl thio | Methacryloyl oxymethyl | Methacryloyl thiomethyl | Allyloxy carbonyl oxy | Methacryloyl thio | Acryloyl thio | Allyloxy carbonyl thio |
| 2,2,/2,2 | G3 | Allyloxy carbonyl oxy | Allyloxy carbonyl oxymethyl | Allyloxy carbonyl thio | Allyloxy carbonyl thiomethyl | Methacryloyl oxymethyl | Acryloyl oxymethyl | Allyloxy carbonyl thiomethyl | Glycidyl oxymethyl |
| | G4 | Allyloxy carbonyl oxy | Allyloxy carbonyl oxymethyl | Allyloxy carbonyl thio | Allyloxy carbonyl thiomethyl | Methacryloyl oxymethyl | Acryloyl oxymethyl | Allyloxy carbonyl thiomethyl | Glycidyl oxymethyl |
| 2,2,/2,2 | G3 | Allylthiocarbonyloxy | Allylthiocarbonyloxymethyl | Allylthiocarbonylthio | Allylthiocarbonylthiomethyl | Acryloyl thiomethyl | Glycidyl oxy | Glycidyl thiomethyl | Thioglycidyl thio |
| | G4 | Allylthiocarbonyloxy | Allylthiocarbonyloxymethyl | Allylthiocarbonylthio | Allylthiocarbonylthiomethyl | Acryloyl thiomethyl | Glycidyl oxy | Glycidyl thiomethyl | Thioglycidyl thio |
| 2,2,/2,2 | G3 | Glycidyl oxy | Glycidyl thio | Glycidyl oxymethyl | Glycidyl thiomethyl | Allylthiocarbonyl thiomethyl | Allylthiocarbonyl oxy | Allylthiocarbonyl thio | Allylthiocarbonyl oxymethyl |
| | G4 | Glycidyl oxy | Gycidyl thio | Glycidyl oxymethyl | Glycidyl thiomethyl | Allylthiocarbonyl thiomethyl | Allylthiocarbonyl oxy | Allylthiocarbonyl thio | Allylthiocarbonyl oxymethyl |
| 2,2,/2,2 | G3 | Thioglycidyl oxy | Thioglycidyl thio | Thioglycidyl oxymethyl | Thioglycidyl thiomethyl | Glycidyl thio | Thioglycidyl oxy | Thioglycidyl thiomethyl | Thioglycidyl oxymethyl |
| | G4 | Thioglycidyl oxy | Thioglycidyl thio | Thioglycidyl oxymethyl | Thioglycidyl thiomethyl | Glycidyl thio | Thioglycidyl oxy | Thioglycidyl thiomethyl | Thioglycidyl oxymethyl |

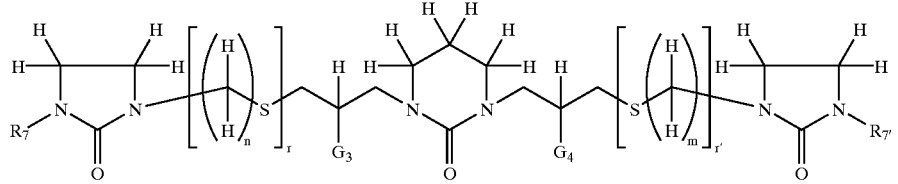

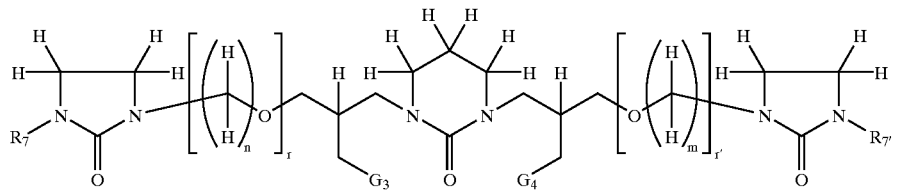

| 2,2,/1,1 | G3 | Hydroxy | Mercapto | Hydroxymethyl | Mercaptomethyl | Mercaptomethyl | Mercaptomethyl | Hydroxy | Mercapto |
| | G4 | Acryloyl oxy | Acryloyl thio | Acryloyl oxymethyl | Acryloyl thiomethyl | Allyloxy carbonyl thiomethyl | Allylthiocarbonyl thiomethyl | Glycidyl oxy | Glycidyl thio |
| 2,2,/1,1 | G3 | Hydroxy | Mercapto | Hydroxymethyl | Mercaptomethyl | Mercaptomethyl | Mercapto | Mercapto | Hydroxy |
| | G4 | Methacryloyl oxy | Methacryloyl thio | Methacryloyl oxymethyl | Methacryloyl thiomethyl | Methacryloyl thiomethyl | Allyloxy carbonyl thio | Allylthiocarbonyl thio | Allylthiocarbonyl oxy |

-continued

| m,n,/r,r' (not in order) | | Methyl, methyl | Methyl, methyl | Methyl, methyl | Methyl, methyl | Methoxyethyl, methyl | Methoxyethyl, methoxyethyl | Methoxyethyl, methoxyethyl | Methylthioethyl, methylthioethyl |
|---|---|---|---|---|---|---|---|---|---|
| 2,2,/1,1 | G3 | Hydroxy | Hydroxymethyl | Mercapto | Mercaptomethyl | Mercaptomethyl | Hydroxymethyl | Hydroxymethyl | Hydroxymethyl |
| | G4 | Allyloxy carbonyl oxy | Allyloxy carbonyl oxymethyl | Allyloxy carbonyl thio | Allyloxy carbonyl thiomethyl | Acryloyl thiomethyl | Methacryloyl oxymethyl | Allyloxy carbonyl oxymethyl | Allylthio carbonyl oxymethyl |
| 2,2,/1,1 | G3 | Hydroxy | Hydroxymethyl | Mercapto | Mercaptomethyl | Hydroxymethyl | Hydroxymethyl | Mercapto | Hydroxy |
| | G4 | Allylthio carbonyl oxy | Allylthio carbonyl oxymethyl | Allylthio carbonyl thio | Allylthio carbonyl thiomethyl | Thioglycidyl thiomethyl | Acryloyl oxymethyl | Methacryloyl thio | Allyloxy carbonyl oxy |
| 2,2,/1,1 | G3 | Hydroxy | Mercapto | Hydroxymethyl | Mercaptomethyl | Hydroxymethyl | Mercaptomethyl | Mercapto | Hydroxy |
| | G4 | Glycidyl oxy | Glycidyl thio | Glycidyl oxymethyl | Glycidyl thiomethyl | Thioglycidyl oxymethyl | Glycidyl thiomethyl | Acryloyl thio | Methacryloyl oxy |
| 2,2,/1,1 | G3 | Hydroxy | Hydroxy | Hydroxymethyl | Hydroxymethyl | Hydroxymethyl | Hydroxy | Hydroxy | Hydroxy |
| | G4 | Thioglycidyl oxy | Thioglycidyl thio | Thioglycidyl oxymethyl | Thioglycidyl thiomethyl | Glycidyl oxymethyl | Thioglycidyl thio | Thioglycidyl oxy | Acryloyl oxy |
| 2,2,/1,1 | G3 | Acryloyl oxy | Acryloyl thio | Acryloyl oxymethyl | Acryloyl thiomethyl | Allyloxy carbonyl oxymethyl | Methacryloyl oxy | Methacryloyl thiomethyl | Acryloyl oxy |
| | G4 | Acryloyl oxy | Acryloyl thio | Acryloyl oxymethyl | Acryloyl thiomethyl | Allyloxy carbonyl oxymethyl | Methacryloyl oxy | Methacryloyl thiomethyl | Acryloyl oxy |
| 2,2,/1,1 | G3 | Methacryloyl oxy | Methacryloyl thio | Methacryloyl oxymethyl | Methacryloyl thiomethyl | Allyloxy carbonyl oxy | Methacryloyl thio | Acryloyl thio | Allyloxy carbonyl thio |
| | G4 | Methacryloyl oxy | Methacryloyl thio | Methacryloyl oxymethyl | Methacryloyl thiomethyl | Allyloxy carbonyl oxy | Methacryloyl thio | Acryloyl thio | Allyloxy carbonyl thio |
| 2,2,/1,1 | G3 | Allyloxy carbonyl oxy | Allyloxy carbonyl oxymethyl | Allyloxy carbonyl thio | Allyloxy carbonyl thiomethyl | Methacryloyl oxymethyl | Acryloyl oxymethyl | Allyloxy carbonyl thiomethyl | Glycidyl oxymethyl |
| | G4 | Allyloxy carbonyl oxy | Allyloxy carbonyl oxymethyl | Allyloxy carbonyl thio | Allyloxy carbonyl thiomethyl | Methacryloyl oxymethyl | Acryloyl oxymethyl | Allyloxy carbonyl thiomethyl | Glycidyl oxymethyl |
| 2,2,/1,1 | G3 | Allylthio carbonyl oxy | Allylthio carbonyl oxymethyl | Allylthio carbonyl thio | Allylthio carbonyl thiomethyl | Acryloyl thiomethyl | Glycidyl oxy | Glycidyl thiomethyl | Thioglycidyl thio |
| | G4 | Allylthio carbonyl oxy | Allylthio carbonyl oxymethyl | Allylthio carbonyl thio | Allylthio carbonyl thiomethyl | Acryloyl thiomethyl | Glycidyl oxy | Glycidyl thiomethyl | Thioglycidyl thio |
| 2,2,/1,1 | G3 | Glycidyl oxy | Glycidyl thio | Glycidyl oxymethyl | Glycidyl thiomethyl | Allylthio carbonyl thiomethyl | Allylthio carbonyl oxy | Allylthio carbonyl thio | Allylthio carbonyl oxymethyl |
| | G4 | Glycidyl oxy | Glycidyl thio | Glycidyl oxymethyl | Glycidyl thiomethyl | Allylthio carbonyl thiomethyl | Allylthio carbonyl oxy | Allylthio carbonyl thio | Allylthio carbonyl oxymethyl |
| 2,2,/1,1 | G3 | Thioglycidyl oxy | Thioglycidyl thio | Thioglycidyl oxy methyl | Thioglycidyl thiomethyl | Glycidyl thio | Thioglycidyl oxy | Thioglycidyl thiomethyl | Thioglycidyl oxy methyl |
| | G4 | Thioglycidyl oxy | Thioglycidyl thio | Thioglycidyl oxy methyl | Thioglycidyl thiomethyl | Glycidyl thio | Thioglycidyl oxy | Thioglycidyl thiomethyl | Thioglycidyl oxy methyl |

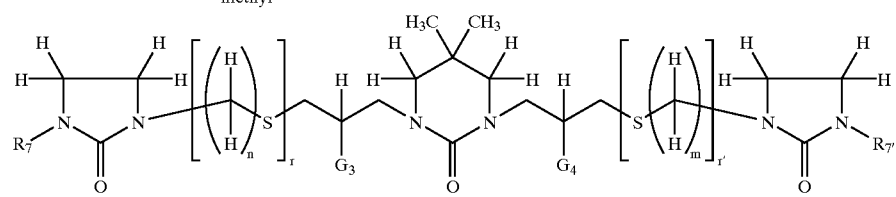

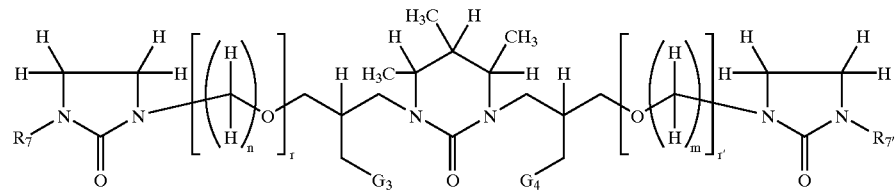

-continued

R7, R7' (not in order)

| m,n/r,r' (not in order) | | Methyl, methyl | Methyl, methyl | Methyl, methyl | Methyl, methyl | Methoxyethyl, methyl | Methoxyethyl, methoxyethyl | Methoxyethyl, methoxyethyl | Methylthio-ethyl, methylthio-ethyl |
|---|---|---|---|---|---|---|---|---|---|
| 2,2,/1,1 | G3 | Hydroxy | Mercapto | Hydroxymethyl | Mercaptomethyl | Mercaptomethyl | Mercaptomethyl | Hydroxy | Mercapto |
| | G4 | Acryloyl oxy | Acryloyl thio | Acryloyl oxymethyl | Acryloyl thiomethyl | Allyloxy carbonyl thiomethyl | Allylthio-carbonyl thiomethyl | Glycidyl oxy | Glycidyl thio |
| 2,2,/1,1 | G3 | Hydroxy | Mercapto | Hydroxymethyl | Mercaptomethyl | Mercaptomethyl | Mercapto | Mercapto | Hydroxy |
| | G4 | Methacryloyl oxy | Methacryloyl thio | Methacryloyl oxymethyl | Methacryloyl thiomethyl | Methacryloyl thiomethyl | Allyloxy carbonyl thio | Allylthio-carbonyl thio | Allylthio-carbonyl oxy |
| 2,2,/1,1 | G3 | Hydroxy | Hydroxymethyl | Mercapto | Mercaptomethyl | Mercaptomethyl | Hydroxymethyl | Hydroxymethyl | Hydroxy-methyl |
| | G4 | Allyloxy carbonyl oxy | Allyloxy carbonyl oxymethyl | Allyloxy carbonyl thio | Allyloxy carbonyl thiomethyl | Acryloyl thiomethyl | Methacryloyl oxymethyl | Allyloxy carbonyl oxymethyl | Allylthio-carbonyl oxymethyl |
| 2,2,/1,1 | G3 | Hydroxy | Hydroxymethyl | Mercapto | Mercaptomethyl | Hydroxymethyl | Hydroxymethyl | Mercapto | Hydroxy |
| | G4 | Allylthio-carbonyl oxy | Allylthio-carbonyl oxymethyl | Allylthio-carbonyl thio | Allylthio-carbonyl thiomethyl | Thioglycidyl thiomethyl | Acryloyl oxymethyl | Methacryloyl thio | Allyloxy carbonyl oxy |
| 2,2,/1,1 | G3 | Hydroxy | Mercapto | Hydroxymethyl | Mercaptomethyl | Hydroxymethyl | Mercaptomethyl | Mercapto | Hydroxy |
| | G4 | Glycidyl oxy | Glycidyl thio | Glycidyl oxymethyl | Glycidyl thiomethyl | Thioglycidyl oxymethyl | Glycidyl thiomethyl | Acryloyl thio | Methacryloyl oxy |
| 2,2,/1,1 | G3 | Hydroxy | Hydroxy | Hydroxymethyl | Hydroxymethyl | Hydroxymethyl | Hydroxy | Hydroxy | Hydroxy |
| | G4 | Thioglycidyl oxy | Thioglycidyl thio | Thioglycidyl oxymethyl | Thioglycidyl thiomethyl | Glycidyl oxymethyl | Thioglycidyl thio | Thioglycidyl oxy | Acryloyl oxy |
| 2,2,/1,1 | G3 | Acryloyl oxy | Acryloyl thio | Acryloyl oxymethyl | Acryloyl thiomethyl | Allyloxy carbonyl oxymethyl | Methacryloyl thiomethyl | Methacryloyl oxy | Acryloyl oxy |
| | G4 | Acryloyl oxy | Acryloyl thio | Acryloyl oxymethyl | Acryloyl thiomethyl | Allyloxy carbonyl oxymethyl | Methacryloyl thiomethyl | Methacryloyl oxy | Acryloyl oxy |
| 2,2,/2,2 | G3 | Hydroxy | Mercapto | Hydroxymethyl | Mercaptomethyl | Mercaptomethyl | Mercaptomethyl | Hydroxy | Mercapto |
| | G4 | Acryloyl oxy | Acryloyl thio | Acryloyl oxymethyl | Acryloyl thiomethyl | Allyloxy carbonyl thiomethyl | Allylthio-carbonyl thiomethyl | Glycidyl oxy | Glycidyl thio |
| 2,2,/2,2 | G3 | Hydroxy | Mercapto | Hydroxymethyl | Mercaptomethyl | Mercaptomethyl | Mercapto | Mercapto | Hydroxy |
| | G4 | Methacryloyl oxy | Methacryloyl thio | Methacryloyl oxymethyl | Methacryloyl thiomethyl | Methacryloyl thiomethyl | Allyloxy carbonyl thio | Allylthio-carbonyl thio | Allylthio-carbonyl oxy |
| 2,2,/2,2 | G3 | Hydroxy | Hydroxymethyl | Mercapto | Mercaptomethyl | Mercaptomethyl | Hydroxymethyl | Hydroxymethyl | Hydroxy-methyl |
| | G4 | Allyloxy carbonyl oxy | Allyloxy carbonyl oxymethyl | Allyloxy carbonyl thio | Allyloxy carbonyl thiomethyl | Acryloyl thiomethyl | Methacryloyl oxymethyl | Allyloxy carbonyl oxymethyl | Allylthio-carbonyl oxymethyl |
| 2,2,/2,2 | G3 | Hydroxy | Hydroxymethyl | Mercapto | Mercaptomethyl | Hydroxymethyl | Hydroxymethyl | Mercapto | Hydroxy |
| | G4 | Allylthio-carbonyl oxy | Allylthio-carbonyl oxymethyl | Allylthio-carbonyl thio | Allylthio-carbonyl thiomethyl | Thioglycidyl thiomethyl | Acryloyl oxymethyl | Methacryloyl thio | Allyloxy carbonyl oxy |
| 2,2,/2,2 | G3 | Hydroxy | Mercapto | Hydroxymethyl | Mercaptomethyl | Hydroxymethyl | Mercaptomethyl | Mercapto | Hydroxy |
| | G4 | Glycidyl oxy | Glycidyl thio | Glycidyl oxymethyl | Glycidyl thiomethyl | Thioglycidyl oxymethyl | Glycidyl thiomethyl | Acryloyl thio | Methacryloyl oxy |
| 2,2,/2,2 | G3 | Hydroxy | Hydroxy | Hydroxymethyl | Hydroxymethyl | Hydroxymethyl | Hydroxy | Hydroxy | Hydroxy |
| | G4 | Thioglycidyl oxy | Thioglycidyl thio | Thioglycidyl oxymethyl | Thioglycidyl thiomethyl | Glycidyl oxymethyl | Thioglycidyl thio | Thioglycidyl oxy | Acryloyl oxy |
| 2,2,/2,2 | G3 | Acryloyl oxy | Acryloyl thio | Acryloyl oxymethyl | Acryloyl thiomethyl | Allyloxy carbonyl oxymethyl | Methacryloyl thiomethyl | Methacryloyl oxy | Acryloyl oxy |
| | G4 | Acryloyl oxy | Acryloyl thio | Acryloyl oxymethyl | Acryloyl thiomethyl | Allyloxy carbonyl oxymethyl | Methacryloyl thiomethyl | Methacryloyl oxy | Acryloyl oxy |

To an extent not causing problem, the hydrogen atoms may be substituted partially or wholly by a like number of halogen atoms such as fluorine atoms. These polymerizable compounds can be used either singly or in combination.

The polymerizable compounds according to the present invention can be synthesized by using numerous general reactions such as those described in series publications of organic chemistry such as "Methoden der Organischen Chemie (1971, Vierte Auflage Herausgegeben von Eugen Muller) and "Shin Jikken Kagaku Koza (Handbook of Experimental Chemistry)" (1975, The Chemical Society of Japan).

A description will be made taking as examples such representative groups of compounds as will be described hereinafter.

Routes, which proceed through substantially the same reaction, will be identified by the same numeral.

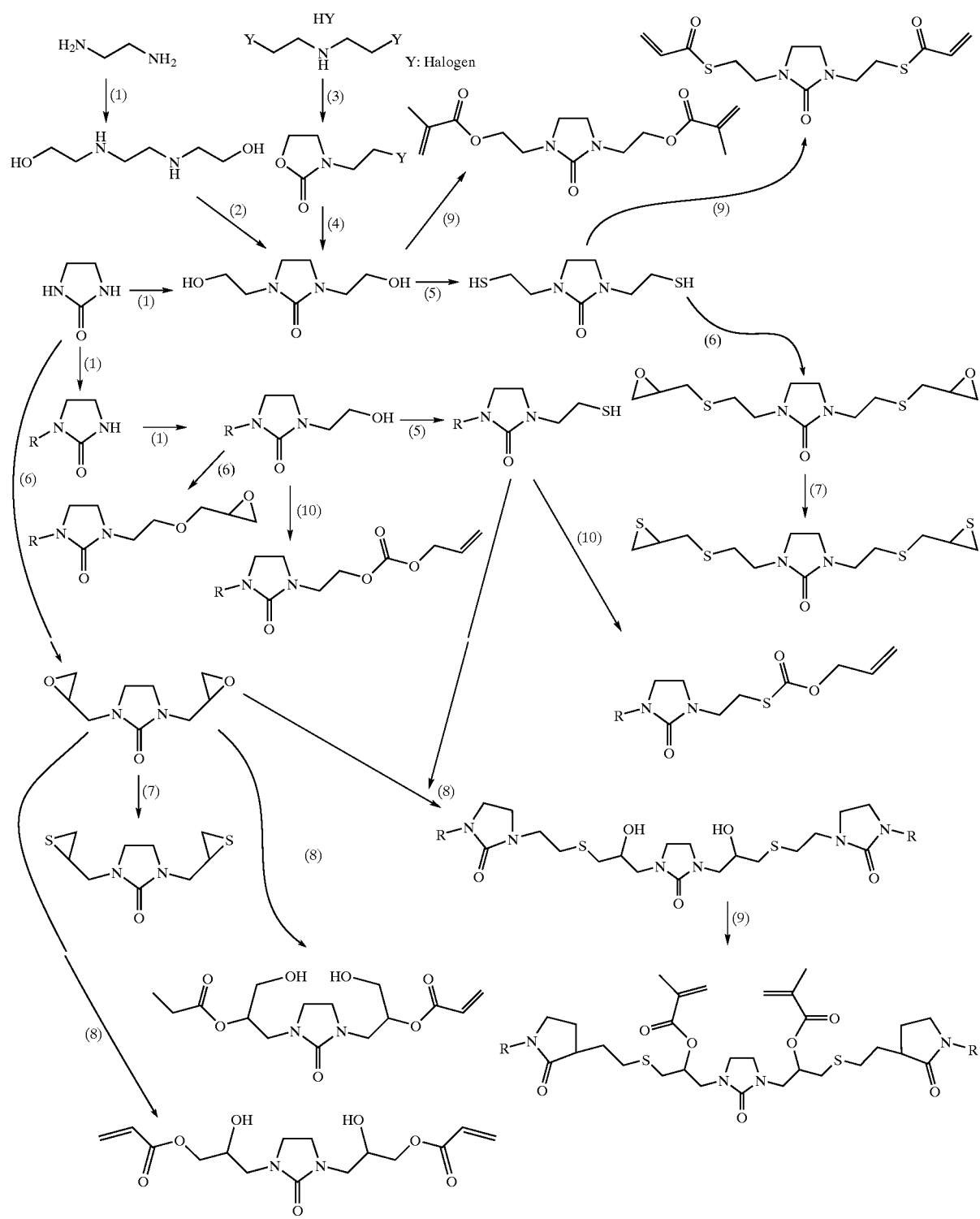

Route (1) is an alkylating reaction of an amine or urea, and a process using, for example, an alkyl halide, alkylene carbonate, alkylene oxide, hydroxyalkyl halide, hydroxyalkyl sulfonate or the like is in common use.

In addition to the alkylation of the amine or urea, an alkyl(thio)urea or alkylamine may be synthesized by reacting an alkylamine or the like to a (thio)carbonyl having an electron attracting group as typified by (thio)phosgene or to an alkane having an electron attracting group as typified by dichloroethane or ethanedibenzene sulfonate.

Incidentally, to conduct mercaptoalkylation, a process using, for example, an alkylene dithiocarbonate, alkylene sulfide, mercaptoalkyl halide, mercaptoalkyl sulfonate or mercaptoalkylamine or the like, can be used in addition to converting a hydroxyl group into a mercapto group.

With a view to improving selectivity, the reactant may be used with its hydroxyl group or mercapto group converted beforehand into a protecting group such as an acetyloxy group, benzoxy group, benzyloxy group, acetylthio group, benzothio group or benzylthio group, and subsequently, a deprotecting reaction such as hydrolysis or reduction may be conducted to synthesize the desired compound.

Route (2) is a reaction that subjects the alkylamine or alkyl(thio)urea, which has been synthesized by Route (1), to ring closure to form an alkylene(thio)urea ring.

When the alkylamine is subjected to ring closure, the number of ring-forming members in the alkylene(thio)urea ring is determined by the length of the alkylene group. The yield tends to drop when the length of the alkylene group is too short or too long. It is relatively preferred that the carbon number of the substituted or unsubstituted methylene structure which makes up the alkylene moiety is in a range of from 2 to 4, with 2 to 3 being more preferred.

For this ring closure of the alkylamine, carbon dioxide, carbon disulfide, (thio)phosgene, an alkylene(arylene) carbonate, (thio)urea or the like is generally employed.

In the process for subjecting the alkyl(thio)urea to ring closure, on the other hand, an alkane having electron attracting groups as typified by 1,2-dichloroethane, 1,2-dibromoethane, 1,2-ethanedibenzene sulfonate (5-membered ring), 1,2-dibromopropane (5-membered ring), 1,3-dibromopropane (6-membered ring), 1,4-diiodobutane (7-membered ring) or the like is generally used.

For the synthesis of N,N'-bis(hydroxyethyl)-ethyleneurea, for example, an illustrative usable process can be to react urea with the N,N'-bis(hydroxyethyl)ethylenediamine, which has been obtained by Route (1), such that the diamine is subjected to ring closure.

The temperature of the above-described ring closing reaction differs between a (thio)carbonyl having an electron attracting group as typified by (thio)phosgene or the like and simple (thio)urea or the like. When urea or the like is reacted, for example, the reaction temperature can be approximately 0 to 300° C, preferably 100 to 250° C., more preferably 150 to 230° C.

To synthesize a compound of the alkylenethiourea structure, thiourea is used in place of urea.

Route (3) is a route to synthesize an N-(2-halogenoethyl)-2-oxazolidone by reacting a bis(2-halogenoethyl)amine hydrohalogenide with an alkaline metal carbonate, alkaline metal hydrogencarbonate or the like.

Use of a bis(3-halogenopropyl)amine hydrohalogenide in this reaction provides an N-(3-halogenopropyl)-oxazinan-2-one having a 6-membered ring structure.

The temperature of this reaction can approximately be in a range of from 20 to 100° C., and a reaction temperature of from 30 to 60° C. may bring about preferred results in some instances.

Route (4) is a reaction to synthesize a target alkylene (thio)urea structure by reacting an amine with a compound of a heterocyclic structure obtained through Route (3), such as a 2-oxazolidone or oxazinan-2-one.

For example, when 2-hydroxyethylamine is reacted with an N-(2-halogenoetyl)-2-oxazolidone, N,N'-bis(2-hydroxyethyl)-ethyleneurea is obtained; when an excess of 3-amino-1,2-propanediol is reacted, N-hydroxyethyl-N'-{2,3-bis(hydroxy)propyl}-ethyleneurea is obtained.

The temperatures in these reactions can be approximately 0 to 250° C., preferably 30 to 200° C., more preferably 60 to 150° C.

As a representative alternative process making use of oxazolidone as a starting raw material other than the above-described process, there is also known a process which comprises reacting a halogenoalkyl isocyanate or the like with an N-halogenoethyl-2-oxazolidone to synthesize an N-halogenoethyl-N'-halogenoalkyl(or aryl)-ethyleneurea which serves as an intermediate in the present invention (JP 41-14991 B).

Route (5) is a reaction to convert hydroxyl groups into mercapto groups.

In general, the hydroxyl groups are converted into electron attracting groups such as halogens or sulfonates by using a reagent such as thionyl chloride, sulfuryl chloride, phosphorus pentoxide, phosphorus tribromide, hydrochloric acid, hydrobromic acid, hydroiodic acid, methane sulfonyl chloride, trifluoromethane sulfonyl chloride, benzene sulfonyl chloride or tosyl chloride.

A process is next used, for example, to react an alkaline metal sulfide such as sodium hydrosulfide, potassium hydrosulfide or sodium sulfide or to react thiourea to form an isothiuronium salt and then to hydrolyze the isothiuronium salt; to react sodium thiosulfate or the like to form a Bunte salt and then to hydrolyze the Bunte salt; to react an alkaline metal N,N-dialkyldithiocarbamate, followed by hydrolysis; to react an alkaline metal O-alkyl dithiocarbonate, followed by hydrolysis; to react a Grignard reagent and then sulfur, followed by final hydrolysis or reduction; or to once react a thiol to synthesize a sulfide and then to cleave the sulfide with an alkaline metal or the like.

Of these processes, the process, which goes through an isothiuronium salt, is used relatively preferably.

To synthesize N-mercaptoethyl-N'-{1,3-dimercapto-2-propyl}-ethyleneurea, for example, an illustrative process can comprise reacting phosphorus tribromide with a liquid mixture of N-hydroxyethyl-N'-{2,3-dihydroxy-propyl}-ethyleneurea, which has been obtained through Route (4), and chlorobenzene at 50 to 132° C., adding thiourea and water to the resulting N-bromoethyl-N'-{2,3-dibromo-propyl}-ethyleneurea and reacting them at 60° C. to under reflux (105° C.) to convert the ethyleneurea into an isothiuronium salt, and subsequent to cooling, adding 25% aqueous ammonium or hydrazine hydrate and hydrolyzing the isothiuronium salt at 40–80° C.

To convert the hydroxyl groups directly into mercapto groups, an illustrative process can comprise reacting thiourea in the presence of a mineral acid such as hydrochloric acid to synthesize an isothiuronium salt and then hydrolyzing the isothiuronium salt; directly reacting hydrogen sulfide; or reacting phosphorus pentasulfide.

To similarly synthesize N-mercaptoethyl-N'-{1,3-dimercapto-2-propyl}-ethyleneurea without conducting halogenation, for example, with phosphorus tribromide or the like, an illustrative process can comprise adding thiourea, hydrochloric acid solution and a catalytic amount of concentrated sulfuric acid to N-hydroxyethyl-N'-{2,3-dihydroxy-propyl}-ethyleneura, reacting them thoroughly under reflux (100 to 110° C.), and subsequent to cooling, adding basic water such as 25% aqueous ammonium or hydrazine hydrate and conducting hydrolysis at 40 to 80° C.

Route (6) is a reaction to introduce epoxy groups. For the introduction of epoxy groups, it is a common practice to react an epihalohydrin with the hydroxy derivative or the thiol derivative to form a halohydrin derivative and then to subject the halohydrin derivative to ring closure with a base to achieve epoxidation. The addition reaction and the ring-closing reaction may be conducted concurrently in a single step, although these reactions are generally conducted in two steps.

Known as an alternative process is to oxidize a corresponding olefin, as typified by allyl groups, directly with hydrogen peroxide, an organic peroxide, air or the like; or to halogenize the olefin in an aqueous solution to synthesize a halohydrin and then to subject it to ring closure with a base.

Route (7) is a reaction to introduce thioepoxy groups.

To convert epoxy groups into thioepoxy groups, for example, it is a common practice to react an alkaline metal thiocyanate, such as sodium thiocyanate or potassium thiocyanate, with the corresponding epoxy groups; to react a thiourea or the like with the corresponding epoxy groups; or to react an aryl (or alkyl) phosphinic acid sulfide with the corresponding epoxy groups.

Among these reactions for converting epoxy groups into thioepoxy groups, relatively preferred is the process which comprises reacting an alkaline metal thiocyanate such as sodium thiocyanate or potassium thiocyanate with the corresponding epoxy groups or the process which comprises reacting a thiourea with the corresponding epoxy groups.

As other processes, there are also a process in which, after an alkaline metal thiocyanate or a thiourea is likewise reacted with a halohydrin derivative as an intermediate for epoxy groups, the reaction product is subjected to ring closure with a base and a process in which a sulfur halide, an aryl (or alkyl) thiosulfenyl halide or thiocyanic acid halide is reacted with an olefin represented by the corresponding allyl group.

To synthesize N-(thioglycidylthioethyl)-N'-{1,3-bis(thioglycidylthio)-2-propyl}-ethyleneurea, for example, there is the following process: Epichlorohydrin is dropwise added to a liquid mixture, which has been formed by adding a catalytic amount of triethylamine to N-mercaptoethyl-N'-{1,3-dimercapto-2-propyl}-ethyleneurea obtained in (5), and reacted at an internal temperature of from 10 to 40° C. to convert the ethyleneurea into a halohydrin derivative, and caustic soda is likewise added dropwise and reacted at an internal temperature of from 20 to 50° C. to obtain N-(glycidylthioethyl)-N'-{1,3-bis(glycidylthio)-2-propyl}-ethyleneurea as an epoxy derivative.

Thiourea is then added to a liquid mixture of the thus-obtained N-(glycidylthioethyl)-N'-{1,3-bis(glycidylthio)-2-propyl}-ethyleneurea and methanol, followed by a reaction at 10 to 40° C.

Route (8) is a reaction to subject the (thio)epoxy groups to ring opening.

Described specifically, an active-hydrogen-containing compound such as an alcohol, thiol, carboxylic acid or primary or secondary amine is reacted with the (thio)epoxy groups to subject the (thio)epoxy groups to ring opening so that the (thio)epoxy compound is converted into a hydroxy compound (mercapto compound).

Preferred results may be obtained in some instances when a general (thio)epoxy ring-opening catalyst—such as a tertiary amine, a quaternary amine halogenide, a quaternary amine hydroxide, a phosphine, an organometal salt, an alkaline metal, an alkaline metal hydroxide, an alkaline metal carbonate, an alkaline metal hydrogencarbonate, an alkaline metal trifurate, a metal halide, a metal oxide, a metal alkoxylate, a boron trifluoride ether complex, or other organic or inorganic acid—is added in the reaction.

Route (9) is a reaction to react an acid halide or halogenochloroformate containing a polymerizable unsaturated group, such as a (meth)acrylic acid halide or an allyl halogenoformate, is reacted.

When synthesis of a (thio)acrylate derivative is desired, for example, acrylic acid chloride is reacted to the hydroxyl groups (or mercapto groups).

Usable as an alternative process can be a two-step process in which a chloropropionic acid halide is once reacted to form a chloropropionate (thio)ester and a base such as a tertiary amine is then added to conduct dehydrohalogenation such that a (thio)acrylate derivative is formed.

To synthesize N-acryloyloxyethyl-N'-{2,3-bis(acryloyloxy)propyl}-ethyleneurea, for example, there is a process that at 20 to 50° C., acrylic acid chloride is added dropwise to and reacted with N-hydroxyethyl-N'-{2,3-dihydroxy-propyl}-ethyleneurea obtained through Route (4).

Upon synthesizing the thio(meth)acrylate derivative, the mercapto derivative available through Route (5) is used as a starting raw material. However, the two-step process described as an alternative process is relatively preferred because Michael addition reaction of the mercapto groups tends to occur.

This applies equally to the synthesis of an allyl carbonate or the like through Route (10). In place of a (meth)acrylic acid halide, allyl chloroformate synthesized from allyl alcohol and phosgene or the like, or similarly, sec-butynyl chloroformate, vinyl chloroformate or isopropenyl chloroformate is reacted.

When a thiocarbonate derivative is desired, such a chloroformate is reacted with the thiol derivative, or phosgene is reacted with allylthiol, sec-butynylthiol, vinylthiol or isopropenylthiol to obtain a thioformate derivative, which is then reacted with a hydroxy derivative.

Further, in the case of a dithiocarbonate, a thiol derivative is reacted with a thiochloroformate are reacted, and in the case of a trithiocarbonate, a dithiochloroformate synthesized from thiophosgene is reacted with the thiol derivative.

The temperatures of these reactions may be approximately −50 to 200° C., preferably −20 to 150° C., more preferably 0 to 100° C.

To synthesize N-allylthiocarbonatoethyl-N'-{1,3-bis(allylthiocarbonato)-2-propyl}-ethyleneurea, for example, there is a process that at 10 to 30° C., ally chloroformate is added to a liquid mixture of N-mercaptoethyl-N'-{1,3-dimercapto-2-propyl}-ethyleneurea, which had been obtained through Route (5), triethylamine and toluene as a solvent and is reacted with the ethyleneurea.

Concerning the alkylene(thio)urea structure in the present invention, some processes have already been described above as processes for synthesizing compounds each of which can be formed into the alkylenethiourea structure. There are, for example, a process in which thiourea, ethylenethiourea and thiophosgene are used in place of urea, ethyleneurea and phosgene, respectively, and also, a process in which a sulfurizing agent such as hydrogen sulfide, boron sulfide, phosphorus pentasulfide or Lawesson's reagent-is reacted with the alkyleneurea structure.

When it is desired to form, as branched structures, the organic linkages connecting the alkylene(thio)urea structure and polymerizable functional groups in the present invention, a process making use of a branched raw material is relatively easy.

To synthesize N,N'-bis(3-methacryloyloxy-2,2-dimethyl-1-propyl)-4-methylimidazolidinone, for example, there is a process in which, after 3-hydroxy-2,2-dimethylpropyl-1-bromide is reacted with 1,2-diaminopropane, the reaction product is subjected to ring closure with urea, followed by a methacrylation reaction.

When it is desired to extend the bond lengths further at the organic linkages, various processes are usable. There are, for example, a process in which an active hydrogen compound containing an unsaturated group, such as hydroxyethyl (meth)acrylate, an alkylene carbonate, an alkylene oxide, an alkylene sulfide, a hydroxyalkyl halide, a hydroxyalkyl sulfonate, an epihalohydrin or the like is reacted with the hydroxy derivative or mercapto derivative available through Route (1), (2), (4) or (5) and also a process in which a halogen is once reacted with the mercapto derivative to convert it into a thiohalide and an unsaturated compound is then reacted.

To synthesize N,N'-bis(5-acryloylthio-3-thiapentyl)-ethyleneurea, for example, there is the following process. N,N'-bis(bromoethyl)-ethyleneurea obtained by brominating N,N'-bis(hydroxyethyl)-ethyleneurea is added dropwise to and reacted with a salt-forming mixture, which has been obtained by adding caustic soda to 2-mercaptoethanol, to synthesize N,N'-bis(5-hydroxy-3-thiapentyl)-ethyleneurea.

Thiourea is next reacted to form N,N'-bis(5-mercapto-3-thiapentyl)-ethyleneurea, followed by the reaction of chloropropionic acid chloride to obtain a chloropropionic acid thioester derivative. Finally, a base such as a tertiary amine is added to conduct a dehydrochlorinating reaction.

When it is desired to introduce halogen atoms such as fluorine atoms into the novel polymerizable compound according to the present invention, there are, as relatively easy processes, a process which uses an already halogenated raw material and a process which uses a halogenating agent such as fluorine gas, hydrogen fluoride, hydrogen chloride, potassium fluoride, potassium iodide, diethylaminosulfur trifluoride, 2,2-difluoro-1,3-dimethylimidazolidine, thionyl chloride, phosphorus tribromide or iodine chloride.

In the above processes, it is possible to use, with a view to improving the reaction velocities of the respective reactions, an acid catalyst—such as sulfuric acid, hydrochloric acid, phosphoric acid, acetic acid, boron trifluoride, aluminum chloride, dibutyltin dioxide, dibutyltin dilaurate or tetrabutyl tin—or a basic catalyst—such as triethylamine, pyridine, triethanolamine, triphenylphosphine, tributylphosphine, sodium hydroxide, potassium hydroxide, sodium carbonate, potassium carbonate, sodium hydrogencarbonate, potassium hydrogencarbonate, calcium carbonate, calcium hydroxide, magnesium hydroxide, sodium formate, sodium methylate, t-butoxy potassium, sodium hydride or sodium—as much as needed to an extent not causing a problem.

A reaction solvent differs depending on the individual reaction. Described basically, however, any solvent can be used insofar as it does not react with the reaction substrate, the reaction agent, the product, the catalyst or the like. Examples of solvents, which are rather commonly employed, can include acetonitrile, dichloromethane, dichloroethane, chloroform, THF, dioxane, glyme, diglyme, dimethylformamide, N,N'-dimethyl-ethyleneurea, benzene, toluene, xylene, chlorobenzene, dichlorobenzene, hexane, cyclohexane, methanol, and water.

The polymerizable composition according to the present invention, which has been described in [8], contains at least one of the novel polymerizable compounds described in [5], [6] and [7].

Especially to improve wettability, an organic (co)polymer available from a composition added with a copolymerizable component tends to be more preferred than an organic polymer available only from the novel polymerizable compound described in [5], [6] or [7]. Illustrative of the copolymerizable component are compounds which contain polymerizable functional groups such as (meth)acryl group, allyl carbonate group, allyl group, isopropenyl group, vinyl group, (thio)epoxy group, iso(thio)cyanate group, mercapto group, hydroxy group and amino group. Use of a compound containing a polymerizable unsaturated group such as (meth)acryl group, allyl carbonate group, allyl group, isopropenyl group or vinyl group may bring about preferred results in some instances.

More preferred copolymerizable components are polymerizable compounds each of which has in its molecule a polar structure the dipolar moment of which is large. Still more preferred are organic polymers each of which has an aprotic polar structure the dipolar moment of which is 3 debyes or greater. Examples of effective elements can include heteroatoms such as oxygen atom, nitrogen atom, phosphorus atom and sulfur atom, while examples of effective structure can include alkylene(thio)urea structure, oxazolidone structure, pyrrolidone structure, lactone structure, sulfone structure, sulfolane structure, amide structure, alkyl(thio)urea structure, sulfone structure, sulfoxide structure, piperazin-2,3-dione structure, acetyleneurea structure, caprolactam structure, alkylene carbonate structure, and phosphoric acid ester structure.

Among these, particularly effective polymerizable compounds are, for example, polymerizable compounds having alkylene(thio)urea structure, oxazolidone structure, pyrrolidone structure, sulfolane structure, amide structure, or sulfone structure.

Describing the copolymerizable components more specifically by compound names, examples can include styrene, isopropenylbenzene, divinylbenzene, diisopropenylbenzene ethylene glycol diallyl carbonate, diethylene glycol diallyl carbonate, glycidyl methacrylate, isocyanatomethacrylate, 3-isopropenyl-α,α-dimethylbenzyl isocyanate, vinyl acetate, vinyl alcohol, allyl alcohol, (meth)acrylic acid, methyl (meth)acrylate, ethyl (meth)acrylate, hydroxyethyl (meth)acrylate, ethylene glycol di(meth)acrylate, diethylene glycol di(meth)acrylate, triethylene glycol di(meth)acrylate, propylene glycol di(meth)acrylate, dipropylene glycol di(meth)acrylate, neopentyl glycol di(meth)acrylate, bis{(meth)acryloyloxy}-benzene, bis{(meth)acryloyloxymethyl}-benzene, 2,2-bis{(meth)acryloyloxy-ethyloxy-ethyloxy-phenyl}-propane, 2,2-bis{(meth)acryloyloxy-ethyloxy-phenyl}-propane, bis{(meth)acryloyloxymethyl}-cyclohexane, bis{(meth)acryloyloxymethyl}-tricyclo[5.2.1.0.$^{26}$] decane, trimethylolpropane tris{(meth)acrylate}, N,N',N"-tris (allyl)-isocyanurate, N,N',N"-tris{(meth)acryloyloxyethyl}-isocyanurate, N-methyl-N'-vinyl-ethyleneurea, N-methoxyethyl-N'-vinyl-ethyleneurea, N,N'-divinyl-ethyleneurea, N-methyl-N'-allyl-ethyleneurea, N-methoxyethyl-N'-allyl-ethyleneurea, N,N'-diallyl-ethyleneurea, N-methyl-N'-allyloxycarbonyl-ethyleneurea, N-methoxyethyl-N'-allyloxycarbonyl-ethyleneurea, N,N'-bis(allyloxycarbonyl)-ethyleneurea, N-methyl-N'-(meth)acryloyl-ethyleneurea, N-methoxyethyl-N'-(meth)acryloyl-ethyleneurea, N,N'-di(meth)acryloyl-ethyleneurea, N-methyl-N'-allyloxycarbonyloxyethyl-ethyleneurea, N-methoxyethyl-N'-allyloxycarbonyloxyethyl-ethyleneurea, N,N'-bis(allyloxycarbonyloxyethyl)-ethyleneurea, N-methyl-N'-(meth)acryloyloxyethyl-ethyleneurea, N-methoxyethyl-N'-(meth)acryloyloxyethyl-ethyleneurea, N,N'-bis{(meth)acryloyloxyethyl}-ethyleneurea, 1-methyl-3-vinyl-tetrahydro-2-pyrrolidine, 1-methoxyethyl-3-vinyl-tetrahydro-2-pyrrolidine, 1,3-divinyl-tetrahydro-2-pyrrolidine, 1-methyl-3-allyl-tetrahydro-2-pyrrolidine, 1-methoxyethyl-3-allyl-tetrahydro-2-pyrrolidine, 1,3-diallyl-tetrahydro-2-pyrrolidine, 1-methyl-3-allyloxycarbonyl-tetrahydro-2-pyrrolidine, 1-methoxyethyl-3-allyloxycarbonyl-tetrahydro-2-pyrrolidine, 1,3-bis(allyloxycarbonyl)-tetrahydro-2-pyrrolidine, 1-methyl-3-(meth)acryloyl-tetrahydro-2-pyrrolidine, 1-methoxyethyl-3-(meth)acryloyl-tetrahydro-2-pyrrolidine, 1,3-di(meth)acryloyl-tetrahydro-2-pyrrolidine, 1-methyl-3-allyloxycarbonyloxyethyl-tetrahydro-2-pyrrolidine, 1-methoxyethyl-3-allyloxycarbonyloxyethyl-tetrahydro-2-pyrrolidine, 1,3-bis(allyloxycarbonyloxyethyl)-tetrahydro-2-pyrrolidine, 1-methyl-3-(meth)acryloyloxyethyl-tetrahydro-2-pyrrolidine, 1-methoxyethyl-3-(meth)acryloyloxyethyl-tetrahydro-2-pyrrolidine, 1,3-bis{(meth)acryloyloxy-ethyl}-tetrahydro-2-pyrrolidine, N-vinyl-oxazolidone, N-allyl-oxazolidone, N-allyloxycarbonyl-oxazolidone, N-(meth)acryloyl-oxazolidone, N-allyloxycarbonyloxyethyl-oxazolidone, N-(meth)acryloyloxyethyl-oxazolidone, N-vinyl-pyrrolidone, N-allyl-pyrrolidone, N-allyloxycarbonyl-pyrrolidine, N-(meth)acryloyl-pyrrolidone, N-allyloxycarbonyloxyethyl-pyrrolidone, N-(meth)acryloyloxyethyl-pyrrolidone, N-vinyl-N-methyl-acetamide, N-allyl-N-methyl-acetamide, N-allyloxycarbonyl-N-methyl-acetamide, N-(meth)acryloyl-N-methyl-acetamide, N-allyloxycarbonyl-oxyethyl-N-methyl-acetamide, N-(meth)acryloyloxyethyl-N-methyl-acetamide, N,N-dimethyl-(meth)acrylamide, N,N-dimethyl-(meth)vinylamide, N,N-dimethyl-(meth)allylamide, N,N-dimethyl-(meth)allyloxycarbonylamide, N,N'-dimethyl-N,N'-divinylurea, N,N'-dimethyl-N,N'-diallylurea, divinylsulfone, and diallylsulfone. It should however also be borne in mind that the present invention is not limited only to these exemplified compounds.

Depending on the desired physical properties, characteristics, purpose, application and the like, it is also possible to optionally contain, polymerizable compounds other than those described above, chain extenders, crosslinking density improvers, curing agents, catalysts, co-catalysts, photopolymerization initiators, photosensitizers, retarders, polymerization inhibitors, ultraviolet absorbers, stabilizers, colorants, paints, pigments, dyes, inks, photosensitizers, luminescent agents, fragrances, bactericides, binders, fillers, polymers, fillers, glass, metals, metal oxides, organometals, salts, extenders, mold releasing agents, surfactants, foaming-agents, carbon dioxide gas, air, inert gas, water, solvents, impurities, additives, and other organic or inorganic compounds, as needed to an extent not causing a problem.

The organic polymer according to the present invention can be obtained by polymerizing the polymerizable compound or the polymerizable composition. As polymerization processes, solution polymerization and bulk polymerization are representative. Bulk polymerization, which does not require any cumbersome operation such as solvent recovery, can be preferably used, although the polymerizable compound or composition according to the present invention can also be polymerized by solution polymerization.

In bulk polymerization, thermal polymerization and radiation-induced polymerization are representative. In the present invention, one of these polymerization processes can also be chosen as desired depending on the purpose.

Compared with thermal polymerization, radiation-induced polymerization is limited in the kind, number and the like of compounds. Nonetheless, polymerization itself proceeds extremely fast and in some instances, may be completed in as short as several seconds. Further, simple and widely-applicable polymerization making use of sunlight or the like is also feasible, and can be considered to be a production process having an extremely high value from the industrial standpoint.

Use examples of these polymerization processes will now be described. For example, thermal polymerization tends to be chosen in the case of large, molded or otherwise formed products. There is however a tendency to choose radiation-induced polymerization when a product to be molded or otherwise formed is small and is desired to be produced in a short time. In the case of ultra-large area painting represented by the painting of an exterior wall, radiation-induced polymerization making use of sunlight tends to be chosen, but for painting a relatively small area, there is a tendency to choose one of thermal polymerization and radiation-induced polymerization as desired.

Thermal polymerization in the present invention is generally conducted by heating and polymerizing a compound according to the present invention, which contains a polymerizable functional group, or a polymerizable composition containing the same. Heating temperature is generally in a range of from room temperature to the Tg of the target polymer or higher or in a range not higher than 300° C. As an alternative, the temperature may be raised gradually from room temperature or so in accordance with the progress of the polymerization.

When thermal polymerization is conducted, a thermal polymerization catalyst such as a radical catalyst, anionic catalyst or cationic catalyst is generally added as needed.

Illustrative of the radical catalyst are azoisobutyronitrile, benzoyl peroxide, di-3-methoxybutyl peroxydicarbonate, diisopropyl peroxydicarbonate, α-cumyl peroxyneodecanoate, t-butyl peroxy-2-ethylhexanoate, dicumyl peroxide, 1,1-di-t-butyl peroxy-3,3,5-trimethylcyclohexane, and t-butylcumyl peroxide.

Illustrative of the anionic catalyst are tetrabutylammonium chloride, tetrabutylammonium hydroxide, triethylamine, tributylamine, pyridine, N-methylpyrrolidone, piperazine, triphenylphosphine, tributylphosphine, triethanolamine, methyldiethanolamine, triisopropanolamine, 4,4"-dimethylamino-benzopheone, 2-dimethylaminoethylbenzoic acid, ethyl dimethylaminobenzoate, isoamyl dimethylaminobenzoate, (n-butoxy)ethyl dimethylaminobenzoate, isoamyl 2-dimethylaminoethylbenzoate, 2-ethylhexyl 2-dimethylaminoethylbenzonate, sodium acetate, potassium phosphate, and sodium methoxide.

Illustrative of the cationic polymerization catalyst are sulfuric acid, hydrochloric acid, p-toluenesulfonic acid, methanesulfonic acid phosphoric acid, acetic acid, propionic acid, dibutyltin dioxide, dimethyltin dichloride, dibutyltin dichloride, dibutyltin dilaurate, tetrabutyl tin, boron trifluoride, boron trifluoride-diethyl ether complex, tetraethoxytitanium, titanium oxide, aluminum oxide, and aluminum fluoride.

The amount of such a thermal polymerization catalyst to be added cannot be specified because it varies considerably depending on the kind of the polymerizable compound or the kind of the composition containing the same. Nonetheless, it can be added preferably in a range of from about 0.0001 to 10 wt. %, more preferably in a range of from 0.001 to 5 wt. %, based on the polymerizable compound or composition according to the present invention.

Examples of radiation usable in the present invention can include visible light of 400 to 800 nm, ultraviolet rays of 400 nm or shorter, and electron beams. In general, use of relatively economical ultraviolet rays or visible light is preferred than electron beams which require a costly apparatus.

Electron beams are, however, extremely effective when ultraviolet rays or visible light does not transmit.

When polymerization is conducted with ultraviolet rays, for example, a light source such as a low-pressure mercury vapor lamp, high-pressure mercury vapor lamp, ultra high-pressure mercury vapor lamp, metal halide lamp, pulsed xenon lamp, ultraviolet laser or electrodeless discharge lamp is preferably employed.

Radiation-induced polymerization in the present invention is performed by exposing the polymerizable compound or composition according to the present invention to radiation. Thermal polymerization may also be used in combination as needed.

In addition to the photopolymerization initiator, the above-described radical catalyst, anionic catalysts or cationic catalyst useful in thermal polymerization may also be used in combination.

Electron beam polymerization may not require any catalyst in some instances. However, a catalyst may be added to an extent not causing a problem.

Illustrative of the photopolymerization initiator are light-activated radical generators, light-activated anion generators, light-activated cation generators, and the like. Among these, light-activated radical generators and light-activated cation generators can be used preferably.

Examples of the light-activated radical generators can include 4- phenoxydichloroacetophenone, 4-t-butyldichloro-acetophenone, diethoxyacetophenone, 2-hydroxy-2-methyl-1-phenylpropan-1-one, 1-(4-isopropylphenyl)-2-hydroxy-2-methylpropan-1-one, 1-(4-dodecylphenyl)-2-hydroxy-2-methylpropan-1-one, 4-(2-hydroxy-2-propyl) ketone, 1-hydroxycyclohexylphenyl ketone, 2-methyl-1-{4-(methylthio)phenyl}-2-morphorylpropane-1, benzoin, benzoin methyl ether, benzoin ethyl ether, benzoin isopropyl ether, benzoin isobutyl ether, benzyldimethylketal, benzophenone, benzoylbenzoic acid, methyl benzoylbenzoate, 4-phenylbenzophenone, hydroxybenzophenone, allylbenzophenone, 4-benzoyl-4'-methyldiphenylsulfide-3,3'-dimethyl-4-methoxybenzophenone, thioxanthone, 2-chlorothioxanthone, 2-methylthioxanthone, isopropylthioxanthone, 2,4-dichiorothioxanthone, 2,4-dimethylthioxanthone, 2,4-diethylthioxanthone, 2,4-diisopropylthioxanthone, 1-phenyl-1,2-propandione-2-(O-ethoxycarbonyl)oxime, 2,4,6-trimethylbenzoyl-diphenylphosphine oxide, methylphenyl glyoxylate, dibenzyl, 9,10-phenanthrenequinone, camphorquinone, dibenzosuberone, 2-ethylanthraquinone, 4',4"-diethylisophthaloquinone, 3,3',4,4'-tetra(t-butyl-peroxycarbonyl)benzophenone.

The amount to be added cannot be specified, because it considerably varies depending on the kind of the polymerizable compound or polymerizable composition. Nonetheless, it can be added preferably in a range of from about 0.0001 to 10 wt. %, more preferably in a range of from 0.001 to 5 wt. %, based on the polymerizable compound or composition according to the present invention.

Examples of the light-activated cation generators can include aromatic diazonium complexes, aromatic sulfonium complexes, aromatic iodonium complexes, Brønsted acid-onium complexes, and Brønsted acid-iron aromatic compound complexes. However, aromatic sulfonium complexes, aromatic iodonium complexes and Brønsted acid-iron aromatic compound complexes can be used preferably in many instances.

Examples of the aromatic sulfonium complexes can include triphenylsulfonium tetrafluoroborate, triphenylsulfonium hexafluorophosphonate, triphenylsulfonium hexafluoroarsenate, triphenylsulfonium hexafluoroantimonate, diphenyliodonium tetrafluoroborate, diphenyliodonium hexafluorophosphonate, diphenyliodonium hexafluoroarsenate, and diphenyliodonium hexafluoroantimonate. There are also "Cyracure UVI-6974" (trade name, product of UCC), "Cyracure UVI-6990" (trade name, product of UCC), "Optomer SP150" (trade name, product of Asahi Denka Kogyo K. K.) and "Optomer SP170" (trade name, product of Asahi Denka Kogyo K. K.), all of which are commercially available as improved products of such aromatic sulfonium complexes and also generate free radicals.

As a Brønsted acid-iron aromatic compound complex, there is "CG24-061" (trade name, product of Ciba Geigy).

The amount of such a light-activated cation generator to be added cannot be specified because it varies considerably depending on the kind of the polymerizable compound or polymerizable composition. Nonetheless, it can be added preferably in a range of from about 0.0001 to 10 wt. %, more preferably in a range of from 0.001 to 5 wt. %, based on the polymerizable compound or composition according to the present invention.

If a desired polymerization rate cannot be achieved, for example, in visible light induced polymerization making combined use of a photopolymerization initiator and a thermal polymerization catalyst, on the other hand, addition of a photosensitizer such as camphorquinone may be effective in some instances.

The organic polymers and the molded or otherwise formed products comprising the same, to both of which the present invention relates, are high in hydrophilicity and tend to be wet with water. Even if ordinary water-insoluble components which remain as pollutants, air-borne hydrophobic substances, or hydrophobic pollutants such as coke components from automobile exhaust, industrial exhaust or the like, sebum and proteins deposit, the pollutants are caused to separate by water such as rain, shower, tear or the like and thus, are eliminated (self-cleaning). In addition, formation of water droplets and mist on window panes, mirrors, agricultural vinyl sheets, spectacle lenses, camera lenses and the like under high-humidity conditions and formation of dews on interior walls and upholstery can also be suppressed. Obviously, they can also be applied as materials for suppressing a reduction in the efficiency of heat exchange due to the formation of water droplets and deposition of fouling substances on cooling fins.

The organic polymers according to the present invention, which are high in water wettability and are hydrophilic, are highly compatible with steam, water and the like and can easily absorb and retain them. Accordingly, they can also be applied as water retaining materials useful for greening deserts or promoting the growth of general plants, and like purposes and also as waste water (liquid) absorbent materials and the like.

In the field of optical materials, such as spectacle lenses, contact lenses, camera lenses and pickup lenses, for which transparency is important, the organic polymers according to the present invention can also improve their dyeability with disperse dyes and contact lens wear comfort in addition to their antifouling properties.

As described above, the organic polymers according to the present invention and the molded or otherwise formed products, which contain the organic polymers and also pertain to the present invention, can be suitably used in the fields of antifouling (including coating) materials (self-cleaning materials), dew preventing materials, water (liquid) absorbent materials, optical materials and the like.

In addition, they can be used in various fields, for example, such as ship bottom painting materials; body fluid absorbents such as gauze, first-aid straps and diapers; plasters such as poultices; medicament-containing adhesive materials such as fragrance preparations; gel materials for cold insulators; road anti-freezing materials; concrete additives; (photocuring) adhesive materials; tape materials; photocuring dental materials; display partition materials; hairdressing additives; additives to surfactants such as hair shampoos, hair rinses, hair conditioners, and body washes or shampoos; surfactants; (photocuring) inks; (photocuring) paints and coating materials; letterpress materials; additives to inkjet inks; additives to inkjet sheets and copy papers; (color) toner materials; binders for magnetic disks and magnetic tapes; photoresist materials; film resist materials; superconductor matrix materials; blood storage containers; materials for molded or otherwise formed plastic products; and curing polymerizable compounds.

The present invention will hereinafter be described in further detail on the basis of Examples. It should however be borne in mind that the present invention is not limited only to these Examples.

Further, a series of operations and the like upon synthesis of polymers were conducted at room temperature unless otherwise specifically indicated.

For the measurement of water contact angles, "CA-X200 Model" (trade name; manufactured by KYOWA INTERFACE SCIENCE CO., LTD.) was used.

EXAMPLE 1

Synthesis of chloroethyloxazolidone (hereinafter abbreviated as "CEOZ") and N-methoxyethyl-N'-hydroxy-ethyl-ethyleneurea (abbreviated as "MHEU")

97% Sodium hydroxide (173.2 g, 4.20 mol), sodium hydrogencarbonate (378.0 g, 4.50 mol) and water (1,500 mL) were mixed into a homogeneous solution.

To the solution, bis(2-chloroethyl)amine hydrochloride (750.0 g, 4.20 mol) was added in portions at internal temperatures of from 30 to 35° C. over 0.5 hour, followed by aging at 40° C. for 4 hours. Chloroform (0.5 L) was added with stirring to the reaction mixture, allowed to stand, a separated lower organic layer was collected. An upper water layer was extracted with three 0.5 L portions of chloroform (total: 1.5 L) to collect organic components. Those chloroform layers were combined and distilled off the solvent to afford CEOZ of 93.2% purity (569.8 g, 3.55 mol, pure yield: 84.5%).

Figure 2:
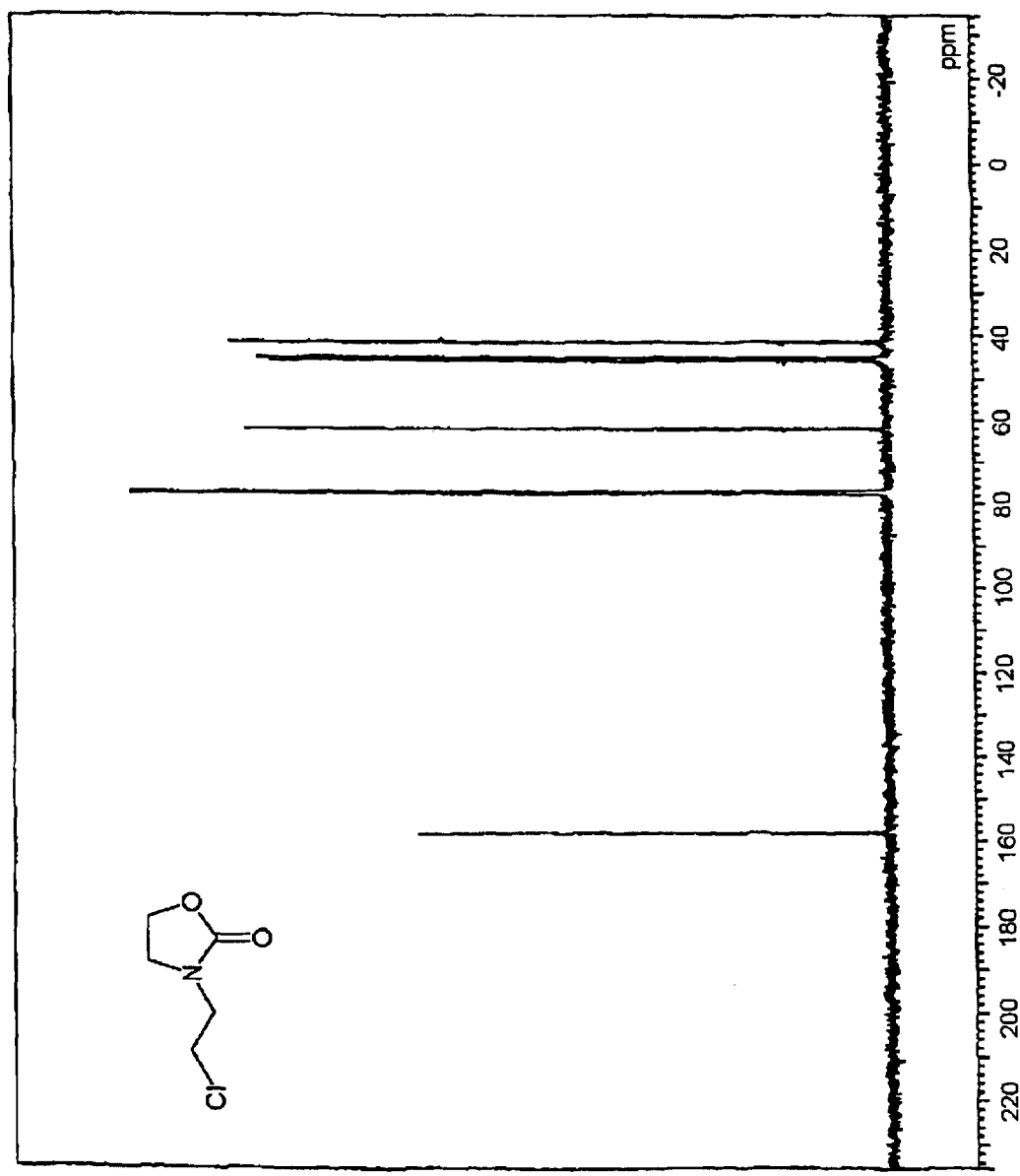
FIG. 2 is a $^{13}$C-NMR chart of chloroethyloxazolidone obtained in Example 1.

The followings are identification data of the thus-obtained CEOZ:
$^1$H-NMR→See FIG. 1
$^{13}$C-NMR→See FIG. 2

To 2-methoxyethylamine (1,350 g, 18.0 mol), the CEOZ of 93.2% purity (3.54 mol) was then added dropwise under reflux (93 to 102° C.) over 1 hour, followed by aging under reflux (102 to 105° C.) for 15 hours.

To the reaction mixture, a 38.7 wt. % aqueous solution of sodium hydroxide (366.0 g, 3.54 mol) was added at internal temperatures of from 20 to 35° C. to neutralize the reaction mixture. Water was eliminated on an evaporator, and the precipitated salt was collected by filtration and washed with ethyl acetate. The resulting filtrate and washings were combined and concentrated again on the evaporator. Finally, the residue was purified by chromatography on a silica gel column to afford MHEU of 99% purity (471.5 g, 2.48 mol, pure yield: 70%).

Figure 3:
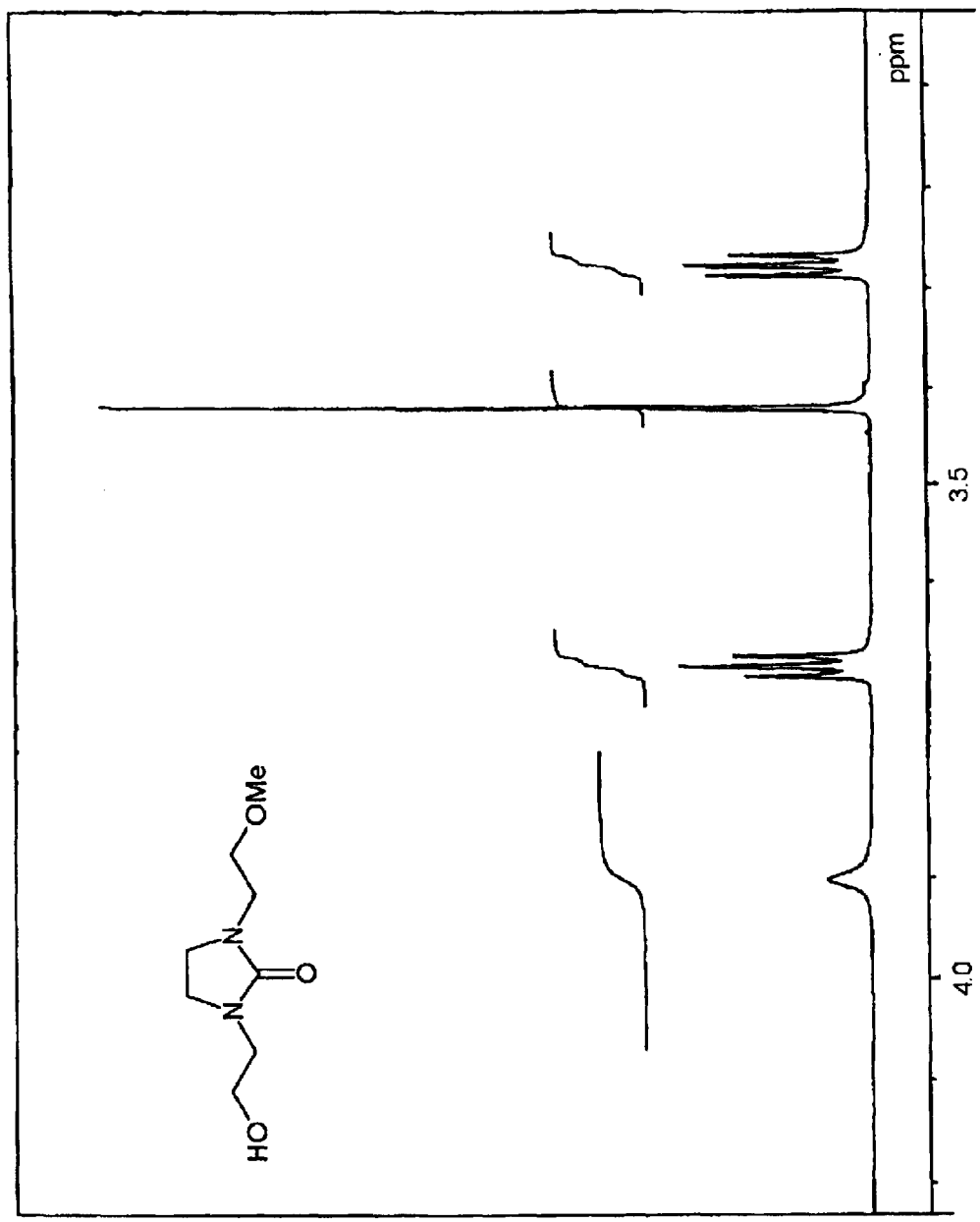
FIG. 3 is a $^1$H-NMR chart of N-methoxyethyl-N'-hydroxyethyl-ethyleneurea obtained in Example 1.
Figure 4:
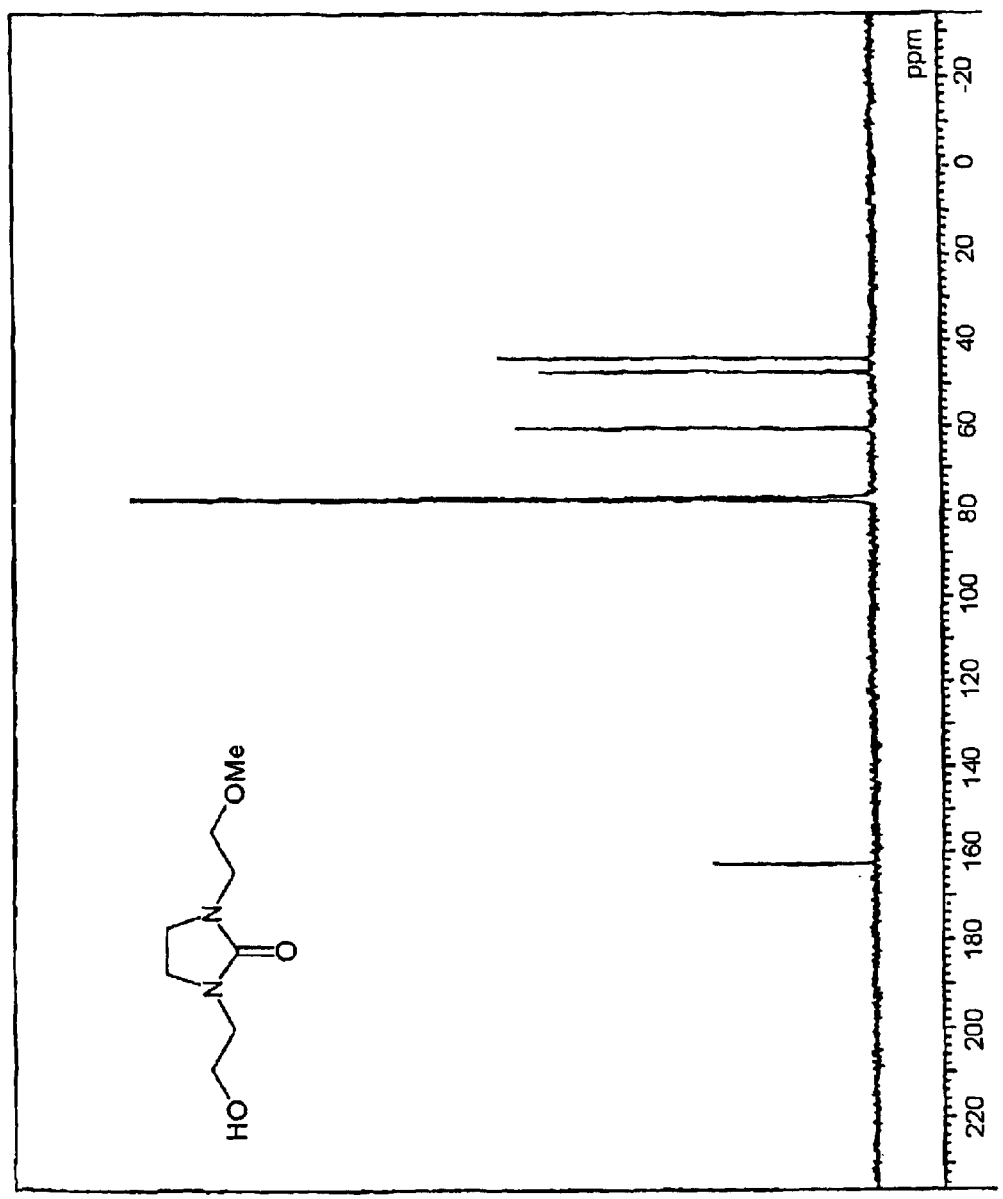
FIG. 4 is a $^{13}$C-NMR chart of N-methoxyethyl-N'-hydroxyethyl-ethyleneurea obtained in Example 1.

The followings are identification data of the thus-obtained CEOZ:
$^1$H-NMR→See FIG. 3
$^{13}$C-NMR→See FIG. 4

EXAMPLE 2

Synthesis of N-methoxyethyl-N'-mercaptoethyl-ethyleneurea (abbreviated as "THEU")

To N-methoxyethyl-N'-hydroxyethyl-ethylene urea (MHEU) of 99% purity (110.0 g, 0.579 mol), phosphorus tribromide (58.0 g, 0.214 mol) was added dropwise at internal temperatures of from 10 to 40° C., followed by aging at 50° C. for 2 hours. Chloroform (200 mL) was added to the reaction mixture, and water (50 mL) was added dropwise at an internal temperature of 60° C. The mixture was allowed to cool down to room temperature and also to separate into layers. The resulting organic layer was concentrated under reduced pressure to afford crude N-methoxyethyl-N'-bromoethyl-ethyleneurea (130.5 g, 0.520 mol, crude yield: 90%).

To the crude N-methoxyethyl-N'-bromoethyl-ethyleneurea, thiourea (69.6 g, 0.914 mol) and water (300 mL) were added, followed by a reaction under reflux (100 to 102° C.) for 3 hours. Subsequent to cooling to 40° C., 28% aqueous ammonia (148.0 g, 2.44 mol) was added dropwise at from 40 to 46° C. and the resulting mixture was allowed to age at 55° C. for 3 hours.

After the reaction mixture was allowed to cool down to room temperature, the resultant reaction mixture was extracted three times with chloroform. The thus-obtained organic layer was washed with hydrochloric acid, an aqueous solution of sodium hydrogencarbonate, and saline, and was then concentrated under reduced pressure. Finally, the resulting residue was purified by chromatography on a silica gel column to afford THEU of 92% purity (68.0 g, 0.306 mol, pure yield: 52.9%/MHEU).

Figure 5:
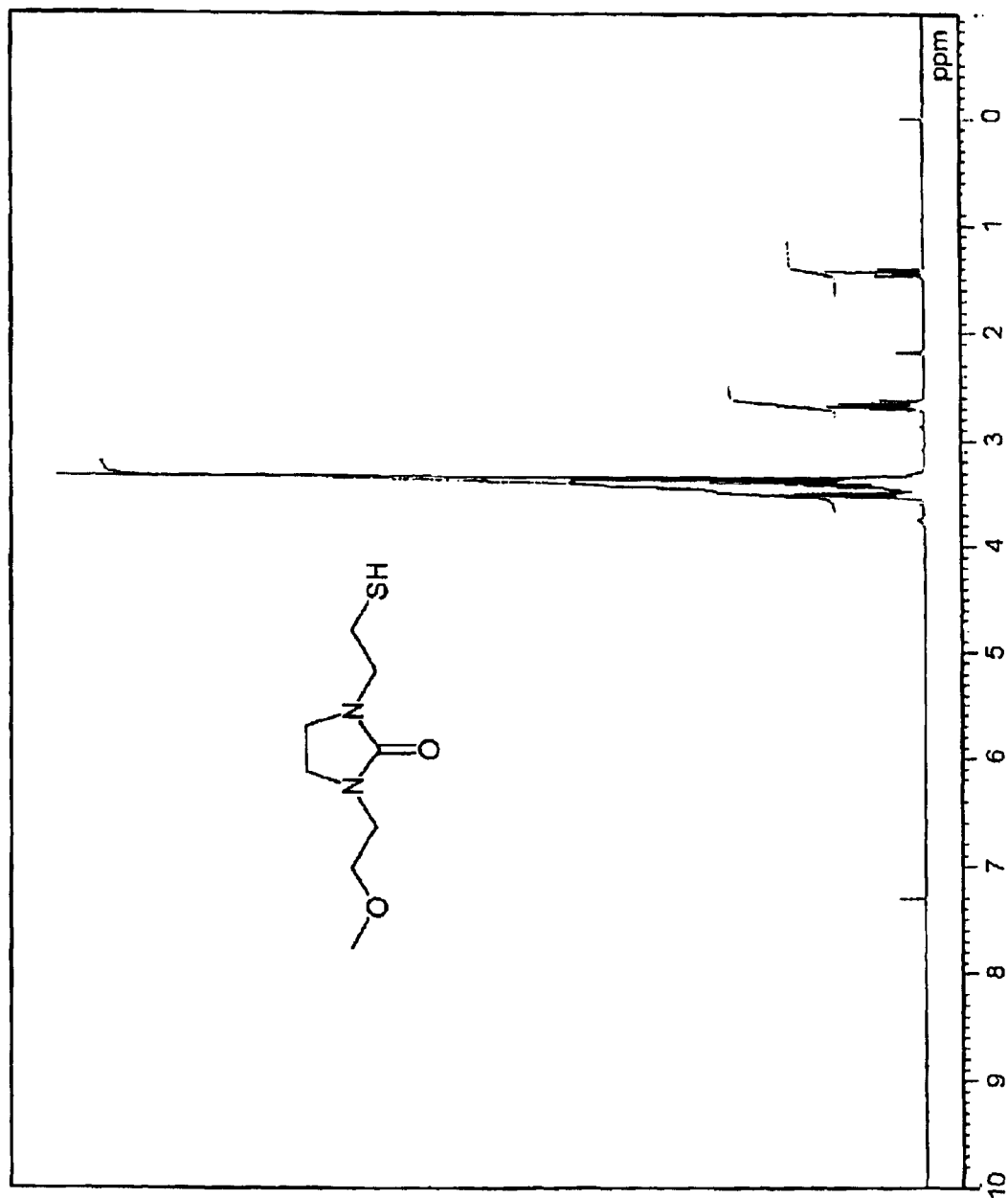
FIG. 5 is a $^1$H-NMR chart of N-methoxyethyl-N'-mercaptoethyl-ethyleneurea obtained in Example 2.
Figure 6:
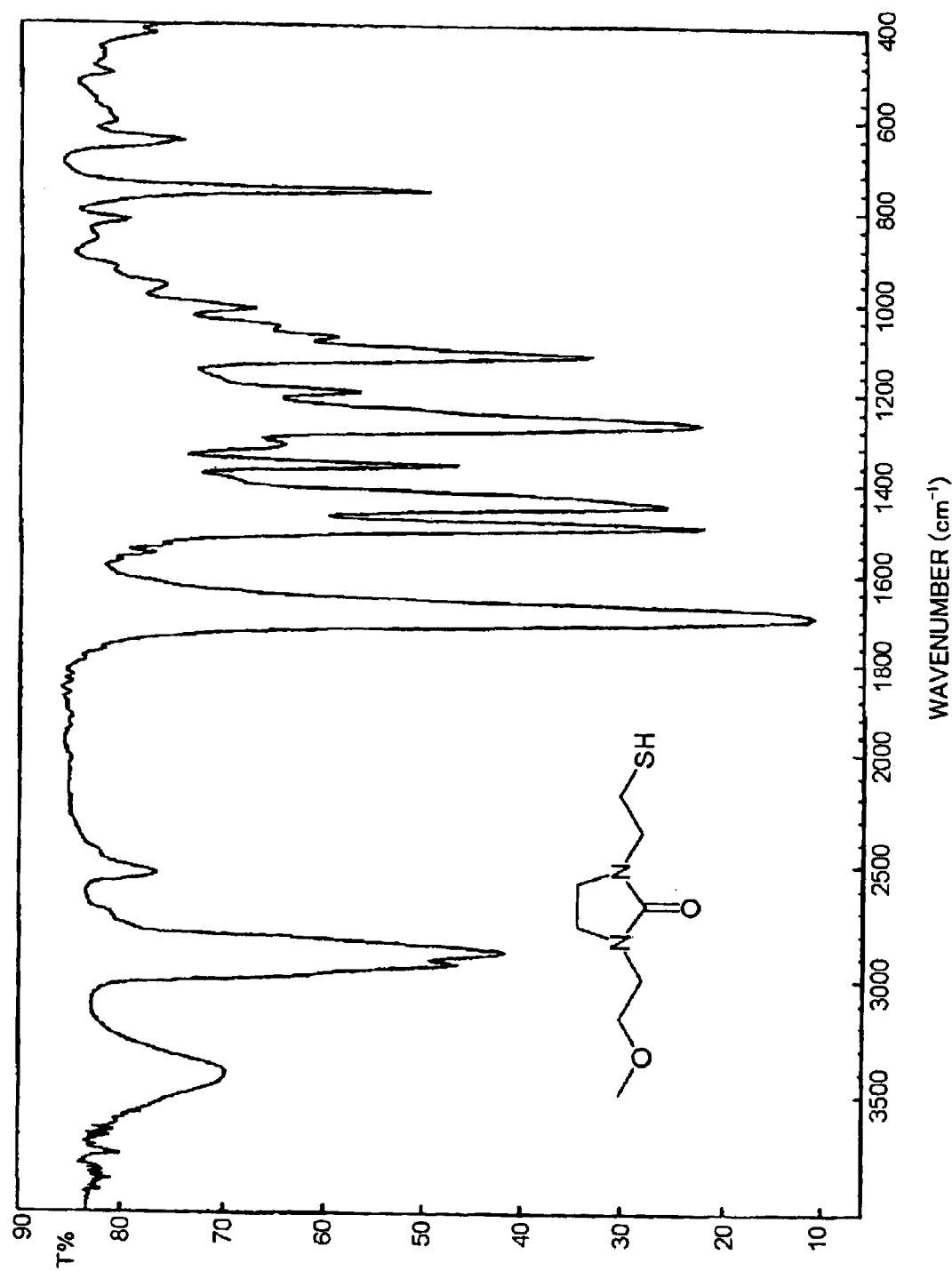
FIG. 6 is an IR chart of N-methoxyethyl-N'-mercaptoethyl-ethyleneurea obtained in Example 2.

The followings are identification data of the thus-obtained THEU:
$^1$H-NMR→See FIG. 5
IR→See FIG. 6

EXAMPLE 3

Synthesis of N,N'-bis(hydroxyethyl)-ethyleneurea (abbreviated as "HEEU") and N,N'-bis(mercaptoethyl)-ethyleneurea (abbreviated as "DMEU")

To 2-aminoethanol (1,180.0 g, 19.3 mol), CEOZ of 93.2% purity (568.0 g, 3.54 mol) was added dropwise at from 105 to 110° C. over 1 hour, followed by aging at 110° C. for 3 hours. Subsequent to cooling, an aqueous solution of 97% sodium hydroxide (146.0 g, 3.54 mol) and water (220 mL) was added, and filtration was then conducted. Anhydrous magnesium sulfate was added to the filtrate, and filtration was conducted again. The filtrate was caused to flow through a silica gel packed column, and the column was washed with methanol. The column effluent and the washing (methanol solution) were combined, and distilled under reduced pressure to distill off the solvent, 2-aminoethanol used in excess, etc. The resulting residue was purified by chromatography on a silica gel column to afford HEEU of 99% purity (469.4 g, 2.67 mol, pure yield: 75.4%).

Figure 7:
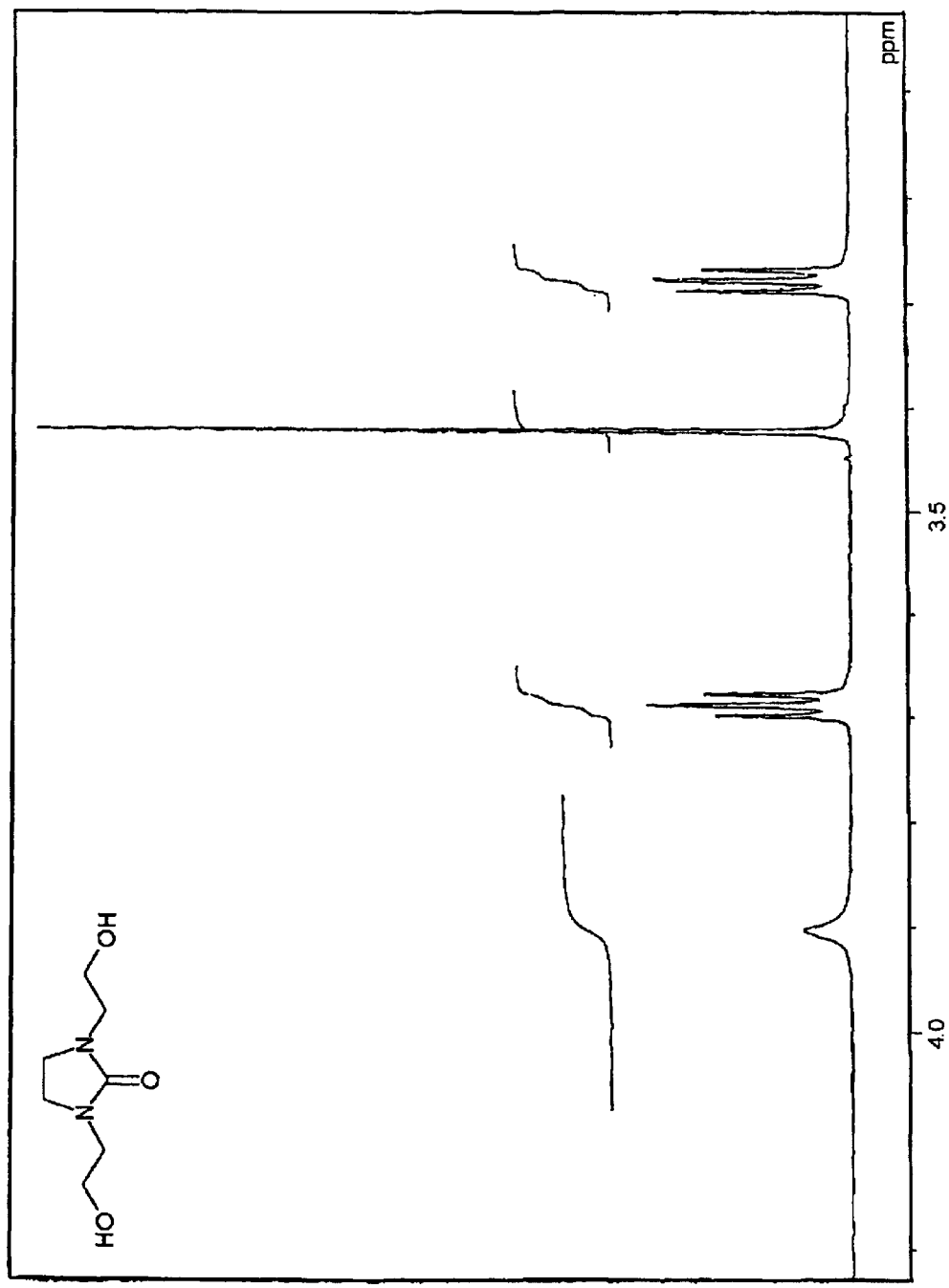
FIG. 7 is a $^1$H-NMR chart of N,N'-bis(hydroxyethyl)-ethyleneurea obtained in Example 3.
Figure 8:
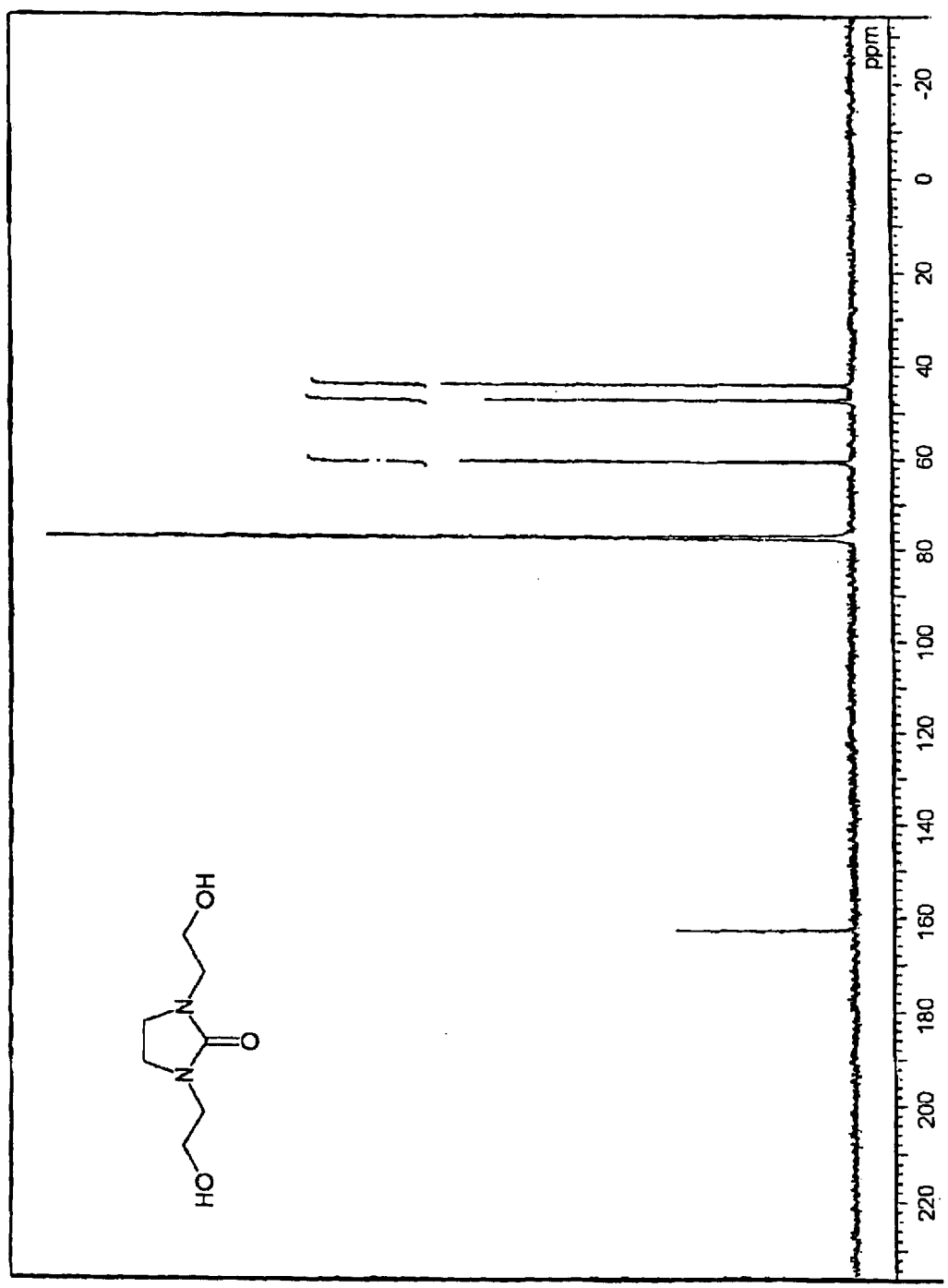
FIG. 8 is a $^{13}$C-NMR chart of N,N'-bis(hydroxyethyl)-ethyleneurea obtained in Example 3.

The followings are identification data of the thus-obtained HEEU:

$^1$H-NMR→See FIG. 7
$^{13}$C-NMR→See FIG. 8

To a liquid mixture of HEEU of 99% purity (150.6 g, 0.856 mol) and chloroform (60 mL), phosphorus tribromide (168.0 g, 0.605 mol) was added dropwise at internal temperatures of from 45 to 60° C., followed by aging at from 50 to 80° C. for 3 hours. The thus-obtained reaction mixture was allowed to cool down to room temperature, and water (30 ml) was added dropwise to hydrolyze excess phosphorus tribromide. Chloroform and water were then added to conduct water washing. The resulting organic layer was concentrated under reduced pressure to afford crude N,N'-bis(bromoethyl)-ethyleneurea (252.7 g, 0.842 mol, crude yield: 98%).

To the crude N,N'-bis(bromoethyl)-ethyleneurea, thiourea (200.0 g, 2.63 mol), 98% sulfuric acid (0.5 mL) and water (250 mL) were added, followed by a reaction under reflux (105° C.) for 3 hours. After being cooled to 40° C., 25% aqueous ammonia (230.0 g, 3.38 mol) was added dropwise at from 40 to 50° C., and a reaction was conducted at 65° C. for 3 hours.

After the reaction mixture was allowed to cool down to room temperature, sodium chloride was added and the resultant solution was extracted three times with chloroform. The thus-obtained organic layer was washed with hydrochloric acid, an aqueous solution of sodium hydrogencarbonate, and saline, and was then concentrated under reduced pressure. The resulting residue was purified by chromatography on a silica gel column to afford DMEU of 95% purity (134.0 g, 0.617 mol, pure yield: 72.1%/MHEU).

Figure 9:
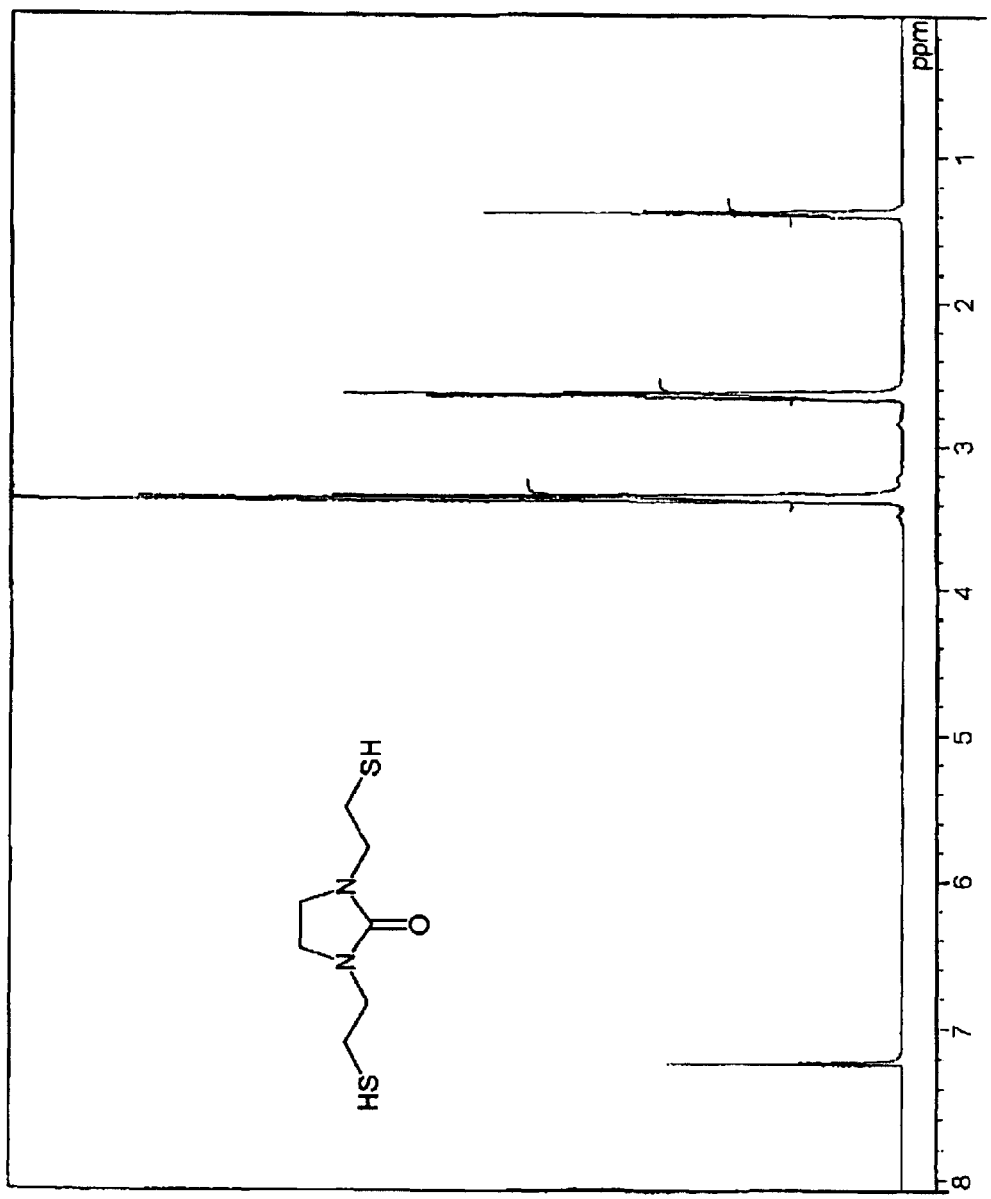
FIG. 9 is a $^1$H-NMR chart of N,N'-bis(mercaptoethyl)-ethyleneurea obtained in Example 3.
Figure 10:
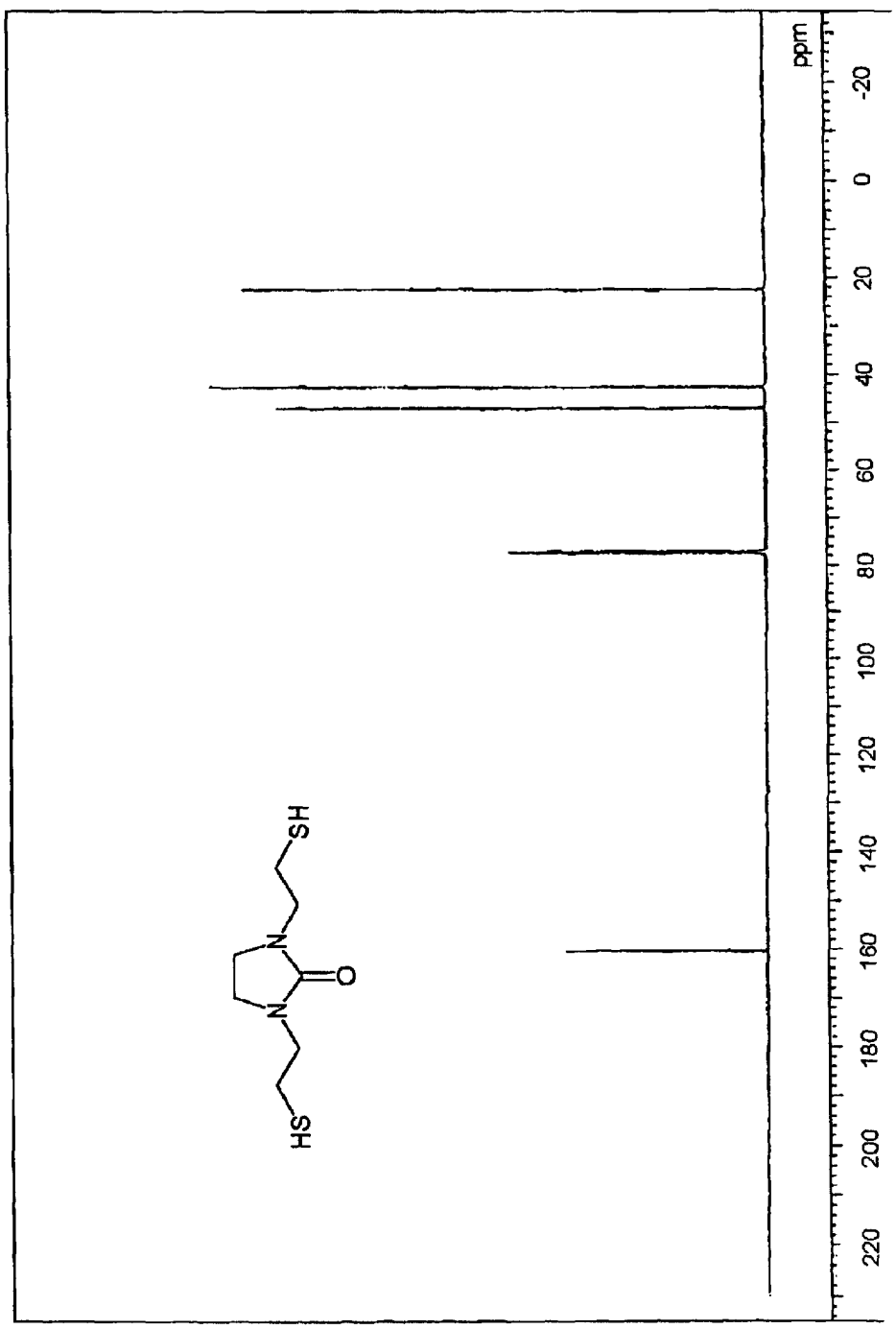
FIG. 10 is a $^{13}$C-NMR chart of N,N'-bis(mercapto-ethyl)-ethyleneurea obtained in Example 3.

The followings are identification data of the thus-obtained DMEU:

$^1$H-NMR→See FIG. 9
$^{13}$C-NMR→See FIG. 10

EXAMPLE 4

Synthesis of N-methoxyethyl-N'-methacryloyloxy-ethyl-ethyleneurea (hereinafter abbreviated as "MEMEU")

To a liquid mixture of MHEU of 99% purity (180.0 g, 0.947 mol), triethylamine (95.7 g, 0.947 mol) and EDC (dichloroethane, 240 g), methacrylic acid chloride (99.0 g, 0.947 mol) was added dropwise at internal temperatures of from 5 to 20° C. over 1 hour, followed by aging at from 10 to 22° C. for 1 hour. The reaction mixture was washed with EDC, water and 35% hydrochloric acid, concentrated under reduced pressure on an evaporator. The residue was purified by chromatography on a silica gel column.

As a result, N-methoxyethyl-N'-methacryloyloxy-ethyl-ethyleneurea (hereinafter abbreviated as "MEMEU") of 97% purity was obtained in an amount of 197.1 g (0.746 mol, pure yield: 78.8%).

Figure 11:
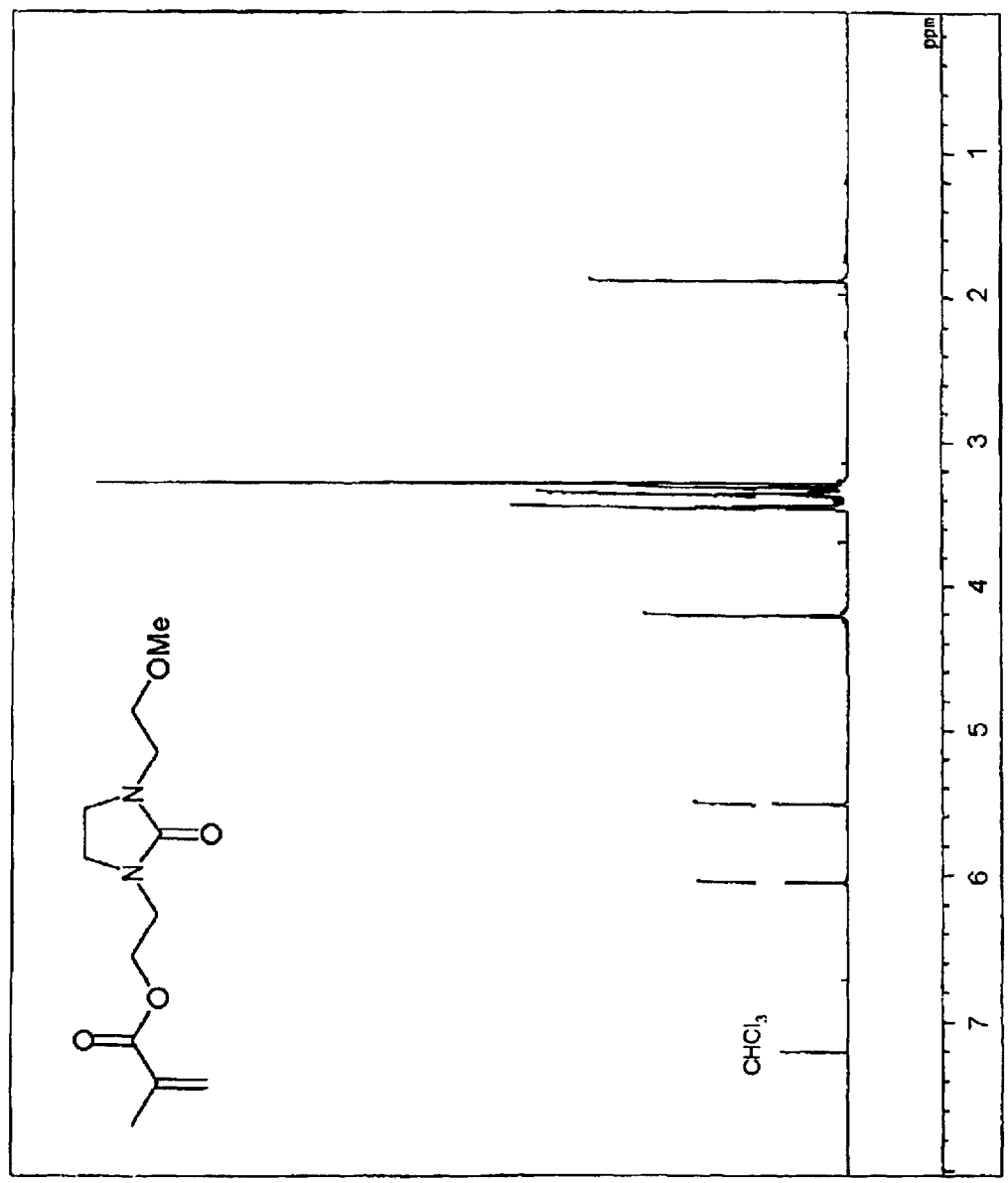
FIG. 11 is a $^1$H-NMR chart of N-methoxyethyl-N'-methacryloyloxyethyl-ethyleneurea obtained in Example 4.
Figure 12:
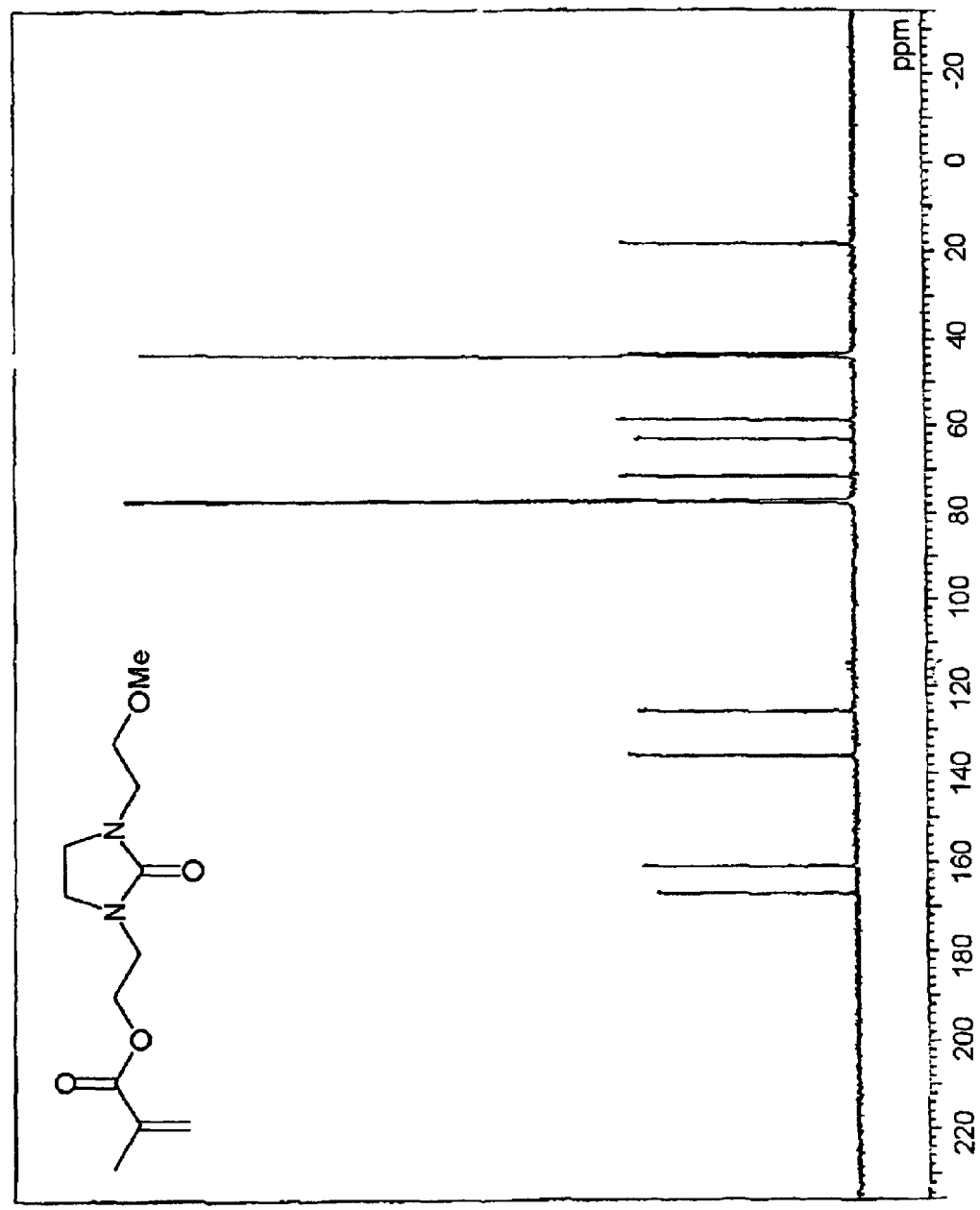
FIG. 12 is a $^{13}$C-NMR chart of N-methoxyethylN'-methacryloyloxyethyl-ethyleneurea obtained in Example 4.

The followings are identification data of the thus-obtained MEMEU:

$^1$H-NMR→See FIG. 11
$^{13}$C-NMR→See FIG. 12

EXAMPLE 5

Synthesis of N-methoxyethyl-N'-acryloylthioethyl-ethyleneurea (abbreviated as "ATEMU")

To MHEU of 99% purity (110.0 g, 0.579 mol), phosphorus tribromide (58.0 g, 0.214 mol) was added dropwise at internal temperatures of from 10 to 40° C., followed by aging at 50° C. for 2 hours. Chloroform (200 mL) was added to the thus-obtained reaction mixture, and water (50 mL) was added dropwise at an internal temperature of 60° C. The thus-prepared mixture was allowed to cool down to room temperature and also to separate into layers. The resulting organic layer was concentrated under reduced pressure to afford crude N-methoxyethyl-N'-bromoethyl-ethyleneurea (130.5 g, crude yield: 88%).

To the N-methoxyethyl-N'-bromoethyl-ethyleneurea, thiourea (69.6, 0.915 mol) and water (300 mL) were added, followed by a reaction under reflux (100 to 102° C.) for 3 hours. Subsequent to cooling to 40° C., 28% aqueous ammonia (148.0 g, 2.44 mol) was added dropwise at 40 to 46° C. and the resulting mixture was allowed to age at 55° C. for 3 hours.

After the reaction mixture was allowed to cool down to room temperature, the resultant reaction mixture was extracted three times with chloroform. The thus-obtained organic layer was washed with hydrochloric acid, an aqueous solution of sodium hydrogencarbonate, and saline, and was then concentrated under reduced pressure to afford crude N-methoxyethyl-N'-mercaptoethyl-ethyleneurea (68.0 g, crude yield: 57.5%/MHEU).

To the crude N-methoxyethyl-N'-mercaptoethyl-ethyleneurea (68.0 g), chloropropionic acid chloride (43.2 g, 0.340 mol) was added dropwise at internal temperatures of from 30 to 40° C., followed by aging at 40° C. for 3 hours.

Chloroform (140 mL) was then added, triethylamine (61.9 g, 0.602 mol) was added dropwise at internal temperatures of from 5 to 15° C. over 1 hour, followed by aging at internal temperatures of from 20 to 30° C. for 1 hour.

To the reaction mixture, chloroform (850 mL) and water (350 mL) were added to extract and wash. The separated organic layer was washed with hydrochloric acid and water, dried over anhydrous magnesium sulfate, and then filtered. The resulting filtrate was concentrated under reduced pressure, and the residue was purified by chromatography on a silica gel column to afford N-methoxyethyl-N'-acryloylthioethyl-ethyleneurea (ATEMU) of 95% purity (65.5 g, 0.241 mol, pure yield: 41.6%/MHEU).

Figure 13:
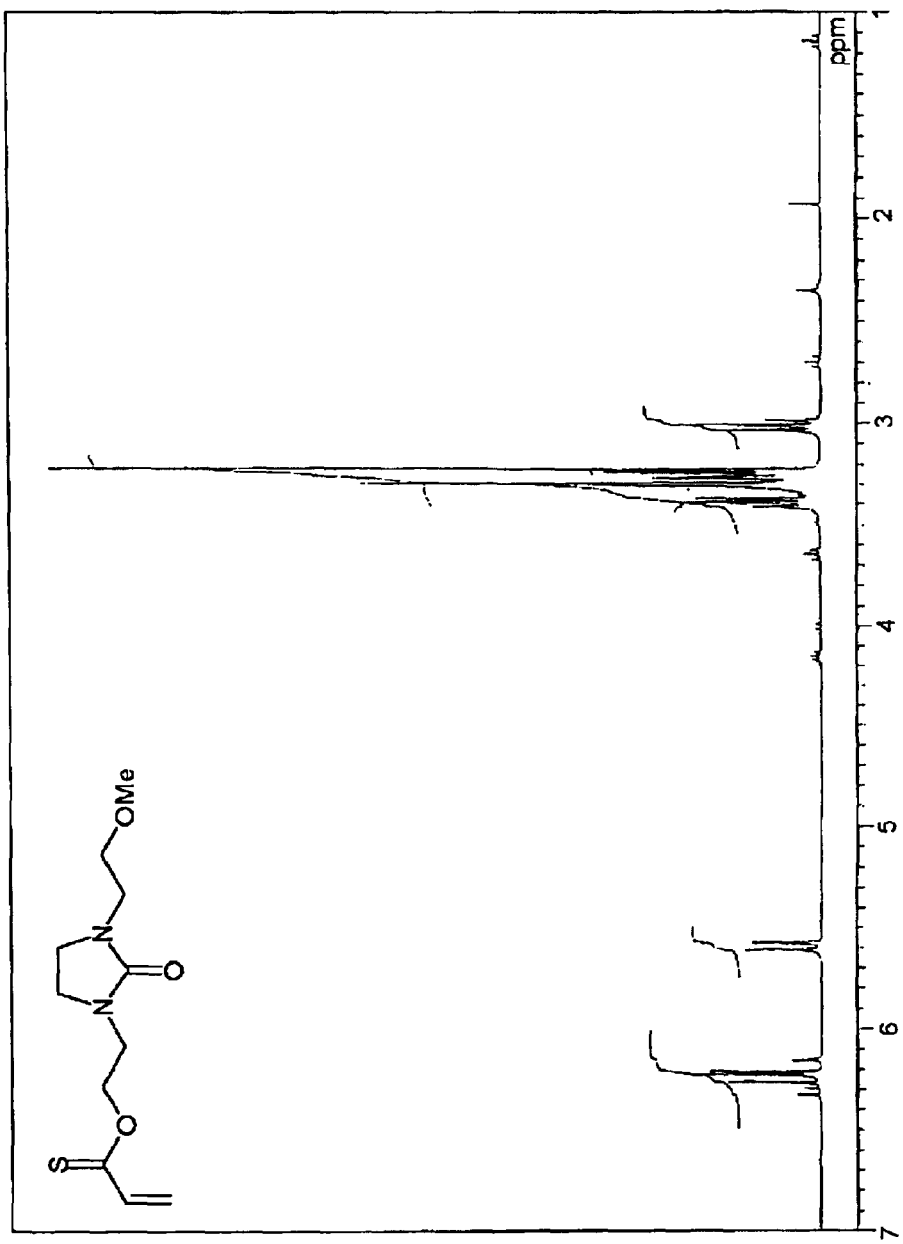
FIG. 13 is a $^1$H-NMR chart of N-methoxyethyl-N'-acryloylthioethyl-ethyleneurea obtained in Example 5.
Figure 14:
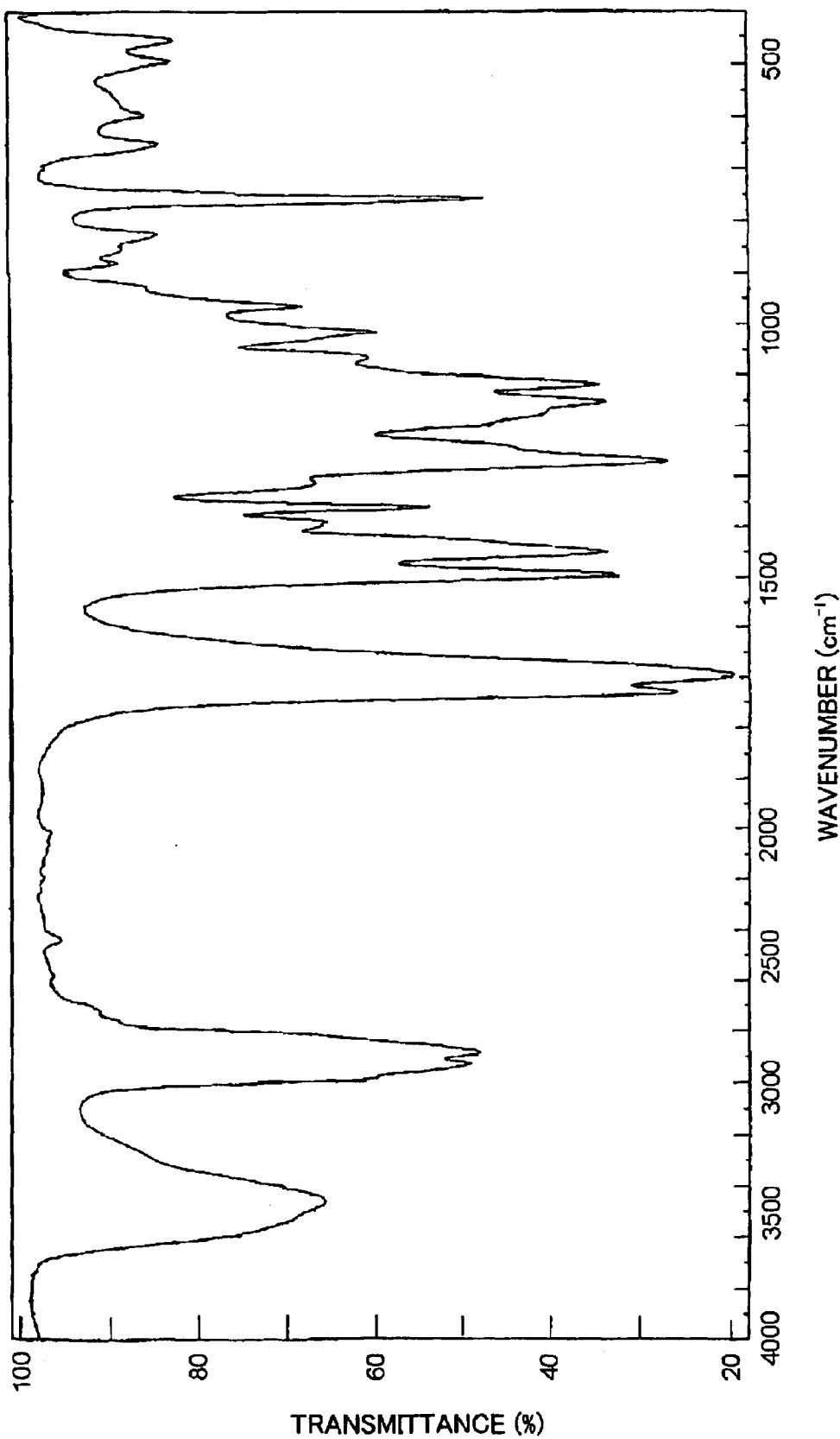
FIG. 14 is an IR chart of N-methoxyethyl-N'-acryloylthioethyl-ethyleneurea obtained in Example 5.

The followings are identification data of the thus-obtained ATEMU:

$^1$H-NMR→See FIG. 13
IR→See FIG. 14

EXAMPLE 6

Synthesis of N-methoxyethyl-N'-allylthiocarbonato-ethyl-ethyleneurea (abbreviated as "ATMEU")

To a liquid mixture of N-methoxyethyl-N'-mercaptoethyl-ethyleneurea (THEU) (80.0 g, 0.392 mol), triethylamine (71.4 g, 0.705 mol) and toluene (200 mL), allyl chloroformate (85.0 g, 0.705 mol) was added dropwise at internal temperatures of from 3 to 15° C. over 2 hours, followed by aging at from 10 to 20° C. for 2 hours. Chloroform (400 mL) and water (400 mL) were then added to extract the reaction mixture and to separate the same into layers. The organic layer was washed twice with water (400 mL), dried over anhydrous magnesium sulfate, and then filtered. The filtrate was concentrated on an evaporator. Finally, the residue was purified by chromatography on a silica gel column to afford N-methoxyethyl-N'-allylthiocarbonatoethyl-ethyleneurea (hereinafter abbreviated as "ATMEU") of 94% purity (105.6 g, 0.344 mol, pure yield: 87.8%/THEU).

Figure 15:
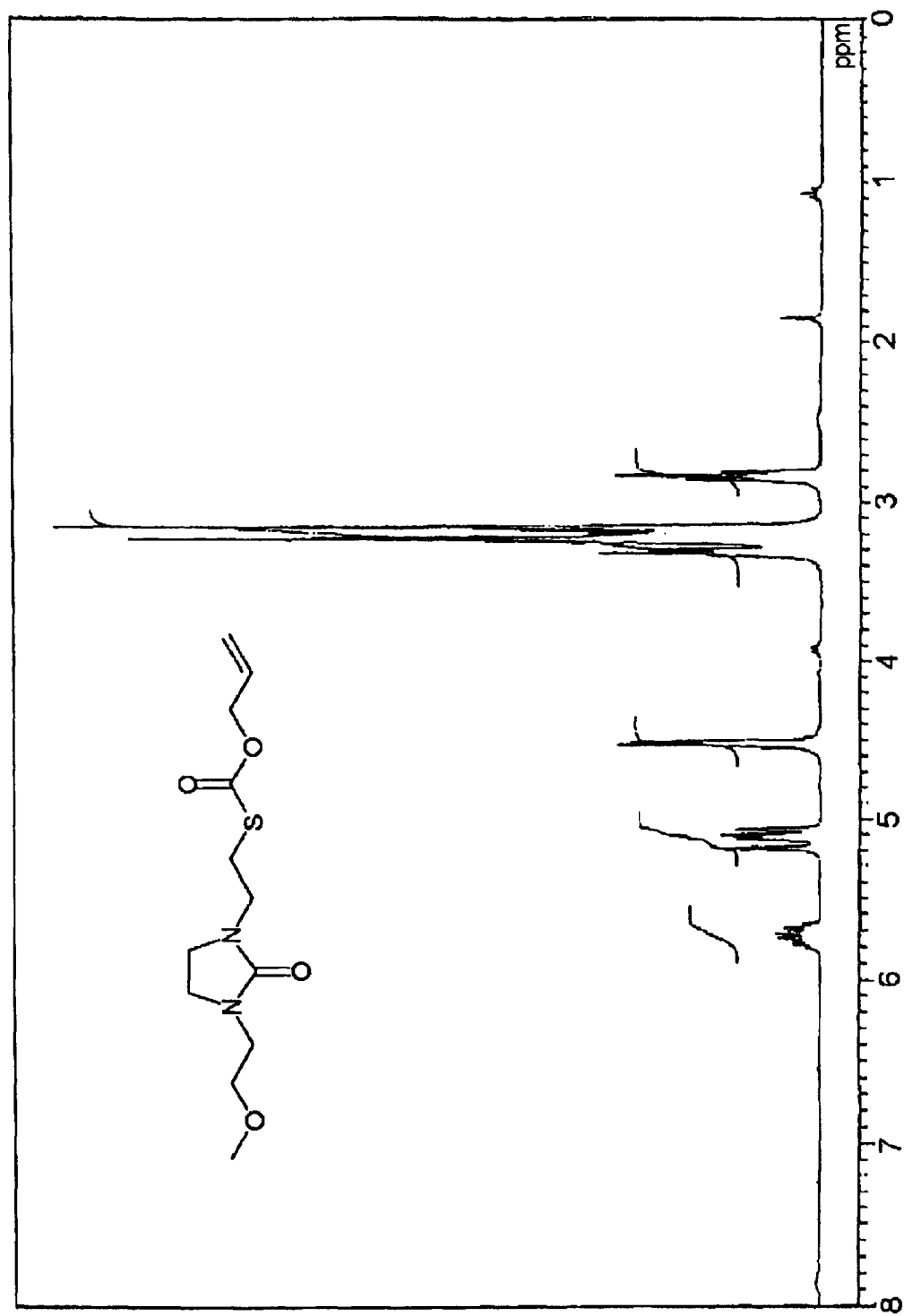
FIG. 15 is a $^1$H-NMR chart of N-methoxyethyl-N'-allylthiocarbonatoethyl-ethleneurea obtained in Example 6.
Figure 16:
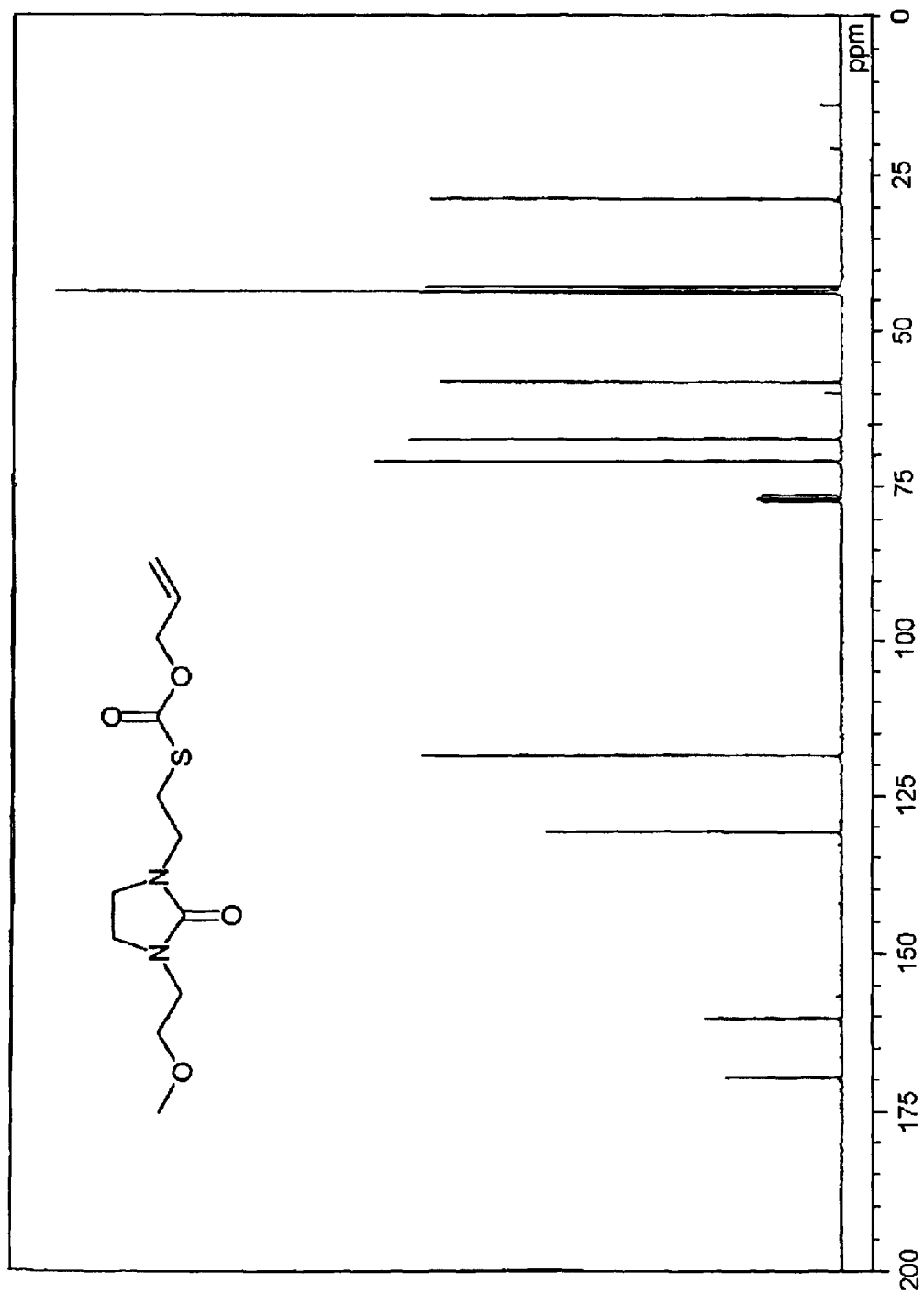
FIG. 16 is a $^{13}$C-NMR chart of N-methoxyethylN'-allylthiocarbonatoethyl-ethyleneurea obtained in Example 6.

The followings are identification data of the thus-obtained ATMEU:

$^1$H-NMR→See FIG. 15
$^{13}$C-NMR→See FIG. 16

EXAMPLE 7

Synthesis of N-methoxyethyl-N'-allylcarbonatoethyl-ethyleneurea (abbreviated as "ACMEU")

To a liquid mixture of N-methoxyethyl-N'-hydroxyethyl-ethyleneurea (MHEU) (73.8 g, 0.392 mol), triethylamine (71.4 g, 0.705 mol) and toluene (200 mL), allyl chloroformate (85.0 g, 0.705 mol) was added dropwise at internal temperatures of from 3 to 15° C. over 2 hours, followed by aging at from 10 to 20° C. for 2 hours. After completion of the reaction, toluene (500 mL) was added, and the resulting mixture was filtered. The filtrate was concentrated on an evaporator. Finally, the residue was purified by chromatography on a silica gel column to afford N-methoxyethyl-N'-allylcarbonatoethyl-ethyleneurea (ACMEU) of 93% purity (100.4 g, 0.343 mol, pure yield: 87.5%/MHEU).

Figure 17:
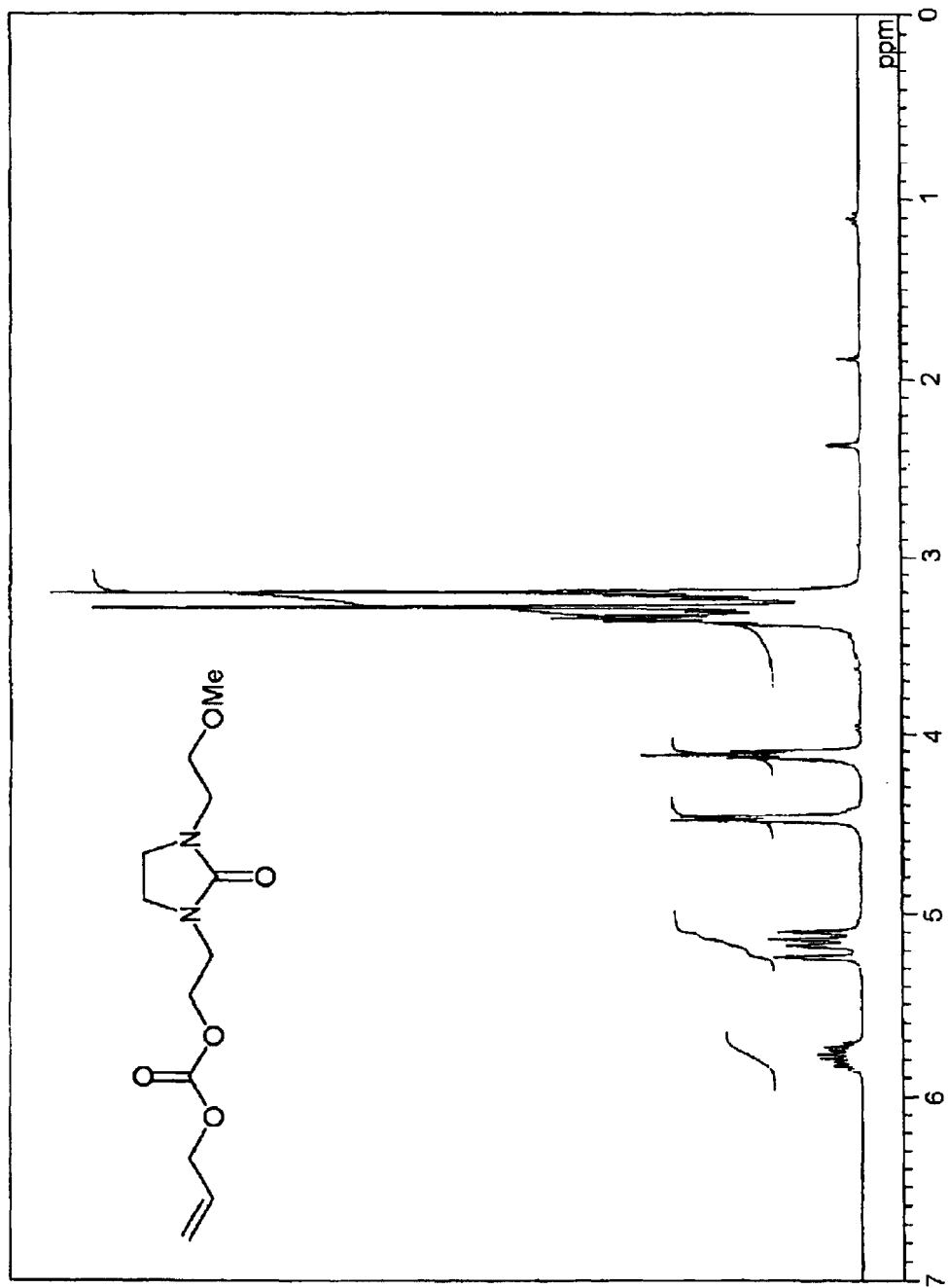
FIG. 17 is a $^1$H-NMR chart of N-methoxyethyl-N'-allylcarbonatoethyl-ethyleneurea obtained in Example 7.
Figure 18:
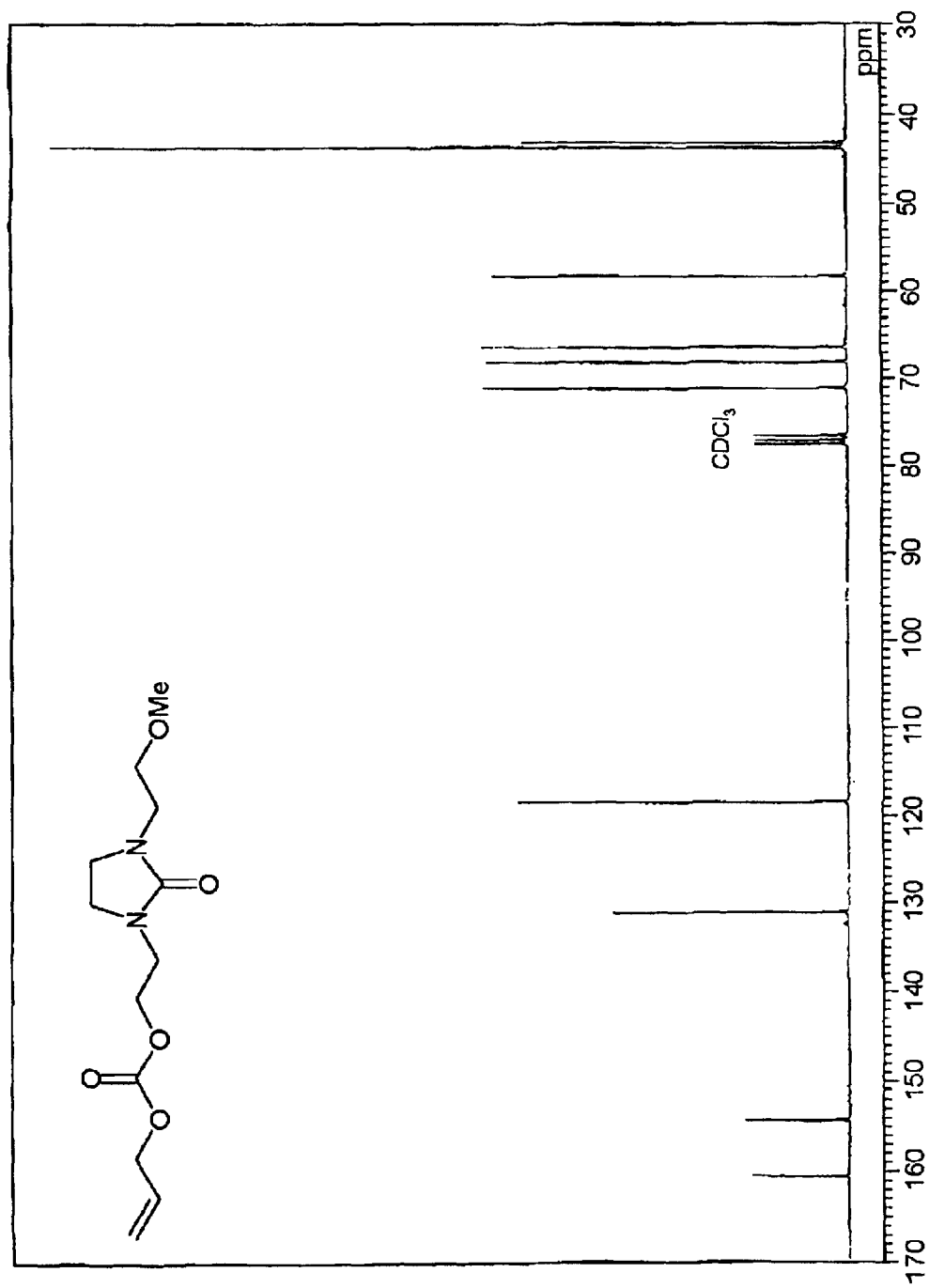
FIG. 18 is a $^{13}$C-NMR chart of N-methoxyethylN'-allylcarbonatoethyl-ethyleneurea obtained in Example 7.

The followings are identification data of the thus-obtained ACMEU:

$^1$H-NMR→See FIG. 17
$^{13}$C-NMR→See FIG. 18

EXAMPLE 8

Synthesis of N-methoxyethyl-N'-(glycidyloxyethyl)-ethyleneurea (abbreviated as "EPMEU")

To a liquid mixture of MHEU of 99% purity (100.0 g, 0.526 mol), epichlorohydrin (147.1 g, 1.59 mol) and dimethyl sulfoxide (30 g), 40% caustic soda (53.0 g, 0.530 mol) was added dropwise at internal temperatures of from 25 to 40° C. over 1 hour, followed by aging at from 40 to 60° C. for 8 hours. The reaction solution was filtered, and the filtrate was concentrated under reduced pressure on an evaporator. Acetonitrile was added to the residue, the resulting mixture was filtered, and the filtrate was again concentrated under reduced pressure on the evaporator. The residue was purified by chromatography on a silica gel. As a result, N-methoxyethyl-N'-(glycidyloxyethyl)-ethyleneurea (EPMEU) of 95% purity was obtained in an amount of 69.0 g (0.268 mol, pure yield: 51%/MHEU).

Figure 19:
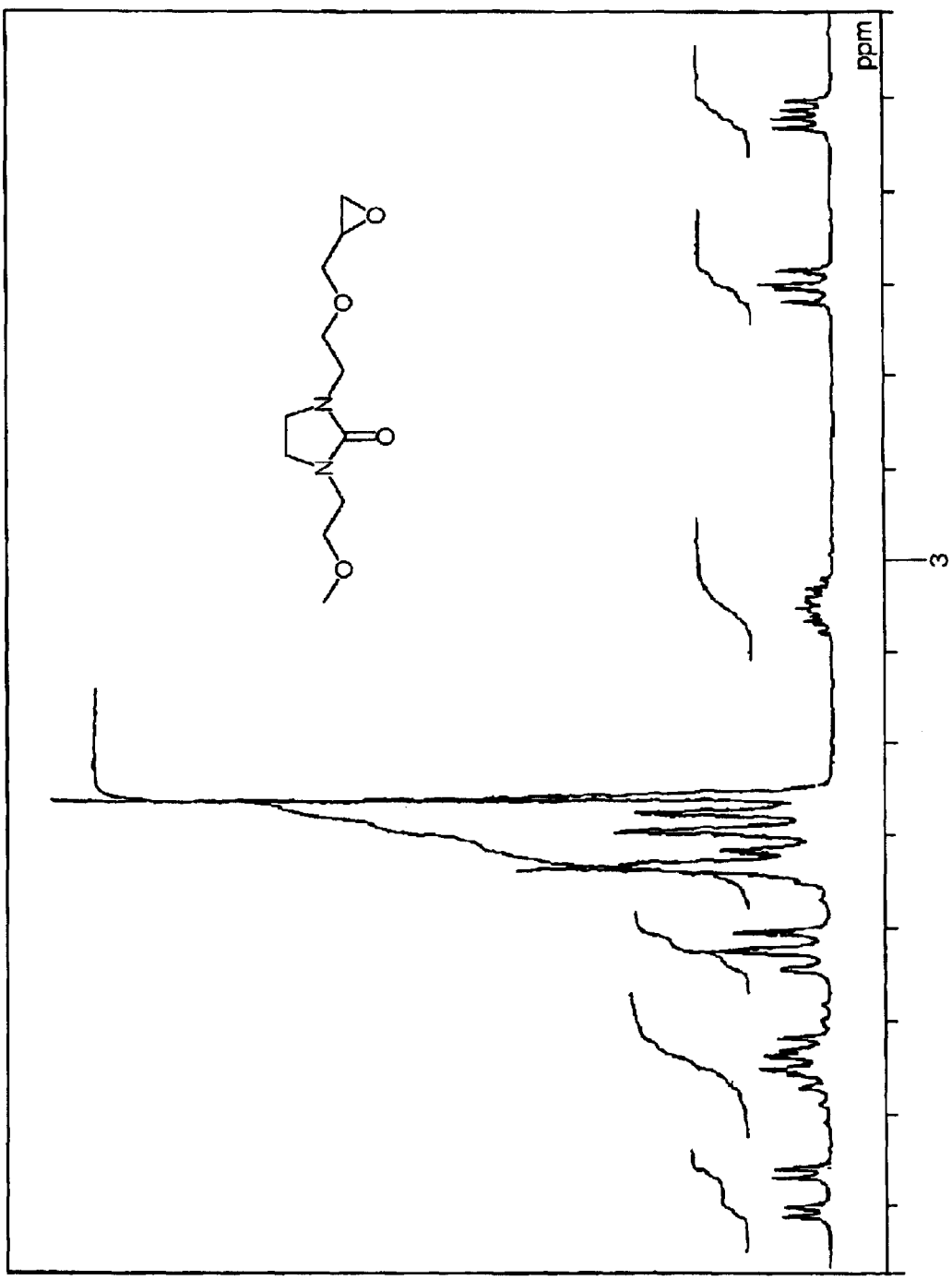
FIG. 19 is a $^1$H-NMR chart of N-methoxyethyl-N'-glycidyloxyethyl-ethyleneurea obtained in Example 8.
Figure 20:
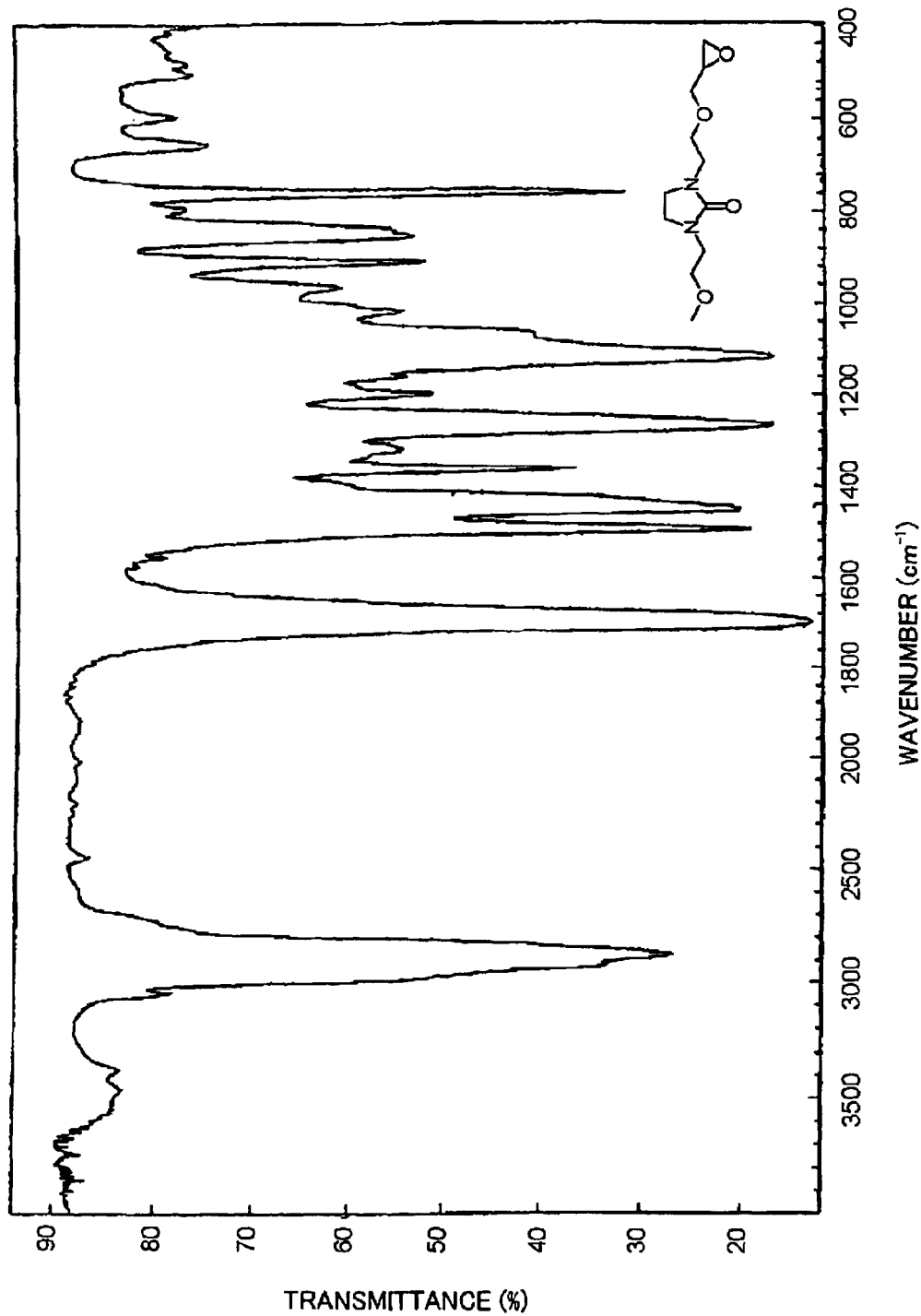
FIG. 20 is an IR chart of N-methoxyethyl-N'-glycidyloxyethyl-ethyleneurea obtained in Example 8.

The followings are identification data of the thus-obtained EPMEU:

$^1$H-NMR→See FIG. 19
IR→See FIG. 20

EXAMPLE 9

Synthesis of N,N'-bis(methacryloyloxyethyl)-ethyleneurea (abbreviated as "MEEU")

To a liquid mixture of HEEU of 99% purity (200.0 g, 1.14 mol), triethylamine (232.7 g, 2.30 mol) and acetonitrile (1,000 mL), methacrylic acid chloride (240.4 g, 2.30 mol) was added dropwise at from 5 to 10° C. over 1 hour, followed by aging at from 10 to 25° C. for 3 hours. After the reaction mixture was filtered, the filtrate was neutralized with acetic acid, p-methoxyphenol (2.0 g) was added, and at 30° C. or lower, distilled off the solvent under reduced pressure. The concentration residue was diluted with toluene, filtered again. The thus-obtained filtrate was distilled off the solvent at 30° C. or lower under reduced pressure. Finally, the resulting residue was purified by chromatography on a silica gel column. In the course of concentration, methoxyphenol (2.0 g) was added once again to afford N,N'-bis(methacryloyloxy-ethyl)-ethyleneurea (MEEU) of 97% purity (211.6 g, 0.661 mol, pure yield: 58.0%).

Figure 21:
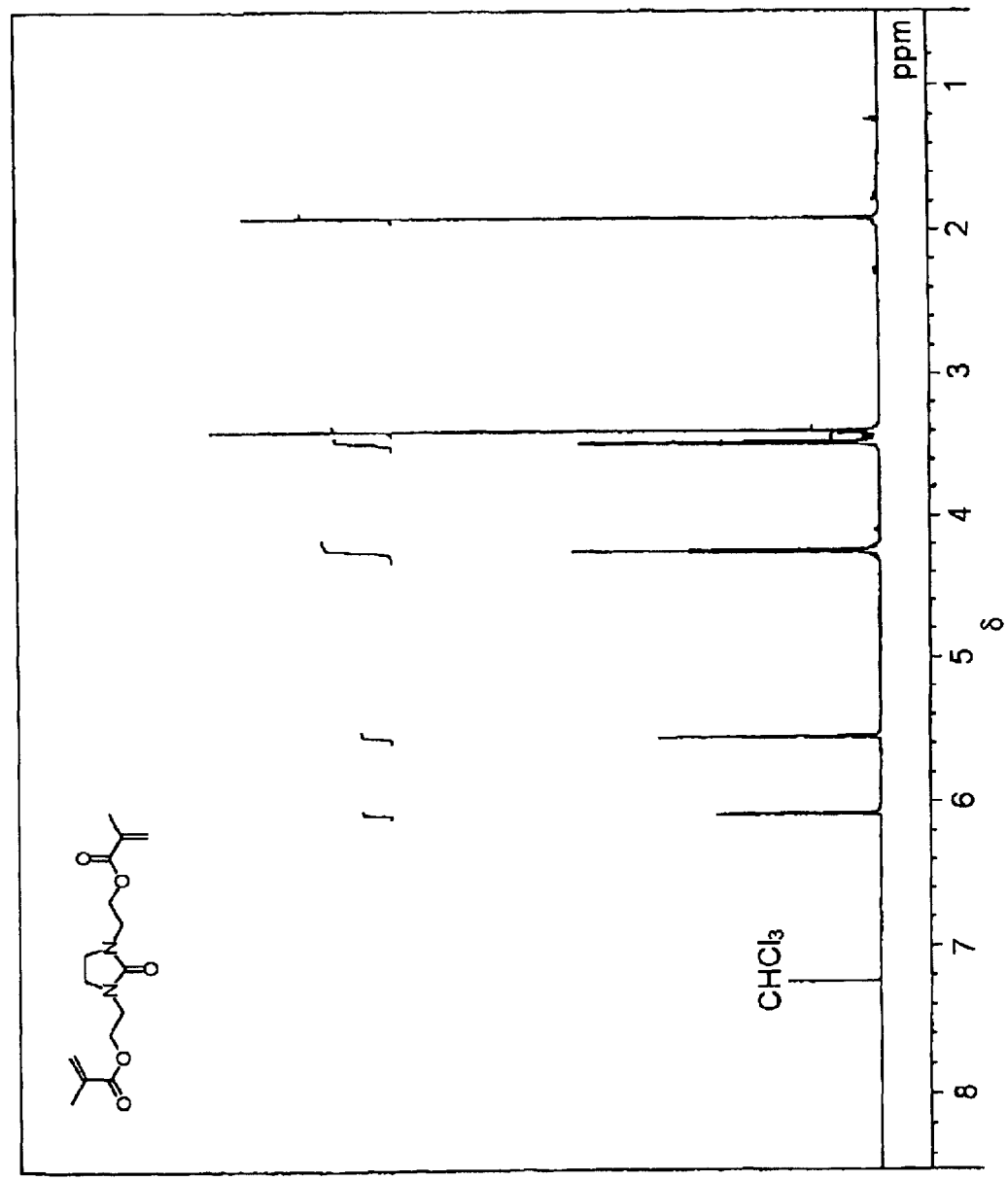
FIG. 21 is a $^1$H-NMR chart of N,N'-bis(methacryloyl-oxyethyl)-ethyleneurea obtained in Example 9.
Figure 22:
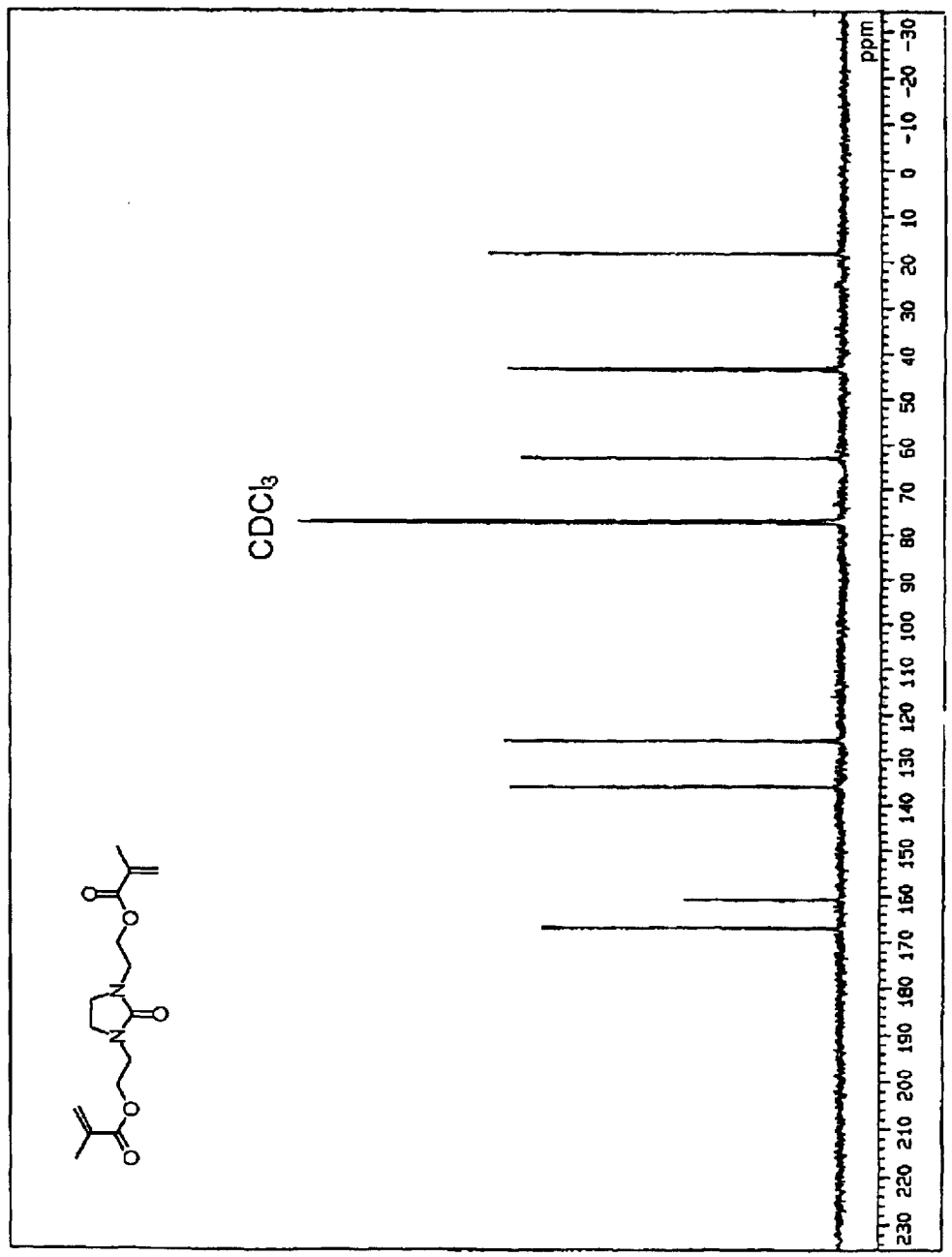
FIG. 22 is a $^{13}$C-NMR chart of N,N'-bis(methacryloyl-oxyethyl)-ethyleneurea obtained in Example 9.

The followings are identification data of the thus-obtained MEEU:

$^1$H-NMR→See FIG. 21
$^{13}$C-NMR→See FIG. 22

EXAMPLE 10

Synthesis of N,N'-bis (allylcarbonatoethyl)-ethyleneurea (abbreviated as "ACEU")

To a liquid mixture of HEEU of 99% purity (100.0 g, 0.568 mol), triethylamine (116.4 g, 1.15 mol) and acetonitrile (500 mL), allyl chloroformate (150.7 g, 1.25 mol) was added dropwise at from 5 to 10° C. over 1 hour, followed by aging at from 10 to 25° C. for 5 hours. After the reaction mixture was filtered, distilled off the solvent at 30° C. or lower under reduced pressure. The concentration residue was diluted with toluene, filtered again. The thus-obtained filtrate was again distilled off the solvent at 30° C. or lower under reduced pressure. The resulting residue was purified by chromatography on a silica gel column to afford N,N'-bis(allylcarbonato-ethyl)-ethyleneurea (ACEU) of 94% purity (160.2 g, 0.440 mol, pure yield: 77.5%).

Figure 23:
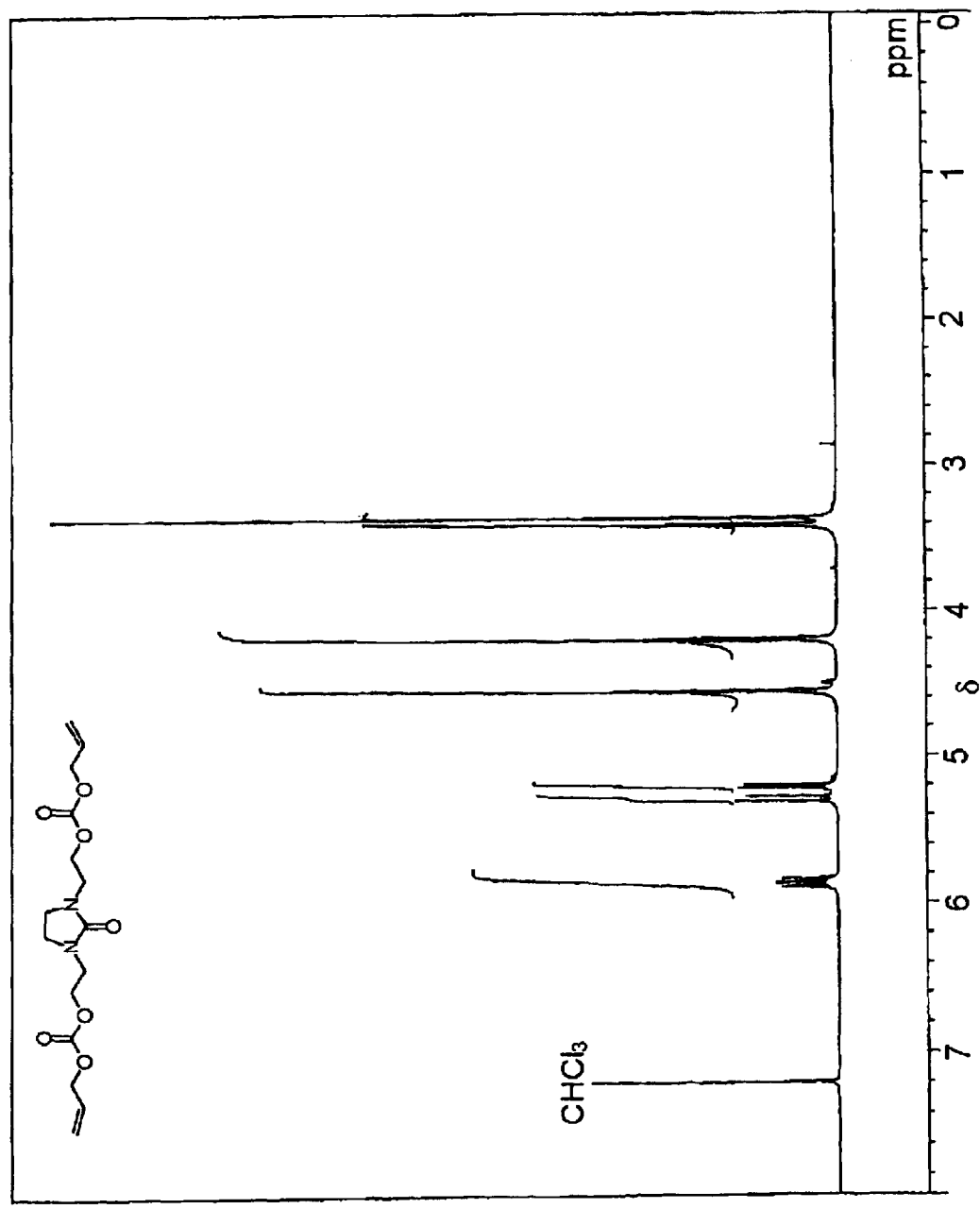
FIG. 23 is a $^1$H-NMR chart of N,N'-bis(allyl-carbonatoethyl)-ethyleneurea obtained in Example 10.
Figure 24:
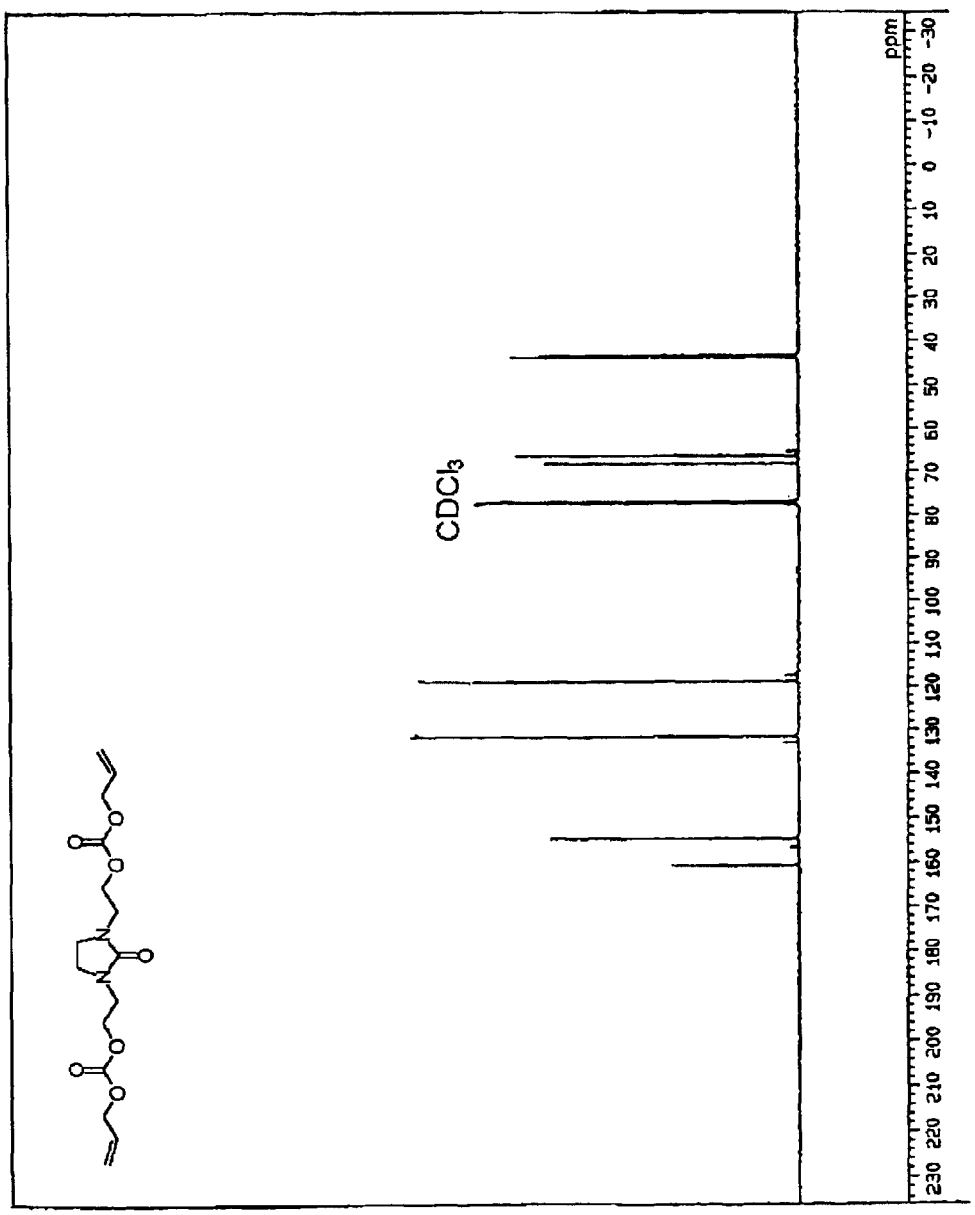
FIG. 24 is a $^{13}$C-NMR chart of N,N'-bis(allyl-carbonatoethyl)-ethyleneurea obtained in Example 10.

The followings are identification data of the thus-obtained ACEU:

$^1$H-NMR→See FIG. 23
$^{13}$C-NMR→See FIG. 24

EXAMPLE 11

Synthesis of N,N'-bis(acryloylthio-ethyl)-ethyleneurea (abbreviated as ATEEU)

To a liquid mixture of DMEU of 95% purity (100.0 g, 0.460 mol) and acetonitrile (120 mL), chloropropionic acid chloride (128.5 g, 1.01 mol) was added dropwise at 40 to 55° C., followed by aging at 40° C. for 6 hours while slightly bubbling the liquid reaction mixture with nitrogen. After the reaction mixture was allowed to cool down to room temperature, toluene (200 mL) was added, triethylamine (144.0 g, 1.42 mol) was added dropwise at from 0 to 10° C., followed by aging at from 10 to 15° C. for 5 hours. To the reaction mixture, water, saline and chloroform were added to extract and wash the same. After the organic layer was washed with hydrochloric acid and water, methoxyphenol (0.1 g) was added, and the solvent was then removed at 20° C. or lower on an evaporator. The remaining residue was purified by chromatography on a silica gel. In the course of concentration, methoxyphenol (0.4 g) was added once again to afford N,N'-bis(acryloylthio-ethyl)-ethyleneurea (ATEEU) of 98% purity (80.0 g, 0.249 mol, pure yield: 54.1%).

Figure 25:
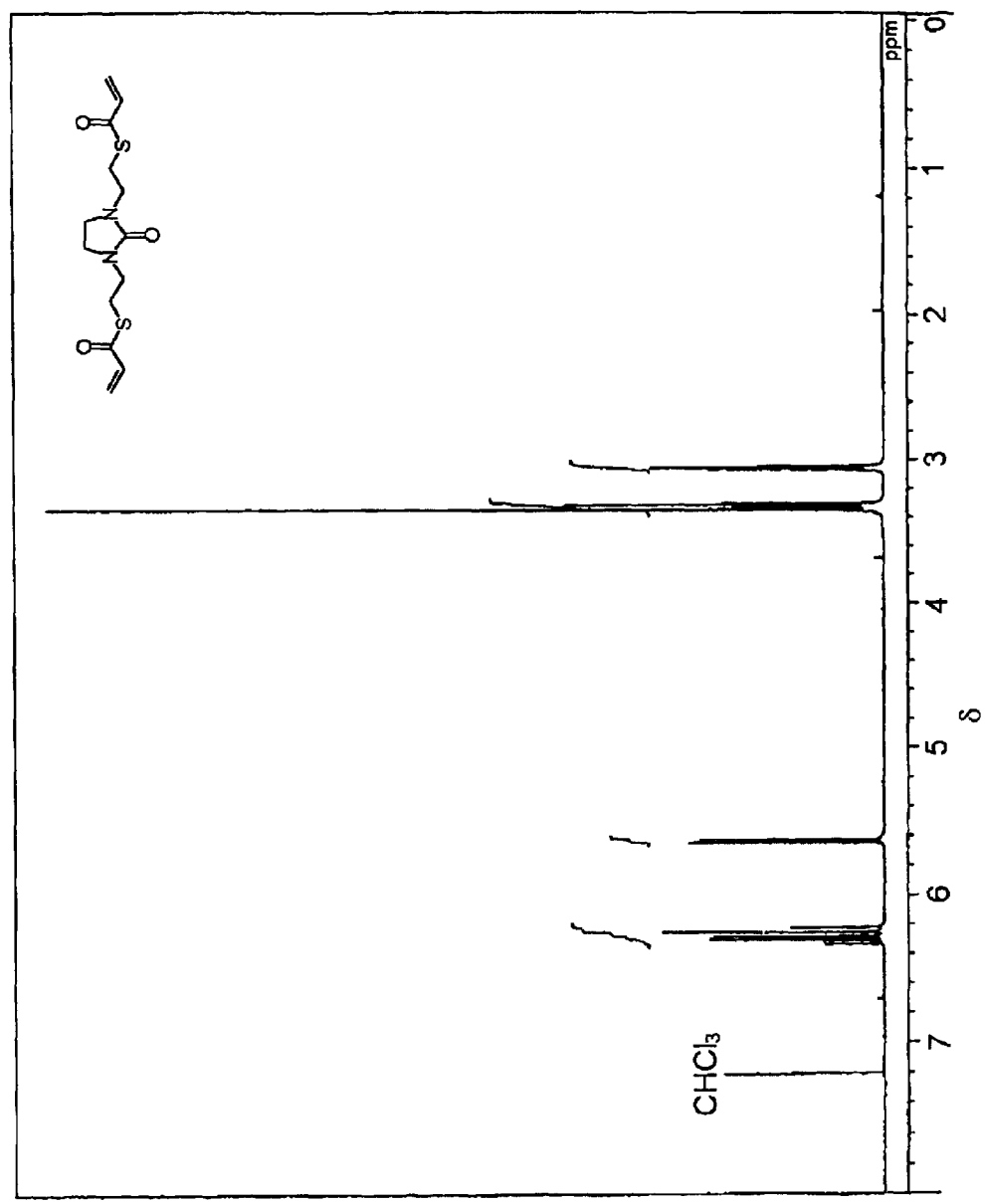
FIG. 25 is a $^1$H-NMR chart of N,N'-bis(acryloylthio-ethyl)-ethyleneurea obtained in Example 11.
Figure 26:
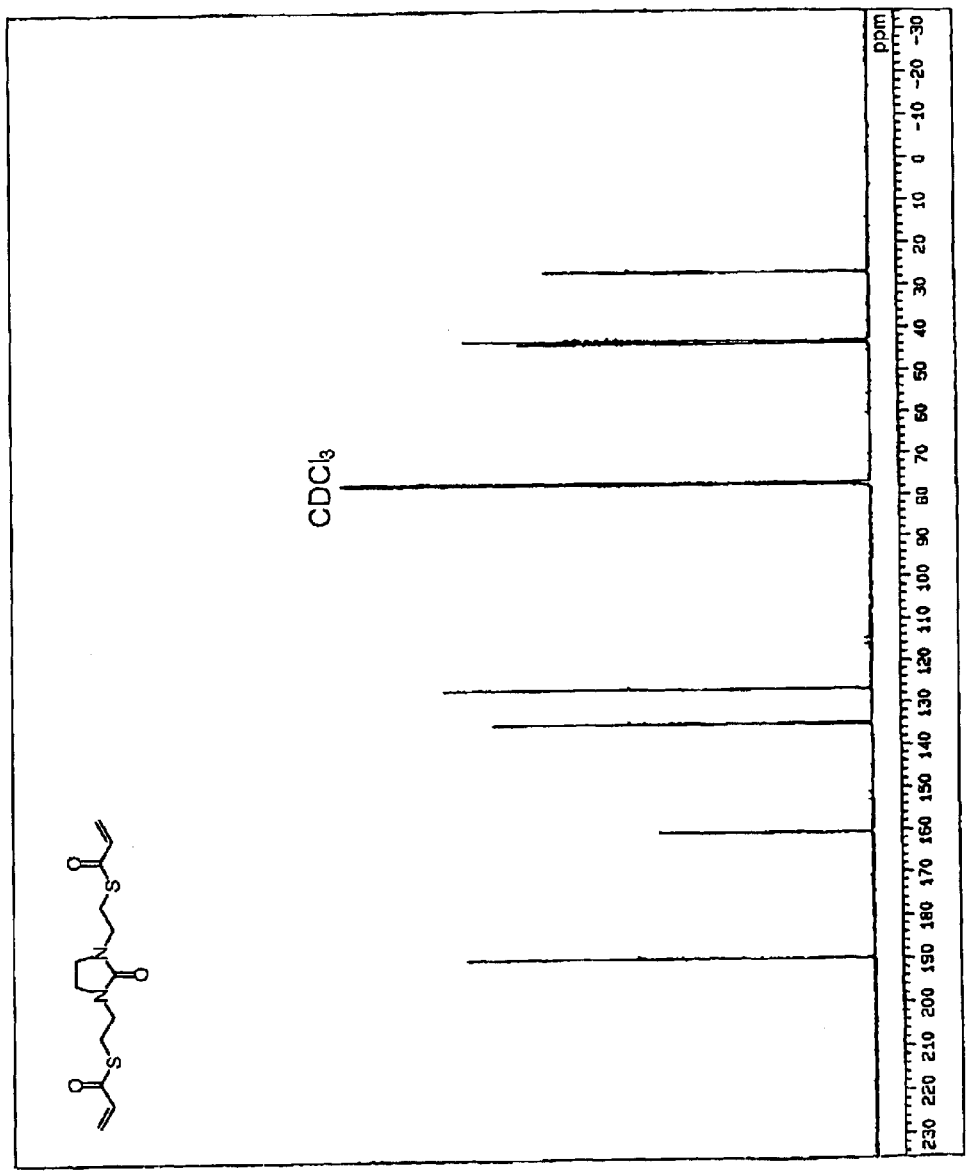
FIG. 26 is a $^{13}$C-NMR chart of N,N'-bis(acryloylthio-ethyl)-ethyleneurea obtained in Example 11.

The followings are identification data of the thus-obtained ATEEU:

$^1$H-NMR→See FIG. 25
$^{13}$C-NMR→See FIG. 26

EXAMPLE 12

Synthesis of N,N'-bis(allylthiocarbonatoethyl)-ethyleneurea (abbreviated as "ATCEU")

To a liquid mixture of DMEU of 95% purity (100.0 g, 0.460 mol), triethylamine (100.0 g, 0.988 mol) and acetonitrile (500 mL), allyl chloroformate (119.1 g, 0.988 mol) was added dropwise at from 5 to 10° C. over 1 hour, followed by aging at from 10 to 25° C. for 5 hours. After the reaction mixture was filtered, concentrated at 30° C. or lower under reduced pressure. The concentration residue was diluted with toluene, and filtered again. The thus-obtained filtrate was concentrated at 30° C. or lower under reduced pressure. Finally, the resulting residue was purified by chromatography on a silica gel column to afford N,N'-bis(allylthiocarbonatoethyl)-ethyleneurea (ATCEU) of 85% purity (141.4 g, 0.321 mol, pure yield: 69.8%).

Figure 27:
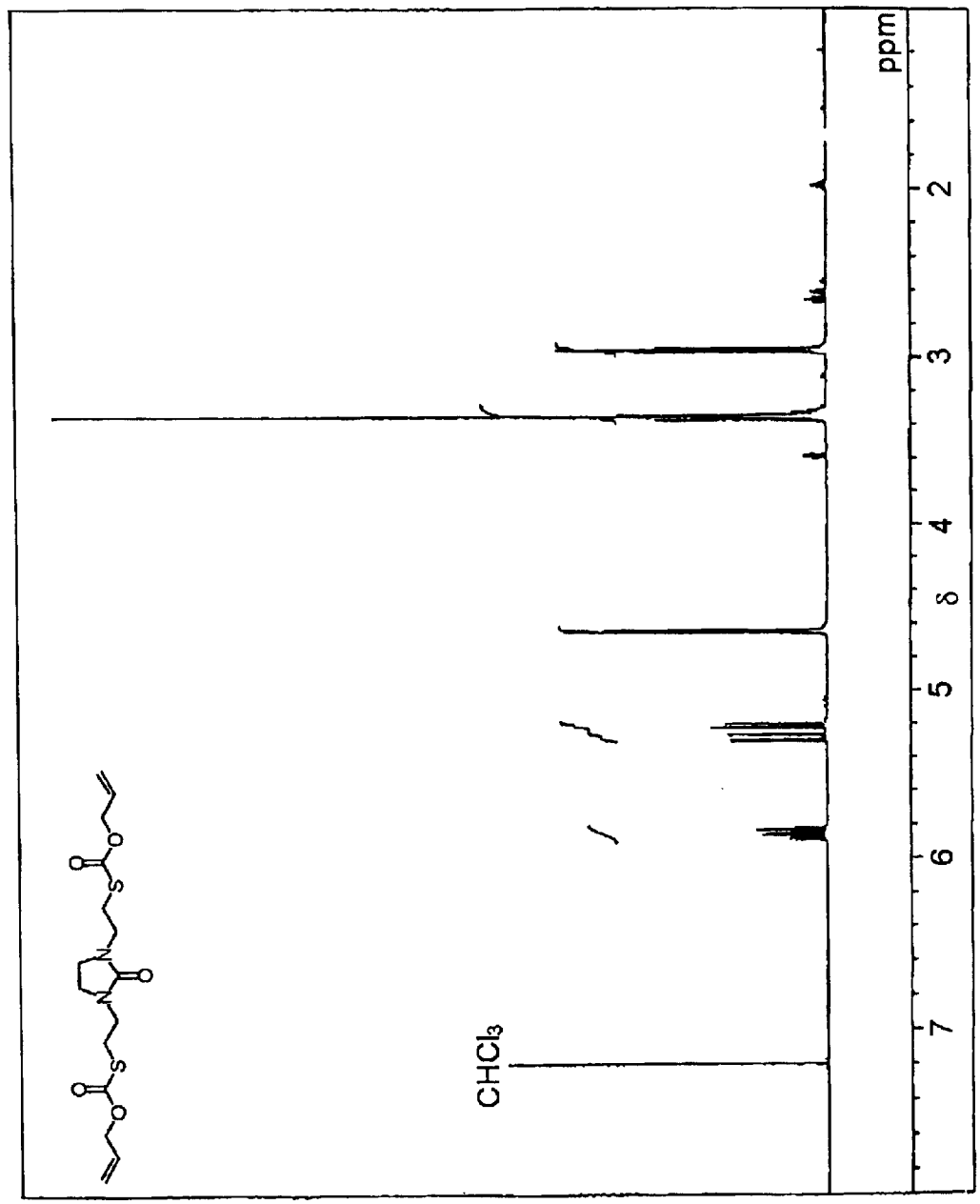
FIG. 27 is a $^1$H-NMR chart of N,N'-bis(allylthio-carbonatoethyl)-ethyleneurea obtained in Example 12.

The followings are identification data of the thus-obtained ATCEU:

$^1$H-NMR→See FIG. 27

Figure 28:
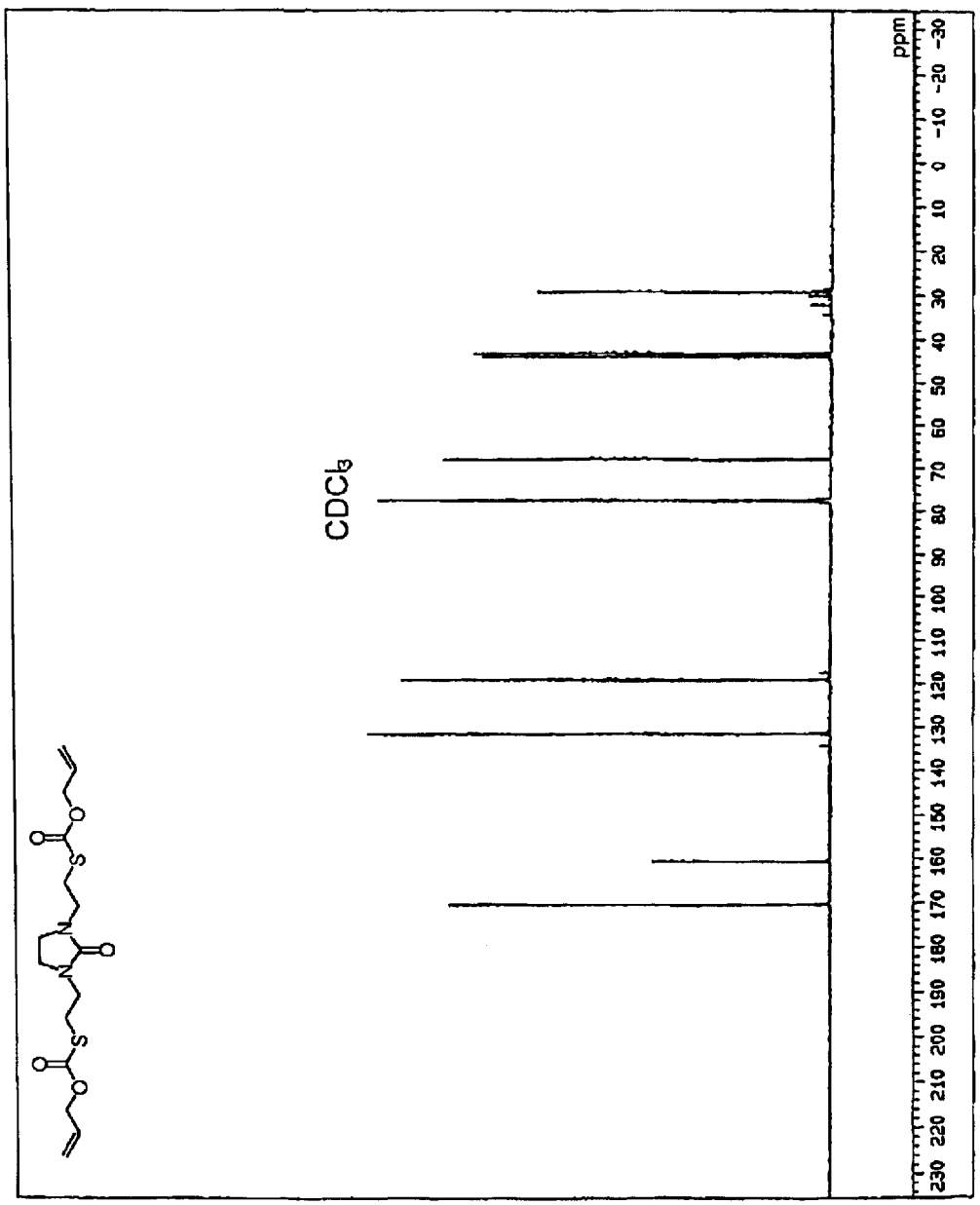
FIG. 28 is a $^{13}$C-NMR chart of N,N'-bis(allylthio-carbonatoethyl)-ethyleneurea obtained in Example 12.

$^{13}$C-NMR→See FIG. 28

EXAMPLE 13

Synthesis of N,N'-bis(glycidylthioethyl)-ethyleneurea (abbreviated as "GTEU")

To DMEU of 95% purity (100.0 g, 0.460 mol), a 49% aqueous solution of sodium hydroxide (75.1 g, 0.920 mol) was added dropwise at from 15 to 25° C. over 1 hour, followed by aging at 20° C. for 0.5 hours. Further, epichlorohydrin (85.1 g, 0.920 mol) was added dropwise at from 30 to 35° C. over 2 hours, followed by aging at 40° C. for 2 hours. To the reaction mixture, chloroform and water were added to extract and wash the same. The thus-obtained organic layer was washed once again with water, dried over anhydrous magnesium sulfate, and filtered. The filtrate was concentrated on an evaporator.

The residue so obtained was purified by chromatography on a silica gel to afford N,N'-bis(glycidylthio-ethyl)-ethyleneurea (GTEU) of 94% purity (11.4 g, 0.034 mol, pure yield: 7.4%).

Figure 29:
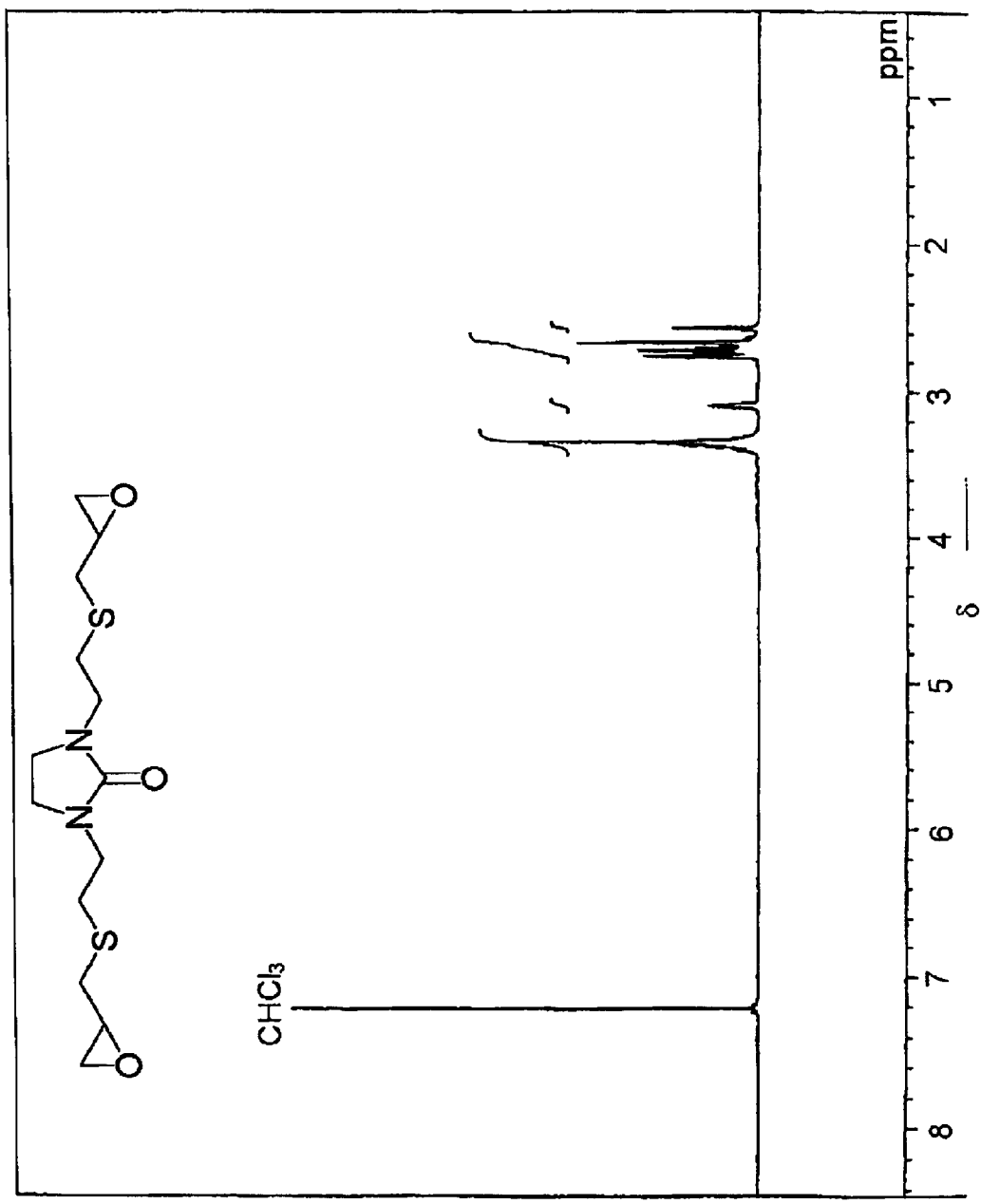
FIG. 29 is a $^1$H-NMR chart of N,N'-bis(glycidylthio-ethyl)-ethyleneurea obtained in Example 13.

The followings are identification data of the thus-obtained GTEU:

$^1$H-NMR→See FIG. 29

Figure 30:
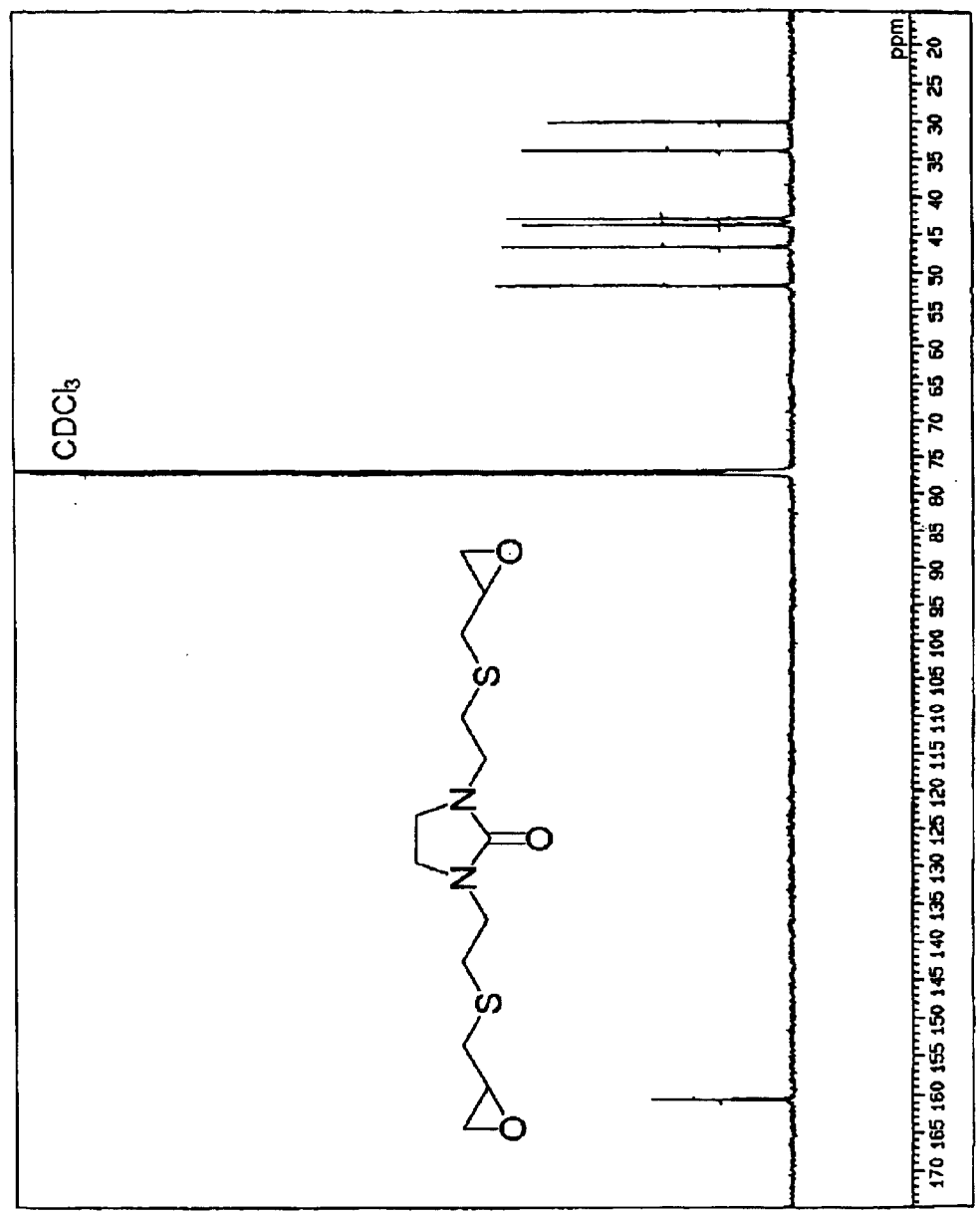
FIG. 30 is a $^{13}$C-NMR chart of N,N'-bis(glycidylthio-ethyl)-ethyleneurea obtained in Example 13.

$^{13}$C-NMR→See FIG. 30

EXAMPLE 14

Synthesis of N,N'-bis(hydroxymethyl)-ethyleneurea (abbreviated as "HMEU") and N,N'-bis(methacryloyloxymethyl)-ethyleneurea (abbreviated as "MMEU")

Ethyleneurea (161.6 g, 1.88 mol), paraformaldehyde (128.5 g, 4.28 mol as formaldehyde), a 28 wt. % solution of sodium methylate in methanol (2.3 g) and methanol (550 mL) were charged in a reactor and reacted at 55° C. for 5 hours. The reaction mixture was concentrated under reduced pressure. The residue was recrystallized form acetonitrile to afford HMEU of 92% purity (168.1 g, 1.06 mol, pure yield: 56.4%).

To a liquid mixture of HMEU of 92% purity (100.0 g, 0.630 mol), triethylamine (138.5 g, 1.37 mol) and acetonitrile (400 mL), methacrylic acid chloride (143.0 g, 1.37 mol) was added dropwise at from 10 to 30° C. over 1 hour, followed by aging at 20° C. for 1 hour. After the reaction mixture was filtered, the filtrate was neutralized, p-methoxyphenol (0.2 g) was added, concentrated at 30° C. or lower under reduced pressure.

To the residue, dichloromethane and diluted hydrochloric acid were added to extract and wash. The thus-obtained organic layer was then washed three times with water, p-methoxyphenol (0.1 g) was added again, and at 30° C. or lower, distilled off the solvent under reduced pressure. Finally, the residue was purified by chromatography on a silica gel column. In the course of concentration, methoxyphenol (0.1 g) was added once again to afford N,N'-bis (methacryloyloxymethyl)-ethyleneurea (MMEU) of 94% purity (58.0 g, 0.193 mol, pure yield: 30.6%).

Figure 31:
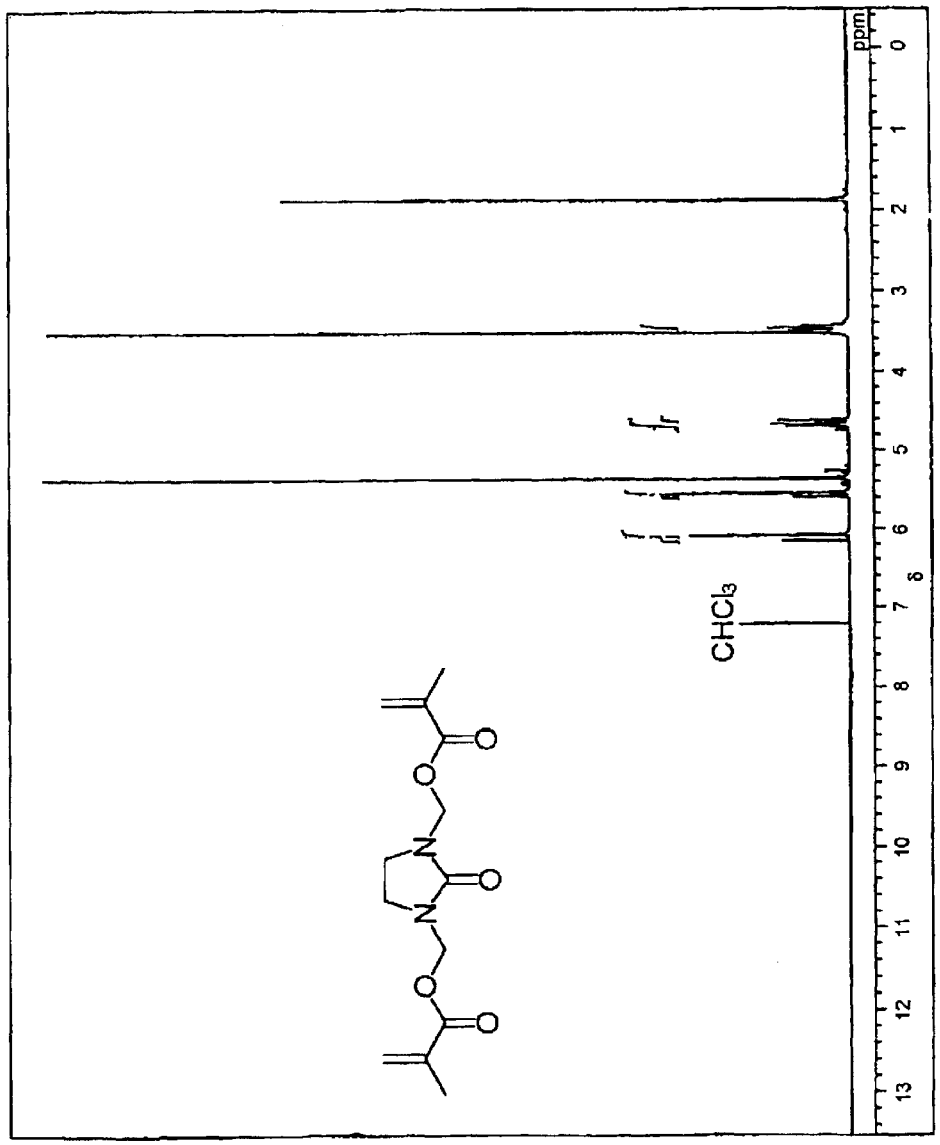
FIG. 31 is a $^1$H-NMR chart of N,N'-bis(methacryloyl-oxymethyl)-ethyleneurea obtained in Example 14.

The followings are identification data of the thus-obtained MMEU:

$^1$H-NMR→See FIG. 31

Figure 32:
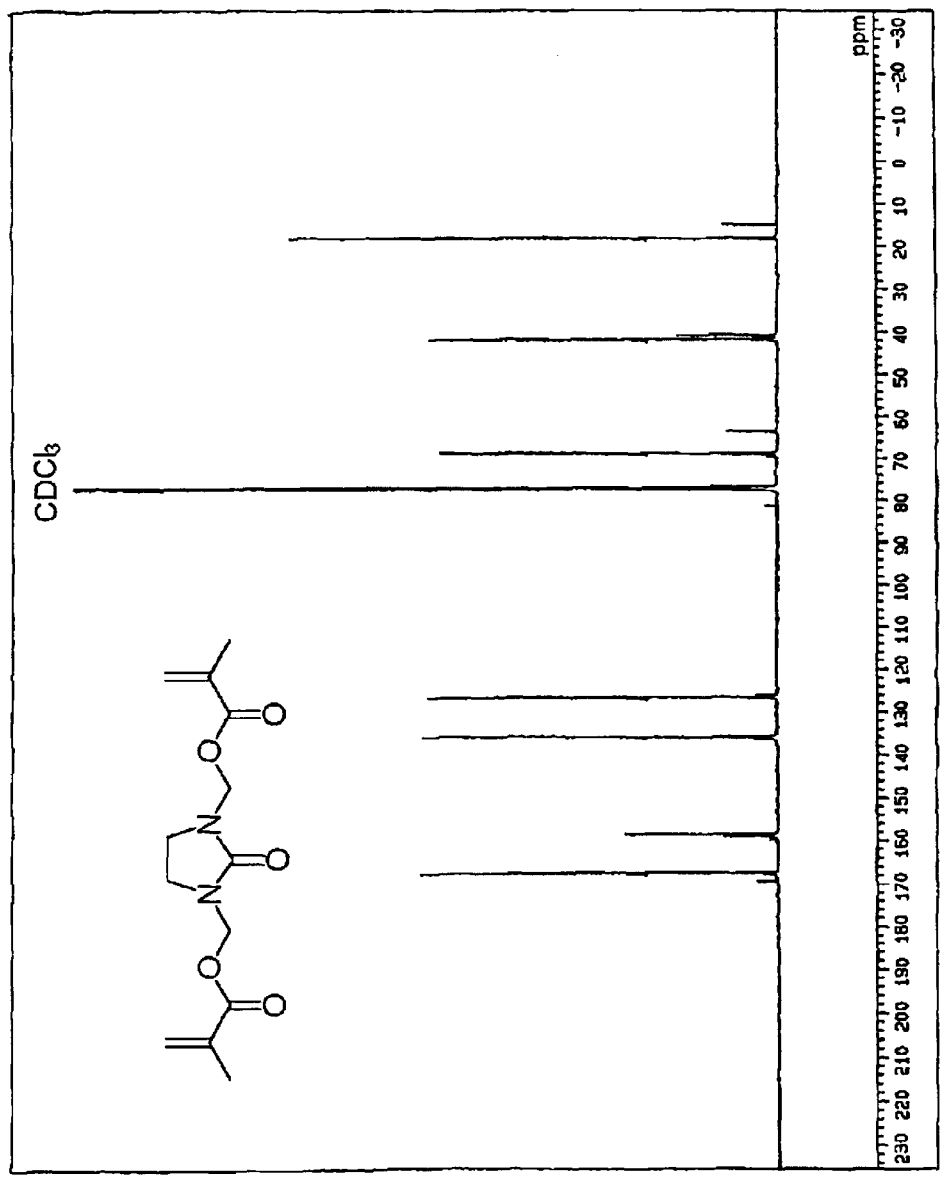
FIG. 32 is a $^{13}$C-NMR chart of N,N'-bis(methacryloyl-oxymethyl)-ethyleneurea obtained in Example 14.

$^{13}$C-NMR→See FIG. 32

EXAMPLE 15

Synthesis of N,N'-bis(glycidyloxyethyl)-ethyleneurea (abbreviated as "DGEEU")

To a liquid mixture of HEEU of 99% purity (500.0 g, 2.84 mol), epichlorohydrin (1,471 g, 15.9 mol) and dimethyl sulfoxide (250 g), 40% caustic soda (574 g, 5.74 mol) was added dropwise at internal temperatures of from 25 to 40° C. over 1 hour, followed by aging at 40° C. for 8 hours. The reaction mixture was filtered, concentrated under reduced pressure on an evaporator. Acetonitrile was added to the residue, the resulting mixture was filtered, concentrated again under reduced pressure on the evaporator. The residue was purified by chromatography on a silica gel. As a result, N,N'-bis(glycidyloxyethyl)-ethyleneurea (DGEEU) of 95% purity was obtained in an amount of 146.0 g (0.484 mol, pure yield: 17%/HEEU).

Figure 33:
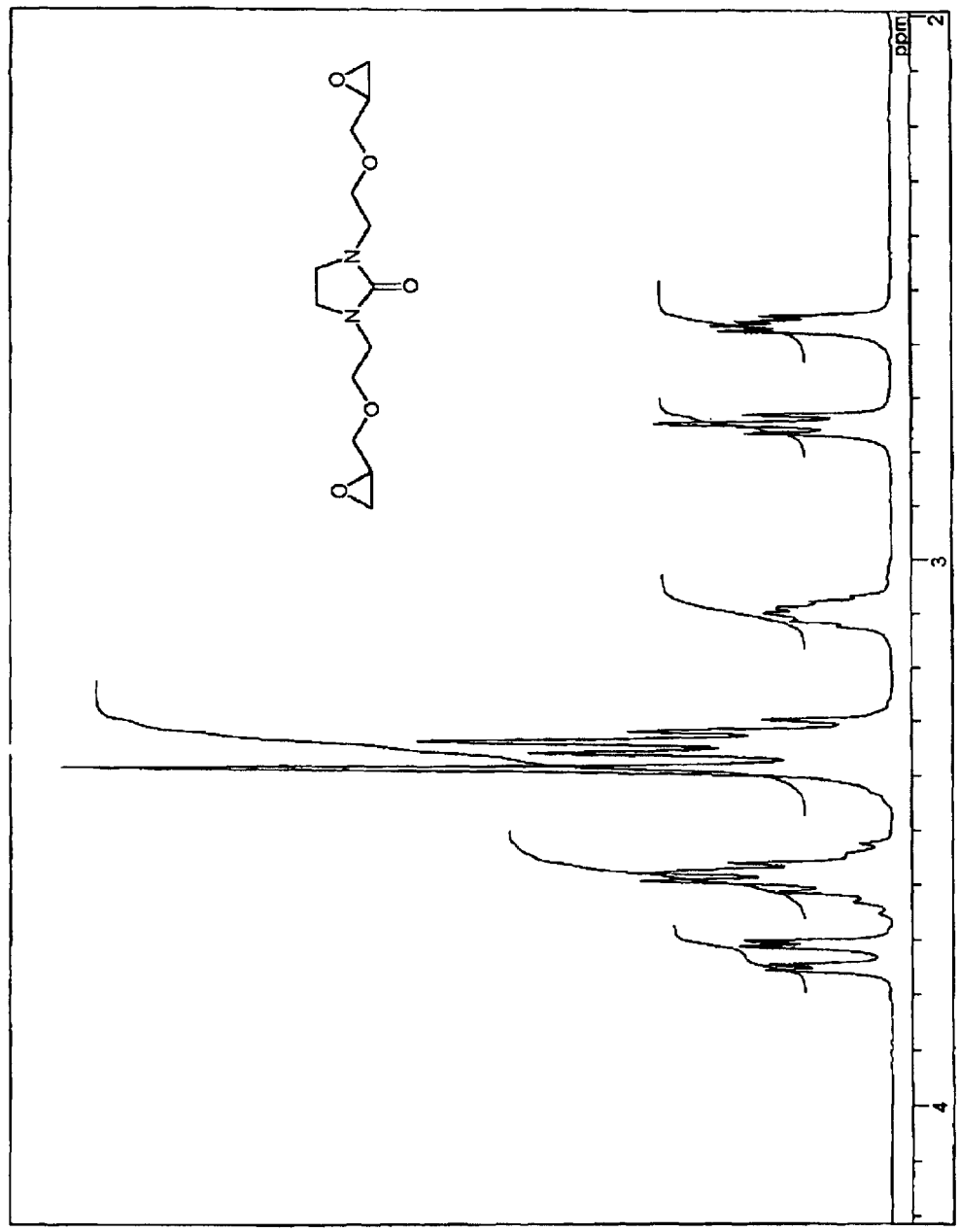
FIG. 33 is a $^1$H-NMR chart of N,N'-bis(glycidyloxy-ethyl)-ethyleneurea obtained in Example 15.

The followings are identification data of the thus-obtained DGEEU:

$^1$H-NMR→See FIG. 33

Figure 34:
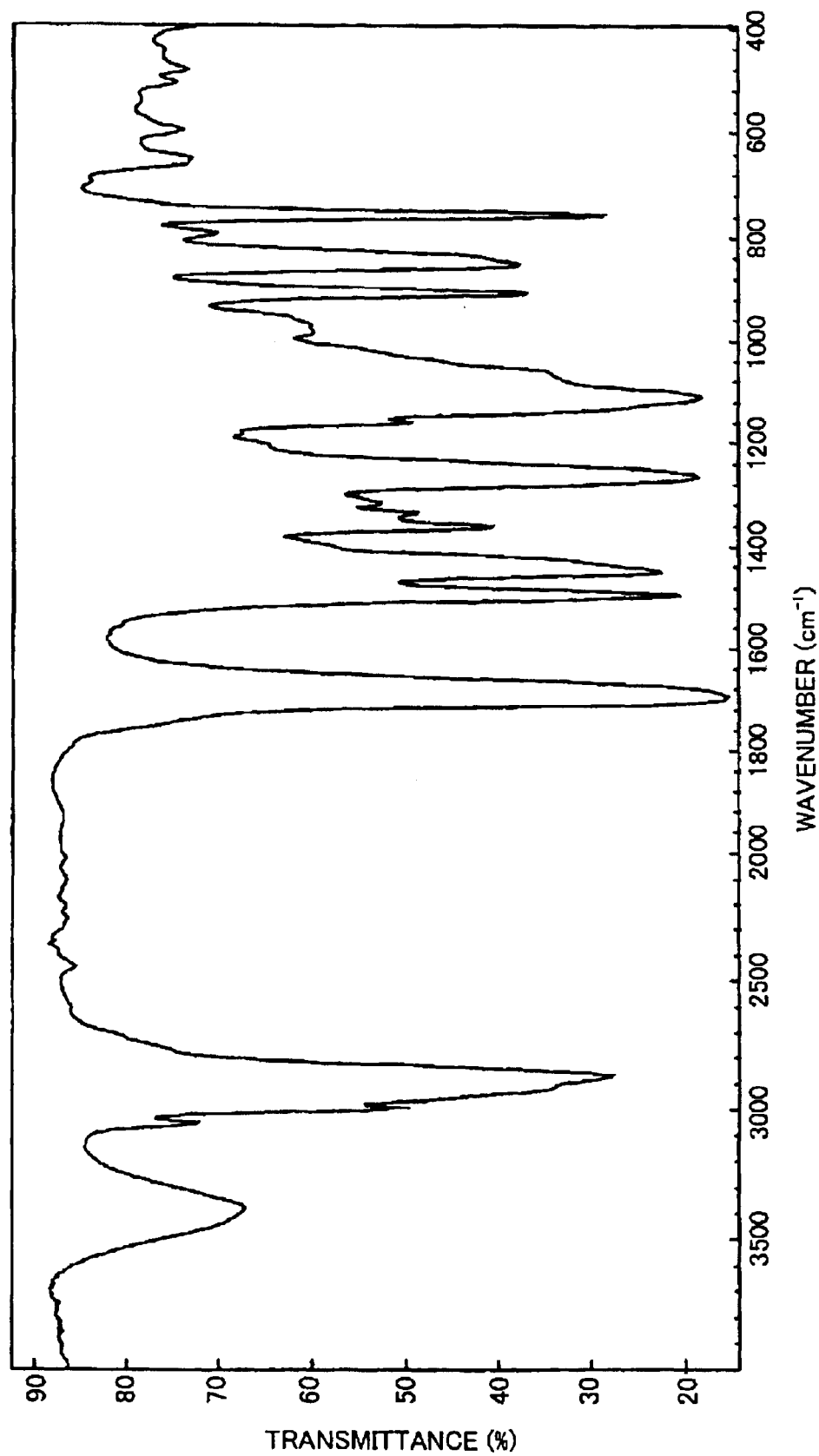
FIG. 34 is an IR chart of N,N'-bis(glycidyloxy-ethyl)-ethyleneurea obtained in Example 15.

IR→See FIG. 34

EXAMPLE 16

Synthesis of N,N'-bis(thioglycidylthioethyl)-ethyleneurea (abbreviated as "TGEU")

To a liquid mixture obtained by adding triethylamine (50 g) to N,N'-bis(mercaptoethyl)-ethyleneurea (DMEU) of 93% purity (600 g, 2.69 mol), epichlorohydrin (550 g, 5.94 mol) was added dropwise at internal temperatures of from 35 to 45° C., followed by aging at from 40 to 55° C. for 7 hours. To the reaction mixture, 42.9% caustic soda (560 g, 6.00 mol) was further added dropwise at internal temperatures of from 25 to 35° C., followed by aging at from 25 to 35° C. for 3 hours. To the thus-obtained reaction mixture, chloroform and water were added to wash the same with water. After washing with diluted hydrochloric acid and washing with water were successively conducted, the reaction mixture was concentrated under reduced pressure on an evaporator to afford crude N,N'-bis(glycidylthioethyl)-ethyleneurea (1,012 g).

To the thus-obtained crude N,N'-bis(glycidyl-thioethyl)-ethyleneurea, thiourea (900 g, 11.8 mol) and methanol (5,000 mL) were added, followed by a reaction at from 25 to 30° C. for 4 hours. After the reaction mixture was concentrated under reduced pressure on an evaporator, chloroform and water were added to wash the residue, separated an organic layer. The organic layer was washed with diluted sulfuric acid and water, dried over anhydrous magnesium sulfate, and filtered. The filtrate was concentrated again under reduced pressure on an evaporator, and the residue was purified by chromatography on a silica gel column. As a result, N,N'-bis(thioglycidylthioethyl)-ethyleneurea (TGEU) of 99% purity was obtained in an amount of 380 g (1.07 mol, pure yield: 40%/DMEU).

Figure 35:
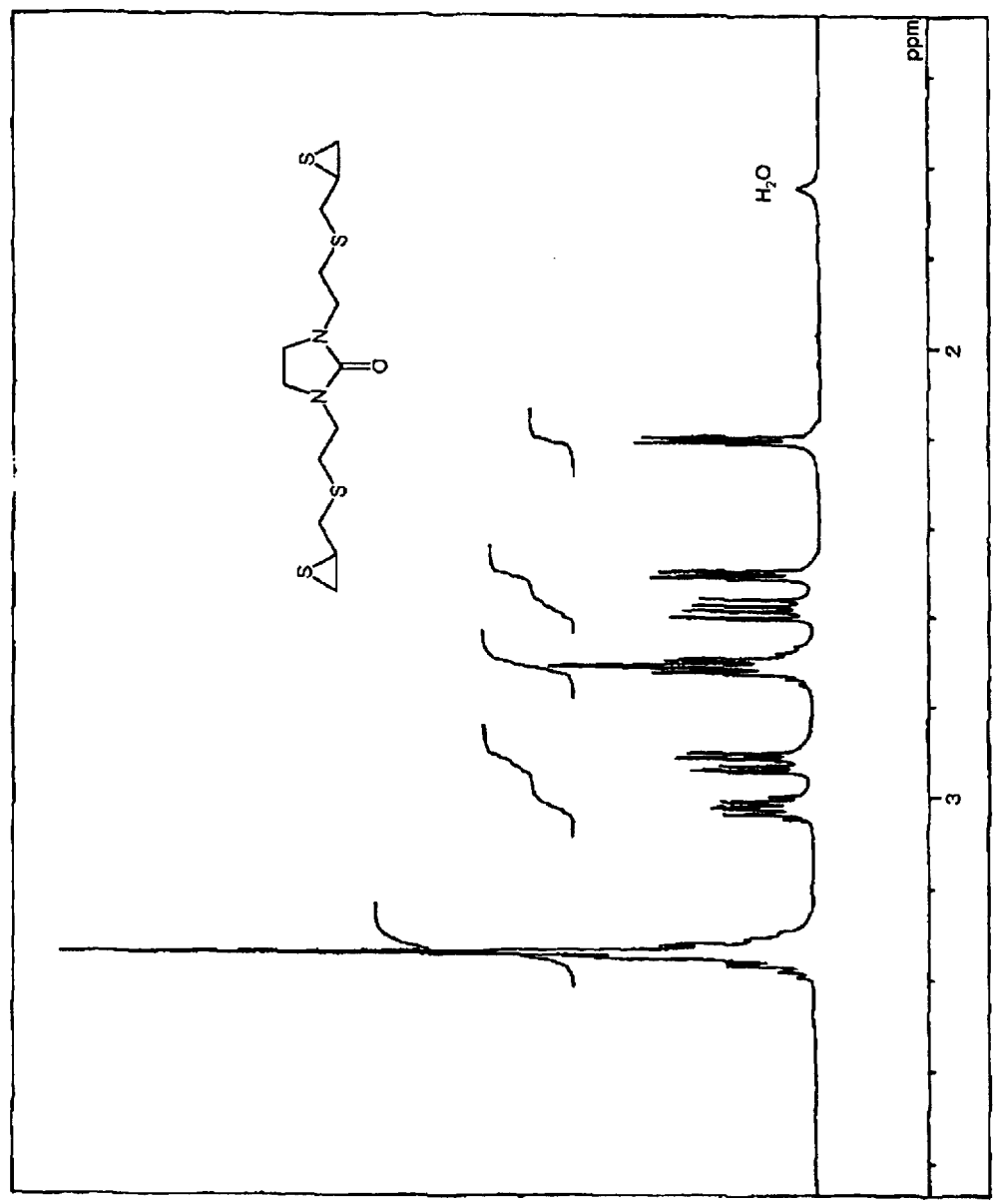
FIG. 35 is a $^1$H-NMR chart of N,N'-bis(thioglycidyl-thioethyl)-ethyleneurea obtained in Example 16.

The followings are identification data of the thus-obtained TGEU:

$^1$H-NMR→See FIG. 35

Figure 36:
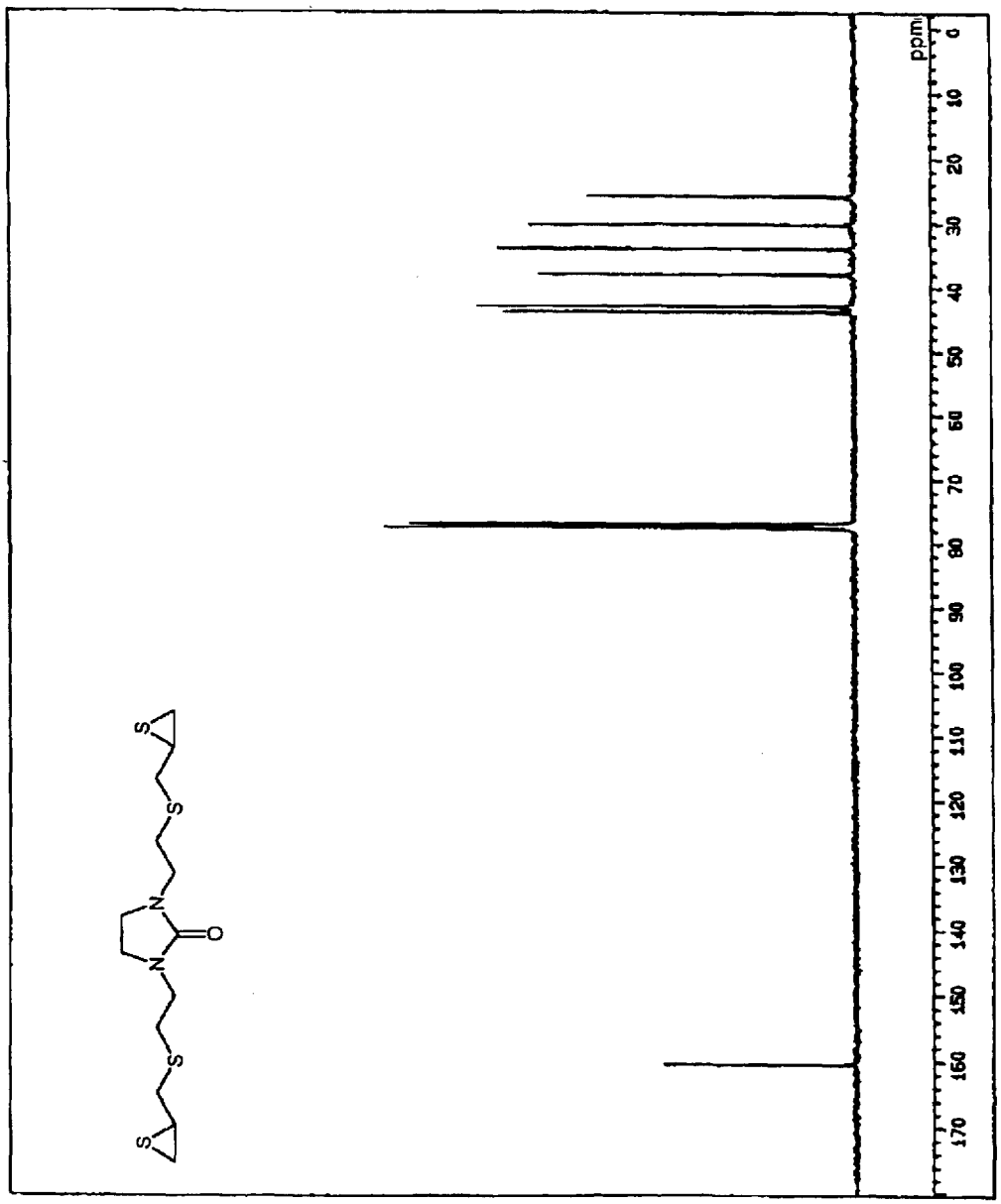
FIG. 36 is a $^{13}$C-NMR chart of N,N'-bis(thioglycidyl-thioethyl)-ethyleneurea obtained in Example 16.

$^{13}$C-NMR→See FIG. 36

EXAMPLE 17

Synthesis of N,N'-bis(2-hydroxy-3-acryloyloxy-propyl)-ethyleneurea (abbreviated as "AHPI")

Into a reaction flask, ethyleneurea (215.0 g, 2.50 mol), epichlorohydrin (2,313.0 g, 25.0 mol) and trimethylbenzyl chloride (6.5 g) were charged. Under heating and reflux (120° C.), they were reacted for 5 hours, and the reaction mixture was cooled to 60° C.

97% Sodium hydroxide flakes (250.0 g, 6.0 mol) was then charged in portions while watching the state of the reaction mixture, and aging was conducted at from 60 to 80° C. for 1.5 hours.

The reaction mixture was allowed to cool down to room temperature, and was then filtered. The resulting filtrate was concentrated on an evaporator, and the residue was purified by chromatography on a silica gel column. As a result, N,N'-bis(glycidyl)-ethyleneurea (DGEU) of 93% purity was obtained in an amount of 290.0 g (1.36 mol, pure yield: 54%/ethyleneurea).

A liquid mixture of the thus-obtained DGEU of 93% purity (105.3 g, 0.494 mol) and trimethylbenzyl chloride (5.0 g) was heated to 60° C. While maintaining the internal temperature, chloropropionic acid (108.5 g, 1.00 mol) was added dropwise, followed by aging at from 65 to 90° C. for 1.5 hours. After the reaction mixture was cooled to 5° C., triethylamine (101.2 g, 1.00 mol) was added dropwise at from 5 to 10° C., followed by aging at from 20 to 30° C. for 1 hour.

The thus-obtained reaction mixture was neutralized with hydrochloric acid, dried over anhydrous magnesium sulfate, and filtered. Finally, the filtrate was concentrated on an evaporator, and the residue was purified by silica gel chromatography. As a result, N,N'-bis(2-hydroxy-3-acryloyloxy-propyl)-ethyleneurea (AHPI) of 92% purity was obtained in an amount of 31.0 g (0.098 mol, pure yield: 20%\/DGEU).

Figure 37:
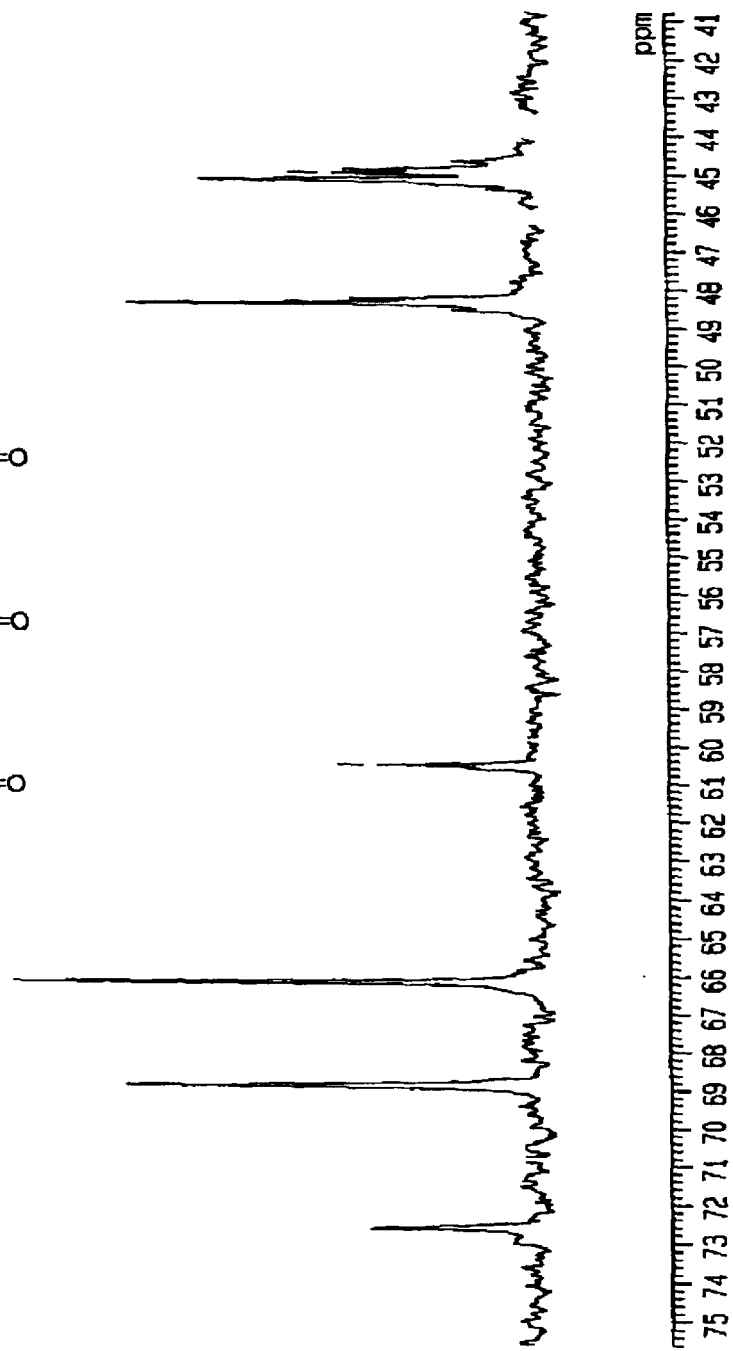
FIG. 37 is a $^1$H-NMR chart of N,N'-bis(2-hydroxy-3-acryloyloxy-propyl)-ethyleneurea obtained in Example 17.

The followings are identification data of the thus-obtained AHPI:

$^{13}$C-NMR→See FIG. 37

Figure 38:
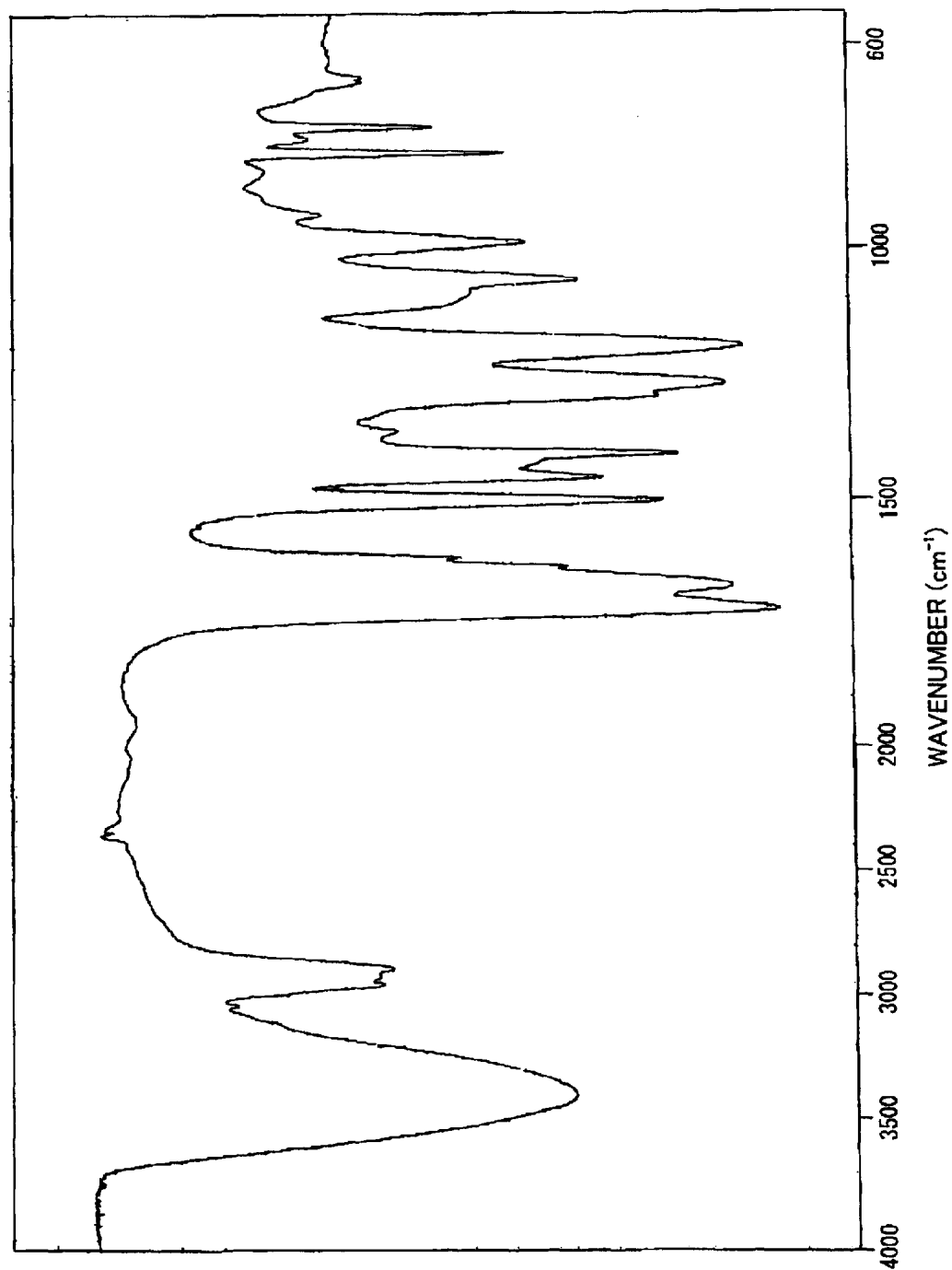
FIG. 38 is an IR chart of N,N'-bis(2-hydroxy-3-acryloyloxy-propyl)-ethyleneurea obtained in Example 17.

IR→See FIG. 38

EXAMPLE 18

Synthesis of N,N'-bis{6-(N-methyl-imidazolidinonyl-N'-)-2-(methacryloyloxy)-4-thiahexyl}-ethyleneurea (abbreviated as "S-3I")

To a liquid mixture of N-methyl-N'-(2-hydroxyethyl)-ethyleneurea (50.0 g, 0.347 mol), which had been synthesized from chloroethyloxazolidone and methylamine, and chlorobenzene (50 mL), phosphorus tribromide (36.5 g, 0.121 mol) was added dropwise at internal temperatures of from 30 to 60° C., followed by aging at from 60 to 70° C. for 1 hour. Thiourea (50.0 g, 0.657 mol) and water (50 mL) were then added, heated under reflux (95 to 96° C.) for 3.5 hours. The reaction mixture was cooled to 40° C. or so, 25% aqueous ammonia (50.0 g, 0.734 mol) was gradually added, hydrolyzed at from 60 to 65° C. for 2.5 hours.

After the reaction mixture was allowed to cool down to room temperature, 35% hydrochloric acid (45.0 g, 0.432 mol) and chloroform (300 mL) were added to wash the reaction mixture. The organic layer was separated. Chloroform (200 mL) was added once again to the water layer to extract it, and an organic layer was allowed to separate. After the separated organic layers were combined and concentrated under reduced pressure, the residue was distilled under reduced pressure to collect a fraction at from 115 to 118° C./200 Pa (1.5 torr). As a result, N-methyl-N'-(2-mercaptoethyl)-ethyleneurea (MEMI) of 99% purity was obtained in an amount of 43.0 g (0.266 mol, pure yield: 77%).

A liquid mixture of DGEU of 93% purity (21.3 g, 0.10 mol), triethylamine (1.0 g) and acetonitrile (50 mL) was then heated to 75° C., and MEMI of 99% purity (32.3 g, 0.20 mol) was added dropwise at from 75 to 80° C., followed by aging at 80° C. for 4 hours. After the reaction mixture was cooled to 5° C., triethylamine (48.0 g, 0.47 mol) was added, methacrylic acid chloride (50.0 g, 0.48 mol) was added dropwise at internal temperatures of from 5 to 10° C., followed by aging at from 20 to 30° C. for 1 hour.

Toluene (100 mL) was added to the thus-obtained reaction mixture, and the resulting mixture was filtered. The filtrate was concentrated on an evaporator, and the resulting residue was purified by silica gel chromatography. As a result, N,N'-bis{6-(N-methyl-imidazolidinonyl-N'-)-2-(methacryloyloxy)-4-thiahexyl}-ethyleneurea (S-3I) of 95% purity was obtained in an amount of 28.6 g (0.042 mol, pure yield: 42%/DGEU).

Figure 39:
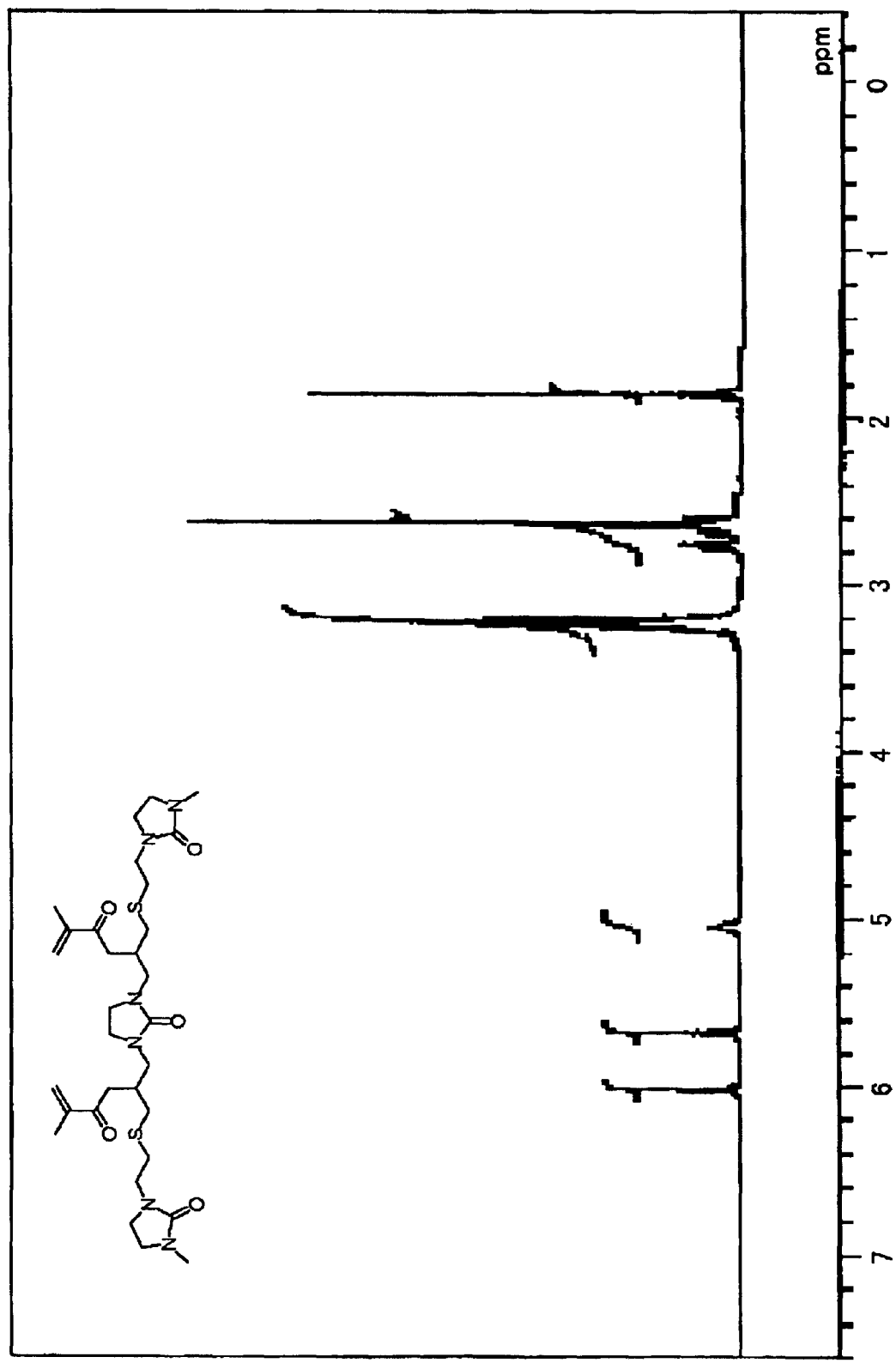
FIG. 39 is a $^1$H-NMR chart of N,N'-bis{6-(N-methyl-imidazolidinonyl-N'-)-2-(methacryloyloxy)-4-thiahexyl}-ethyleneurea obtained in Example 18.

The followings are identification data of the thus-obtained S-3I:

$^1$H-NMR→See FIG. 39

Figure 40:
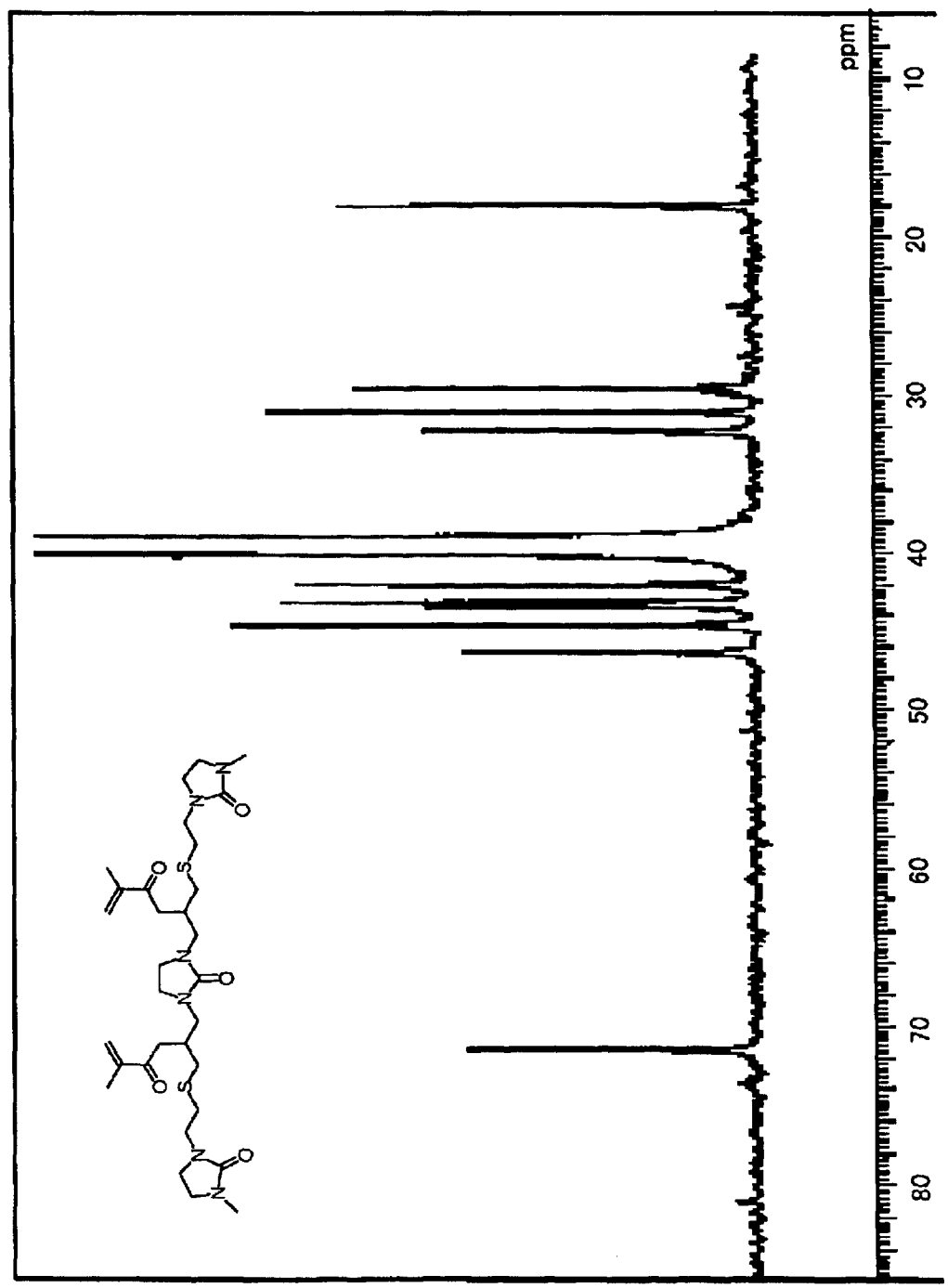
FIG. 40 is a $^{13}$C-NMR chart of N,N'-bis{6-(N-methyl-imidazolidinonyl-N'-)-2-(methacryloyloxy)-4-thiahexyl}-ethyleneurea obtained in Example 18.

$^{13}$C-NMR→See FIG. 40

EXAMPLE 19

Synthesis of N,N'-bis(acryloyloxyethyl)-ethyleneurea (abbreviated as "AEEU")

To a liquid mixture of HEEU of 99% purity (200.0 g, 1.14 mol), triethylamine (232.7 g, 2.30 mol) and acetonitrile (1,000 mL), acrylic acid chloride (208.2 g, 2.30 mol) was added dropwise at from 5 to 10° C. over 1 hour, followed by aging at from 10 to 25° C. for 3 hours. After the reaction mixture was filtered, the filtrate was neutralized with acetic acid and concentrated at 30° C. or lower under reduced pressure. Toluene was added to the residue, and filtered again. The filtrate was again concentrated at 30° C. or lower under reduced pressure. Finally, the thus-obtained residue was purified by chromatography on a silica gel column. In the course of concentration, methoxyphenol (0.2 g) was added to afford N,N'-bis(acryloyloxyethyl)-ethyleneurea (AEEU) of 96% purity (191.1 g, 0.650 mol, pure yield: 57.0%).

Figure 41:
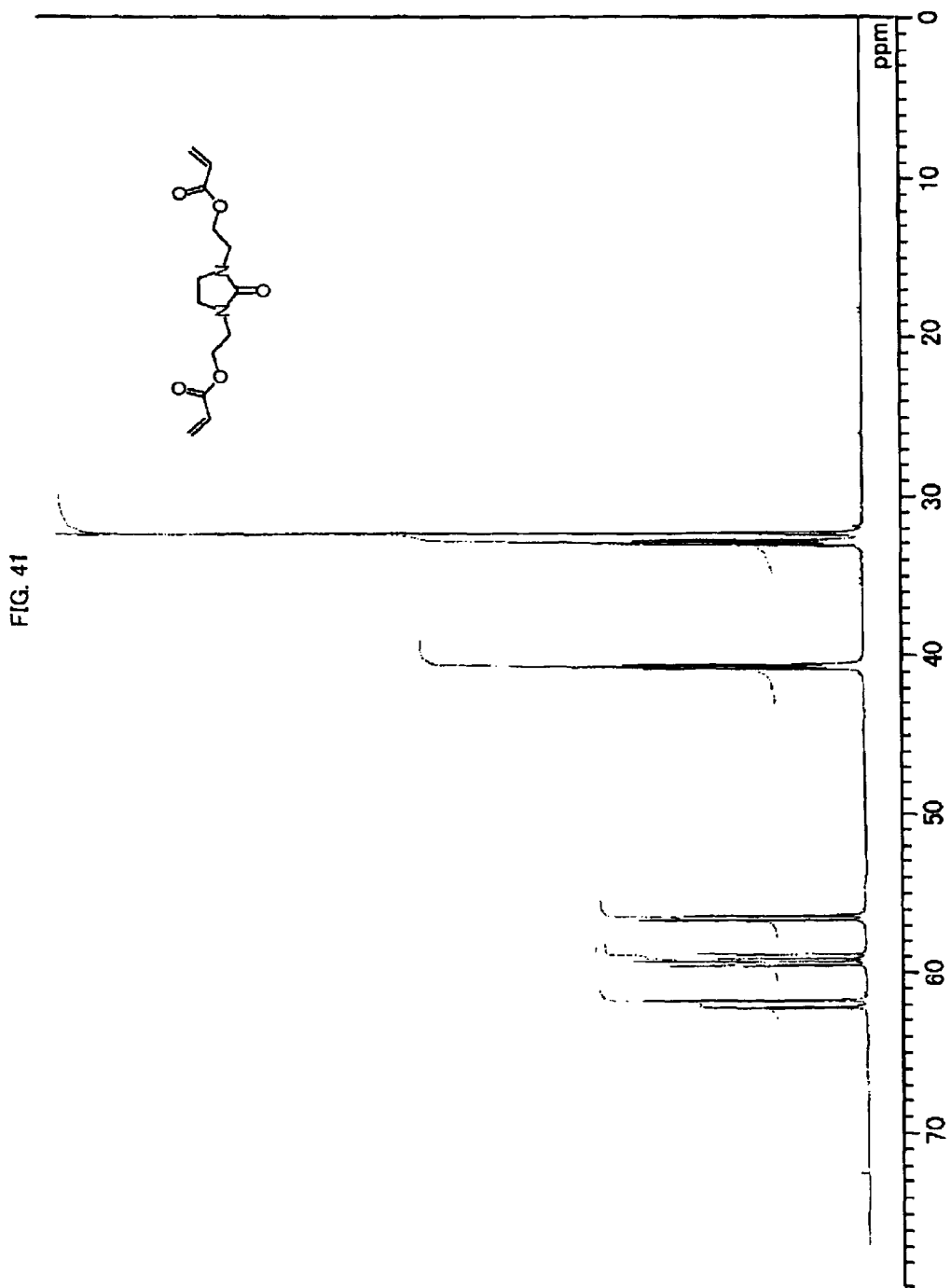
FIG. 41 is a $^1$H-NMR chart of N,N'-bis(acryloyloxy-ethyl)-ethyleneurea obtained in Example 19.

The followings are identification data of the thus-obtained AEEU:

$^1$H-NMR→See FIG. 41

Figure 42:
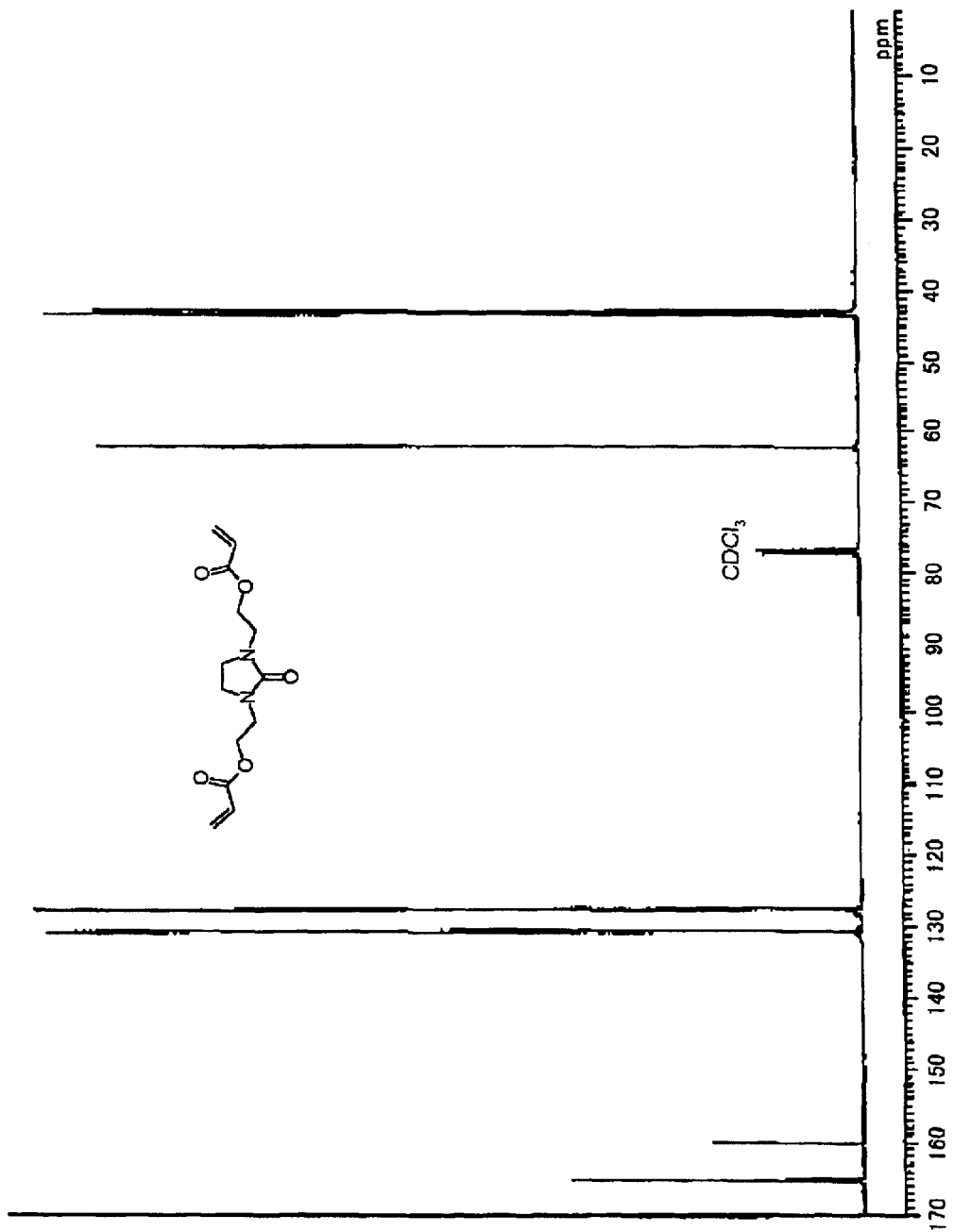
FIG. 42 is a $^{13}$C-NMR chart of N,N'-bis(acryloyloxy-ethyl)-ethyleneurea obtained in Example 19.

$^{13}$C-NMR→See FIG. 42

EXAMPLE 20

Synthesis of N,N'-bis{2-mercaptomethyl-2-(2-mercaptoethylthio)-ethyl}-ethyleneurea (abbreviated as "MESPI")

A liquid mixture of N,N'-diglycidyl-ethyleneurea (DGEU) (59.4 g, 0.30 mol) and triethylamine (3.0 g) was heated to 50° C., and 2-mercaptoethanol (47.8 g, 0.61 mol) was added dropwise at from 50 to 80° C., followed by aging at 60° C. for 1 hour.

After the reaction mixture was allowed to cool down to room temperature, phosphorus tribromide (109.4 g, 0.40 mol) was added dropwise at from 20 to 30° C. over 1 hour, followed by aging at 60° C. for 4 hours. To the thus-obtained reaction mixture, chloroform (400 mL) and water (200 mL) were added for extraction, and the organic layer was concentrated under reduced pressure to afford crude N,N'-bis{2-bromo-3-(2-bromoethylthio)-propyl}-ethyleneurea (165.0 g, 0.272 mol, crude yield: 90.6%/DGEU).

Thiourea (166 g, 2.19 mol) and water (200 mL) were next added to the resulting bromo derivative (155.0 g, 0.26 mol), and the resulting mixture was heated under stirring and reflux for 4 hours (internal temperature: 100 to 102° C.).

After the reaction mixture was cooled to 40° C., 28 wt. % aqueous ammonia (198.0 g, 3.27 mol) was added dropwise at internal temperatures of from 40 to 45° C. over 30 minutes, followed by aging at 50° C. for 2 hours.

The thus-obtained reaction mixture was extracted with chloroform (300 mL) three times (900 mL in total). The combined organic layer was washed with hydrochloric acid, an aqueous solution of sodium carbonate and water, and was then concentrated under reduced pressure to afford MESPI (109.3 g, 0.26 mol). Finally, the crude MESPI was purified by silica gel chromatography to afford crude N,N'-bis{2-mercaptomethyl-2-(2-mercaptoethylthio)-ethyly}-ethyleneurea (MESPI) (73.0 g, 0.17 mol, pure yield: 60%/DGEU).

Figure 43:
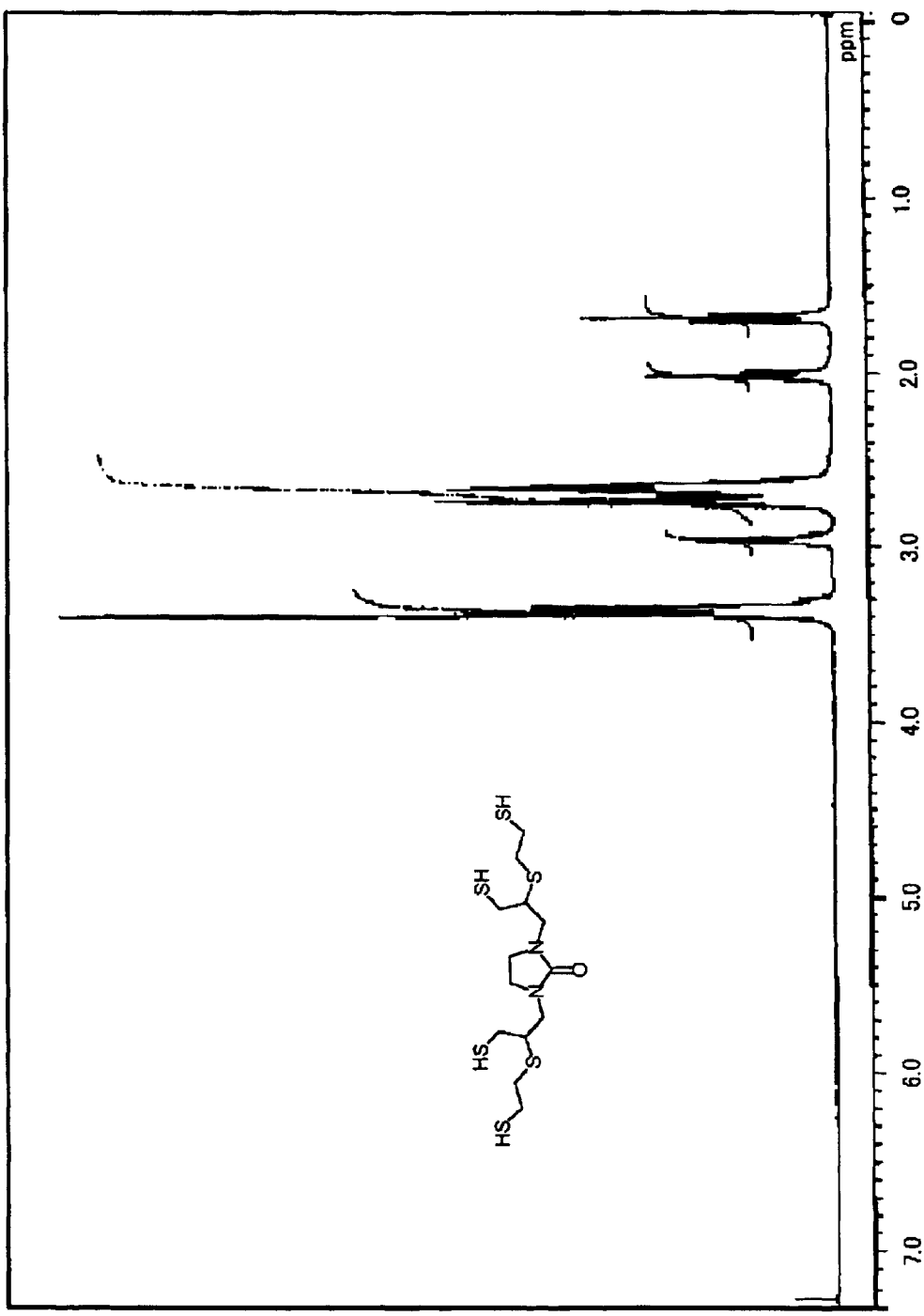
FIG. 43 is a $^1$H-NMR chart of N,N'-bis{2-mercapto-methyl-2-(2-mercaptoethylthio)-ethyl}-ethyleneurea obtained in Example 20.
Figure 44:
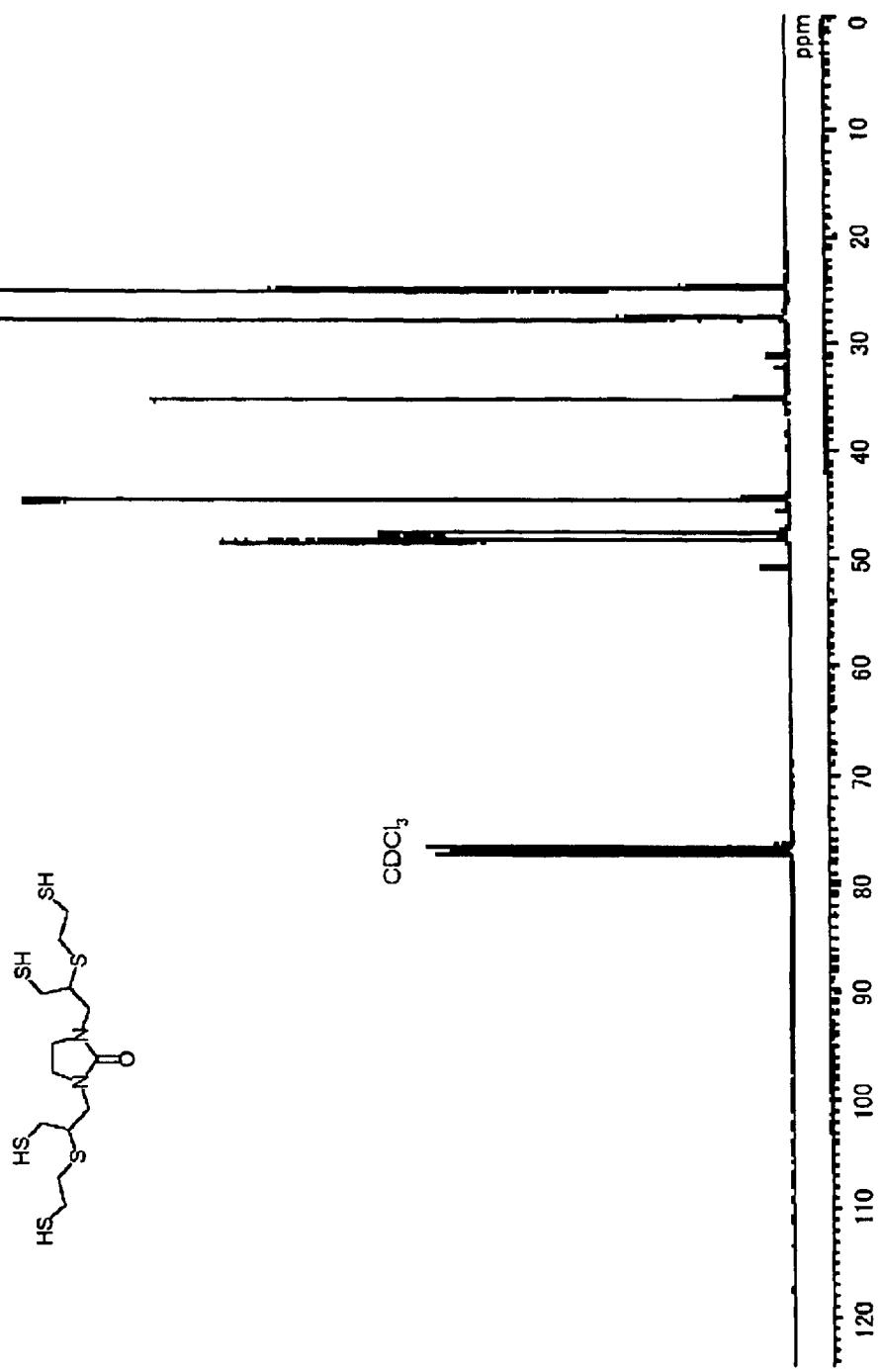
FIG. 44 is a $^{13}$C-NMR chart of N,N'-bis{2-mercapto-methyl-2-(2-mercaptoethylthio)-ethyl}-ethyleneurea obtained in Example 20.

The followings are identification data of the thus-obtained MESPI:
$^1$H-NMR→See FIG. 43
$^{13}$C-NMR→See FIG. 44

EXAMPLE 21

Synthesis of N,N'-diallyl-ethyleneurea (abbreviated as "DAEU")

To a liquid mixture of 60 wt. % sodium hydride (101.0 g, 2.5 mol) and THF (800 mL), ethyleneurea (EU) (100.0 g, 1.16 mol) was added at internal temperatures of from 40 to 50° C. over 1 hour or longer, maintained at 50° C. for 1 hour. Allyl bromide (305.5 g, 2.5 mol) was then added dropwise at internal temperature of from 40 to 50° C. over 1 hour, and the thus-obtained mixture was maintained at 53° C. for 1 hour.

Under cooling, methanol (50 mL) was gradually added at room temperature. The resulting mixture was filtered, and the thus-obtained filtrate was concentrated under reduced pressure. Hexane was added to the remaining residue. Subsequent to thorough stirring, the mixture was filtered, and the filtrate was concentrated under reduced pressure. Hexane was added once again to the residue, followed by thorough mixing. The mixture was filtered, and the filtrate was concentrated under reduced pressure to afford a concentration residue (109.8 g).

Finally, sodium sulfite (0.1 g) was added to the concentration residue, and reduced-pressure distillation was conducted to collect a fraction at from 95 to 105° C./0.12 kPa. As a result, N,N'-diallyl-ethyleneurea (DAEU) of 98% purity was obtained in an amount of 78.3 g (0.46 mol, pure yield: 40%/EU).

Figure 45:
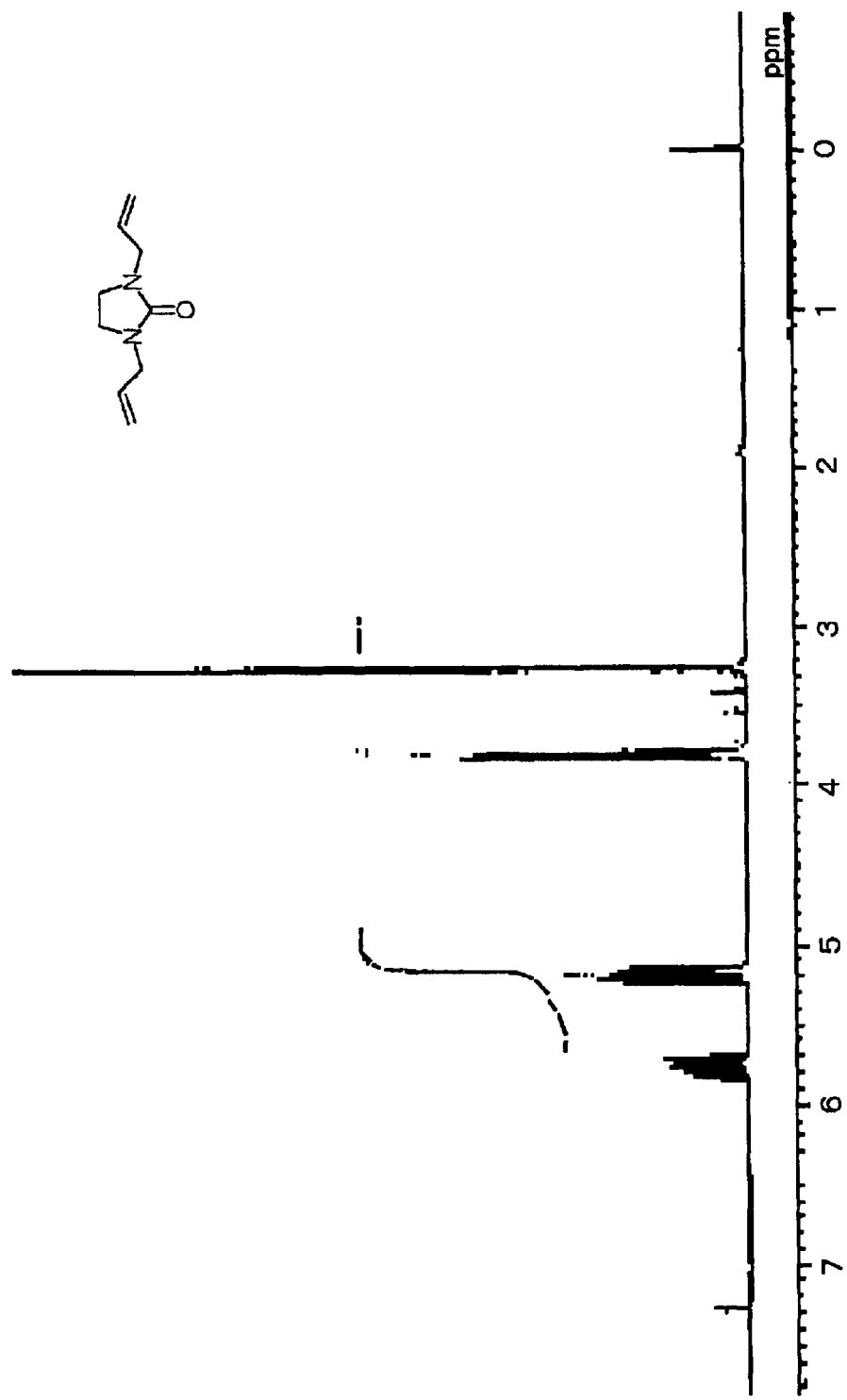
FIG. 45 is a $^1$H-NMR chart of N,N'-diallyl-ethyleneurea obtained in Example 21.
Figure 46:
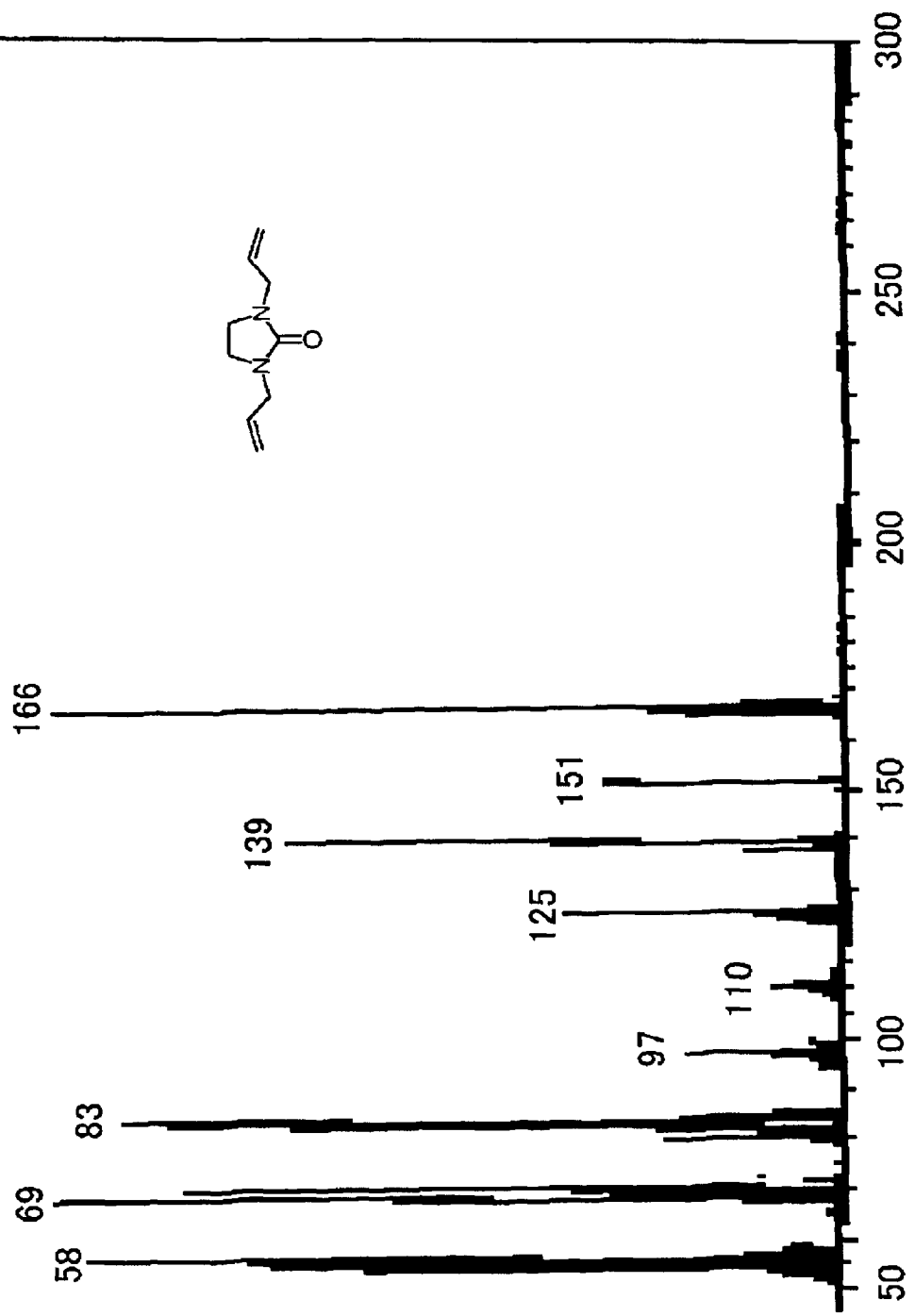
FIG. 46 is an MS spectrum of N,N'-diallyl-ethyleneurea obtained in Example 21.

The followings are identification data of the thus-obtained DAEU:
$^1$H-NMR→See FIG. 45
MS spectrum→See FIG. 46

EXAMPLE 22

Synthesis of N-mono(allyloxycarbonyl)-ethyleneurea (abbreviated as "MACI")

To a liquid mixture of pyridine (200.0 g, 2.5 mol), ethyleneurea (EU) (100.0 g, 1.16 mol) and dichloroethane (1,000 mL), allyl chloroformate (303.8 g, 2.52 mol) was added dropwise at internal temperatures of from 25 to 30° C. over 0.5 hours or longer, and the resulting mixture was maintained under reflux (86 to 88° C.) for 6 hours.

Subsequent to cooling, dichloroethane (500 mL) and water (400 mL) were added. The resulting mixture was thoroughly mixed and allowed to stand, and an organic layer was separated. The thus-obtained organic layer was washed with 16 wt. % saline, and a water layer was then removed. The resulting organic layer was dried over magnesium sulfate, and filtered. The filtrate was concentrated under reduced pressure. Finally, the remaining residue was recrystallized from toluene, and then dried under reduced pressure to afford N-mono(allyloxycarbonyl)-ethyleneurea (MACI) of 88% purity (69.0 g, 0.36 mol, pure yield: 31%/EU).

Figure 47:
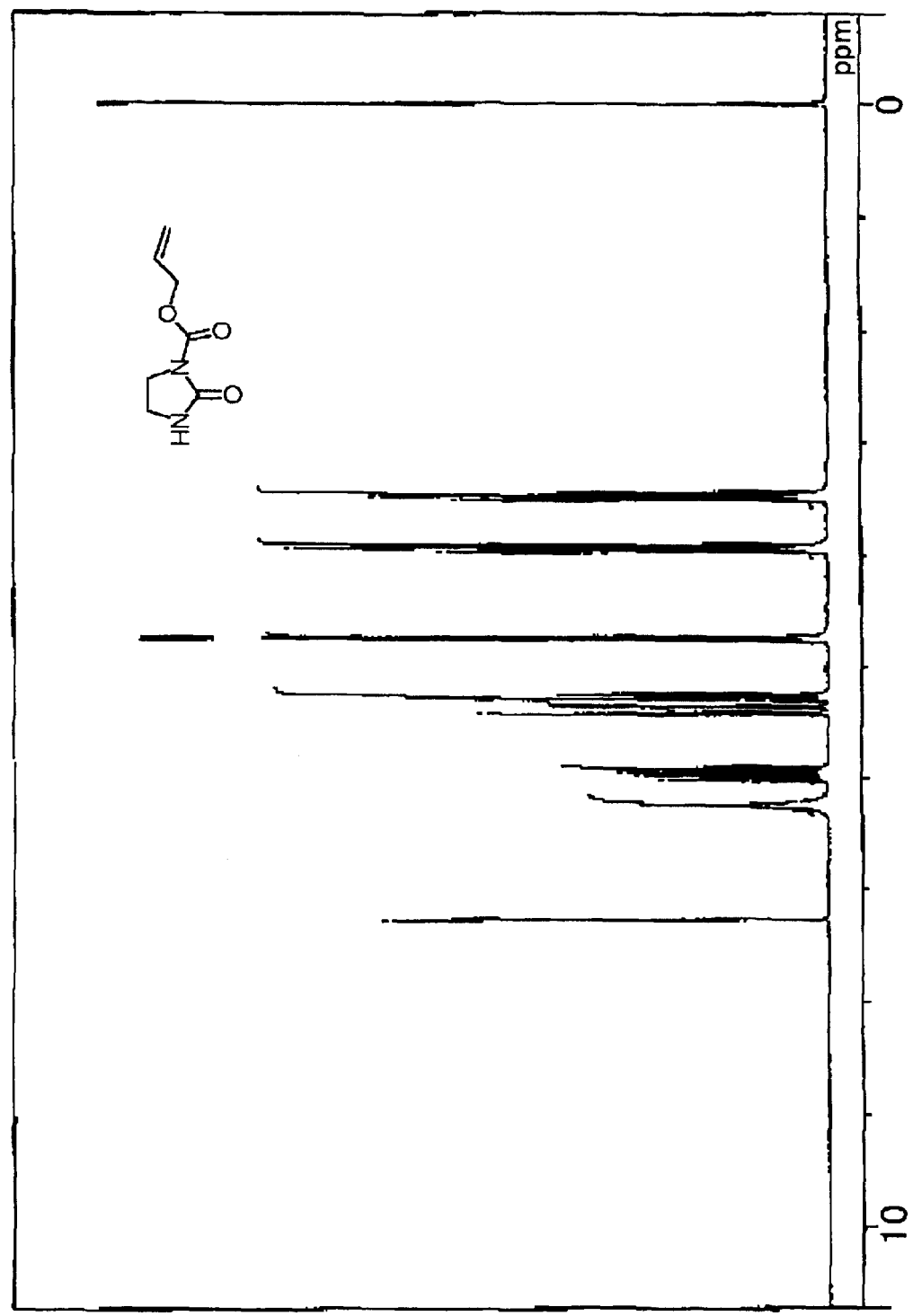
FIG. 47 is a $^1$H-NMR chart of N-mono(allyloxy-carbonyl)-ethyleneurea obtained in Example 22.
Figure 48:
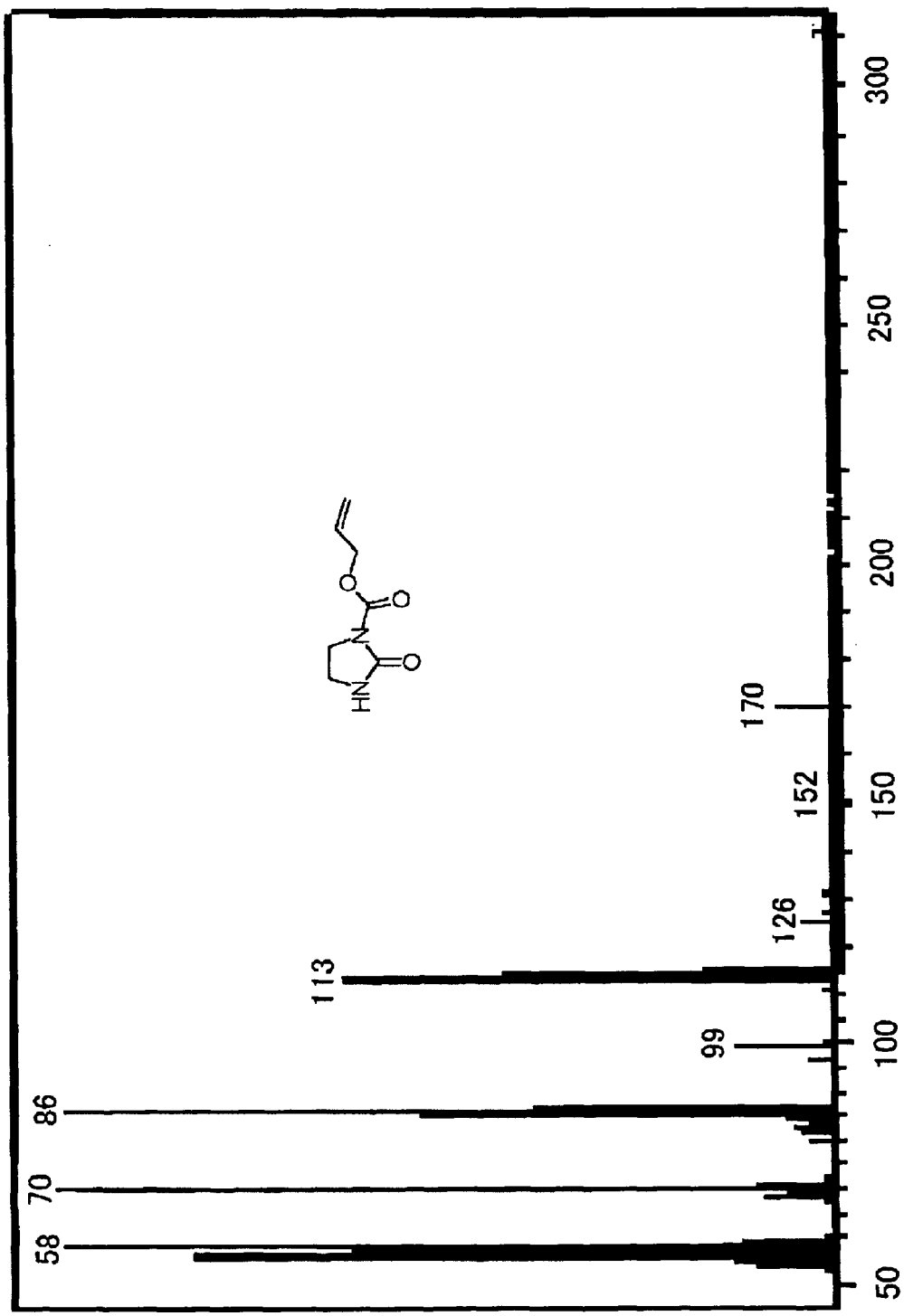
FIG. 48 is an MS spectrum of N-mono(allyloxy-carbonyl)-ethyleneurea obtained in Example 22.

The followings are identification data of the thus-obtained MACI:
$^1$H-NMR→See FIG. 47
MS spectrum→See FIG. 48

EXAMPLE 23

Synthesis of N,N'-di(allyloxycarbonyl)-ethyleneurea (abbreviated as "DACI")

To a liquid mixture of 60 wt. % sodium hydride (50.0 g, 1.25 mol) and THF (1,000 mL), ethyleneurea (EU) (50.0 g, 0.58 mol) was added at internal temperatures of from 40 to 50° C. over 0.5 hours or longer, maintained at from 50 to 52° C. for 1 hour. To the mixture, allyl chloroformate (150.7 g, 1.25 mol) was added dropwise at internal temperatures of from 25 to 30° C. over 1.5 hours or longer, maintained under reflux (66° C.) for 2 hours.

After the reaction mixture was allowed to cool down to room temperature, insoluble matter was filtered off, and the filtrate was concentrated under reduced pressure. Hexane (400 mL) and toluene (500 mL) were added to the concentration residue, heated to 65° C. At the same temperature, insoluble matter was filtered off, and the filtrate was allowed to slowly cool down to room temperature to conduct recrystallization. Filtration was then conducted. Finally, hexane was added to the thus-obtained filter cake to perform sludgish precipitation. The resulting mixture was filtered again, and the thus-obtained filter cake was dried under reduced pressure to afford N,N'-di(allyloxycarbonyl)-ethyleneurea (DACI) of 92% purity (72.2 g, 0.26 mol, pure yield: 45%/EU).

Figure 49:
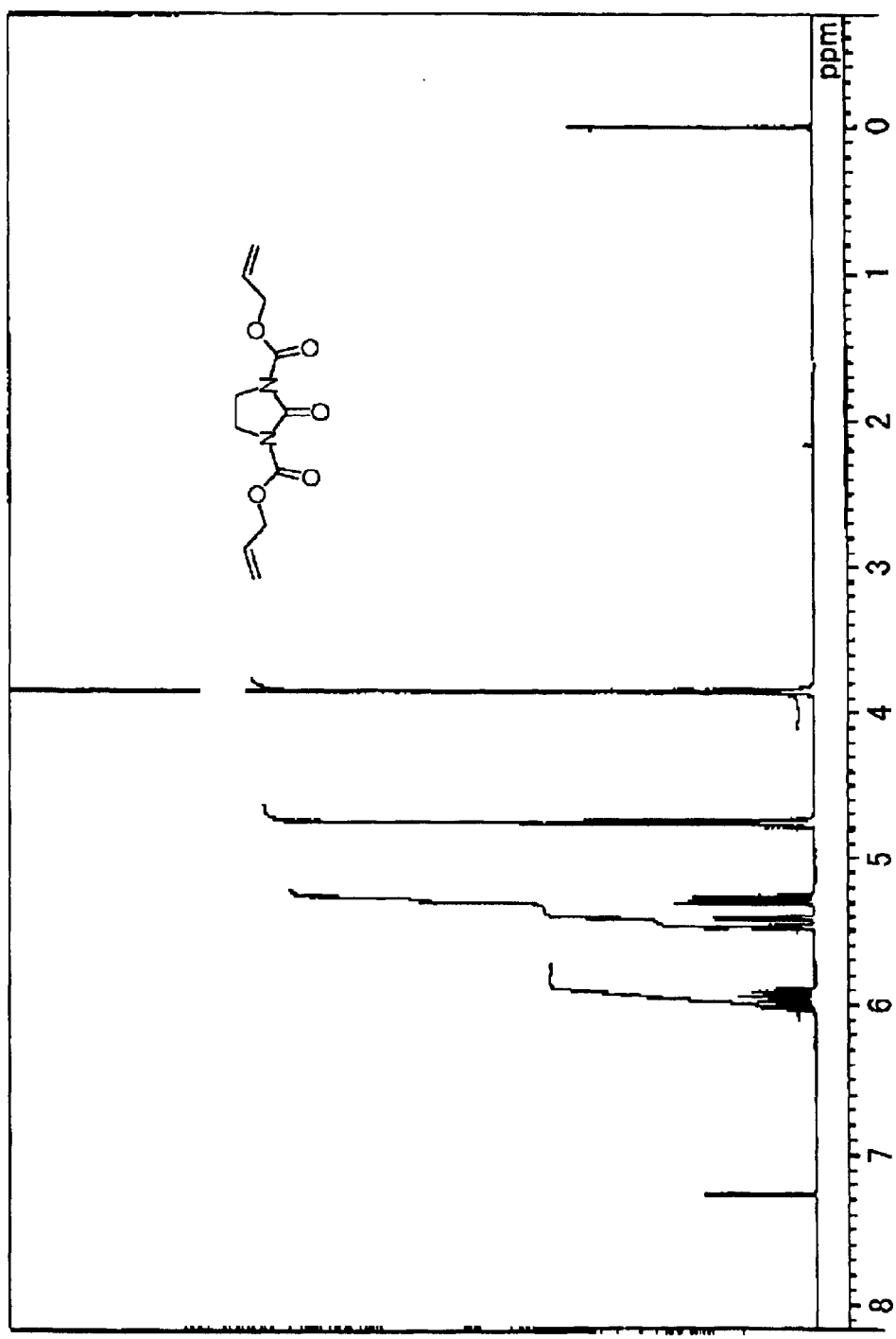
FIG. 49 is a $^1$H-NMR chart of N,N'-di(allyloxy-carbonyl)-ethyleneurea obtained in Example 23.
Figure 50:
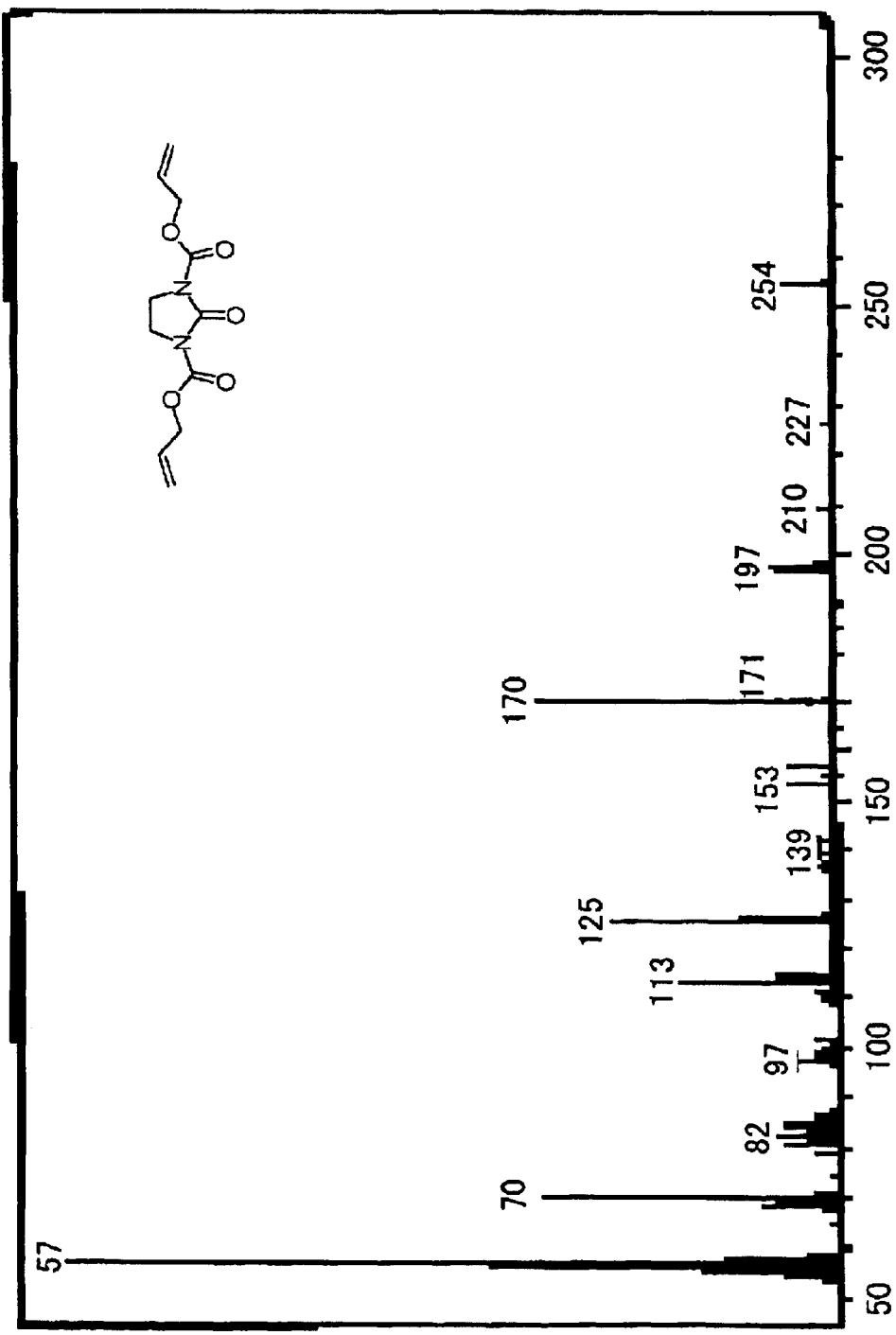
FIG. 50 is an MS spectrum of N,N'-di(allyloxy-carbonyl)-ethyleneurea obtained in Example 23.

The followings are identification data of the thus-obtained DACI:
$^1$H-NMR→See FIG. 49
MS spectrum→See FIG. 50

EXAMPLE 24

Synthesis of N-mono(methacryloyl)-ethyleneurea (abbreviated as "EUM")

To a liquid mixture of pyridine (158.2 g, 2.0 mol), ethyleneurea (EU) (172.2 g, 2.0 mol) and acetonitrile (1,000 mL), methacrylic acid chloride (209.1 g, 2.0 mol) was added dropwise at internal temperatures of from 15 to 20° C. over 0.5 hours or longer, maintained at from 20 to 25° C. for 3 hours.

The reaction mixture was then filtered, and the filtrate was concentrated under reduced pressure. The remaining residue was purified by chromatography on a silica gel column to give a crystalline residue. The residue was recrystallized from a mixed solvent of toluene and hexane to afford N-mono(methacryloyl)-ethyleneurea (EUM) of 99% purity (35.0 g, 0.23 mol, pure yield: 11%/EU).

Figure 51:
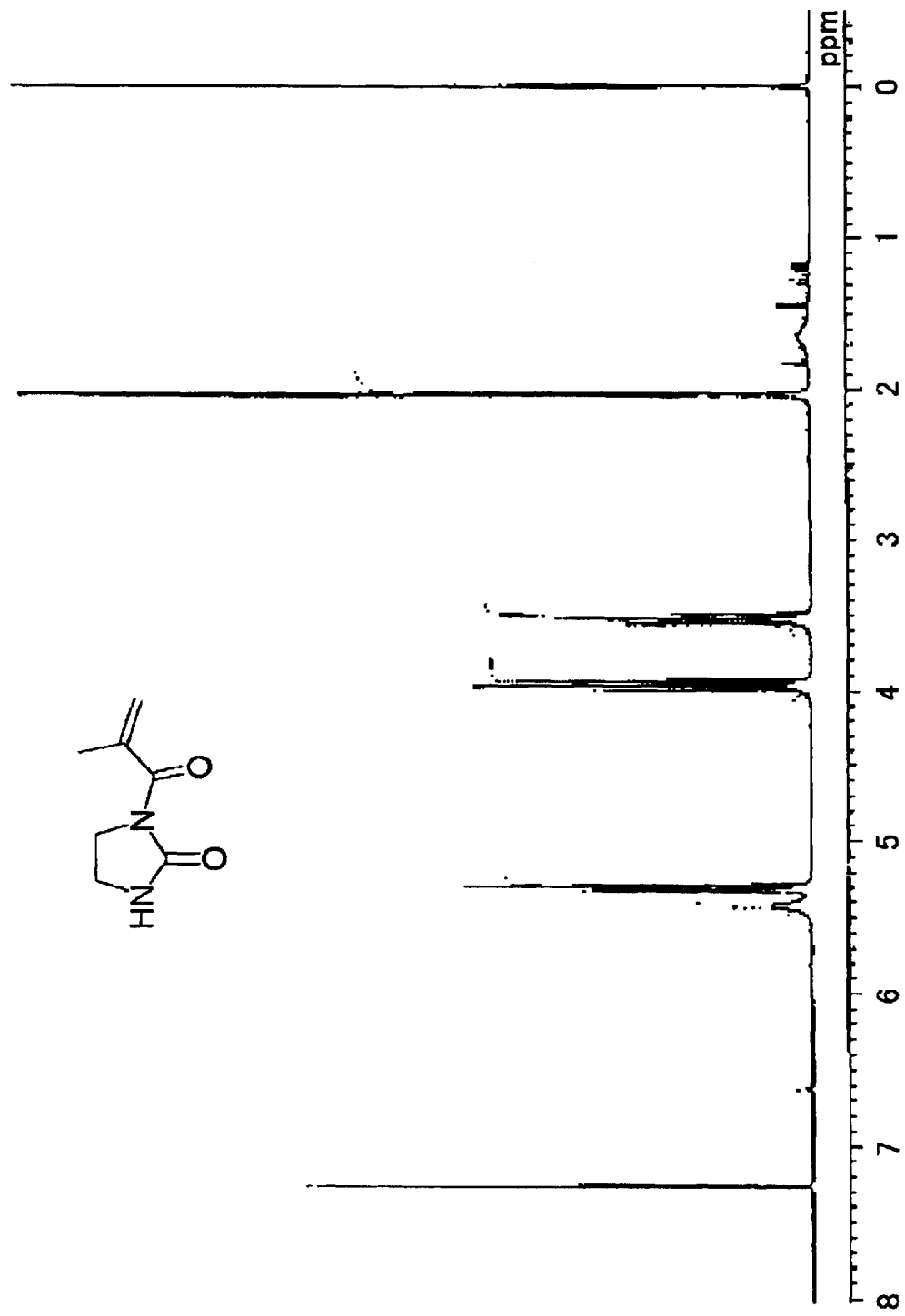
FIG. 51 is a $^1$H-NMR chart of N-mono(methacryloyl)-ethyleneurea obtained in Example 24.
Figure 52:
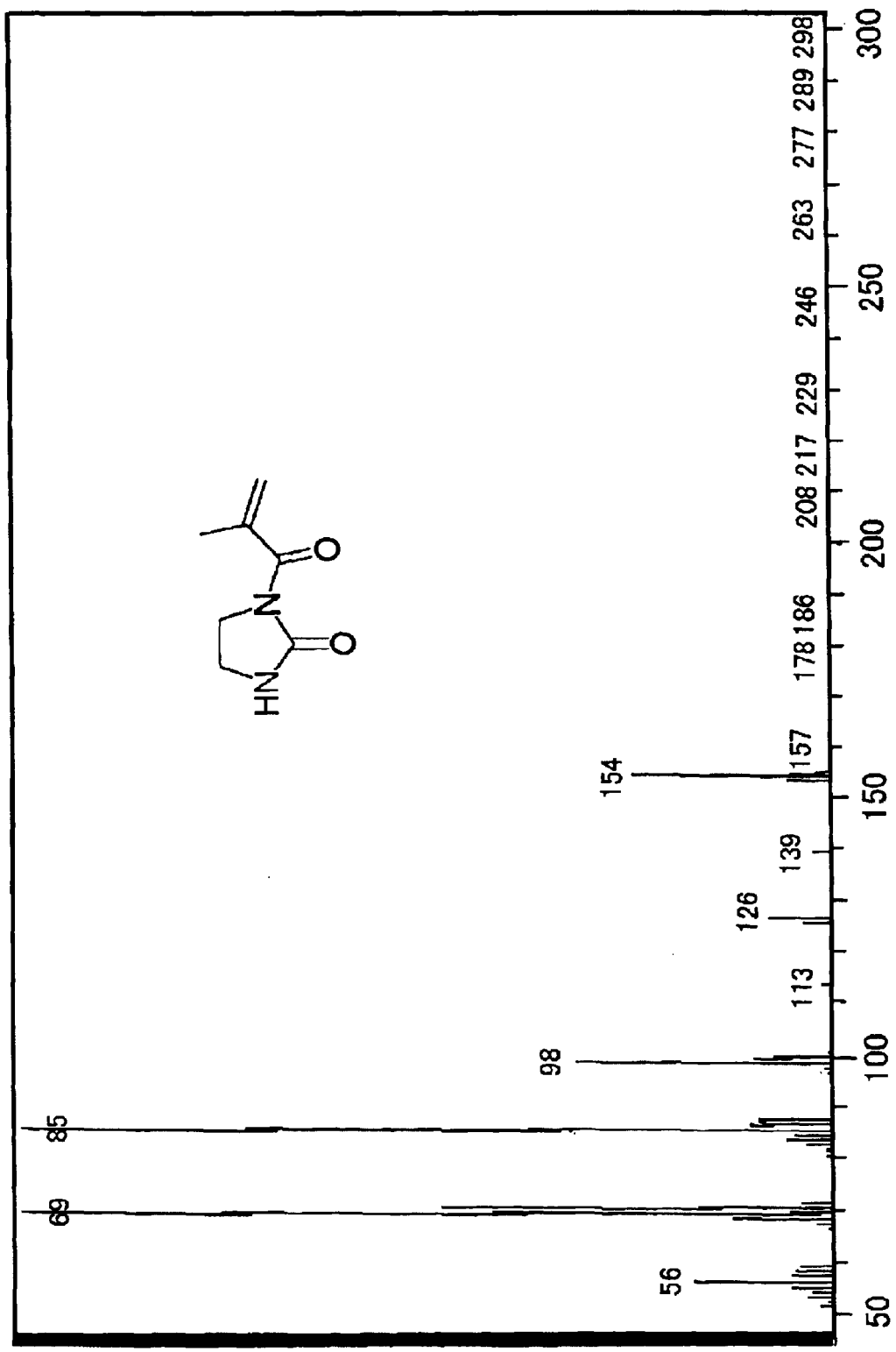
FIG. 52 is an MS spectrum of N-mono(methacryloyl)-ethyleneurea obtained in Example 24.

The followings are identification data of the thus-obtained EUM:
$^1$H-NMR→See FIG. 51
MS spectrum→See FIG. 52

EXAMPLE 25

Synthesis of N,N'-di(methacryloyl)-ethyleneurea (abbreviated as "DMAI")

To a liquid mixture of 60 wt. % sodium hydride (100.0 g, 2.50 mol) and THF (1,600 mL), ethyleneurea (EU) (100.0 g, 1.16 mol) was added at internal temperatures of from 40 to 50° C. over 2 hours or longer, maintained at from 40 to 50° C. for 4 hours. After the mixture was allowed to cool down to room temperature, methacrylic acid chloride (250.0 g, 2.39 mol) was added dropwise at an internal temperature of 40° C. over 2 hours, maintained at 40° C. for 2 hours.

To the reaction mixture, methanol (50 mL) was carefully added at internal temperatures of from 20 to 25° C. Subsequently, 35 wt. % hydrochloric acid (200 g) was likewise gradually added at internal temperatures of from 20 to 25° C. The thus-obtained mixture was then concentrated under reduced pressure.

Hexane (1,000 mL) was then added to the concentration residue, followed by thorough mixing. After the mixture was allowed to stand, the separated hexane layer was discarded. To the separated water layer, ethyl acetate (1,000 mL) was added, followed by thorough mixing. After the mixture was allowed to stand, the separated ethyl acetate layer was collected and concentrated again under reduced pressure.

Finally, toluene (800 mL) and hexane (800 mL) were added. Subsequent to heating under stirring, the mixture was subjected to hot filtration. The filtrate was slowly cooled to 5° C. to conduct recrystallization. Crystals were collected by filtration, and then dried under reduced pressure to afford N,N'-di(methacryloyl)-ethyleneurea (DMAI) of 95% purity (10.0 g, 0.043 mol, pure yield: 3.7%/EU).

Figure 53:
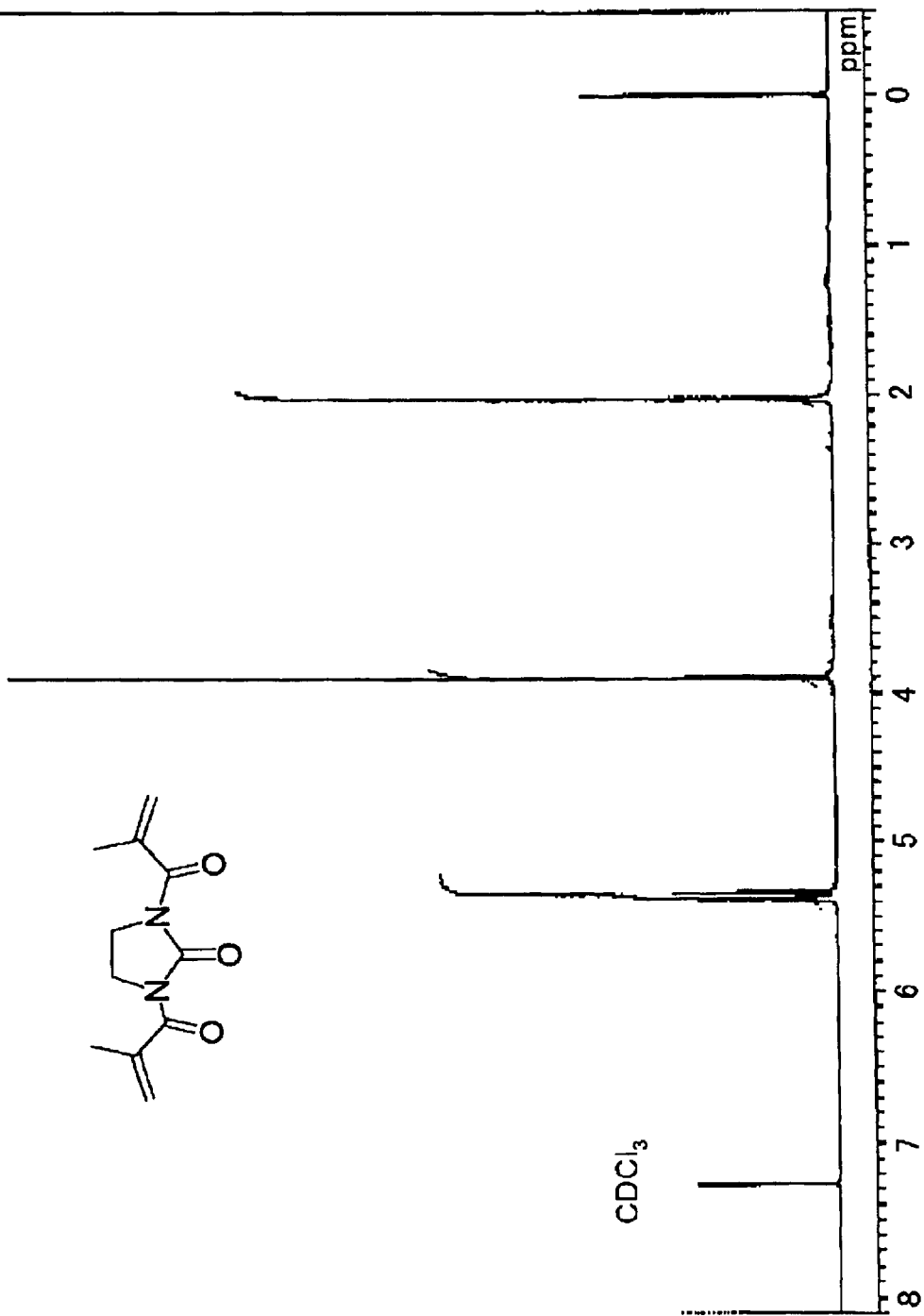
FIG. 53 is a $^1$H-NMR chart of N,N'-di(methacryloyl)-ethyleneurea obtained in Example 25.

The followings are identification data of the thus-obtained DMAI:

$^1$H-NMR→See FIG. 53

Figure 54:
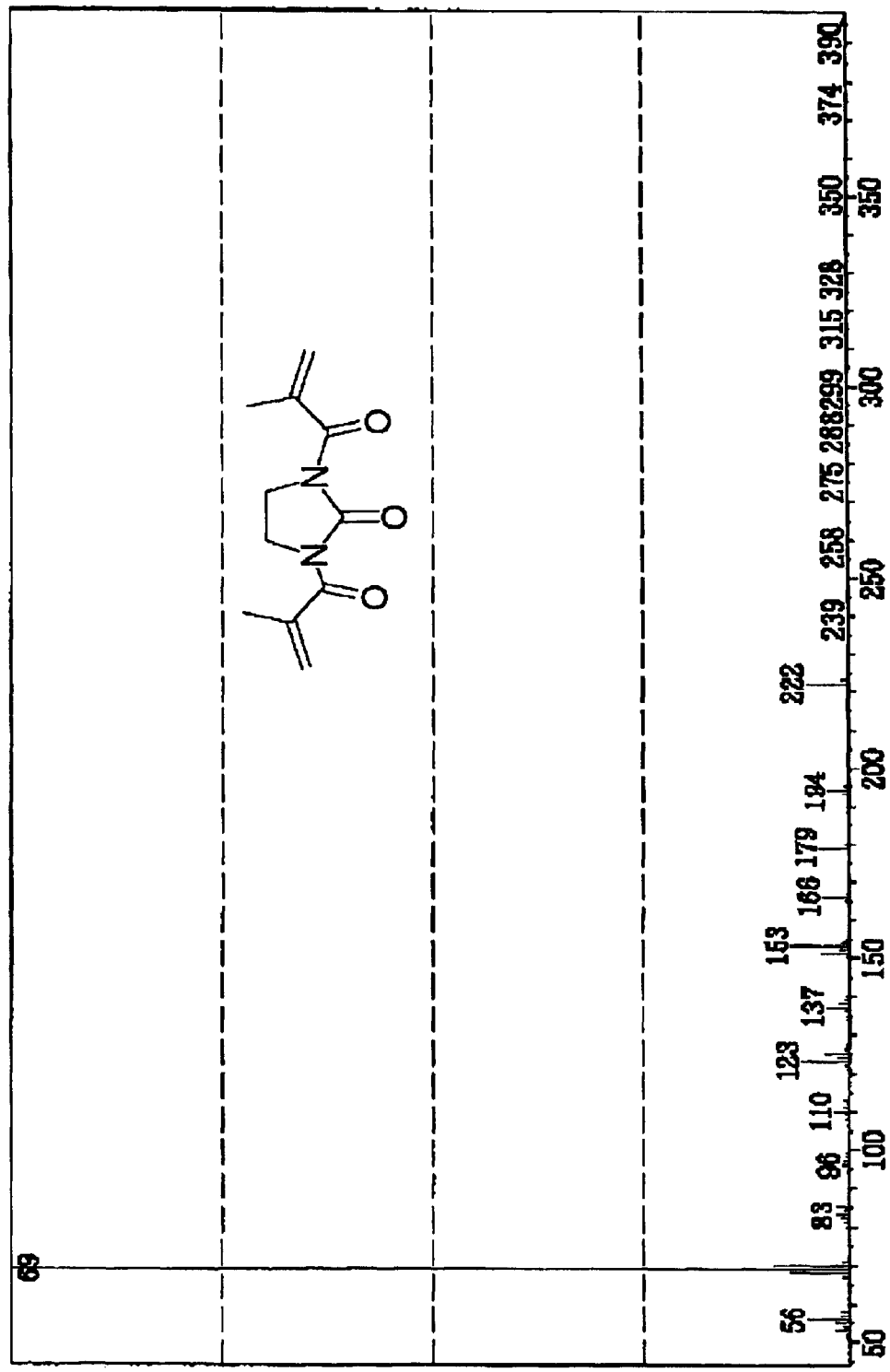
FIG. 54 is an MS spectrum of N,N'-di(methacryloyl)-ethyleneurea obtained in Example 25.

MS spectrum→See FIG. 54

EXAMPLE 26

Synthesis of N-methyl-N'-glycidyl-ethyleneurea (abbreviated as "MGI")

Into a reaction flask, N-methyl-ethyleneurea (450.0 g, 4.05 mol), epichlorohydrin (2,082.0 g, 25.5 mol) and trimethylbenzyl chloride (15 g) were charged. Under heating and reflux (115–120° C.), they were reacted for 5 hours, and the reaction mixture was cooled to 60° C.

A 39% aqueous solution of sodium hydroxide (625.0 g, 6.09 mol) was then added dropwise, followed by aging at 80° C. for 1 hour.

The reaction mixture was allowed to cool down to room temperature, and then filtered. To the resulting filtrate, chloroform and water were added. After the resulting mixture was allowed stand, the chloroform layer was collected. The thus-obtained chloroform layer was concentrated on an evaporator, and the residue was purified by silica gel chromatography. As a result, N-methyl-N'-glycidyl-ethyleneurea (abbreviated as "MGI") of 92% purity was obtained in an amount of 56.2 g (0.33 mol, pure yield: 8.2%/N-methyl-ethyleneurea).

Figure 55:
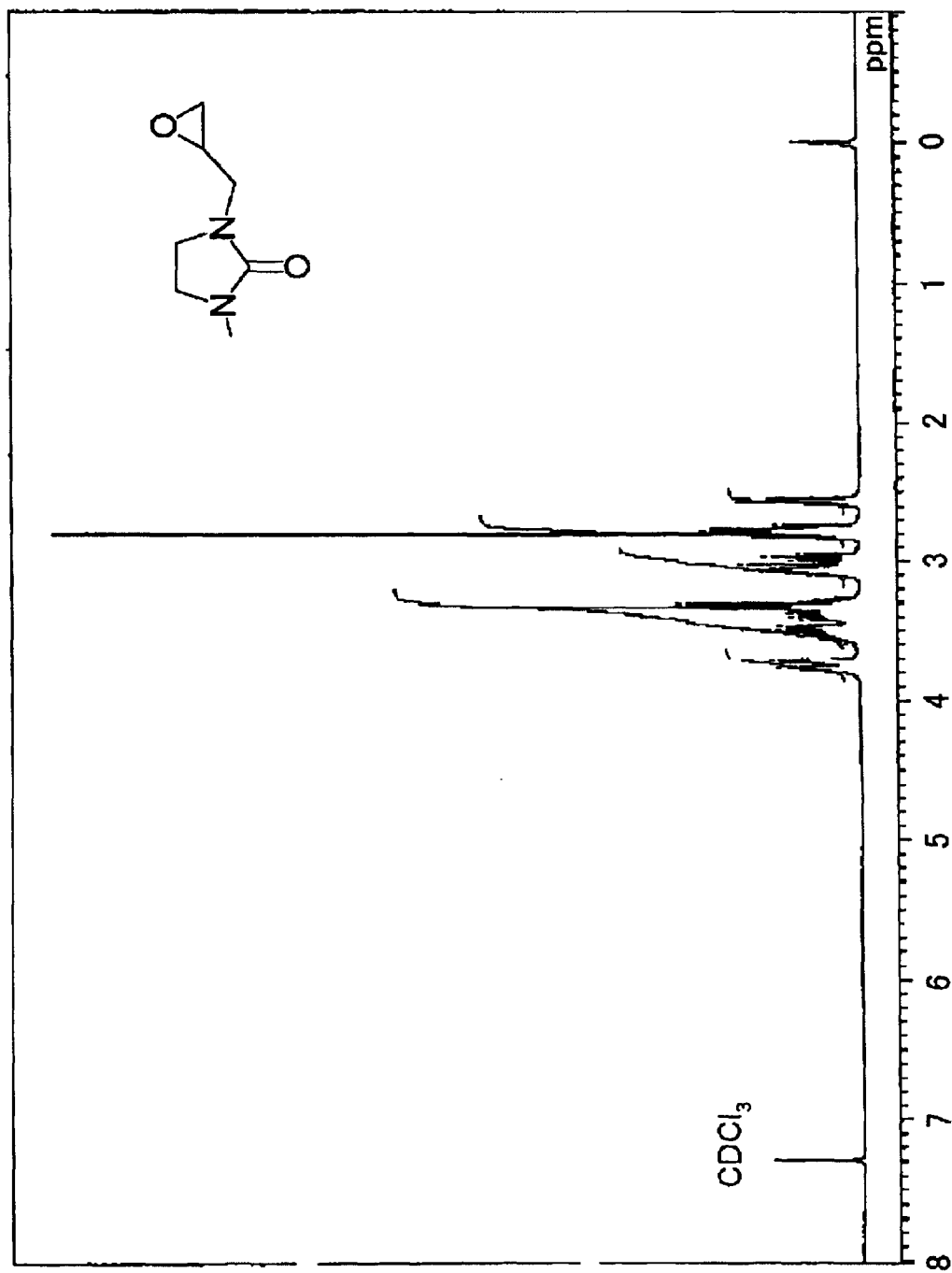
FIG. 55 is a $^1$H-NMR chart of N-methyl-N'-glycidyl-ethyleneurea obtained in Example 26.

The followings are identification data of the thus-obtained MGI:

$^1$H-NMR→See FIG. 55

Figure 56:
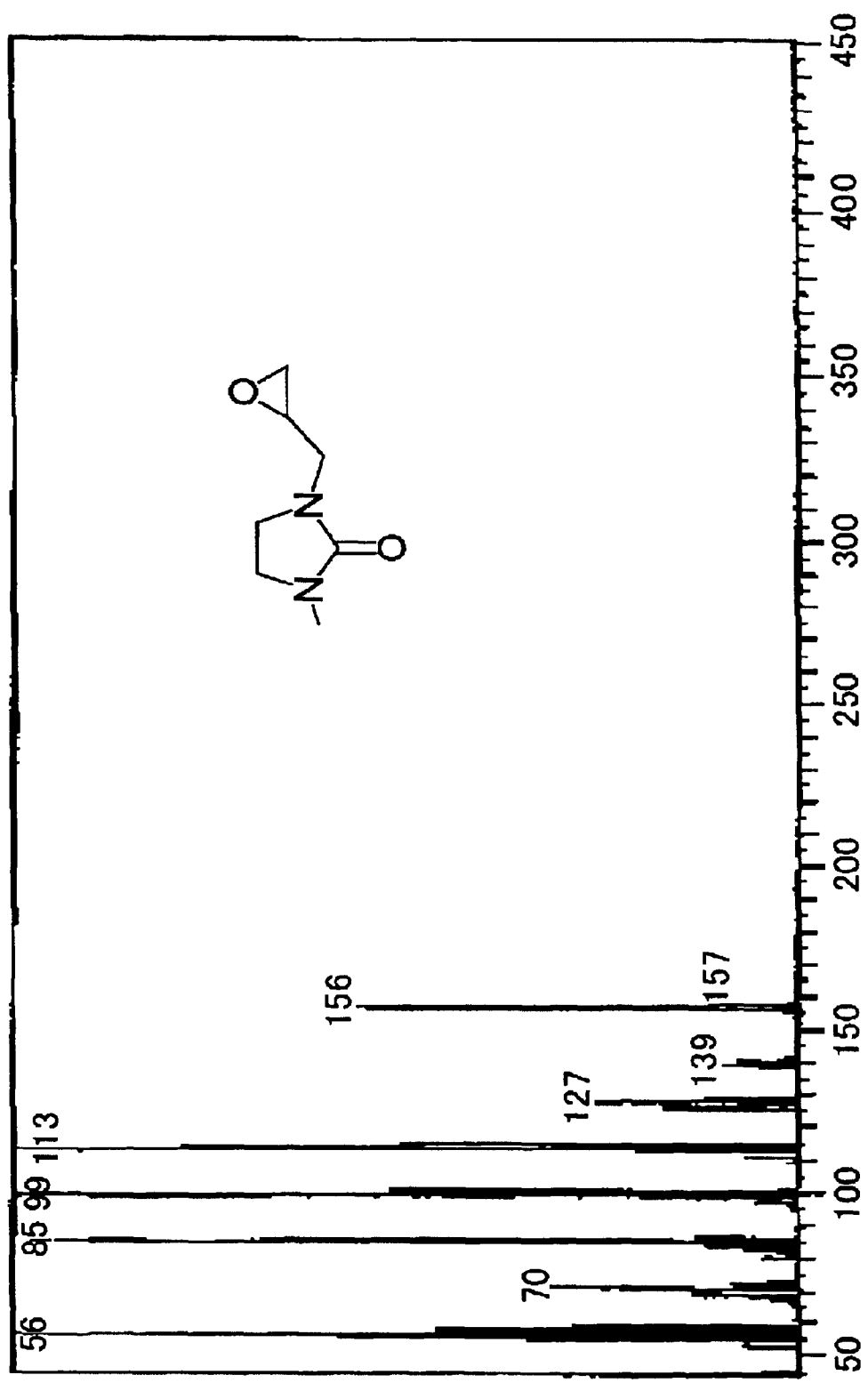
FIG. 56 is an MS spectrum of N-methyl-N'-glycidyl-ethyleneurea obtained in Example 26.

MS spectrum→See FIG. 56

EXAMPLE 27

Synthesis of N-methyl-N'-acryloyloxyethyl-ethyleneurea (abbreviated as "MAEI")

To a liquid mixture of N-methyl-N'-(2-hydroxyethyl)-ethyleneurea (HEMI) (421 g, 2.90 mol), which had been synthesized from chloroethyloxazolidone and methylamine, triethylamine (302 g, 2.98 mol) and chloroform (1,000 g), acrylic acid chloride (270 g, 2.98 mol) was added dropwise at internal temperatures of from 3 to 13° C. over 2 hours or longer, followed by aging at from 5 to 12° C. for 2 hours. To the reaction mixture, chloroform and water were added to wash the same. An organic layer was separated and collected, and then washed with saturated saline. An organic layer was obtained again and concentrated under reduced pressure on an evaporator. Finally, the residue was purified by chromatography on a silica gel column to afford N-methyl-N'-acryloyloxyethyl-ethyleneurea (abbreviated as "MAEI") of 98% purity (261 g, 1.29 mol, pure yield: 44.5%).

Figure 57:
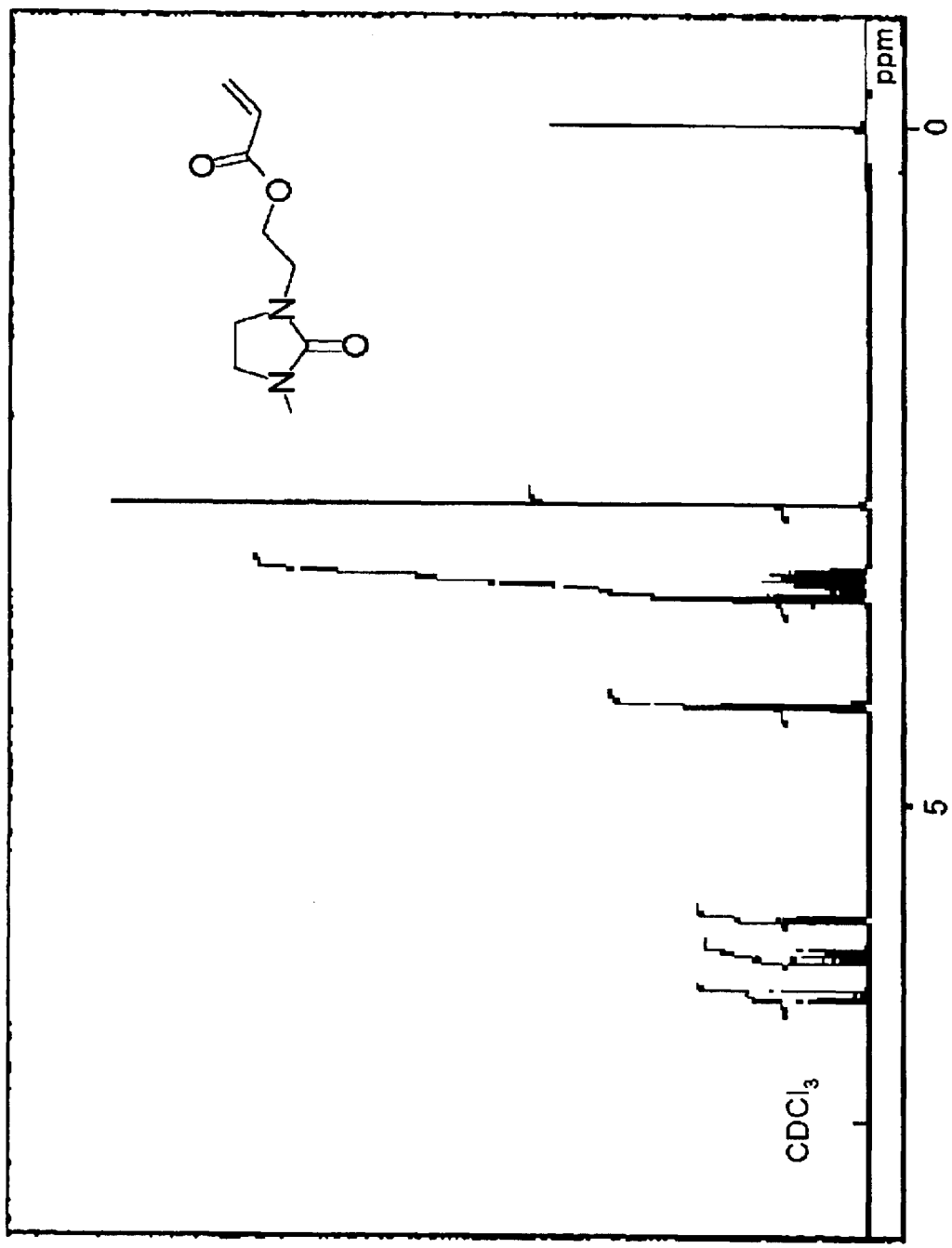
FIG. 57 is a $^1$H-NMR chart of N-methyl-N'-acryloyl-oxyethyl-ethyleneurea obtained in Example 27.

The following is an identification datum of the thus-obtained MAEI:

$^1$H-NMR→See FIG. 57

EXAMPLE 28

Synthesis of N-acryloyl-oxazolidone (abbreviated as "ACOZ")

To a liquid mixture of 2-oxazolidone (43.5 g, 0.50 mol) and acetonitrile (200 mL), β-chloropropionic acid chloride (65.4 g, 0.52 mol) was added dropwise at internal temperatures of from 13 to 18° C. over 0.5 hours or longer, maintained at 45° C. for 4 hours. After the mixture was cooled to 10° C., triethylamine (104.2 g, 1.03 mol) was added dropwise at internal temperatures of from 10 to 20° C. over 1 hour or longer, maintained at 20° C. for 1 hour.

The thus-obtained reaction mixture was filtered, the filtrate was concentrated under reduced pressure, and chloroform (300 mL) and water (100 mL) were added to the concentration residue, followed by thorough mixing. The resulting mixture was allowed to stand, and the organic layer was collected.

The organic layer was then concentrated under reduced pressure, and the concentration residue was purified by chromatography on a silica gel column. As a result, N-acryloyl-oxazolidone (ACOZ) of 98% purity was obtained in an amount of 20.5 g (0.14 mol, pure yield: 29%/oxazolidone).

Figure 58:
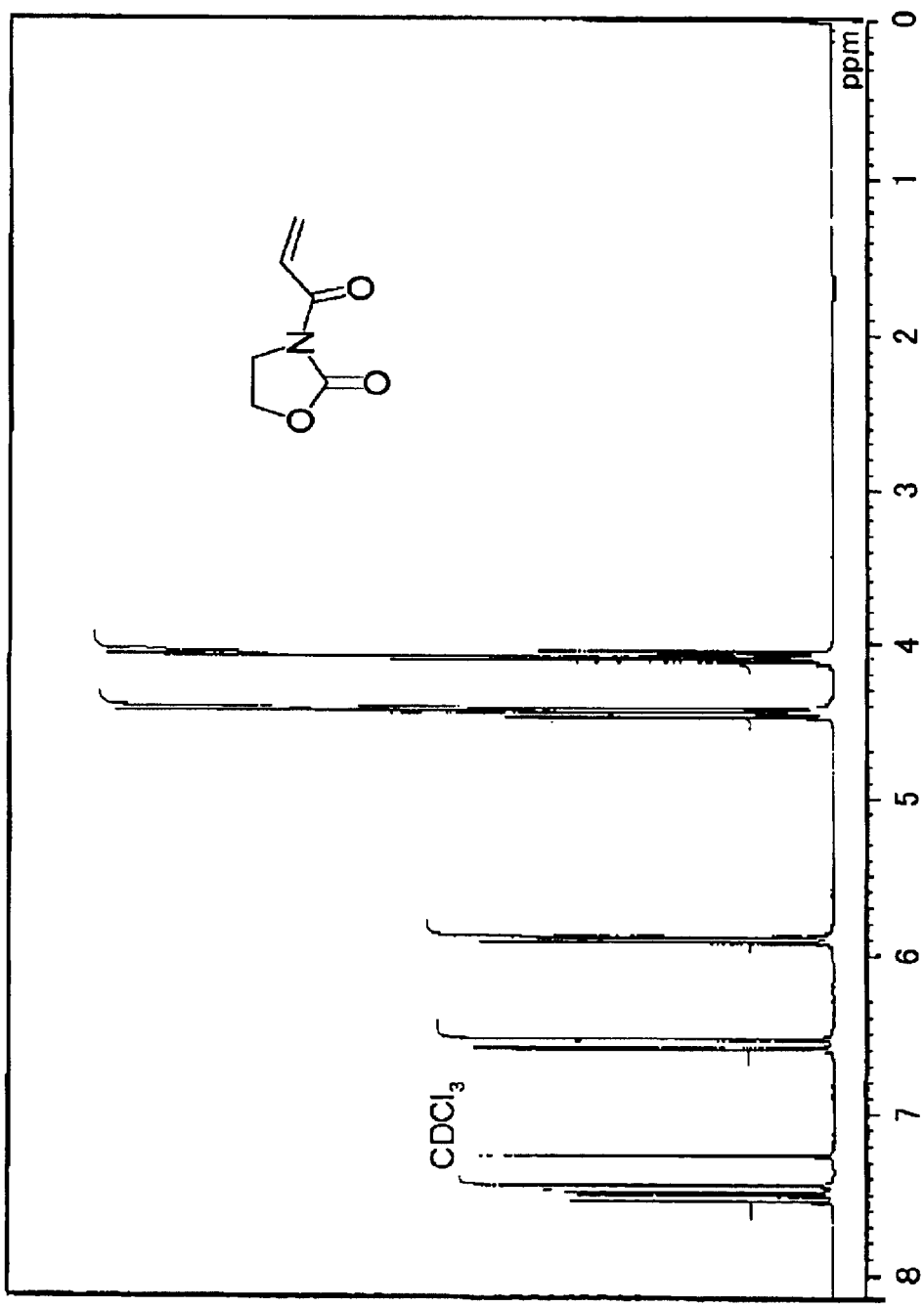
FIG. 58 is a $^1$H-NMR chart of N-acryloyl-oxazolidone obtained in Example 28.

The followings are identification data of the thus-obtained ACOZ:

$^1$H-NMR→See FIG. 58

Figure 59:
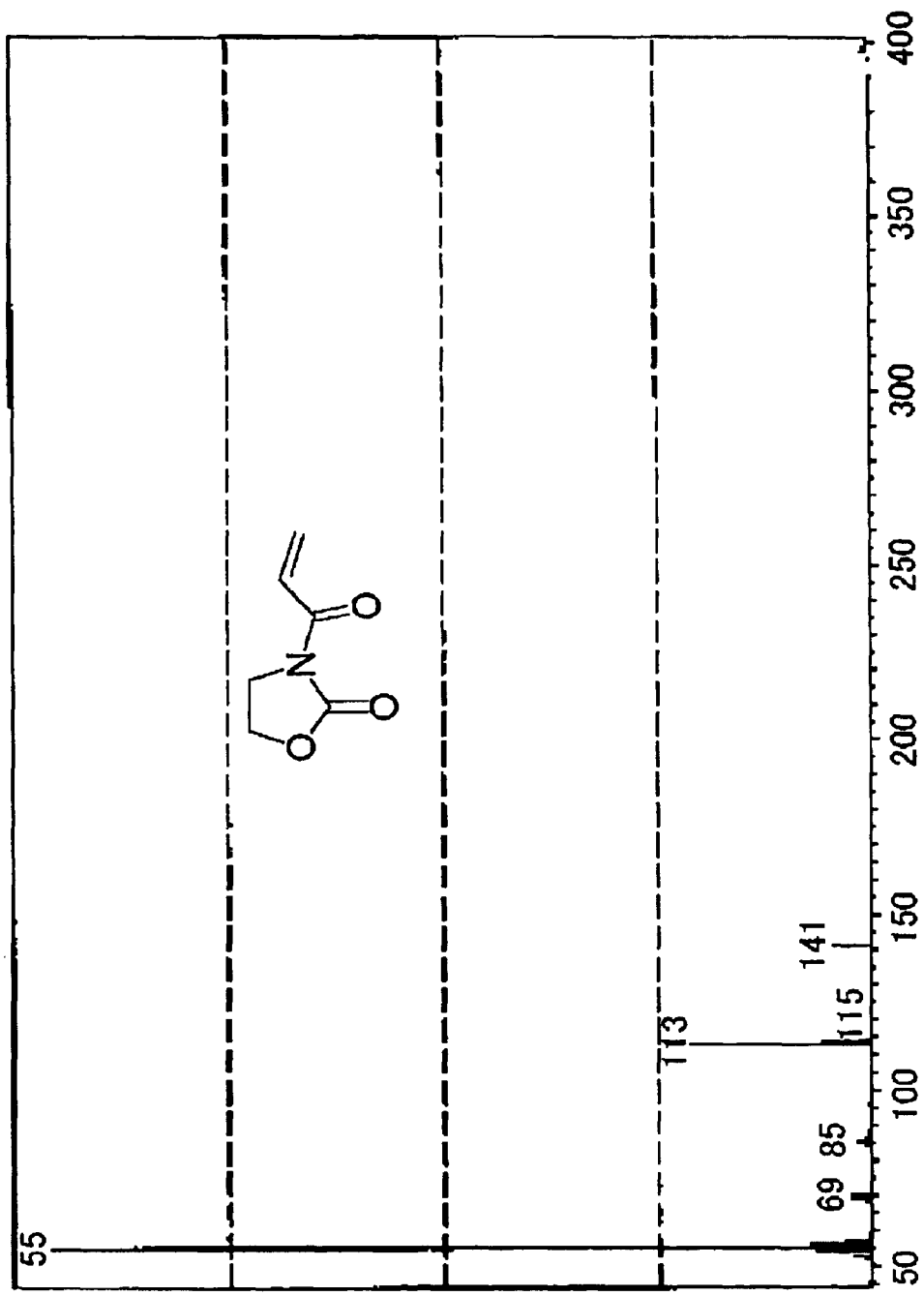
FIG. 59 is an MS spectrum of N-acryloyl-oxazolidone obtained in Example 28.

MS spectrum→See FIG. 59

EXAMPLE 29

Synthesis of N-allyl-oxazolidone (abbreviated as "ALOZ")

To a liquid mixture of 60 wt. % sodium hydride (20.0 g, 0.50 mol) and THF (700 mL), 2-oxazolidone (43.5 g, 0.50 mol) was added at internal temperatures of from 25 to 35° C. over 0.5 hours or longer, maintained at 60° C. for 2 hours. After the mixture was allowed to cool down to room temperature, allyl bromide (60.5 g, 0.50 mol) was added dropwise to the mixture at internal temperatures of from 25 to 30° C. over 0.5 hours or longer, maintained at 50° C. for 2 hours.

The thus-obtained reaction mixture was filtered, the filtrate was concentrated under reduced pressure, and the remaining concentration residue was purified by chromatography on a silica gel column. As a result, N-allyl-oxazolidone (ALOZ) of 96% purity was obtained in an amount of 37.2 g (0.28 mol, pure yield: 56%/oxazolidone).

Figure 60:
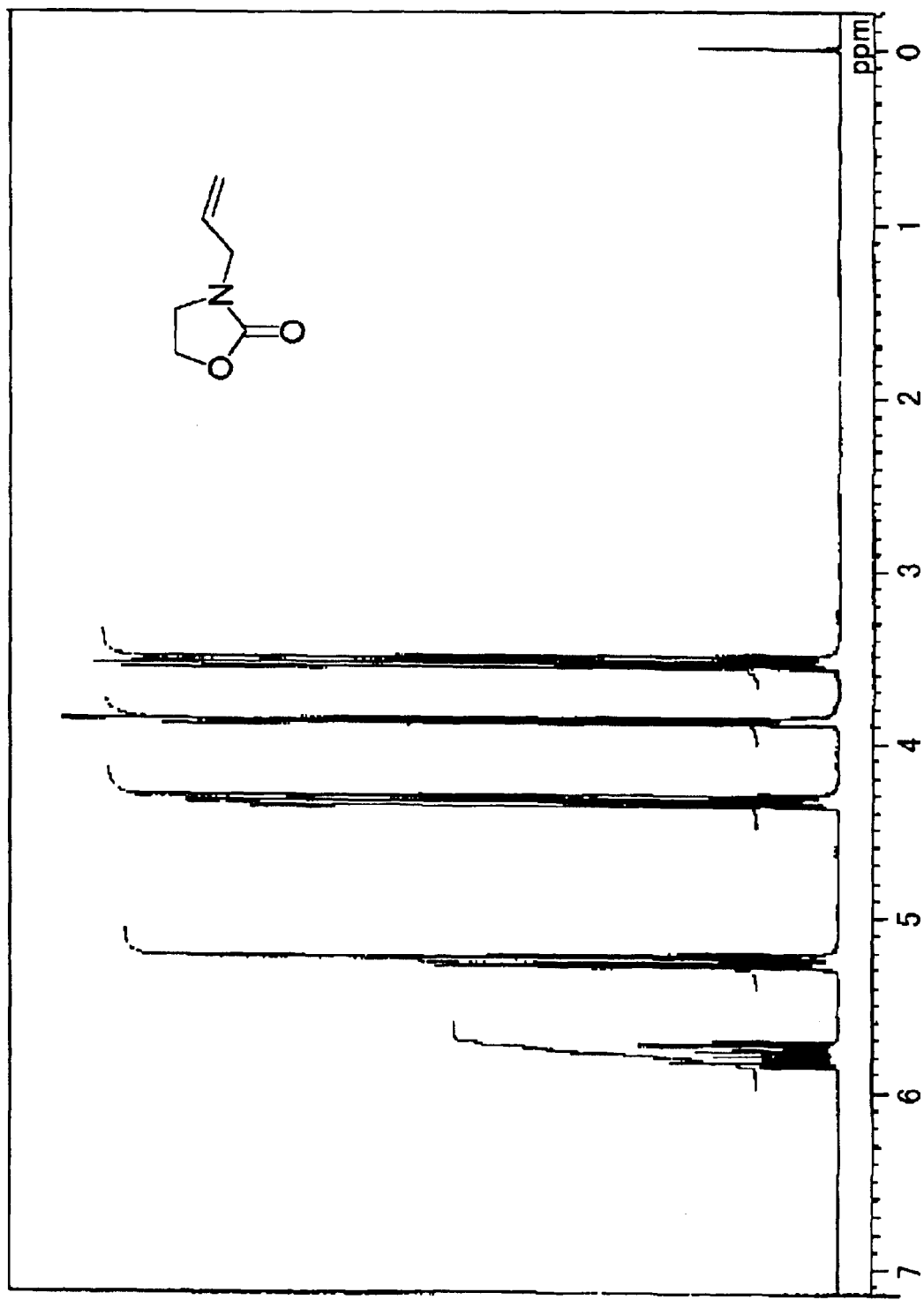
FIG. 60 is a $^1$H-NMR chart of N-allyl-oxazolidone obtained in Example 29.

The followings are identification data of the thus-obtained ALOZ:

$^1$H-NMR→See FIG. 60

Figure 61:
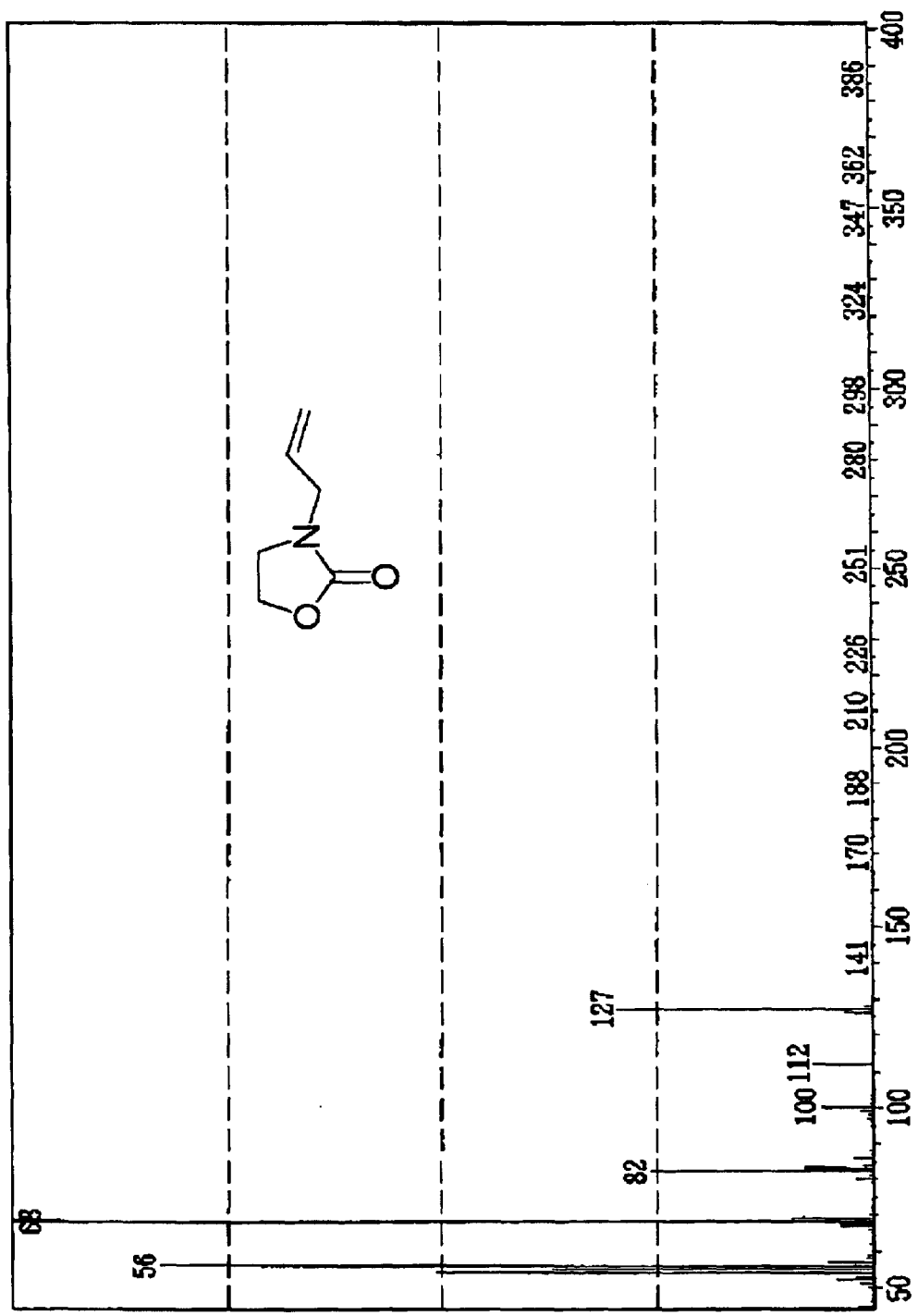
FIG. 61 is an MS spectrum of N-allyl-oxazolidone obtained in Example 29.

MS spectrum→See FIG. 61

EXAMPLE 30

Synthesis of N-vinyl-oxazolidone (abbreviated as "VOZ")

Into a reaction flask, ethylene carbonate (176.1 g, 2.00 mol) and diethanolamine (210.3 g, 2.00 mol) were charged.

At from 160 to 165° C., they were reacted for 5 hours. After cooling, the reaction mixture was purified by chromatography on a silica gel column to afford crude N-hydroxyethyl-oxazolidone (310 g).

To the crude product, potassium carbonate (6.9 g, 0.05 mol) and diethyl carbonate (945 g, 8.00 mol) were then added. They were reacted at from 100 to 106° C. for 5 hours while drawing formed methanol. Subsequent to cooling, the reaction mixture was filtered, and the filtrate was concentrated under reduced pressure to afford crude N-(ethylcarbonatoethyl)-oxazolidone (163 g).

The crude N-(ethylcarbonatoethyl)-oxazolidone was next added dropwise under reduced pressures of from 2.0 to 2.7 kPa (15 to 20 torr) into a flask which had been added with potassium carbonate (6.9 g, 0.05 mol) and was controlled at 190° C., and distilled fractions were collected. Finally, the thus-obtained fractions were distilled once again under a reduced pressure of 1.3 kPa (10 torr), and a 120–130° C. fraction was collected to afford N-vinyl-oxazolidone of 95% purity (63.0 g, 0.53 mol, pure yield: 26%/ethylenecarbonate).

Figure 62:
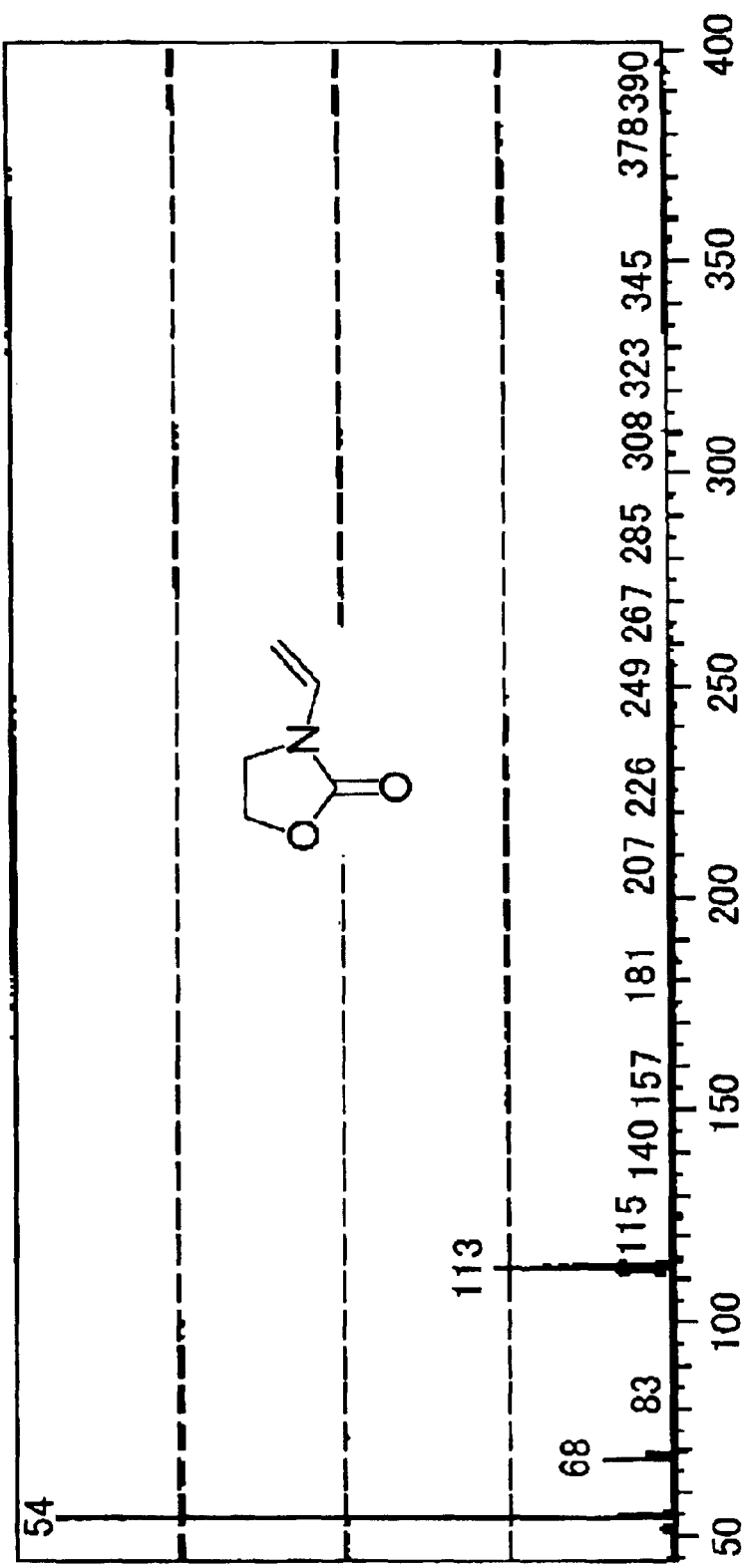
FIG. 62 is an MS spectrum of N-vinyl-oxazolidone obtained in Example 30.

The following is an identification datum of the thus-obtained VOZ:

MS spectrum→See FIG. 62

EXAMPLE 31

Synthesis of N-acryloyl-pyrrolidone (abbreviated as "NAPD")

To a liquid mixture of 2-pyrrolidone (42.6 g, 0.50 mol) and chloroform (75 mL), β-chloropropionic acid chloride (65.4 g, 0.52 mol) was added dropwise at internal temperatures of from 25 to 30° C. over 0.5 hours or longer, maintained at 40° C. for 4 hours. After the mixture was cooled to 10° C., triethylamine (104.2 g, 1.03 mol) was added dropwise at internal temperatures of from 10 to 20° C. over 1 hour or longer, maintained at 20° C. for 1 hour.

To the thus-obtained reaction mixture, chloroform (300 mL) and water (200 mL) were added, followed by thorough mixing. The resulting mixture was allowed to stand, and the organic layer was collected.

The organic layer was then concentrated under reduced pressure, and the concentration residue was purified by chromatography on a silica gel column. As a result, N-acryloyl-pyrrolidone (NAPD) of 85% purity was obtained in an amount of 50.5 g (0.31 mol, pure yield: 62%/pyrrolidone).

Figure 63:
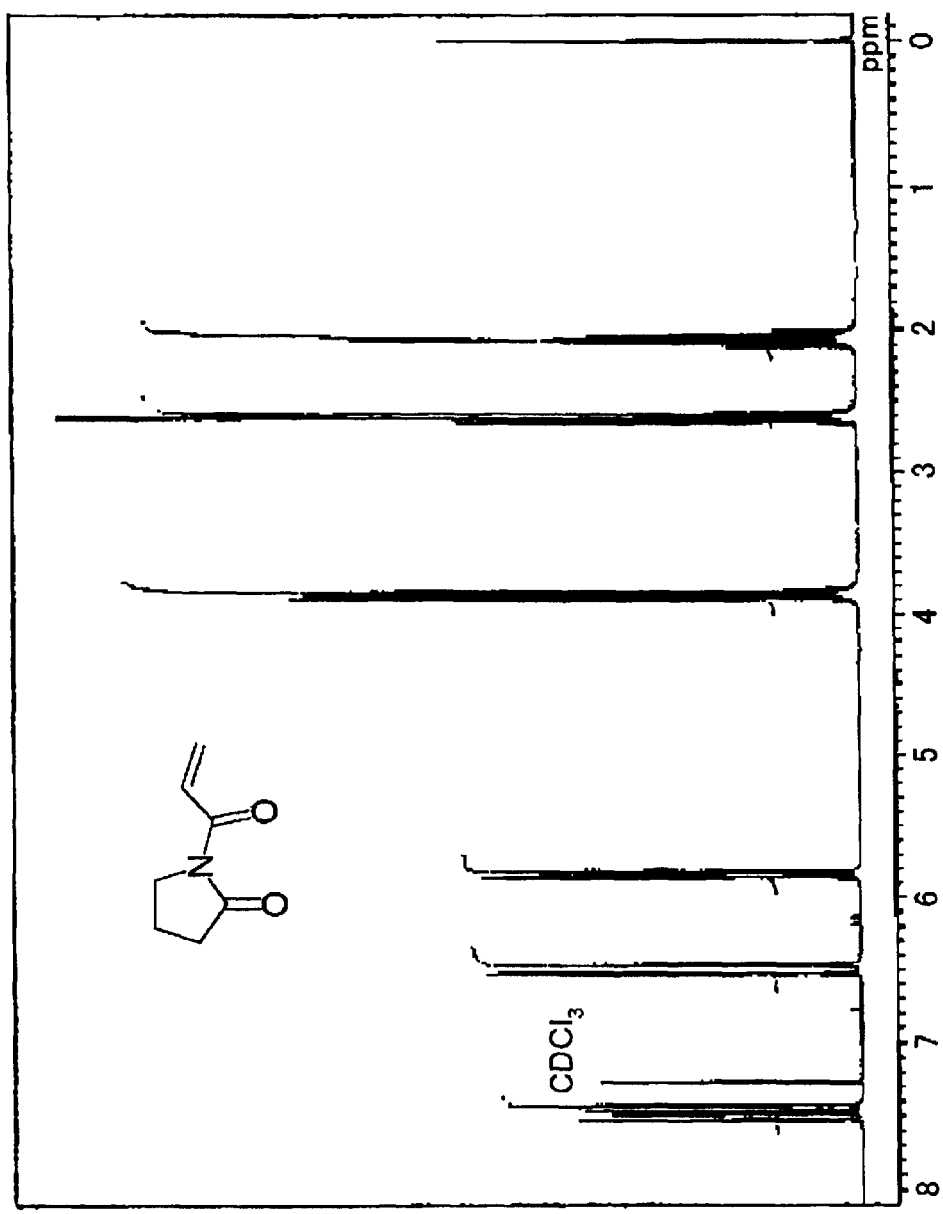
FIG. 63 is a $^1$H-NMR chart of N-acryloyl-pyrrolidone obtained in Example 31.

The followings are identification data of the thus-obtained NAPD:

$^1$H-NMR→See FIG. 63

Figure 64:
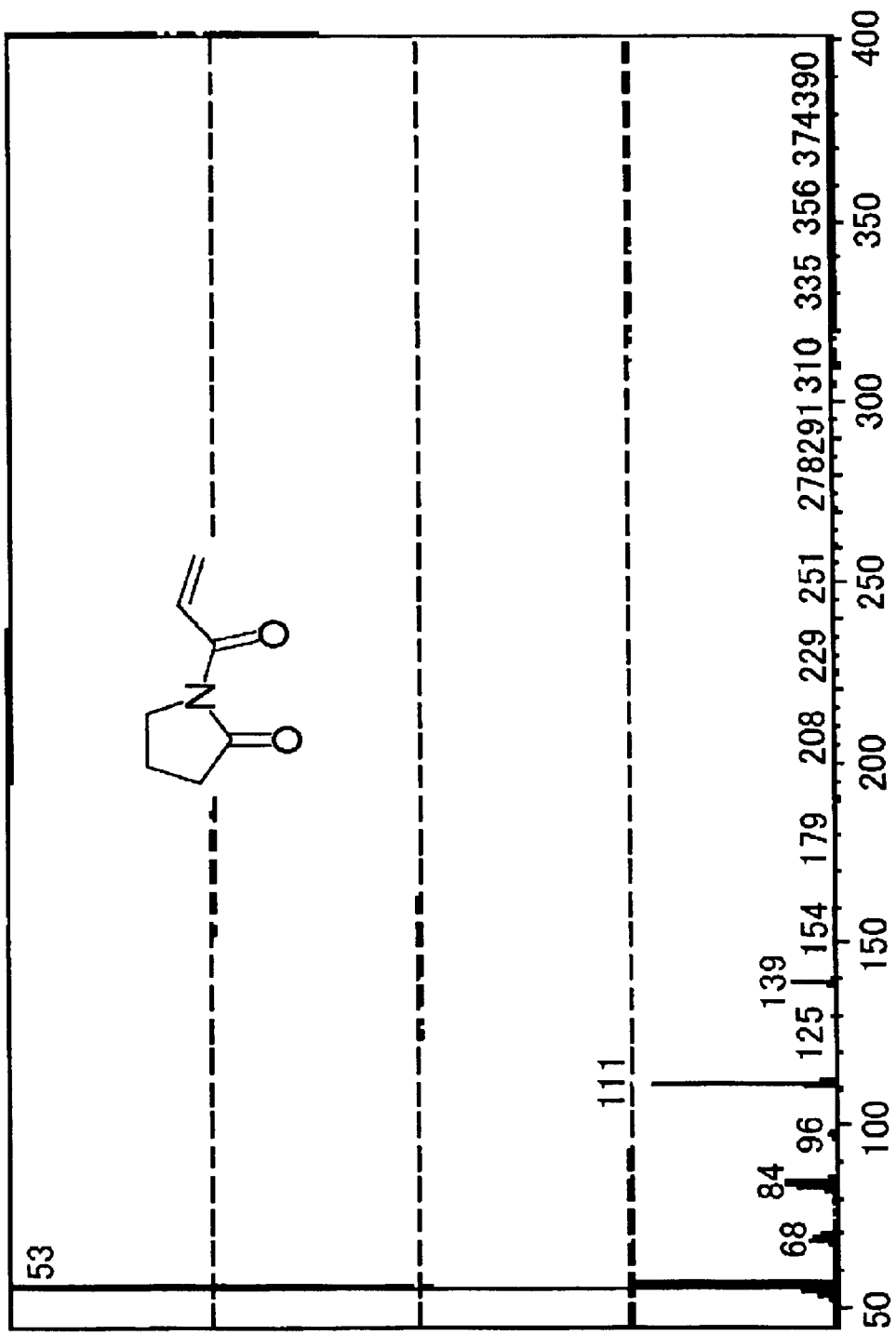
FIG. 64 is an MS spectrum of N-acryloyl-pyrrolidone obtained in Example 31.

MS spectrum→See FIG. 64

EXAMPLE 32

Synthesis of N-allyl-pyrrolidone (abbreviated as "ALPD")

To a liquid mixture of 60 wt. % sodium hydride (40.0 g, 1.00 mol) and THF (600 mL), 2-pyrrolidone (85.1 g, 1.00 mol) was added at internal temperatures of from 24 to 33° C. over 1 hour or longer, maintained at 60° C. for 2 hours. After cooling, allyl bromide (121.0 g, 1.00 mol) was added dropwise to the mixture at internal temperatures of from 30 to 35° C. over 1 hour or longer, maintained at 45° C. for 2 hours.

The thus-obtained reaction mixture was filtered, the filtrate was concentrated under reduced pressure, and the remaining concentration residue was purified by chromatography on a silica gel column. As a result, N-allyl-pyrrolidone (ALPD) of 97% purity was obtained in an amount of 75.3 g (0.58 mol, pure yield: 58%/pyrrolidone).

Figure 65:
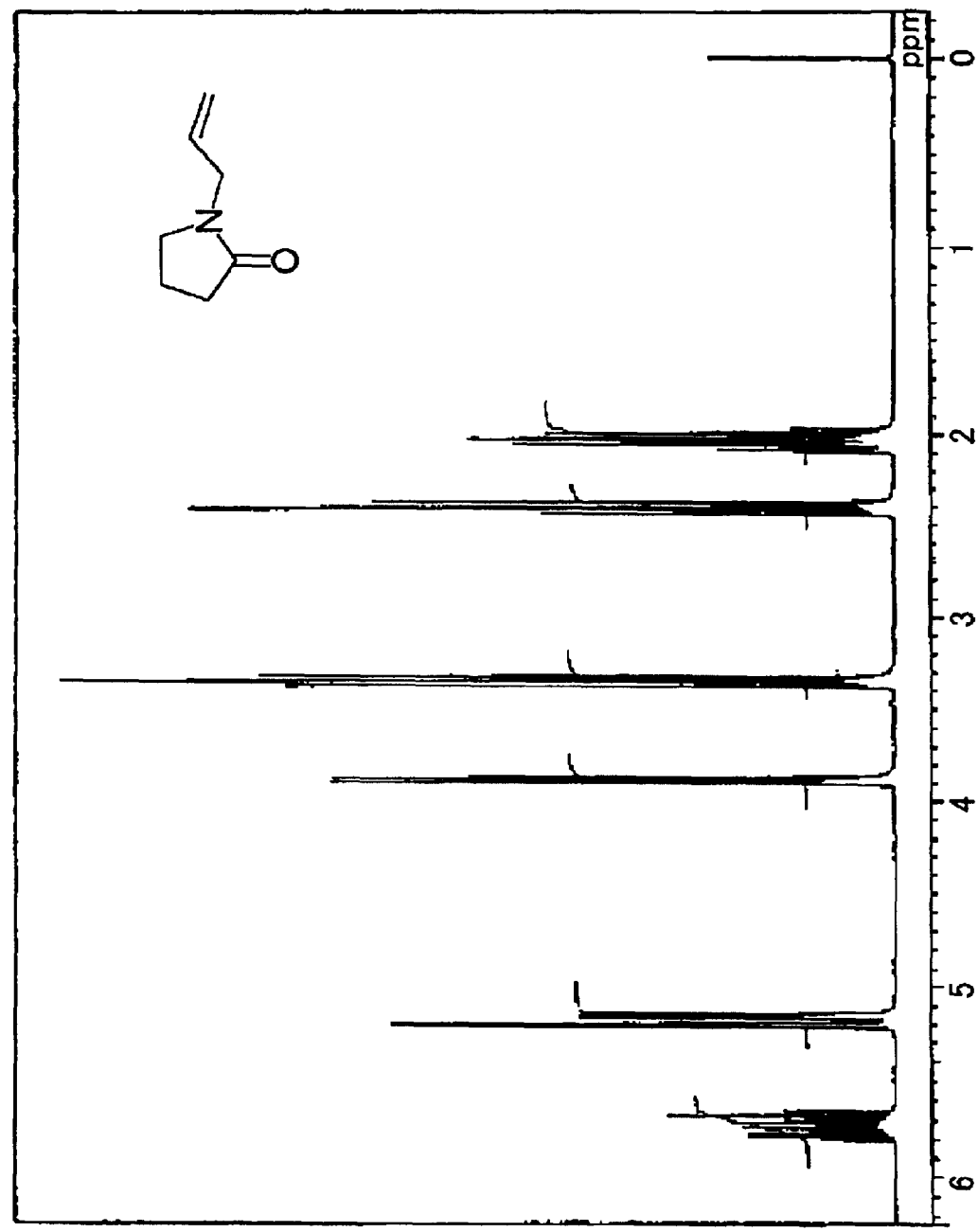
FIG. 65 is a $^1$H-NMR chart of N-allyl-pyrrolidone obtained in Example 32.

The followings are identification data of the thus-obtained ALPD:

$^1$H-NMR→See FIG. 65

Figure 66:
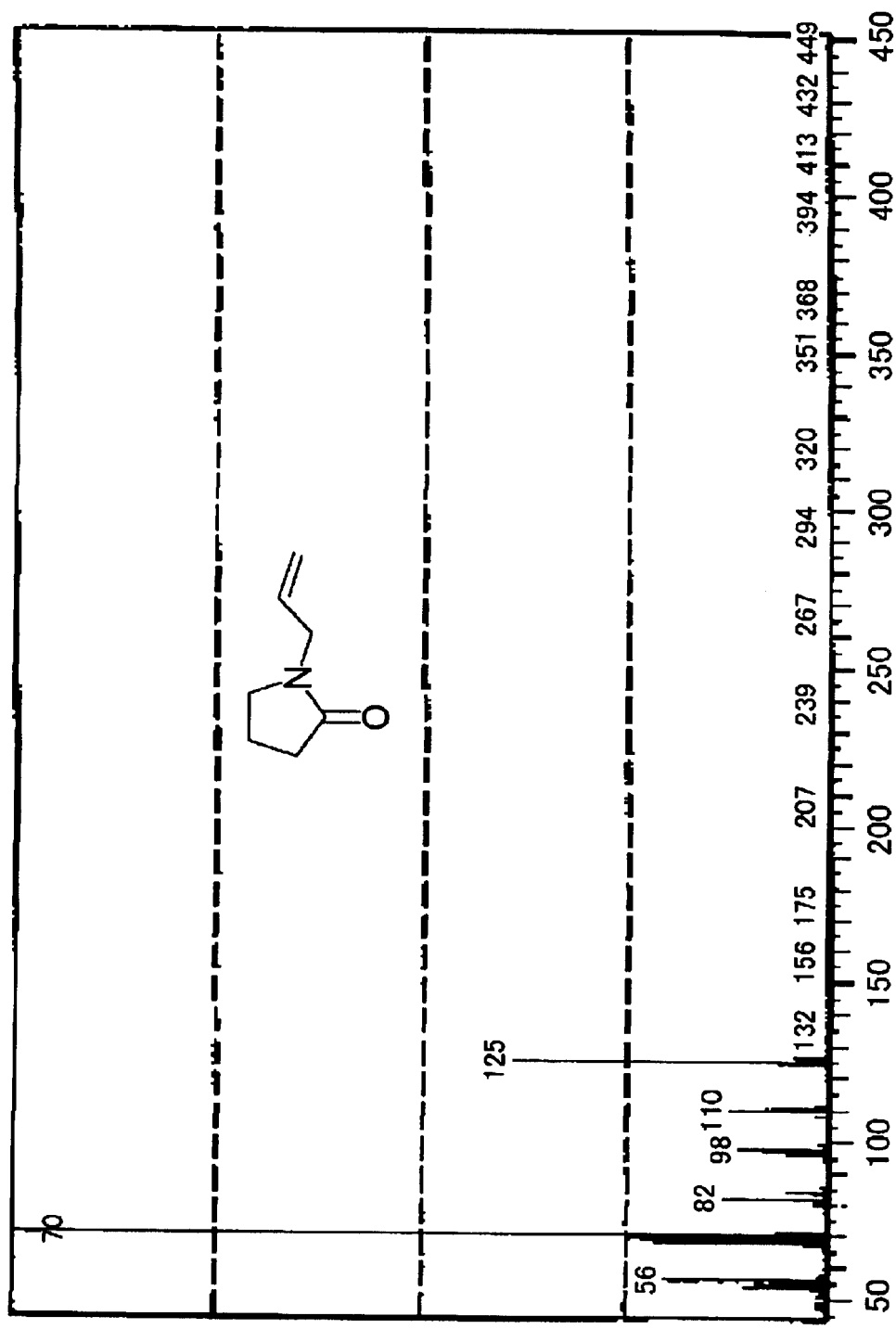
FIG. 66 is an MS spectrum of N-allyl-pyrrolidone obtained in Example 32.

MS spectrum→See FIG. 66

EXAMPLE 33

Synthesis of N-allyl-N-methyl-acetamide (abbreviated as "ALACM")

To a liquid mixture of 60 wt. % sodium hydride (40.0 g, 1.00 mol) and THF (500 mL), N-methyl-acetamide (73.1 g, 1.00 mol) was added at internal temperatures of from 21 to 27° C. over 40 minutes or longer, maintained at 60° C. for 2 hours. After cooling, allyl bromide (121.0 g, 1.00 mol) was added dropwise to the mixture at internal temperatures of from 29 to 31° C. over 40 minutes or longer, maintained at 50° C. for 2 hours.

The thus-obtained reaction mixture was filtered, the filtrate was concentrated under reduced pressure, and the remaining concentration residue was purified by chromatography on a silica gel column. As a result, N-allyl-N-methyl-acetamide (ALACM) of 97% purity was obtained in an amount of 65.0 g (0.56 mol, pure yield: 56%/N-methyl-acetamide).

Figure 67:
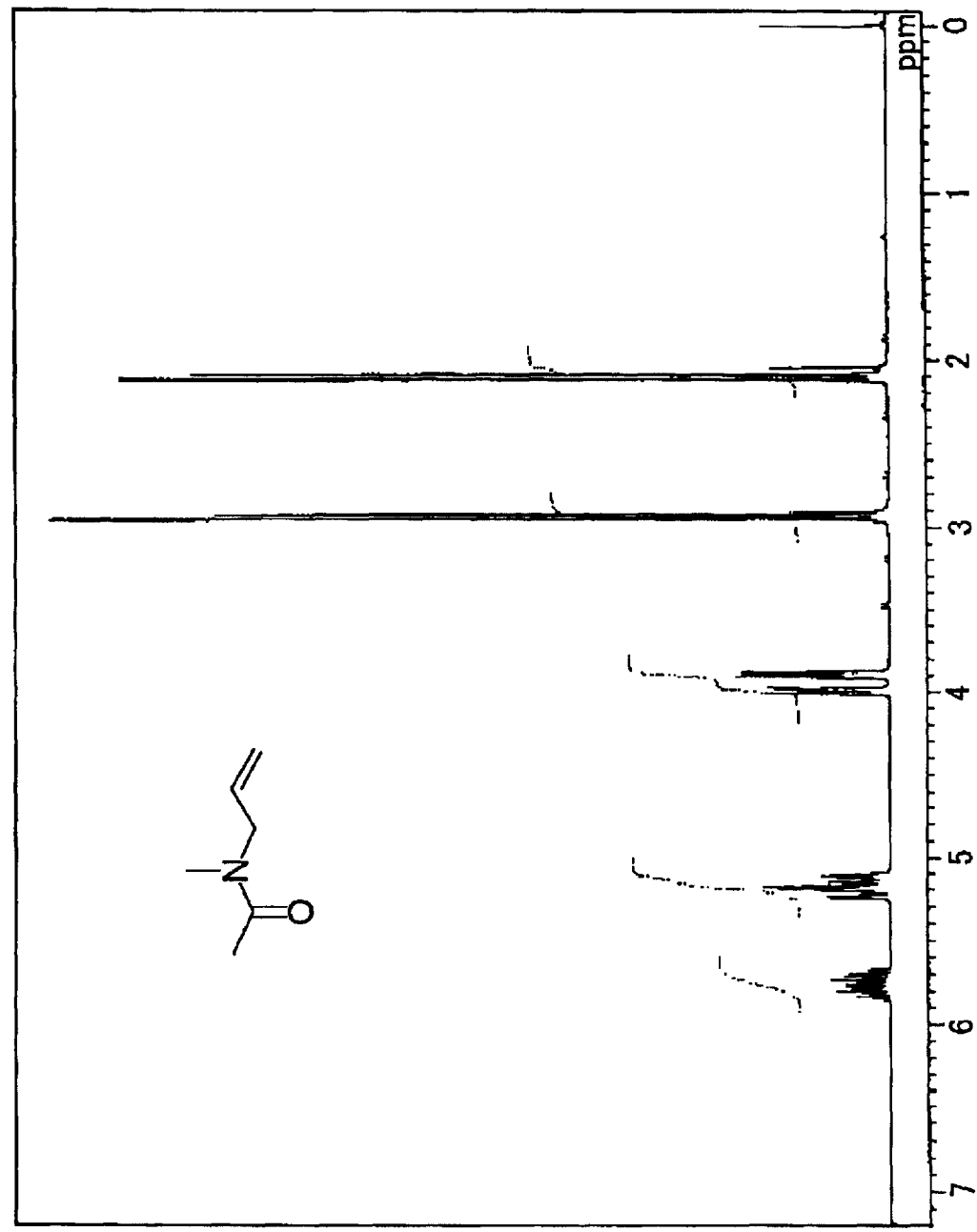
FIG. 67 is a $^1$H-NMR chart of N-allyl-N-methyl-acetamide obtained in Example 33.

The followings are identification data of the thus-obtained ALACM:

$^1$H-NMR→See FIG. 67

Figure 68:
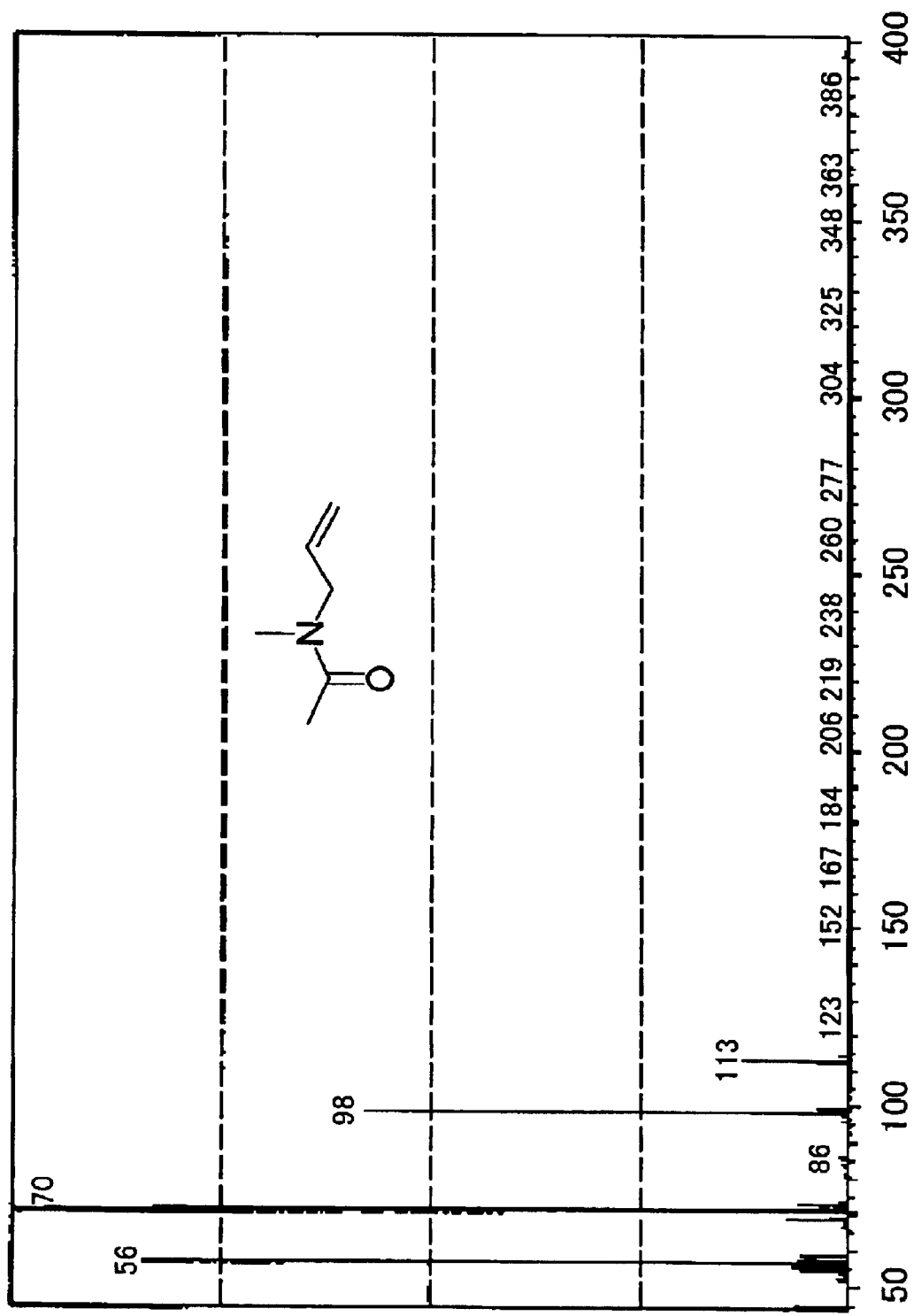
FIG. 68 is an MS spectrum of N-allyl-N-methyl-acetamide obtained in Example 33.

MS spectrum→See FIG. 68

EXAMPLE 34

Production of Polymer 1

To cyclohexane (50 mL) which had been bubbled with nitrogen, azobisisobutyronitrile (AIBN) (265 mg) was added, followed by bubbling with nitrogen. MEMEU of 97% purity (20.0 g) was charged into the resultant mixture at an internal temperature of 20° C., and thermal polymerization was conducted at 70° C. for 4 hours.

After completion of the polymerization, the solvent, cyclohexane, was decanted. To the remaining white solid, methanol (100 mL) was added to dissolve the same. The thus-obtained solution was added dropwise under stirring into diethyl ether (500 mL) which had been placed beforehand. The precipitated white solid was taken out and dried under reduced pressure.

As a result, an MEMEU polymer (17.3 g) of an average molecular weight of 120,000 (converted based on polystyrene) as measured by GPC analysis was obtained.

As a result of a measurement of this polymer by DSC, neither Tg nor Tm was observed within a range of from −180 to 250° C. ($1^{st}$—Heat, $1^{st}$—Cool, $2^{nd}$—Heat).

Concerning the solubility of the polymer in solvents, it was dissolved at room temperature in ethanol and chloroform as desired (tested range: 1 to 100 wt. %/solvent weight).

EXAMPLE 35

Production of Polymer 2

To a liquid mixture of N,N'-bis(methacryloyloxy-ethyl)-ethyleneurea (MEEU) of 97% purity (10.0 g) and N-methyl-N'-vinyl-ethyleneurea (MVI) (10.0 g), were added 2,2-dimethoxy-2-phenylacetophenone (100 mg, 0.5 wt. %) as a photopolymerization initiator, t-butyl peroxy-2-ethylhexanoate (60 mg, 0.5 wt. %) as a radical catalyst, and di(5-n-butoxy-1,4-dimethyl-3-oxypentyl)phosphoric acid (60 mg, 0.5 wt. %) as an internal mold releasing agent. They were mixed, degassed under reduced pressure, and exposed to ultraviolet ray of from 100 to 130 mW/cm$^2$ intensity for curing, and then annealed at from 80 to 120° C.

The thus-obtained resin was transparent, and its water contact angle was 10°.

EXAMPLE 36

Production of Polymer 3

To a liquid mixture of N,N'-bis(acryloyloxyethyl)-ethyleneurea (AEEU) of 96% purity (10.0 g) and N-methyl-N'-acryloyloxyethyl-ethyleneurea (MAEI) (10.0 g), were added 2,2-dimethoxy-2-phenylacetophenone (10 mg, 500 ppm) as a photopolymerization initiator, t-butyl peroxy-2-ethylhexanoate (40 mg, 2,000 ppm) as a radical catalyst, and di(5-n-butoxy-1,4-dimethyl-3-oxypentyl)phosphoric acid (40 mg, 2,000 ppm) as an internal mold releasing agent. They were mixed, degassed under reduced pressure, and exposed to ultraviolet ray of from 80 to 110 mW/cm² intensity for curing, and then annealed at from 80 to 120° C. The thus-obtained resin was transparent, and its water contact angle was 7°.

EXAMPLES 37–49

Production of polymers 4–16

Polymerization was conducted in a similar manner as in Example 35 or Example 36. Physical properties of the resultant resins are shown in Table-1.

COMPARATIVE EXAMPLES 1–4

Contact angles of commercially-available slide glass and general-purpose resins were measured. The results are shown in Table-1.

COMPARATIVE EXAMPLES 5–7

Polymerization was conducted in a similar manner as in Example 35 or Example 36. Physical properties of the resultant resins are shown in Table-1.

COMPARATIVE EXAMPLE 8

Resinification of acrylic acid was attempted under the conditions of Example 36. Polymerization took place, but the resulting resin contained numeral crazing and cracks and was in a foamed form. Measurement of its contact angle was not feasible.

TABLE 1

| Example Comp. Ex. | Polymer No. | Monomer-1 | Amount | Monomer-2 | Amount | External appearance | Water contact angle |
|---|---|---|---|---|---|---|---|
| Ex. | | | | | | | |
| 35 | 2 | MEEU | 10 parts | MVI | 10 parts | Transparent | 10° |
| 37 | 4 | same as above | 10 parts | VP | 10 parts | Transparent | 6° |
| 38 | 5 | same as above | 10 parts | ALPD | 10 parts | Transparent | 7° |
| 39 | 6 | same as above | 10 parts | VOZ | 10 parts | Transparent | 20° |
| 40 | 7 | same as above | 10 parts | ALOZ | 10 parts | Transparent | 9° |
| 36 | 3 | AEEU | 10 parts | MAEI | 10 parts | Transparent | 7° |
| 41 | 8 | same as above | 10 parts | DAEU | 10 parts | Transparent | 15° |
| 42 | 9 | same as above | 10 parts | VOZ | 10 parts | Transparent | 6° |
| 43 | 10 | same as above | 10 parts | ALOZ | 10 parts | Transparent | 20° |
| 44 | 11 | same as above | 10 parts | MVA | 10 parts | Transparent | 17° |
| 45 | 12 | S-3I | 10 parts | MVI | 10 parts | Transparent | 9° |
| 46 | 13 | EGMA | 10 parts | MVI | 10 parts | Transparent | 12° |
| 47 | 14 | same as above | 10 parts | MAEI | 10 parts | Transparent | 18° |
| 48 | 15 | same as above | 10 parts | ALPD | 10 parts | Transparent | 17° |
| 49 | 16 | same as above | 10 parts | MVA | 10 parts | Transparent | 19° |
| Comp. Ex. | | | | | | | |
| 1 | | Slide glass | | None | | | 25° |
| 2 | | Nylon | | None | | | 60° |
| 3 | | Polycarbonate | | None | | | 61° |
| 4 | | Polypropylene | | None | | | 81° |
| 5 | | EGMA | 20 parts | None | | Transparent | 69° |
| 6 | | same as above | 10 parts | HEMA | 10 parts | Transparent | 48° |
| 7 | | same as above | 10 parts | Acrylic acid | 10 parts | Transparent | 40° |

Abbreviations in the table are as will be defined hereinafter.

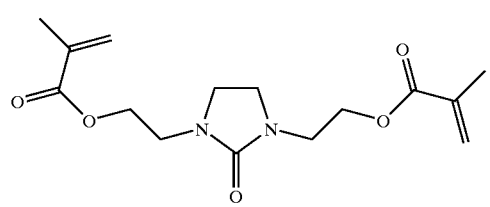

MEEU

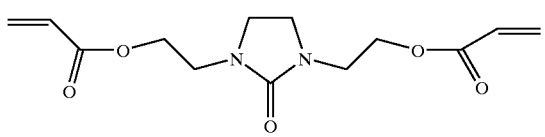

AEEU

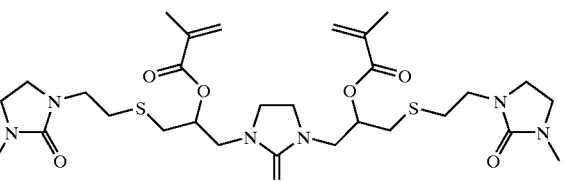

S-3I

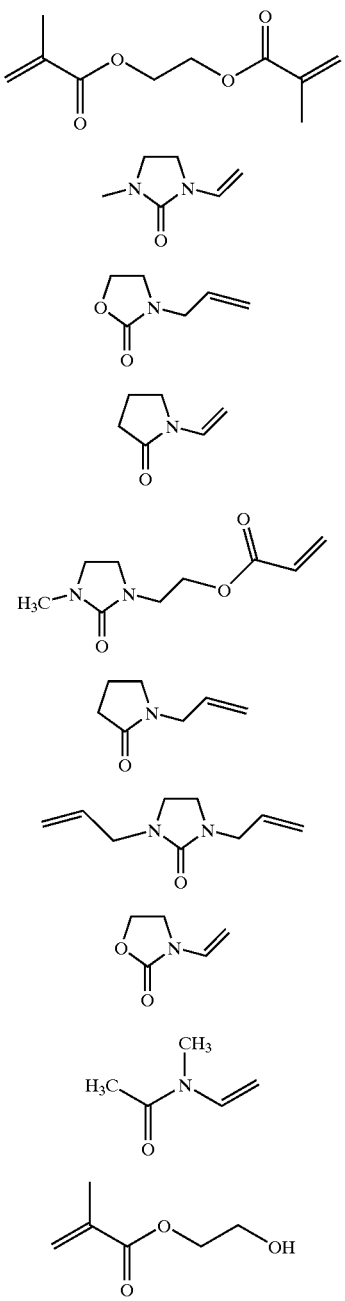

EGMA

MVI

ALOZ

VP

MAEI

ALPD

DAEU

VOZ

MVA

HEMA

EXAMPLE 50

Production of Polymer 17

To a liquid mixture of N,N'-bis{2-mercaptomethyl-2-(2-mercaptothio)-ethyl}-ethyleneurea (MESPI) of 98% purity (10.1 g) and bis(isocyanatomethyl)norbornane(NBDI) (9.9 g), were added dibutyltin dichloride (6 mg, 300 ppm) as a catalyst, 2-(2H-benzotriazol-2-yl)-4-(t-octyl)phenol (10 mg, 500 ppm) as an ultraviolet absorber, di(5-n-butoxy-1,4-dimethyl-3-oxypentyl)phosphoric acid (60 mg, 3,000 ppm) as an internal mold releasing agent. They were mixed, degassed under reduced pressure, and subjected to thermal polymerization at room temperature to 120° C. for 18 hours. The thus-obtained resin board of 10 mm thickness was transparent, and had a refractive index of 1.62 (e beam; 546 nm), an Abbe number (e) of 39, Tg (TMA) of 137° C. and a density (d) of 1.30 (g/cc).

Further, the above-obtained resin was immersed at from 91 to 93° C. for 60 minutes in a liquid mixture which consisted of dispersion dyes, "MLP Blue-2" (MITSUI BASF DYES LIMITED) (2.0 g), "MLP Red-2" (MITSUI BASF DYES LIMITED) (2.0 g) and "MLP Yellow-2" (MITSUI BASF DYES LIMITED) (4.0 g), and water (1,000 mL). The resin was then taken out of the liquid mixture, washed and dried.

As a result, it was found that the resin had been dyed to 79% (before the dyeing test: 85%) in terms of transmission at 500 nm. The results are shown in Table-2.

COMPARATIVE EXAMPLE 9

Bis{2-mercaptomethyl-2-(2-mercaptothio)-ethyl}sulfide (FSH) (9.4 g) and bis(isocyanatomethyl)norbornane (NBDI) (10.6 g) were mixed, and subjected to thermal polymerization in a similar manner as in Example 42. The resulting resin board of 10 mm thickness was transparent, and had a refractive index of 1.63 (e beam; 546 nm), an Abbe number (ve) of 38, Tg (TMA) of 130° C. and a density (d) of 1.31 (g/cc).

Further, a dyeing test was conducted in a similar manner as in Example 50. As a result, its transmittance at 500 nm was 84% (before the dyeing test: 85%). The resin was not dyed under the conditions although its heat resistance was lower than the resin of Example 50.

The results are shown in Table-2.

EXAMPLE 51

Production of Polymer 18

To a liquid mixture of N,N'-bis(thioglycidylthio-ethyl)-ethyleneurea (TGEU) of 99% purity (20.0 g) and N,N'-bis(mercaptoethyl)-ethylurea (DMEU) of 95% purity (1.0 g), triethylamine (21 mg, 1,000 ppm) was added as a catalyst. Under reduced pressure, they were mixed and degassed. The thus-degassed liquid mixture was charged in a mold and then gradually heated from 25° C. to 120° C. over 20 hours to cure the polymerizable compounds, and annealing was conducted at 120° C. for 2 hours. The thus-obtained resin was transparent, and had a refractive index of 1.66 (e beam; 546 nm), an Abbe number (ve) of 36, Tg (TMA) of 74° C. and a density (d) of 1.32 (g/cc).

Further, the above-obtained resin was immersed at 92° C. for 3 minutes in a liquid mixture of a dispersion dye, "MLP Blue-2", (MITSUI BASF DYES LIMITED), (5.0 g) and water (1,000 mL). The resin was then taken out of the liquid mixture, washed and dried. As a result, a resin evenly dyed in a dark blue color was obtained.

The results are shown in Table-2.

COMPARATIVE EXAMPLE 10

Bis(thioglycidyl) disulfide (abbreviated as "ETDS") (18.0 g), bis{2-mercaptomethyl-2-(2-mercaptothio)-ethyl}sulfide (FSH) (2.0 g), N,N-dimethyl-cyclohexylamine (4 mg, 200 ppm) and N,N-dicyclohexyl-methylamine (20 mg, 1,000 ppm) and 2-(2H-benzotriazol-2-yl)-4-(t-octyl)phenol (220 mg, 1.1 wt. %) were mixed, and subjected to thermal polymerization in a similar manner as in Example 28. The resulting resin board of 10 mm thickness was transparent, and had a refractive index of 1.74 (e beam; 546 nm), an Abbe number (ve) of 33, Tg (TMA) of 80° C. and a density (d) of 1.46 (g/cc). Dyeing of the above-obtained resin was attempted under the conditions of Example 51, but the resin was not dyed practically.

The results are shown in Table-2.

TABLE 2
| Example Comp. Ex. | Monomer-1 | Amount | Monomer-2 | Amount | Ne | ve | Tg | Remarks |
|---|---|---|---|---|---|---|---|---|
| Ex. 50 | 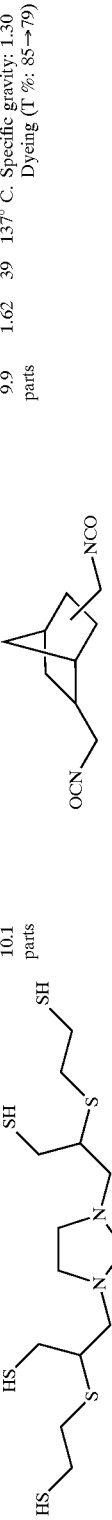<br>MESPI | 10.1 parts | 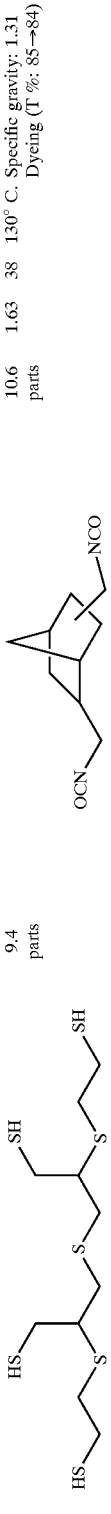<br>NBDI | 9.9 parts | 1.62 | 39 | 137° C. | Specific gravity: 1.30<br>Dyeing (T %: 85→79) |
| Comp. Ex. 9 | 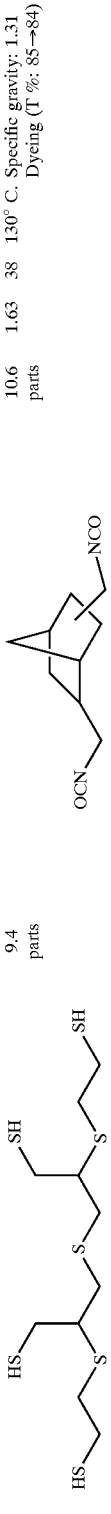<br>FSH | 9.4 parts | 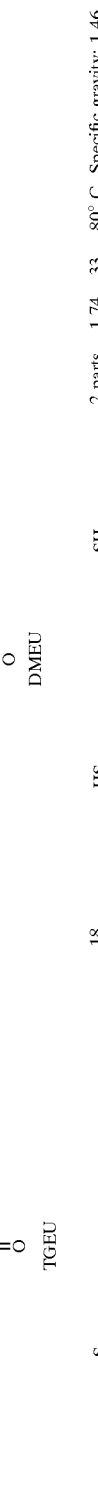<br>NBDI | 10.6 parts | 1.63 | 38 | 130° C. | Specific gravity: 1.31<br>Dyeing (T %: 85→84) |
| Ex. 51 | 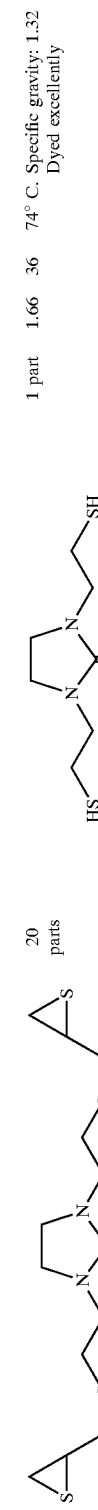<br>TGEU | 20 parts | 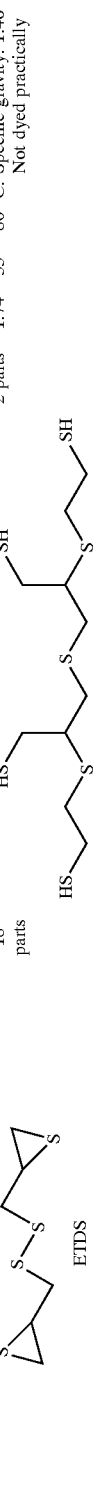<br>DMEU | 1 part | 1.66 | 36 | 74° C. | Specific gravity: 1.32<br>Dyed excellently |
| Comp. Ex. 10 | 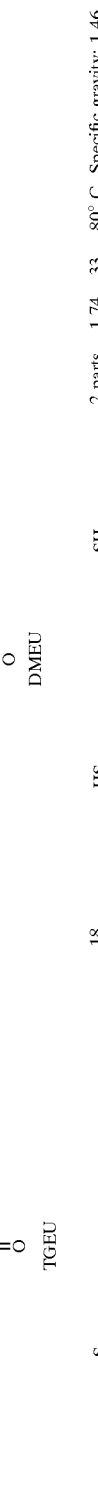<br>ETDS | 18 parts | <br>FSH | 2 parts | 1.74 | 33 | 80° C. | Specific gravity: 1.46<br>Not dyed practically |

EXAMPLE 52

COMPARATIVE EXAMPLE 11
(Water Absorption Test)

With respect to the resin of Example 37 and the resin of Comparative Example 6, a submerged water absorption test was conducted (purified water, 23° C.). The results are shown in Table-3.

TABLE 3

| Example Comp. Ex. | Monomer-1 | Amount | Monomer-2 | Amount | Water contact angle | Percent weight increase after 5 hours (based on the weight before test) |
|---|---|---|---|---|---|---|
| Ex. 52 | MEEU | 10 parts | VP | 10 parts | 6° | 116 wt % |
| Comp. Ex. 11 | EGMA | 10 parts | HEMA | 10 parts | 48° | 102 wt % |

Industrial Applicability

The organic polymers according to the present invention are physically and chemically stable, and have high wettability, water (liquid) absorbing capability, transparency and dyeability. They can, therefore, be suitably used in the field of functional materials such as antifouling materials, anti-mist materials, dew preventing materials, water (liquid) absorbent materials and optical materials. Different from the conventional art, they do not require special ingenuity, apparatus and cumbersome conversion to assure high wettability and high transparency.

What is claimed is:

1. A polymerizable compound comprising, in a molecule thereof, one or more of the following partial structural formula (A):

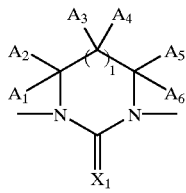

(A)

wherein $A_1$ to $A_6$ each independently represent a hydrogen atom or an alkyl group having 1 to 6 carbon atoms, $X_1$ represents O or S, and 1 stands for an integer of 0 to 2, and one or more thioepoxy groups or allylthio-carbonyl groups, or two or more allyloxycarbonyl groups, or one allyloxycarbonyloxy group or alloxycarbonylthio group.

2. A polymerizable compound comprising, in a molecule thereof, one or more of the following partial structural formula (A):

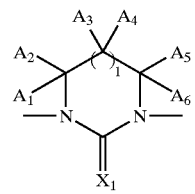

(A)

wherein $A_1$ to $A_6$ each independently represent a hydrogen atom or an alkyl group having 1 to 6 carbon atoms, $X_1$ represents O or S, and 1 stands for an integer of 0 to 2, and two or more mercapto groups, glycidylthio groups or (metb)acryloylthio groups.

3. A polymerizable compound represented by the following formula (B):

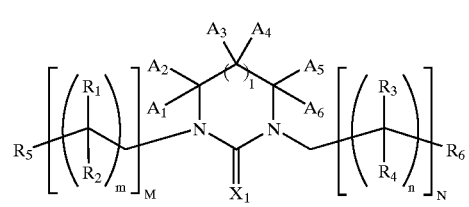

(B)

wherein $A_1$ to $A_6$ each independently represent a hydrogen atom or an alkyl group having 1 to 6 carbon atoms, $X_1$ represents O or S, 1 stands for an integer of 0 to 2, $R_1$ to $R_4$ each independently represent a hydrogen atom, a hydroxy group, a mercapto group, an alkyl group having 1 to 6 carbon atoms, an alkoxy group having 1 to 6 carbon atoms, an alkylthio group having 1 to 6 carbon atoms, or the below-described formulas (C) to (F), m and n each independently stand for an integer of from 0 to 10, M and N each independently stand for an integer of from 1 to 10, $R_5$ and $R_6$ each independently represent an alkoxy group having 1 to 6 carbon atoms, an alkylthio group having 1 to 6 carbon atoms, or the below-described formulas (C) to (F), with a proviso that any one or more of $R_1$ to $R_4$ are any of the below-described formulas (C) to (E)

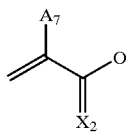
(C)

wherein $A_7$ represents a hydrogen atom or a methyl group, and $X_2$ represents O or S;

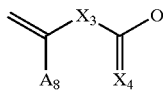
(D)

wherein $A_8$ represents a hydrogen atom or a methyl group, and $X_3$ and $X_4$ each independently represent O or S; and

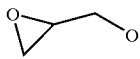
(E)

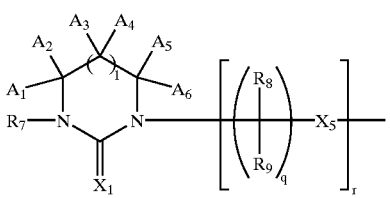
(F)

wherein $A_1$ to $A_6$ each independently represent a hydrogen atom or an alkyl group having 1 to 6 carbon atoms, $X_1$ or $X_5$ represents O or S, 1 stands for an integer of 0 to 2, $R_7$ each independently represents a hydrogen atom, an alkyl group having 1 to 6 carbon atoms, an alkoxyalkyl group having 2 to 12 carbon atoms or an alkylthioalkyl group having 2 to 12 carbon atoms, $R_8$ and $R_9$ each independently represent a hydrogen atom, a hydroxy group, a mercapto group, an alkyl group having 1 to 6 carbon atoms, an alkoxy group having 1 to 6 carbon atoms or an alkylthio group having 1 to 6 carbon atoms, q stands for an integer of from 1 to 6, and r stands for an integer of an integer of from 0 to 3.

4. A polymerizable composition comprising a polymerizable compound according to claim 3.

5. An organic polymer available from polymerization of a polymerizable compound according to claim 3 having a water contact angle of 20° or smaller.

6. An organic polymer available from polymerization of a polymerizable compound according to claim 5 having a water contact angle of 7° or smaller.

7. A molded or otherwise formed product comprising an organic polymer according to claim 5.

8. A polymerizable composition comprising a polymerizable compound according to claim 1.

9. A polymerizable composition comprising a polymerizable compound according to claim 2.

10. An organic polymer available from polymerization of a polymerizable compound according to claim 1 and having a water contact angle of 20° or smaller.

11. An organic polymer available from polymerization of a polymerizable compound according to claim 2 and having a water contact angle of 20° or smaller.

12. An organic polymer available from polymerization of a polymerizable composition according to claim 4 and having a water contact angle of 20° or smaller.

13. An organic polymer available from polymerization of a polymerizable composition according to claim 8 and having a water contact angle of 20° or smaller.

14. An organic polymer available from polymerization of a polymerizable composition according to claim 9 and having a water contact angle of 20° or smaller.

15. An organic polymer according to claim 10 wherein the organic polymer has a water contact angle of 7° or smaller.

16. An organic polymer according to claim 11 wherein the organic polymer has a water contact angle of 7° or smaller.

17. An organic polymer according to claim 12 wherein the organic polymer has a water contact angle of 7° or smaller.

18. An organic polymer according to claim 13 wherein the organic polymer has a water contact angle of 7° or smaller.

19. An organic polymer according to claim 14 wherein the organic polymer has a water contact angle of 7° or smaller.

20. A molded or otherwise formed product comprising an organic polymer according to claim 10.

21. A molded or otherwise formed product comprising an organic polymer according to claim 11.

22. A molded or otherwise formed product comprising an organic polymer according to claim 12.

23. A molded or otherwise formed product comprising an organic polymer according to claim 13.

24. A molded or otherwise formed product comprising an organic polymer according to claim 14.

* * * * *